US011629128B2

(12) United States Patent
Beatty et al.

(10) Patent No.: US 11,629,128 B2
(45) Date of Patent: Apr. 18, 2023

(54) COMPOUND AND DIMER COMPLEX EMBODIMENTS FOR SUPRAMOLECULAR SENSING

(71) Applicant: UVic Industry Partnerships Inc., Victoria (CA)

(72) Inventors: Meagan Beatty, Victoria (CA); Fraser Hof, Victoria (CA); Allison Selinger, Victoria (CA)

(73) Assignee: UVic Industry Partnerships Inc., Victoria (CA)

( * ) Notice: Subject to any disclaimer, the term of this patent is extended or adjusted under 35 U.S.C. 154(b) by 248 days.

(21) Appl. No.: 16/911,250

(22) Filed: Jun. 24, 2020

(65) Prior Publication Data
US 2020/0407318 A1 Dec. 31, 2020

Related U.S. Application Data

(60) Provisional application No. 62/866,473, filed on Jun. 25, 2019.

(51) Int. Cl.
*C07D 213/20* (2006.01)
*C07D 401/04* (2006.01)
*C07D 215/10* (2006.01)
*C07D 209/08* (2006.01)
*C07D 271/12* (2006.01)
*C07D 263/56* (2006.01)
*C07D 285/06* (2006.01)
*C07D 221/06* (2006.01)
*C07D 277/66* (2006.01)

(52) U.S. Cl.
CPC ......... *C07D 213/20* (2013.01); *C07D 209/08* (2013.01); *C07D 215/10* (2013.01); *C07D 221/06* (2013.01); *C07D 263/56* (2013.01); *C07D 271/12* (2013.01); *C07D 277/66* (2013.01); *C07D 285/06* (2013.01); *C07D 401/04* (2013.01)

(58) Field of Classification Search
CPC .. C07D 213/20; C07D 209/08; C07D 215/10; C07D 221/06; C07D 263/56; C07D 271/12; C07D 277/66; C07D 285/06; C07D 401/04
See application file for complete search history.

(56) References Cited

U.S. PATENT DOCUMENTS

| 5,770,453 A * | 6/1998 | Beer ................ G01N 27/3335 436/103 |
| 5,952,526 A | 9/1999 | Lamartine |
| 9,879,300 B2 | 1/2018 | Hof et al. |
| 10,338,037 B2 | 7/2019 | Hof et al. |
| 2004/0127722 A1* | 7/2004 | Parola ................ C07D 409/14 549/3 |
| 2006/0019311 A1 | 1/2006 | Moussa et al. |
| 2010/0062540 A1 | 3/2010 | Cecillon et al. |
| 2017/0052154 A1* | 2/2017 | Hof .......................... C08B 15/00 |

FOREIGN PATENT DOCUMENTS

| WO | WO 2008/001116 | 1/2008 |
| WO | WO 2013/091074 | 6/2013 |

OTHER PUBLICATIONS

Krebs; J. Chem. Soc., Perkin Trans. 2, 2000, 1935-1941. (Year: 2000).*
Beatty; J. Am. Chem. Soc. 2018, 140, 10, 3500-3504, with Supporting Information pp. S1-S24. (Year: 2018).*
Bitter; Tetrahedron 1997, 53, 16867-16876. (Year: 1997).*
Chawla; Tetrahedron 2006, 62, 2901-2911. (Year: 2006).*
Jin; Synthesis 2001, 7, 1023-1026. (Year: 2001).*
Kachkovskiy; Journal of Inclusion Phenomena and Macrocyclic Chemistry 2006, 56, 315-321. (Year: 2006).*
Klimentova; Journal of Molecular Structure 2007, 826, 48-63. (Year: 2007).*
Koh; Tetrahedron Letters 1994, 35, 8255-8258. (Year: 1994).*
Krebs; J. Chem. Soc., Perkin Trans. 2, 2000, 1929-1934. (Year: 2000).*
Kubinyi; Journal of Molecular Structure 1997, 408-409, 543-546. (Year: 1997).*
Verbiest; Special Publication—Royal Society of Chemistry 1993, 137, 326-31. (Year: 1993).*
Allen et al., "Inhibition of histone binding by supramolecular hosts," *Biochem. J.*, 459(3): 505-512, May 1, 2014.
Beatty et al., "Analyte-driven disassembly and turn-on fluorescent sensing in competitive biological media," *J. Am. Chem. Soc.*, 140(10): 3500-3504, Feb. 20, 2018.
Beshara et al., "A Simple Calixarene Recognizes Post-translationally Methylated Lysine," *ChemBioChem*, 11(1): 63-66, Nov. 20, 2009.
Coleman et al., "Enhanced detection of the pathogenic prion protein by its supramolecular associate with para-sulfonato-calix[n]arene derivatives," *New Journal of Chemistry*, vol. 31, pp. 711-717, 2007.
Daze et al., "Determining the effects of salt, buffer, and temperature on the complexation of methylated ammonium ions and methyllysines by sulfonated calixarenes," *Can. J. Chem.*, 91(11): 1072-1076, Jul. 4, 2013.
Daze et al., "Supramolecular hosts that recognize methyllysines and disrupt the interaction between a modified histone tail and its epigenetic reader protein," *Chemical Science*, vol. 3, pp. 2695-2699, Jun. 21, 2012.

(Continued)

*Primary Examiner* — Daniel R Carcanague
(74) *Attorney, Agent, or Firm* — Klarquist Sparkman, LLP

(57) ABSTRACT

Disclosed herein are embodiments of a compound that can be used as a supramolecular sensor for determining the presence of analytes (e.g., illicit drugs), and for identifying and/or quantifying the analytes. Also disclosed herein is a parallel synthesis method for making compound embodiments, as well as method embodiments for using the compound embodiments. Array embodiments comprising one or more compound embodiments disclosed herein also are described.

16 Claims, 62 Drawing Sheets
(2 of 62 Drawing Sheet(s) Filed in Color)

(56) References Cited

OTHER PUBLICATIONS

Daze et al., "Synthesis of New Trisulfonated Calix[4]arenes Functionalized at the Upper Rim, and Their Complexation with the Trimethyllysine Epigenetic Mark," *Organic Letters*, 14(6): 1512-1515, Mar. 7, 2012.

Daze et al., "The Cation-π Interaction at Protein-Protein Interaction Interfaces: Developing and Learning from Synthetic Mimics of Proteins That Bind Methylated Lysines," *Accounts of Chemical Research*, 46(4): 937-945, Jun. 22, 2012.

Daze, "Synthesis and evaluation of supramolecular chemical tools to study and disrupt epigenetic pathways," Thesis Dissertation submitted at Simon Fraser University, Apr. 28, 2014.

Florea et al., "A Fluorescence-Based Supramolecular Tandem Assay for Monitoring Lysine Methyltransferase Activity in Homogeneous Solution," *Chem. Eur. J.*, 18(12): 3521-3528, Feb. 24, 2012.

Garnett, "Substitutions of sulfonatocalix[4]arenes that lead to applications in biomolecular recognition and give rise to novel self-association phenomena," Thesis Abstract submitted at University of Victoria, circa Dec. 23, 2014.

Guo et al., "Operational calixarene-based fluorescent sensing systems for choline and acetylcholine and their application to enzymatic reactions," *Chem. Sci.*, vol. 2, pp. 1722-1734, Jun. 23, 2011.

International Search Report and Written Opinion issued for International Application No. PCT/CA2012/001174, dated Mar. 8, 2013.

Kim et al., "Calixarene-derived fluorescent probes," *Chem. Rev.*, vol. 107, pp. 3780-3799, Aug. 21, 2007.

Lee et al., "Supramolecular fishing for plasma membrane proteins using an ultrastable synthetic host-guest binding pair," *Nature Chemistry*, vol. 3, pp. 154-159, 2011.

McGovern et al., "Structural study of a small molecule receptor bound to dimethyllysine in lysosome," *Chem. Sci.*, 6(1): 442-449, Jan. 1, 2015.

Minaker et al., "Antibody-Free Reading of the Histone Code Using a Simple Chemical Sensor Array," *Journal of the American Chemical Society*, 134(28): 11674-11680, Jun. 14, 2012.

Tabet et al., "Synthetic trimethyllysine receptors that bind histone 3, trimethyllysine 27 (H3K27me3) and disrupt its interaction with the epigenetic reader protein CBX7," *Bioorganic & Medicinal Chemistry*, 21(22): 6857-7230, Sep. 19, 2013.

Tabet, "Development of fluorescence-based supramolecular tools for studying histone post-translational modifications," Thesis Dissertation submitted at Department of Chemistry, University of Victoria, circa Apr. 29, 2014.

\* cited by examiner

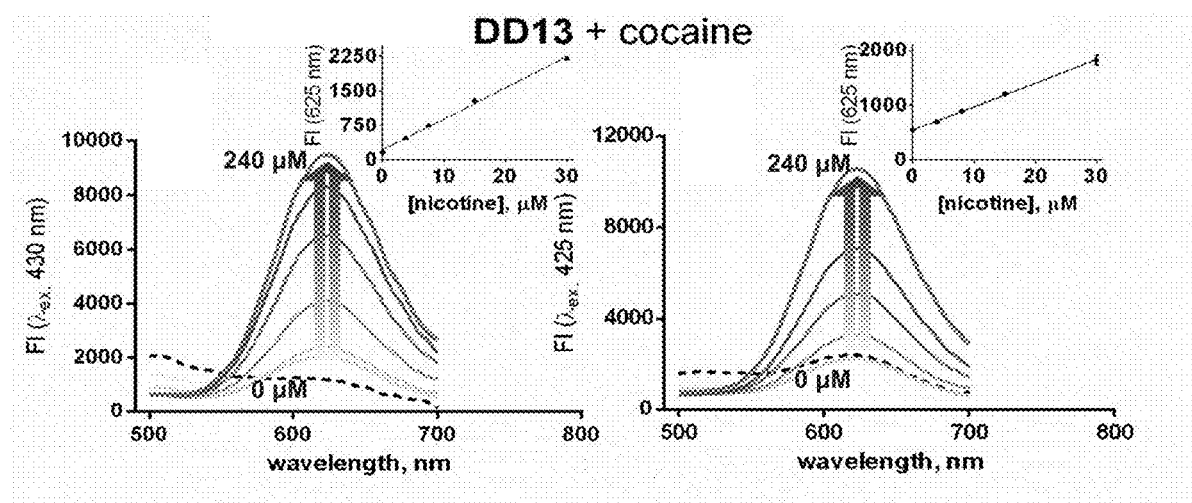
FIG. 7A  FIG. 7B
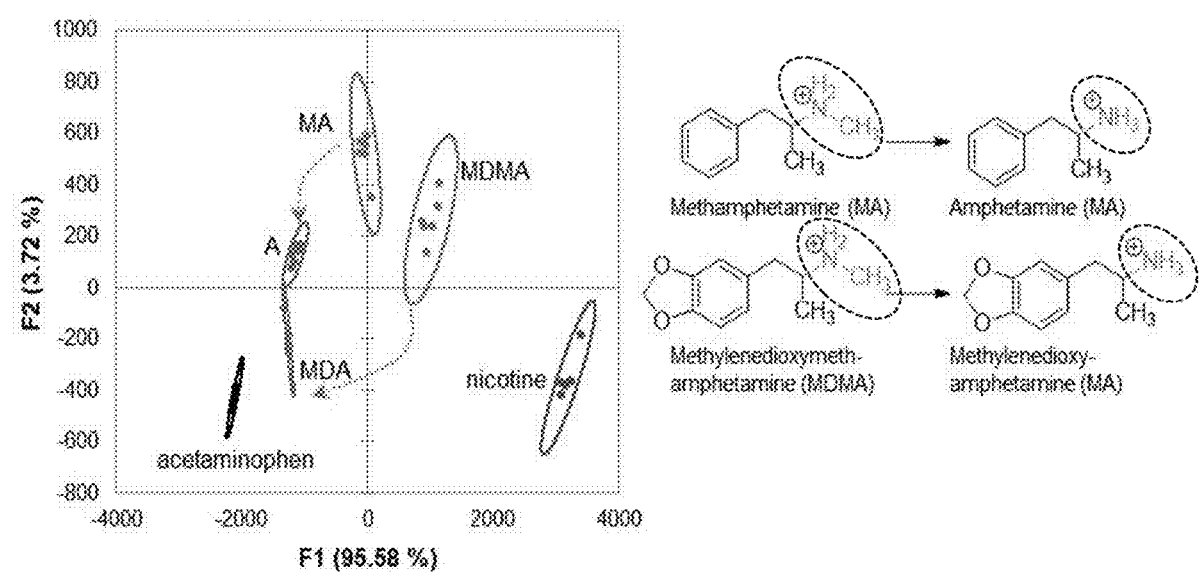
FIG. 8A

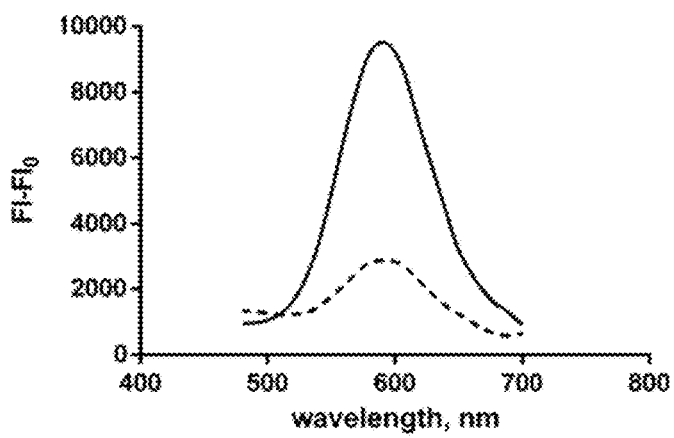
FIG. 14A
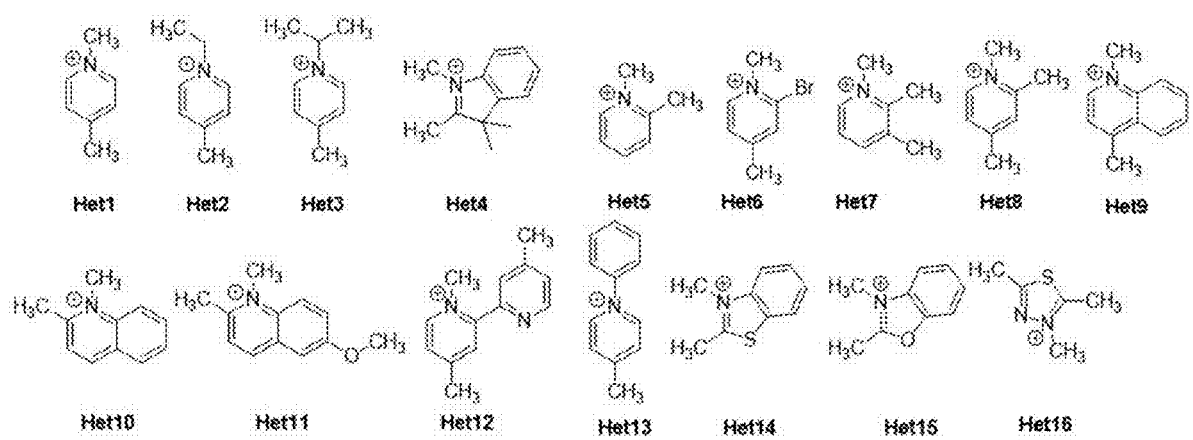
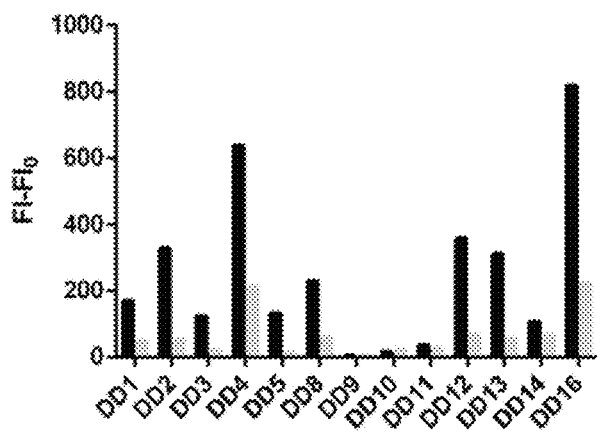
FIG. 14B

COMPOUND AND DIMER COMPLEX EMBODIMENTS FOR SUPRAMOLECULAR SENSING

CROSS REFERENCE TO RELATED APPLICATION

This application claims the benefit of the earlier filing date of U.S. Provisional Patent Application No. 62/866,473, filed on Jun. 25, 2019, the entirety of which is incorporated herein by reference.

FIELD

Disclosed herein are embodiments of compounds and dimer complexes for analyte detection in various media and methods of making and using the same.

BACKGROUND

Analyte detection using supramolecular sensors is often limited to organic solvents and aqueous/organic solvent mixtures as detection is difficult when the analyte is in complex aqueous biological media. Additionally, methods of making such supramolecular sensors can be difficult and are often limited to synthesizing singular sensors individually. There exists a need in the art for supramolecular sensors that can accurately detect analytes, even those present in complex biological media, using aqueous solutions and methods of making such sensors that provide the ability to rapidly and efficiently make such sensors.

SUMMARY

Disclosed herein are embodiments of compounds and dimer complexes that can be used for supramolecular sensing. In some embodiments, the compound has a structure satisfying any one or more of the structural formulas described herein. The dimer complex can comprise a first compound having such a structure and a second compound having such a structure, wherein the first compound and the second compound can be identical or different. Also disclosed herein are embodiments of methods for using the compounds and/or the dimer complexes for determining the presence of an analyte. Representative analytes that can be detected using such methods are disclosed herein. Also disclosed are embodiments of an array comprising a plurality of compound and/or dimer complex embodiments and methods of using such arrays.

The foregoing and other objects and features of the present disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2C show results obtained from using method embodiments to make certain compound embodiments disclosed herein, wherein FIG. 2A is a photographic image showing color changes resulting upon synthesis of certain compound embodiments disclosed herein and FIGS. 2B and 2C show ultra performance liquid chromatography/mass spectrometry (UPLC-MS) traces for particular compound embodiments (DD12 and DD6, respectively).

FIG. 3A shows an exemplary high through-put reaction set-up wherein each compound synthesis reaction occurs in a separate vial heated by an aluminium block; (ii) FIG. 3B shows an assay after the crude mixture from FIG. 3A is aliquoted (10 µL) into a black-walled 96-well plate, and the methanol is evaporated to leave dried compound pellets; and (iii) FIG. 3C shows results after the compound pellets are re-dissolved in buffered water, in which they spontaneously assemble to form a dimer complex, and the drug is added (wherein fluorescence is measured before and after drug addition and the difference in fluorescence is represented in FIG. 3C); with reference to FIG. 3C, the black bars=10 µM nicotine, and the grey bars=10 µM acetaminophen.

FIGS. 4A-4C show results obtained from using nicotine titrations to determine the ability of dimer complex embodiments disclosed herein to disassemble and form fluorescent compound-nicotine complexes, wherein FIG. 4A shows $^1$H NMR titration results for embodiments where nicotine (10 mM) is added to a composition comprising a dimer complex comprising compound embodiment DD12 (500 µM), showing fluorophore resonances in either fast exchange by shifting downfield (dotted lines) or in intermediate exchange and broadening (stars), which is indicative of disassembly and formation of nicotine complex; FIG. 4B shows a photographic image of NMR tubes containing dimer complex comprising compound embodiment DD12 without nicotine (labeled as "−" in FIG. 4B, which does not exhibit fluorescence) and with nicotine (labeled as "+" in FIG. 4B, which exhibits fluorescence when irradiated by a hand-held lamp); and FIG. 4C shows a graph of fluorescence titration curves upon addition of nicotine into a solution comprising a dimer complex comprising compound embodiment DD12 (12 µM).

FIGS. 7A and 7B are fluorescence titration curves showing results obtained after adding cocaine to a dimer complex embodiment comprising compound embodiment DD13 in buffered water (NaH$_2$PO$_4$/Na$_2$HPO$_4$ (10 mM, pH 7.4), FIG. 7A) and saliva (1:1 dilution of saliva with water, FIG. 7B).

FIGS. 8A-8C show principal component analysis (PCA) score plots, which show that dimer complex embodiments comprising compound embodiments DD1, DD4, DD8, DD12, DD13—each at 12 µM—can distinguish between different amphetamines (FIG. 8A), anaesthetics (FIG. 8B), and opioids (FIG. 8C)—each drug at a concentration of 100 µM in a NaH$_2$PO$_4$/Na$_2$HPO$_4$ (10 mM, pH 7.4) buffer—and wherein the dotted lines map the parent drug to its main metabolite; structures in each class are shown to the right of the PCA plot, with the motifs that are recognized by the calixarene pocket being circled; and each sample cluster is enclosed by 95% confidence ellipses.

FIGS. 14A and 14B provide results for different dimer complex embodiments upon exposure to nicotine; FIG. 14A shows combined fluorescence spectra ($\lambda_{ex.}$ 390 nm) of a dimer complex comprising compound embodiment DD1 with nicotine (50 µM), which shows that fluorescence increases when changing the reaction time from 1.5 hours (dotted line) to 6 hours (solid line); FIG. 14B shows results for the response of different dimer complex embodiments upon exposure to nicotine (10 µM) after making the compound embodiment of the dimer complex using either 40 eq. of morpholine (black bars) or 20 eq. of morpholine (gray bars), and without having to purify the synthesized compound/dimer complex embodiment prior to nicotine addition.

FIG. 37A shows results obtained using media comprising $NaH_2PO_4/Na_2HPO_4$ buffered water (10 mM, pH 7.4, $\lambda_{ex.}$=385 nm) and FIG. 37B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 37B) and water (FIG. 37A).

FIG. 38A shows results obtained using media comprising $NaH_2PO_4/Na_2HPO_4$ buffered water (10 mM, pH 7.4, $\lambda_{ex.}$=385 nm) and FIG. 38B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 38B) and water (FIG. 38A).

FIG. 39A shows results obtained using media comprising $NaH_2PO_4/Na_2HPO_4$ buffered water (10 mM, pH 7.4, $\lambda_{ex.}$=385 nm) and FIG. 39B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 39B) and water (FIG. 39A).

FIG. 40A shows results obtained using media comprising $NaH_2PO_4/Na_2HPO_4$ buffered water (10 mM, pH 7.4, $\lambda_{ex.}$=385 nm) and FIG. 40B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 40B) and water (FIG. 40A).

FIG. 41A shows results obtained using media comprising $NaH_2PO_4/Na_2HPO_4$ buffered water (10 mM, pH 7.4, $\lambda_{ex.}$=385 nm) and FIG. 41B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 41B) and water (FIG. 41A).

FIG. 42A shows results obtained using media comprising $NaH_2PO_4/Na_2HPO_4$ buffered water (10 mM, pH 7.4, $\lambda_{ex.}$=385 nm) and FIG. 42B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 42B) and water (FIG. 42A).

FIG. 43A shows results obtained using media comprising $NaH_2PO_4/Na_2HPO_4$ buffered water (10 mM, pH 7.4, $\lambda_{ex.}$=385 nm) and FIG. 43B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 43B) and water (FIG. 43A).

FIG. 44A shows results obtained using media comprising $NaH_2PO_4/Na_2HPO_4$ buffered water (10 mM, pH 7.4, $\lambda_{ex.}$=385 nm) and FIG. 44B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 44B) and water (FIG. 44A).

FIG. 45A shows results obtained using media comprising $NaH_2PO_4/Na_2HPO_4$ buffered water (10 mM, pH 7.4, $\lambda_{ex.}$=385 nm) and FIG. 45B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 45B) and water (FIG. 45A).

FIG. 46A shows results obtained using media comprising $NaH_2PO_4/Na_2HPO_4$ buffered water (10 mM, pH 7.4, $\lambda_{ex.}$=385 nm) and FIG. 46B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 46B) and water (FIG. 46A).

FIG. 47A shows results obtained using media comprising $NaH_2PO_4/Na_2HPO_4$ buffered water (10 mM, pH 7.4, $\lambda_{ex.}$=385 nm) and FIG. 47B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 47B) and water (FIG. 47A).

FIG. 48A shows results obtained using media comprising $NaH_2PO_4/Na_2HPO_4$ buffered water (10 mM, pH 7.4, $\lambda_{ex.}$=385 nm) and FIG. 48B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 48B) and water (FIG. 48A).

FIG. 49A shows results obtained using media comprising $NaH_2PO_4/Na_2HPO_4$ buffered water (10 mM, pH 7.4, $\lambda_{ex.}$=385 nm) and FIG. 49B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 49B) and water (FIG. 49A).

FIG. 50A shows results obtained using media comprising $NaH_2PO_4/Na_2HPO_4$ buffered water (10 mM, pH 7.4, $\lambda_{ex.}$=385 nm) and FIG. 50B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 50B) and water (FIG. 50A).

FIG. 51A shows results obtained using media comprising $NaH_2PO_4/Na_2HPO_4$ buffered water (10 mM, pH 7.4, $\lambda_{ex.}$=385 nm) and FIG. 51B shows results obtained using diluted saliva (1:1, saliva:water, $\lambda_{ex.}$=390 nm); insets show binding isotherms monitored at fluorescence maximum, $\lambda_{max.}$=590 nm in both saliva (FIG. 51B) and water (FIG. 51A).

FIGS. 52A and 52B show DD1Cx5 color changing properties with a shift in $\lambda_{max\,ex}$ from 380 nm to 414 nm upon cocaine binding and FIGS. 52C and 52D show fluorescence responses for both nicotine and cocaine with a $\lambda_{max\,em}$ of 598 nm.

FIGS. 53A and 53B show DD4Cx5 color changing properties with a shift in $\lambda_{max\,ex}$ from 480 nm to 540 nm upon nicotine binding and a shift to 544 nm upon cocaine binding and and FIGS. 53C and 53D show fluorescence responses for both nicotine and cocaine with a $\lambda_{max\,em}$ of 574 nm.

FIGS. 53A-53D are graphs of titration curves showing absorbance (FIG. 55A) and fluorescence (FIGS. 55B-55D) results after combining a mixture of HemiDD1, DD4 and DD13Cx5 (12 µM each) in $NaH_2PO_4/Na_2HPO_4$ buffered water (10 mM, pH 7.4) with human serum albumin.

DETAILED DESCRIPTION

I. Overview of Terms

Figure 1A:
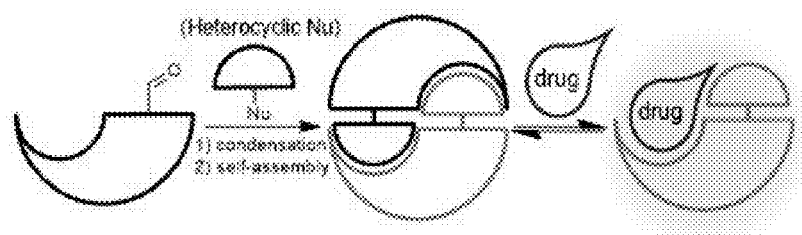
FIGS. 1A-1C are schematic illustrations of embodiments of using dimer complex embodiments as sensors for analytes according to embodiments of the present disclosure.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a symbol "–" which is used to show how the defined functional group attaches to, or within, the compound to which it is bound.

Also, a dashed bond (i.e., "---") as used in certain formulas described herein indicates an optional bond (that is, a bond that may or may not be present). A wavy bond (i.e., "-") as used in certain formulas or structures described herein indicates a bond disconnection. A person of ordinary skill in the art would recognize that the definitions provided below and the compounds and formulas included herein are not intended to include impermissible substitution patterns (e.g., methyl substituted with 5 different groups, and the like). Such impermissible substitution patterns are easily recognized by a person of ordinary skill in the art. In formulas and compounds disclosed herein, a hydrogen atom is present and completes any formal valency requirements (but may not necessarily be illustrated) wherever a functional group or other atom is not illustrated. For example, a phenyl ring that is drawn as

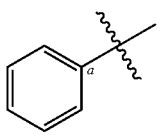 [SMILES: *c1ccccc1]

comprises a hydrogen atom attached to each carbon atom of the phenyl ring other than the "a" carbon, even though such hydrogen atoms are not illustrated. Any functional group disclosed herein and/or defined above can be substituted or unsubstituted, unless otherwise indicated herein.

Acyl Halide: —C(O)X, wherein X is a halogen, such as Br, F, I, or Cl.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Aliphatic-aromatic: An aromatic group that is or can be coupled to a compound disclosed herein, wherein the aromatic group is or becomes coupled through an aliphatic group.

Aliphatic-aryl: An aryl group that is or can be coupled to a compound disclosed herein, wherein the aryl group is or becomes coupled through an aliphatic group.

Aliphatic-heteroaryl: A heteroaryl group that is or can be coupled to a compound disclosed herein, wherein the heteroaryl group is or becomes coupled through an aliphatic group.

Alkenyl: An unsaturated monovalent hydrocarbon having at least two carbon atoms to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: —O-aliphatic, such as —O-alkyl, —O-alkenyl, —O-alkynyl; with exemplary embodiments including, but not limited to, methoxy, ethoxy, n-propoxy, isopropoxy, n-butoxy, t-butoxy, sec-butoxy, n-pentoxy (wherein any of the aliphatic components of such groups can comprise no double or triple bonds, or can comprise one or more double and/or triple bonds).

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atoms to 50 carbon atoms ($C_{2-5}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —C(O)NR$^a$R$^b$ or —NR$^a$C(O)R$^b$ wherein each of R$^a$ and R$^b$ independently is selected from hydrogen, aliphatic, heteroaliphatic, haloaliphatic, haloheteroaliphatic, aromatic, or an organic functional group.

Amino: —NR$^a$R$^b$, wherein each of R$^a$ and R$^b$ independently is selected from hydrogen, aliphatic, heteroaliphatic, haloaliphatic, haloheteroaliphatic, aromatic, or an organic functional group.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

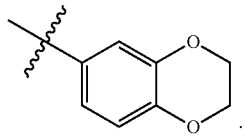 [SMILES: *c1ccc2c(c1)OCCO2]

However, in certain examples, context or express disclosure may indicate that the point of attachment is through a non-aromatic portion of the condensed ring system. For example,

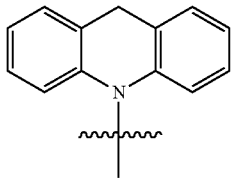

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Aromatic groups may be substituted with one or more groups other than hydrogen, such as aliphatic, heteroaliphatic, haloaliphatic, haloheteroaliphatic, aromatic, or an organic functional group.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, haloaliphatic, haloheteroaliphatic, aromatic, or an organic functional group.

Aryloxy: —O-aromatic.

Azo: —N=$NR^a$ wherein $R^a$ is hydrogen, aliphatic, heteroaliphatic, haloaliphatic, haloheteroaliphatic, aromatic, or an organic functional group.

Carbamate: —OC(O)$NR^aR^b$, wherein each of $R^a$ and $R^b$ independently is selected from hydrogen, aliphatic, heteroaliphatic, haloaliphatic, haloheteroaliphatic, aromatic, or an organic functional group.

Carboxyl: —C(O)OH.

Carboxylate: —C(O)O— or salts thereof, wherein the negative charge of the carboxylate group may be balanced with an $M^+$ counterion, wherein $M^+$ may be an alkali ion, such as K+, Na+, Li+; an ammonium ion, such as $^+N(R^b)_4$ where $R^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Cyano: —CN.

Detectable Moiety: A component of a compound embodiment that provides a detectable signal. In some embodiments, the detectable moiety can provide the detectable signal when attached to a compound embodiment and after an analyte has interacted with the compound, such as when the analyte disrupts a dimer comprising the compound, or when the analyte acts to unfold a folded structure of the compound embodiment wherein the detectable moiety folds into a binding pocket of the compound embodiment. In yet additional embodiments, the detectable moiety can be present in a dimer complex as described herein and can emit a detectable signal that is different (e.g., different in wavelength or color and/or fluorescence intensity) from any detectable signal emitted by the first and/or second compounds in the dimer complex.

Detectable Signal: A signal (e.g., a color change, an increase or decrease in fluorescence, an increase or decrease in phosphorescence or other type of luminescence, and the like) that occurs when a dimer comprising a compound embodiment disclosed herein, or a folded compound embodiment is disrupted by an analyte that binds to or otherwise interacts with the compound embodiment. In some embodiments, the detectable signal occurs after a homodimer or heterodimer comprising two compound embodiments (which can be the same in the case of a homodimer, or different in the case of a heterodimer) is disrupted by binding of an analyte to a portion of at least one of the compound embodiments providing the homodimer or heterodimer. In yet additional embodiments, the detectable signal occurs after a folded compound embodiment is unfolded by an analyte binding to (or otherwise associating with) the compound embodiment. In such embodiments, the folding can occur wherein the detectable moiety is bound or otherwise attracted to a binding pocket of the compound embodiment; and the unfolding can occur wherein the analyte displaces the detectable moiety from the binding pocket. In yet additional embodiments, a dimer complex can emit a detectable signal that is different (e.g., different in wavelength or color and/or fluorescence intensity) from a detectable signal emitted by the first and/or second compounds in the dimer complex. In some embodiments, a detectable signal is visible to the naked eye or is visible using an analytical detection technique.

Disulfide: —$SSR^a$, wherein $R^a$ is selected from hydrogen, aliphatic, heteroaliphatic, haloaliphatic, haloheteroaliphatic, aromatic, or an organic functional group.

Dithiocarboxylic: —C(S)$SR^a$ wherein $R^a$ is selected from hydrogen, aliphatic, heteroaliphatic, haloaliphatic, haloheteroaliphatic, aromatic, or an organic functional group.

Ester: —C(O)$OR^a$ or —OC(O)$R^a$, wherein $R^a$ is selected from aliphatic, heteroaliphatic, haloaliphatic, haloheteroaliphatic, aromatic, or an organic functional group.

Ether: -aliphatic-O-aliphatic, -aliphatic-O-aromatic, -aromatic-O-aliphatic, or -aromatic-O-aromatic.

Fluorophore: A compound or functional group capable of emitting fluorescence.

Representative fluorophores can include, but are not limited to, a xanthene derivative (e.g., fluorescein, rhodamine, eosin, Texas red, Oregon green, or the like), cyanine or a cyanine derivative (e.g., indocarbocyanine, oxacarbocyanine, thiacarbocyanine, merocyanine, Cy3, or Cy5), a naphthalene derivative (e.g., dansyl, prodan, and the like), coumarin and derivatives thereof (e.g., hydroxycoumarin, aminocoumarin, methoxycoumarin, and the like), oxadiazole derivatives (e.g., pyridyloxazole, nitrobenzoxadiazole, benzoxadiazole, and the like), anthracene derivatives, pyrene derivatives (e.g., cascade blue), oxazine derivatives (e.g., Nile red, Nile blue, cresyl violet, and the like), acridine derivatives (e.g., auramine, crystal violet, malachite green, and the like), fluorone dyes (e.g., rhodamine, rhodol, methylrhodol), isoquinoline dyes (e.g., 2-(2-methoxyethyl)-1H-benzo[de]isoquinoline-1,3(2H)-dione), a naphthalimide compound (e.g., naphthalimide or 4-(2-methoxyethoxy)-N-butyl-1,8-naphthalimide), a chromenone dye (e.g., 4-methyl-2H-chromen-2-one), styryl derivatives (e.g. stilbene, tetraarylethene, triarylethene, 4-(hydroxystyryl)-N-methylpyridinium, 4-(aminostyryl)-N-methylpyridinium, and the like), BODIPY derivatives (e.g. 2,4-dimethyl-BODIPY), and tetrapyrrole derivatives (e.g., porphin, phthalocyanine, and the like) and in some embodiments can be methylrhodol, 2-(2-methoxyethyl)-1H-benzo[de]isoquinoline-1,3(2H)-dione, 4-methyl-2H-chromen-2-one, coumarin, naphthalimide, fluorescein, rhodamine, rhodol, Cy3, or Cy5. In some embodiments, compound embodiments of the present disclosure comprise a precursor to such fluorophore groups. Also, fluorophore compound embodiments can be described as heteroaryl and/or heteroaliphatic (e.g., heterocyclic) groups in the present disclosure.

Halo (or halide or halogen): Fluoro, chloro, bromo, or iodo.

Haloaliphatic: An aliphatic group wherein one or more hydrogen atoms, such as one to 10 hydrogen atoms, independently is replaced with a halogen atom, such as fluoro, bromo, chloro, or iodo.

Haloaliphatic-aryl: An aryl group that is or can be coupled to a compound disclosed herein, wherein the aryl group is or becomes coupled through a haloaliphatic group.

Haloaliphatic-heteroaryl: A heteroaryl group that is or can be coupled to a compound disclosed herein, wherein the heteroaryl group is or becomes coupled through a haloaliphatic group.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a CX₃ group, wherein each X independently can be selected from fluoro, bromo, chloro, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group. Alkoxy, ether, amino, disulfide, peroxy, and thioether groups are exemplary (but non-limiting) examples of heteroaliphatic. In some embodiments, a fluorophore can also be described herein as a heteroaliphatic group, such as when the heteroaliphatic group is a heterocyclic group.

Heteroaliphatic-aryl: An aryl group that is or can be coupled to a compound disclosed herein, wherein the aryl group is or becomes coupled through a heteroaliphatic group.

Heteroaryl: An aryl group comprising at least one heteroatom to six heteroatoms, such as one to four heteroatoms, which can be selected from, but not limited to oxygen, nitrogen, sulfur, silicon, boron, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. Heteroaryl groups may be substituted with one or more groups other than hydrogen, such as aliphatic, heteroaliphatic, haloaliphatic, haloheteroaliphatic, aromatic, or an organic functional group. In some embodiments, a fluorophore can also be described herein as a heteroaryl group.

Heteroatom: An atom other than carbon or hydrogen, such as (but not limited to) oxygen, nitrogen, sulfur, silicon, boron, selenium, or phosphorous. In particular disclosed embodiments, such as when valency constraints do not permit, a heteroatom does not include a halogen atom.

Hydrophobic Cation: A functional group comprising a positively charged atom and one or more groups that exhibit hydrophobic characteristics (e.g., aliphatic groups or other neutral or non-polar functional groups). In some embodiments, a hydrophobic cation includes quaternary amine groups (e.g., an amine comprising at least one aliphatic group bound to the nitrogen and three other groups bound to the nitrogen).

Ketone: —C(O)R$^a$, wherein R$^a$ is selected from aliphatic, heteroaliphatic, haloaliphatic, haloheteroaliphatic, aromatic, or an organic functional group.

Organic Functional Group: A functional group that may be provided by any combination of aliphatic, heteroaliphatic, aromatic, haloaliphatic, and/or haloheteroaliphatic groups, or that may be selected from, but not limited to, aldehyde; arylroxy; acyl halide; halogen; nitro; cyano; azide; carboxyl (or carboxylate); amide; ketone; carbonate; imine; azo; carbamate; hydroxyl; thiol; sulfonyl (or sulfonate); oxime; ester; thiocyanate; thioketone; thiocarboxylic acid; thioester; dithiocarboxylic acid or ester; phosphonate; phosphate; silyl ether; sulfinyl; thial; or combinations thereof.

Oxime: —CR$^a$=NOH, wherein R$^a$ is hydrogen, aliphatic, heteroaliphatic, haloaliphatic, haloheteroaliphatic, aromatic, or an organic functional group.

Peroxy: —O—OR$^a$ wherein R$^a$ is hydrogen, aliphatic, heteroaliphatic, haloaliphatic, haloheteroaliphatic, aromatic, or an organic functional group.

Phosphate: —O—P(O)(OR$^a$)$_2$, wherein each R$^a$ independently is hydrogen, aliphatic, heteroaliphatic, haloaliphatic, haloheteroaliphatic, aromatic, or an organic functional group; or wherein one or more R$^a$ groups are not present and the phosphate group therefore has at least one negative charge, which can be balanced by a counterion, M$^+$, wherein each M$^+$ independently can be an alkali ion, such as K$^+$, Na$^+$, Li$^+$; an ammonium ion, such as $^+$N(R$^b$)$_4$ where R$^b$ is H, aliphatic, heteroaliphatic, haloaliphatic, haloheteroaliphatic, or aromatic; or an alkaline earth ion, such as [Ca$^{2+}$]$_{0.5}$, [Mg$^{2+}$]$_{0.5}$, or [Ba$^{2+}$]$_{0.5}$.

Phosphonate: —P(O)(OR$^a$)$_2$, wherein each R$^a$ independently is hydrogen, aliphatic, heteroaliphatic, haloaliphatic, haloheteroaliphatic, aromatic, or an organic functional group; or wherein one or more R$^a$ groups are not present and the phosphate group therefore has at least one negative charge, which can be balanced by a counterion, M$^+$, wherein each M$^+$ independently can be an alkali ion, such as K$^+$, Na$^+$, Li$^+$; an ammonium ion, such as +N(R$^b$)$_4$ where R$^b$ is H, aliphatic, heteroaliphatic, haloaliphatic, haloheteroaliphatic, or aromatic; or an alkaline earth ion, such as [Ca$^{2+}$]$_{0.5}$, [Mg$^{2+}$]$_{0.5}$, or [Ba$^{2+}$]$_{0.5}$.

Silyl Ether: —OSiR$^a$R$^b$, wherein each of R$^a$ and R$^b$ independently is selected from hydrogen, aliphatic, heteroaliphatic, haloaliphatic, haloheteroaliphatic, aromatic, or an organic functional group.

Subject: Mammals and other animals, such as humans, companion animals (e.g., dogs, cats, rabbits, etc.), utility animals, and feed animals; thus, disclosed methods are applicable to both human therapy and veterinary applications.

Sulfinyl: —S(O)R$^a$, wherein R$^a$ is selected from hydrogen, aliphatic, heteroaliphatic, haloaliphatic, haloheteroaliphatic, aromatic, or an organic functional group.

Sulfonyl: —SO$_2$R$^a$, wherein R$^a$ is selected from hydrogen, aliphatic, heteroaliphatic, haloaliphatic, haloheteroaliphatic, aromatic, or an organic functional group.

Sulfonamide: —SO$_2$NR$^a$R$^b$ or —N(R$^a$)SO$_2$R$^b$, wherein each of R$^a$ and R$^b$ independently is selected from hydrogen, aliphatic, heteroaliphatic, haloaliphatic, haloheteroaliphatic, aromatic, or an organic functional group.

Sulfonate: —SO$_3$, wherein the negative charge of the sulfonate group may be balanced with an M$^+$ counter ion, wherein M$^+$ may be an alkali ion, such as K$^+$, Na$^+$, Li$^+$; an ammonium ion, such as $^+$N(R$^b$)$_4$ where R$^b$ is H, aliphatic, heteroaliphatic, haloaliphatic, haloheteroaliphatic, or aromatic; or an alkaline earth ion, such as [Ca$^{2+}$]$_{0.5}$, [Mg$^{2+}$]$_{0.5}$, or [Ba$^{2+}$]$_{0.5}$.

Thial: —C(S)H.

Thiocarboxylic acid: —C(O)SH, or —C(S)OH.

Thiocyanate: —S—CN or —N=C=S.

Thioester: —C(O)SR$^a$ or —C(S)OR$^a$ wherein R$^a$ is selected from hydrogen, aliphatic, heteroaliphatic, haloaliphatic, haloheteroaliphatic, aromatic, or an organic functional group.

Thioether: —S-aliphatic or —S-aromatic, such as —S-alkyl, —S-alkenyl, —S-alkynyl, —S-aryl, or —S-heteroaryl; or -aliphatic-S-aliphatic, -aliphatic-S-aromatic, -aromatic-S-aliphatic, or -aromatic-S-aromatic.

Thioketone: —C(S)R$^a$ wherein R$^a$ is selected from hydrogen, aliphatic, heteroaliphatic, haloaliphatic, haloheteroaliphatic, aromatic, or an organic functional group.

II. Introduction

Analyte detection in water is made more difficult and less predictable when the target is found in complex biological media. And, de novo design of new sensing systems for biological media possess fallbacks that have prevented methods of making supramolecular sensors efficiently.

Compound embodiments disclosed herein can be used as supramolecular sensors. In some embodiments, the unique topology of the disclosed compound embodiments can lead to self-assembly in water, aqueous-based solutions and/or organic solutions, into dimer complexes comprising a first compound and a second compound, wherein each of the first and the second compound can have a structure satisfying formulas disclosed herein. In some embodiments, the aqueous solutions can be water, or a buffered solution (e.g., solutions comprising a buffer, such as a phosphate buffer). In some embodiments, the disclosed compound embodiments can self-assemble into non-emissive dimers (e.g., dimers that do not exhibit a detectable signal) and/or dimers that exhibit a dimer detectable signal, wherein the dimer detectable signal is different from any signal emitted by the first compound and/or the second compound. Upon the addition of an analyte from a sample, such as a biological sample, the dimers can disassemble and provide a fluorescent or colorimetric complex. For example, see FIGS. 1A and/or 1B for exemplary schematic illustrations. As shown in FIG. 1B, a compound embodiment 100 can comprise a binding pocket 102 and a reporter moiety 104 that provides a detectable signal. The compound embodiment can self-assemble into a dimer complex 106, thereby quenching any signal from the respective reporter moieties of the compound embodiments. Upon exposure to an analyte 108, the dimer complex 106 is disrupted and the analyte binds to the binder pocket, providing a different detectable signal produced by interaction between the compound embodiment and the analyte and the dimer complex disruption (shown for product 110). Due to the salt tolerance of the disclosed compounds, they can operate in the presence of high concentrations, of biologically relevant concentrations, or of physiological concentrations of NaCl, proteins, peptides, organic co-solutes, reducing agents, transition metal salts, and other enzyme co-factors.

In some embodiments the disclosed compounds comprise a (i) host element capable of binding an analyte and (ii) a detectable moiety (ex. chromophore or ring system) capable of producing a detectable signal, wherein the compounds self-assemble into dimers with control over the chromophore-chromophore interactions. In some embodiments, self-assembled dimers are in a quenched state wherein the quenched state may be non-emissive or may be characterized by a fluorescent or colorimetric signal at multiple wavelengths that is characteristic of the starting dimeric state. The dimers disassemble and produce a turn-on response when brought into contact with a sample containing an analyte capable of binding the host element. In additional embodiments the turn-on response produces a detectable signal that is fluorescent or colorimetric. In further embodiments the analyte comprises or consists of a cation or a hydrophobic cation. In yet some additional embodiments, the compound embodiments can be used to provide dimer complexes that can exhibit two detectable signals, including a fluorescent and colorimetric signal.

Also disclosed herein are embodiments of a parallel synthesis-driven approach to creating a family of new compounds capable of acting as supramolecular sensors, and their use for the rapid identification of sensors for illicit drugs. Many classes of drugs including opioids, amphetamines, tropane alkaloids, and anaesthetics contain a hydrophobic cation in their structure that can be recognized by sulfonate/carboxylate-calix[4]arene-based cores contained in certain compound embodiments. In some embodiments, the parallel synthesis method embodiments and a highly efficient crude screening process can be used to quickly identify new sensors for the detection of a given analyte in a given solution. Also disclosed herein are embodiments of an analyte-identifying sensor array that operates on multiple classes of illicit drugs.

The parallel approach described here gives access to new agents with a supramolecular sensing mechanism, but with varying photophysical properties, guest binding properties, and salt responses.

The new supramolecular sensor disclosed herein have sensitivities in real biological solutions that meet or approach the values seen in real human samples. Drug concentrations in saliva reach low μM within an hour of consumption and it has been shown that the compound embodiment sensors can detect at or near these concentrations. For example, 3,4-methyl enedioxymethamphetamine (MDMA) concentrations reaches 34 μM in saliva after 1.5 hours while cocaine can be present in saliva at 3 μM after 1 hour. The sensors were able to detect these concentrations in saliva. Compound embodiments remain functional in saliva that often contains 3 g/L of proteins and 20-100 mM concentrations of various salts.

The power of a sensor array to detect many analytes without the need for excellent specificity or rational design was demonstrated with the combination of five different compound embodiments (DD1, DD4, DD8, DD12, DD13). From the nicotine, MDMA, and cocaine titrations, it was noticed that subtle changes in drug structure induced small but significant changes in fluorescence responses. Those differences translated into substantial success when the DDs were deployed in a sensor array. With the combination of the five sensors and PCA plots, it was possible to reasonably distinguish between each member within a drug class. Through Linear Discriminant Analysis (LDA) 100% of members within the opioid and anaesthetics family were classified and 96% in the amphetamines were classified.

III. Compound and Array Embodiments

Disclosed herein are embodiments of a compound that can be used as a sensor capable of detecting biologically-relevant analytes in various media environments. In some embodiments, a plurality of such compound embodiments can be used together to provide embodiments of a sensing array, which is described in more detail herein.

Compound embodiments disclosed herein can have structures satisfying Formula I below.

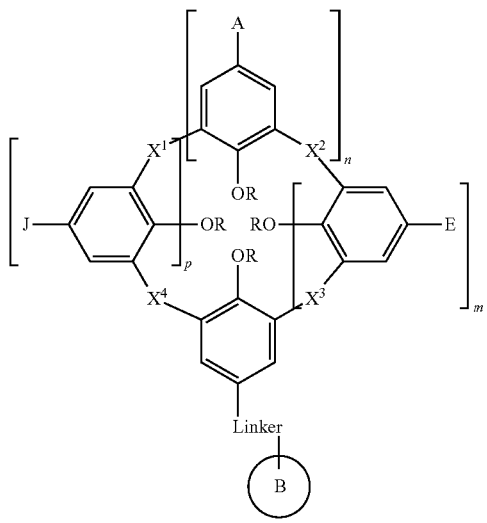

Formula I

With reference to Formula I, the following variable recitations can apply:

each A independently can be selected from C(O)H; CH$_2$OH; CO$_2$R' or SO$_3$R', wherein each R' independently is H or a counterion; or linker'-Ring$_{B'}$, wherein linker' is aliphatic or heteroaliphatic and Ring$_{B'}$ is a ring system capable of producing a detectable signal;

each E independently can be selected from CO$_2$R' or SO$_3$R', wherein each R' independently is H or a counterion;

each J independently can be selected from CO$_2$R' or SO$_3$R', wherein each R' independently is H or a counterion;

each of X$^1$, X$^2$, X$^3$, and X$^4$ independently is CH$_2$, O, S, CH$_2$OCH$_2$, CH$_2$SCH$_2$, or NR$^b$ wherein each R$^b$ independently is hydrogen, aliphatic, heteroaliphatic, or aromatic;

each R independently is H, aliphatic, or a counterion;

the linker group is aliphatic or heteroaliphatic;

the B ring is a ring system capable of producing a detectable signal; and each of n, m, and p independently is an integer selected from 1 to 3, such as 1, 2, or 3.

In some embodiments, the linker group and/or the linker' group independently comprise an alkenyl group, a heteroalkenyl group, or a combination thereof. In particular disclosed embodiments, the linker group and/or the linker' group independently have a structure satisfying a Formula IA

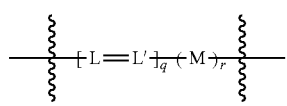

Formula IA wherein each L and L' independently is CH or N; M is NH; q is an integer selected from 1 to 3, such as 1, 2, or 3; and r is 0 or 1. In exemplary embodiments, the linker and/or linker' group independently are —CH=CH—, —N=N—NH—, —N=CH—NH—, or —CH=N—NH—.

In some embodiments, the Ring B and/or the Ring$_{B'}$ groups independently comprise a detectable moiety, such as a detectable moiety capable of producing a colorimetric signal, a fluorescent signal, or other luminescent signal. In particular embodiments, the Ring B and/or the Ring$_{B'}$ groups independently comprise an N-functionalized nitrogen-containing ring system, a 2-ethyl-1H-benzo[de]isoquinoline-1,3(2H)-dione functional group, or a nitrobenzo[c][1,2,5]oxadiazole functional group. In such embodiments, the N-functionalized nitrogen-containing ring system can be 5- to 10-membered ring system, such as a 5- to 10-membered aromatic ring system comprising at least one nitrogen atom that is functionalized with H, aliphatic, or aromatic. Representative N-functionalized nitrogen-containing ring system embodiments are illustrated in Table 1 below:

TABLE 1

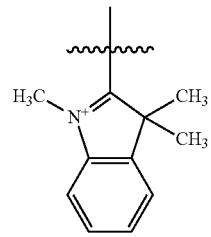

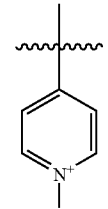

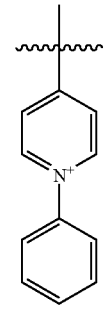

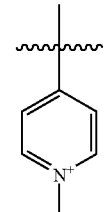

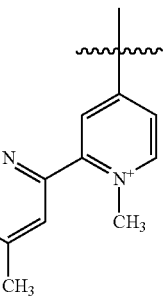

19
TABLE 1-continued
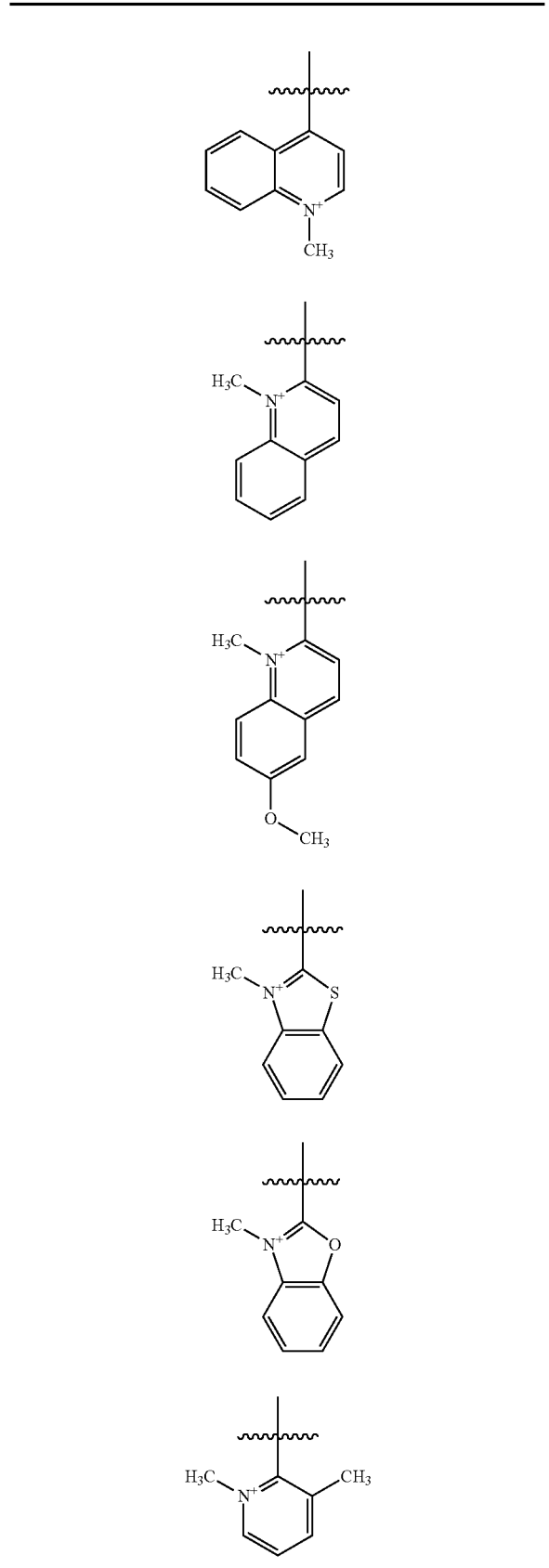
20
TABLE 1-continued
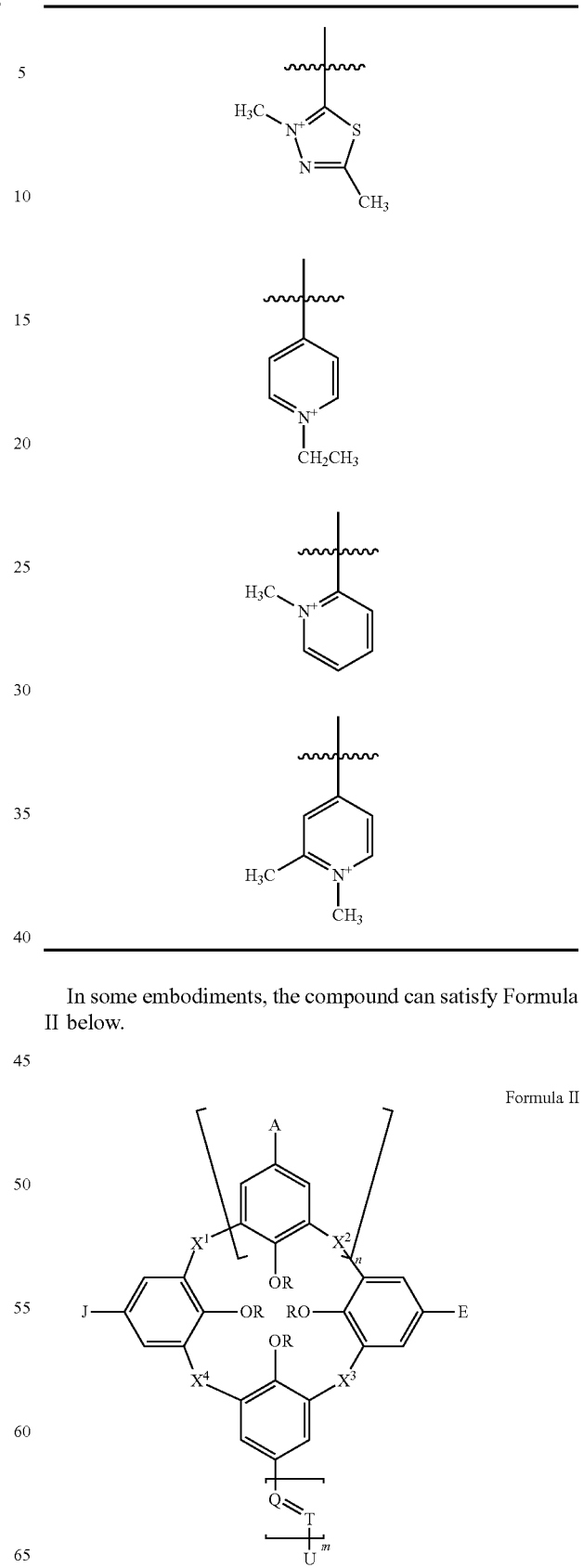
In some embodiments, the compound can satisfy Formula II below.

With reference to Formula II, n is an integer selected from 0, 1, or 2; m is an integer selected from 0, 1, 2, or 3; each R independently is H or an aliphatic group (e.g., $C_{1-12}$aliphatic); each of $X^1$, $X^2$, $X^3$, and $X^4$ independently is $CH_2$, O, S, $CH_2OCH_2$, or $CH_2SCH_2$; each A and each of E and J independently is $SO_3H$ or $CO_2H$ (or $SO_3$- or $CO_2$- balanced with a counterion provided by an aqueous solution, buffered aqueous solution, or any other counterion that may exist in the environment in which the compound is provided); each of Q and T independently is N or CH; and U is a heteroaryl group that produces a colorimetric or fluorescent signal.

In additional embodiments, the compound can have a structure satisfying Formula III below.

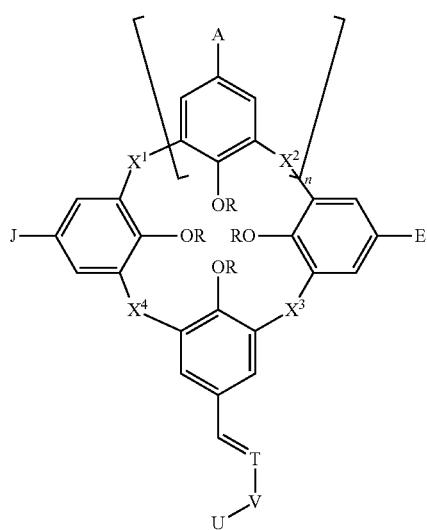

Formula III

With reference to Formula III, n independently is an integer selected from 0, 1, or 2; each R independently is H or an aliphatic group (e.g., $C_{1-12}$aliphatic); each of $X^1$, $X^2$, $X^3$, and $X^4$ independently is $CH_2$, O, S, $CH_2OCH_2$, or $CH_2SCH_2$; each of E and J independently is $SO_3H$ or $CO_2H$ (or $SO_3$- or $CO_2$- balanced with a counterion provided by an aqueous solution, buffered aqueous solution, or any other counterion that may exist in the environment in which the compound is provided); T is N or CH; V is NH; and U is a heteroaryl group that produces a colorimetric signal or fluorescent signal (e.g., a fluorescent dye or color-generating dye). Such compound embodiments have a dynamic, fluxional nature that provides facilitate their use in reversible sensing.

In additional embodiments, the compound can have a structure satisfying Formula IV below.

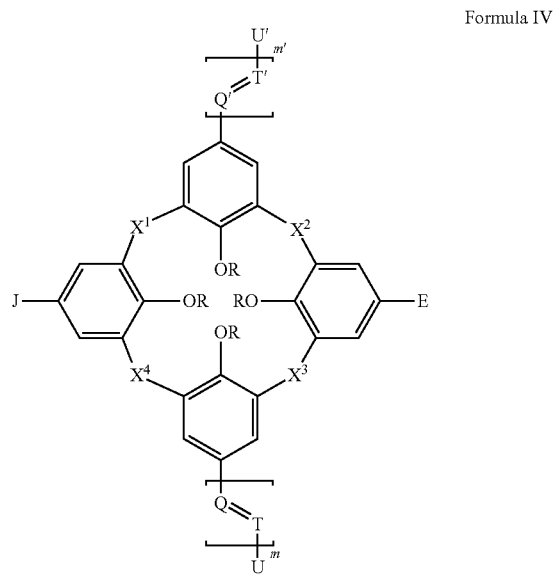

Formula IV

With reference to Formula IV, each of m and m' independently is an integer selected from 0, 1, 2, or 3; each R independently is H or an aliphatic group (e.g., $C_{1-12}$aliphatic); each of $X^1$, $X^2$, $X^3$, and $X^4$ independently is $CH_2$, O, S, $CH_2OCH_2$, or $CH_2SCH_2$; each of E and J independently is $SO_3H$ or $CO_2H$ (or $SO_3$- or $CO_2$- balanced with a counterion provided by an aqueous solution, buffered aqueous solution, or any other counterion that may exist in the environment in which the compound is provided); each of Q, T, Q', and T' independently is N or CH; and U and U' independently are a heteroaryl group that produces a colorimetric or fluorescent signal. Such compound embodiments can provide useful changes in wavelengths of sensor responses, as well as sensor responses with unique and useful photophysical mechanisms.

In additional embodiments, the compound can have a structure satisfying Formula V or Formula VA below.

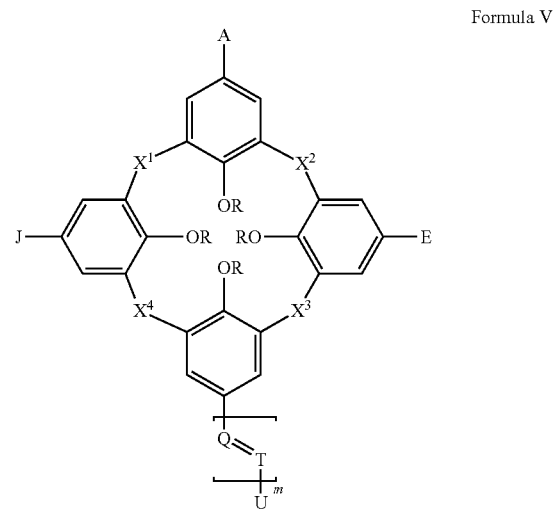

Formula V

TABLE 2

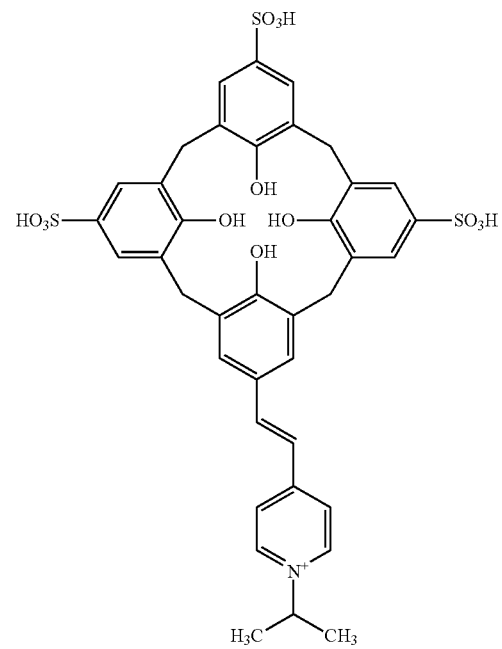 [SMILES: CC(C)[n+]1ccc(/C=C/c2cc3c(O)c(c2)Cc2cc(S(=O)(=O)O)cc(c2O)Cc2cc(S(=O)(=O)O)cc(c2O)Cc2cc(S(=O)(=O)O)cc(c2O)C3)cc1]

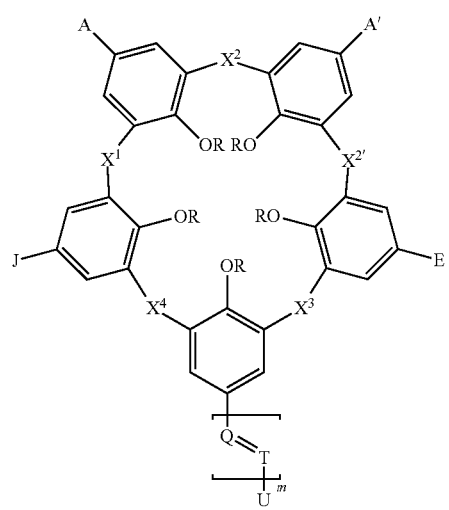

Formula VA

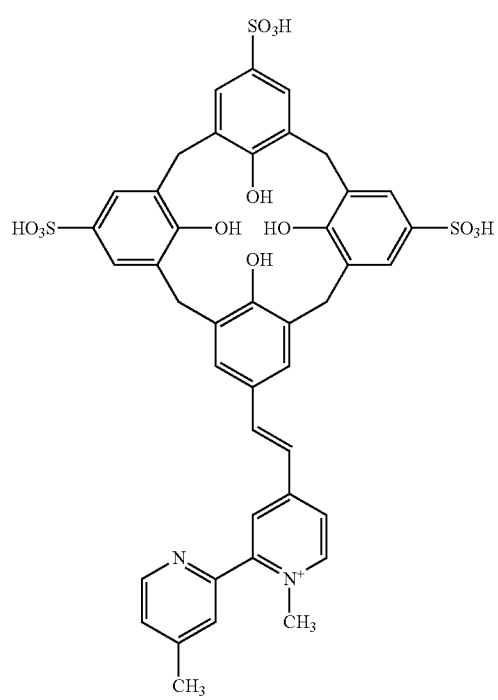 [SMILES: Cc1ccnc(-c2cc(/C=C/c3cc4c(O)c(c3)Cc3cc(S(=O)(=O)O)cc(c3O)Cc3cc(S(=O)(=O)O)cc(c3O)Cc3cc(S(=O)(=O)O)cc(c3O)C4)cc[n+]2C)c1]

With reference to Formulas V and VA, m independently is an integer selected from 0, 1, 2, or 3; each R independently is H or an aliphatic group (e.g., $C_{1-12}$ aliphatic); each of $X^1$, $X^2$, $X^{2'}$ $X^3$, and $X^4$ independently is $CH_2$, O, S, $CH_2OCH_2$, or $CH_2SCH_2$; each of E and J independently is $SO_3H$ or $CO_2H$ (or $SO_3$- or $CO_2$- balanced with a counterion provided by an aqueous solution, buffered aqueous solution, or any other counterion that may exist in the environment in which the compound is provided); each of Q and T independently is N or CH; U is a heteroaryl group that produces a colorimetric or fluorescent signal; and each of A and A' independently is C(O)H, $CH_2OH$, or $CO_2H$. Such compound embodiments have different interactions with analytes and with each other that provide enhanced analyte selectivity, improved detection limits, and useful new photophysical mechanisms. In particular embodiments of compounds having structures according to Formula VA, the compounds can form dimer complexes that can interact with an analyte to provide both a fluorescent and colorimetric signal.

Exemplary compound embodiments are illustrated in Table 2 below.

TABLE 2-continued
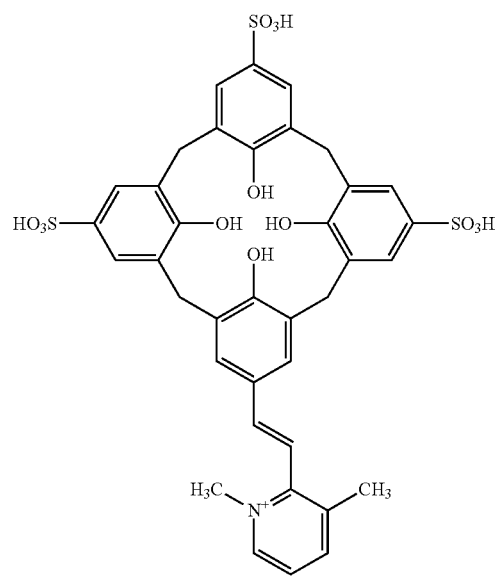 [SMILES: Cc1ccc[n+](C)c1/C=C/c1cc2c(O)c(c1)Cc1cc(S(=O)(=O)O)cc(c1O)Cc1cc(S(=O)(=O)O)cc(c1O)Cc1cc(S(=O)(=O)O)cc(c1O)C2]
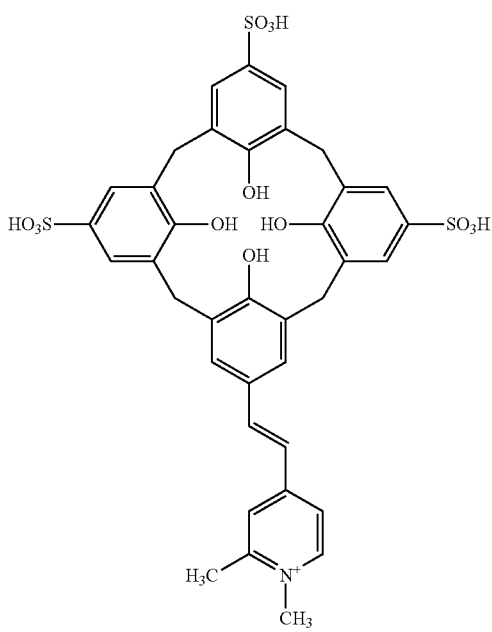
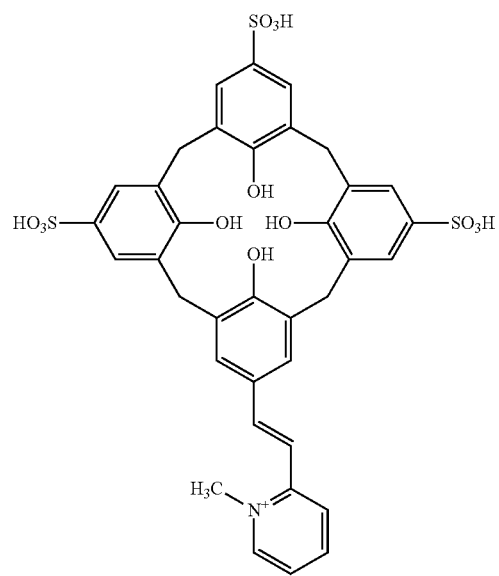 [SMILES: C[n+]1ccccc1/C=C/c1cc2c(O)c(c1)Cc1cc(S(=O)(=O)O)cc(c1O)Cc1cc(S(=O)(=O)O)cc(c1O)Cc1cc(S(=O)(=O)O)cc(c1O)C2]
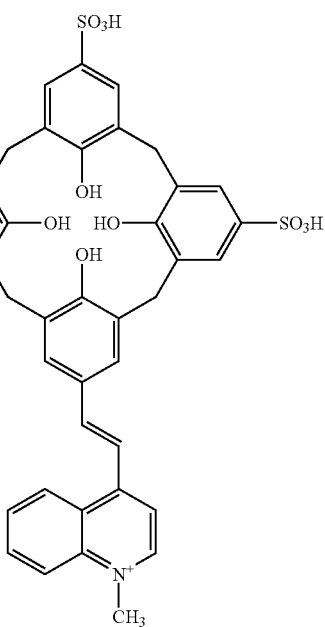

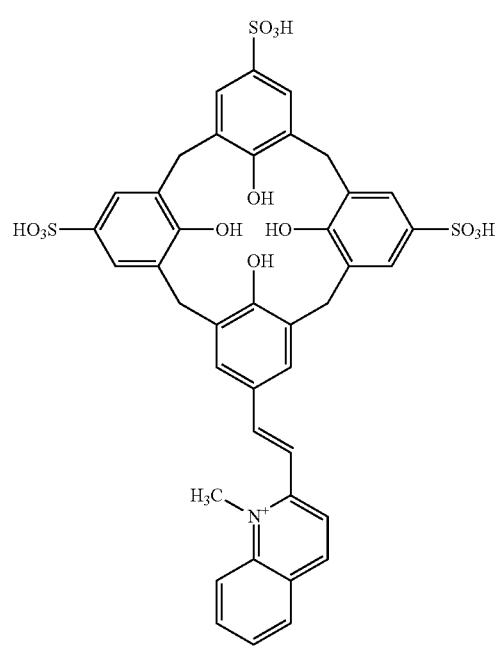 [SMILES: C[n+]1c(/C=C/c2cc3c(O)c(c2)Cc2cc(S(=O)(=O)O)cc(c2O)Cc2cc(S(=O)(=O)O)cc(c2O)Cc2cc(S(=O)(=O)O)cc(c2O)C3)ccc2ccccc21]
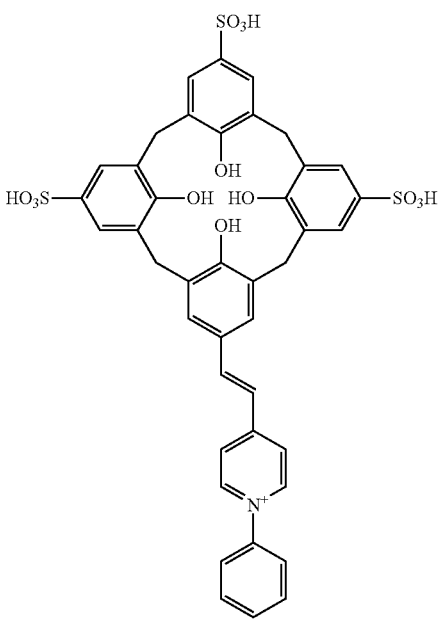
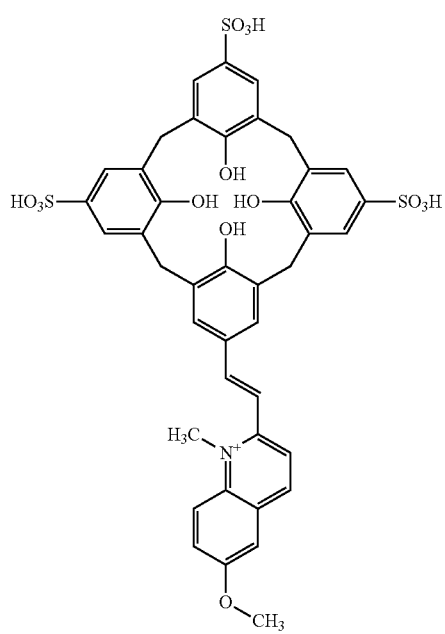 [SMILES: COc1ccc2c(ccc(/C=C/c3cc4c(O)c(c3)Cc3cc(S(=O)(=O)O)cc(c3O)Cc3cc(S(=O)(=O)O)cc(c3O)Cc3cc(S(=O)(=O)O)cc(c3O)C4)[n+]2C)c1]
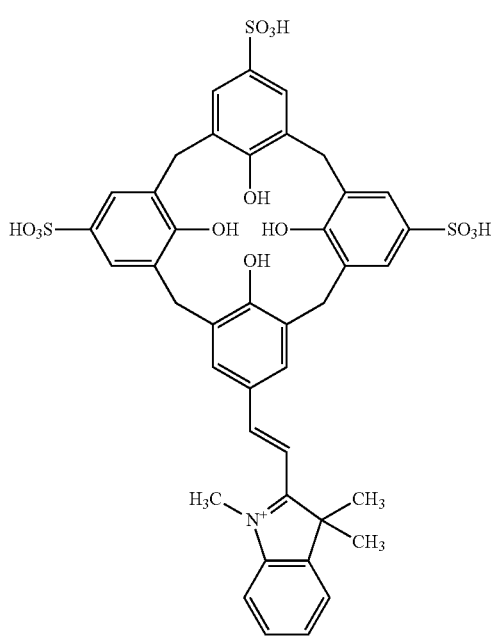 [SMILES: C[N+]1=C(/C=C/c2cc3c(O)c(c2)Cc2cc(S(=O)(=O)O)cc(c2O)Cc2cc(S(=O)(=O)O)cc(c2O)Cc2cc(S(=O)(=O)O)cc(c2O)C3)C(C)(C)c2ccccc21]

TABLE 2-continued
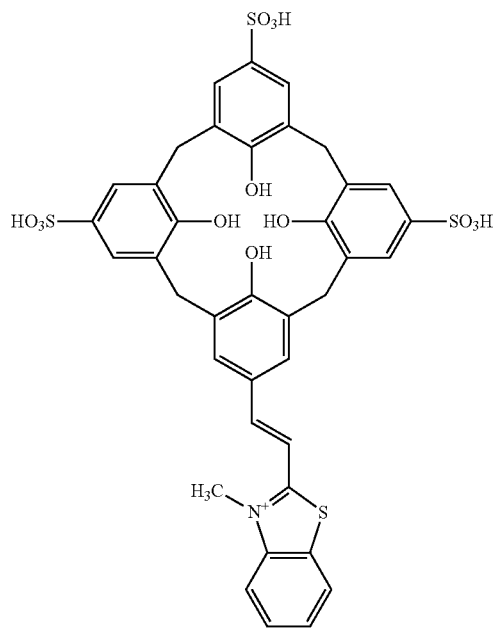 [SMILES: C[n+]1c(/C=C/c2cc3c(O)c(c2)Cc2cc(S(=O)(=O)O)cc(c2O)Cc2cc(S(=O)(=O)O)cc(c2O)Cc2cc(S(=O)(=O)O)cc(c2O)C3)oc2ccccc21]
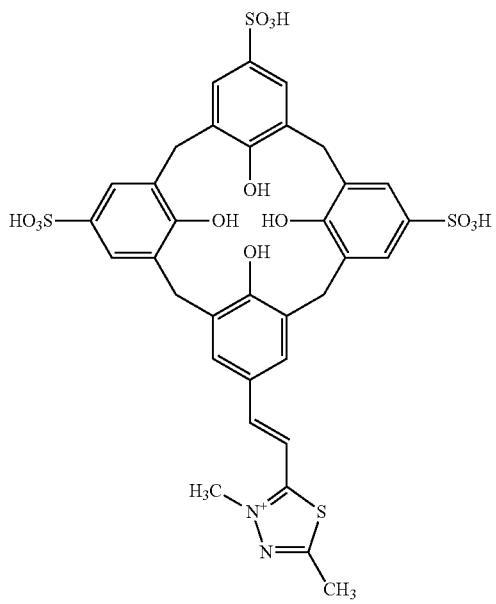 [SMILES: Cc1n[n+](C)c(/C=C/c2cc3c(O)c(c2)Cc2cc(S(=O)(=O)O)cc(c2O)Cc2cc(S(=O)(=O)O)cc(c2O)Cc2cc(S(=O)(=O)O)cc(c2O)C3)s1]

TABLE 2-continued
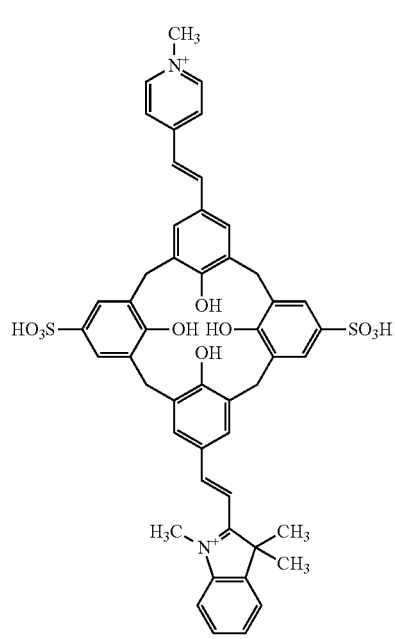 [SMILES: C[N+]1=C(/C=C/c2cc3c(O)c(c2)Cc2cc(S(=O)(=O)O)cc(c2O)Cc2cc(/C=C/c4cc[n+](C)cc4)cc(c2O)Cc2cc(S(=O)(=O)O)cc(c2O)C3)C(C)(C)c2ccccc21]
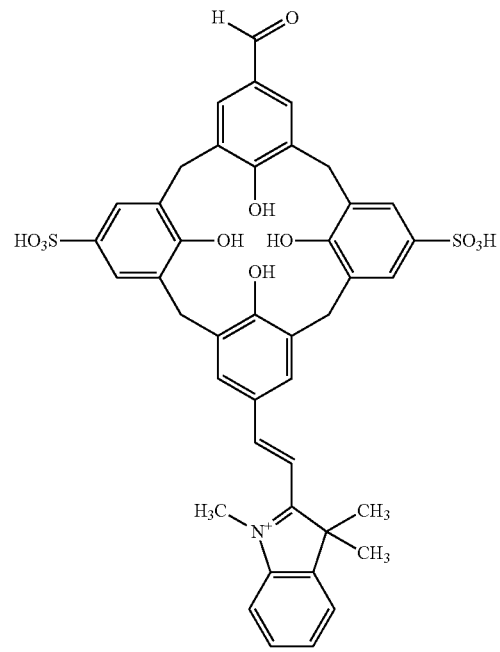
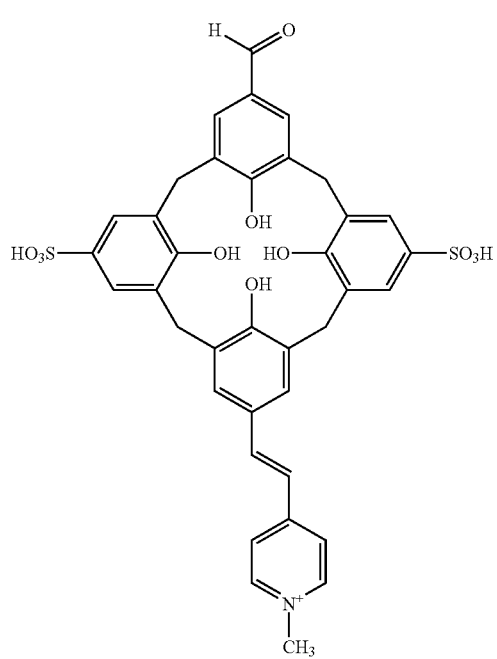 [SMILES: C[n+]1ccc(/C=C/c2cc3c(O)c(c2)Cc2cc(S(=O)(=O)O)cc(c2O)Cc2cc(C=O)cc(c2O)Cc2cc(S(=O)(=O)O)cc(c2O)C3)cc1]

TABLE 2-continued
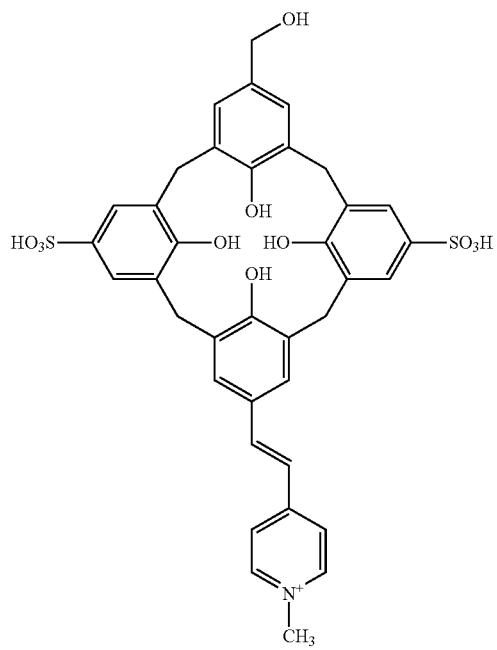 [SMILES: C[n+]1ccc(/C=C/c2cc3c(O)c(c2)Cc2cc(S(=O)(=O)O)cc(c2O)Cc2cc(CO)cc(c2O)Cc2cc(S(=O)(=O)O)cc(c2O)C3)cc1]
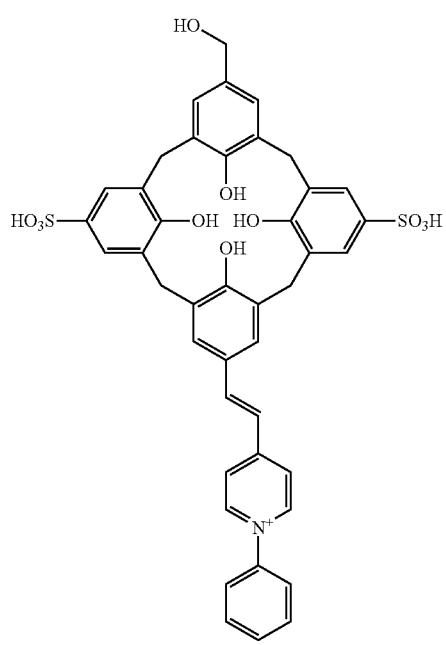
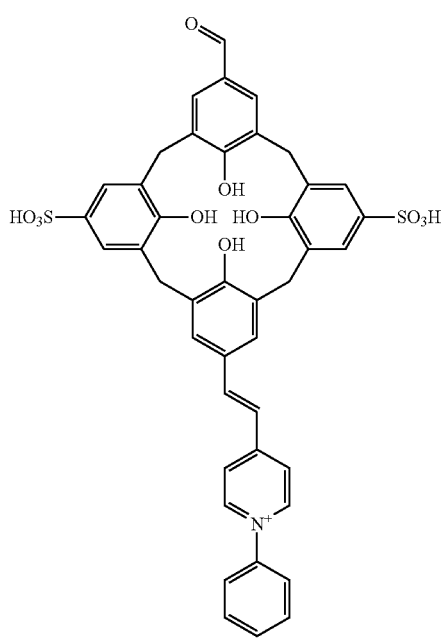 [SMILES: O=Cc1cc2c(O)c(c1)Cc1cc(S(=O)(=O)O)cc(c1O)Cc1cc(/C=C/c3cc[n+](-c4ccccc4)cc3)cc(c1O)Cc1cc(S(=O)(=O)O)cc(c1O)C2]
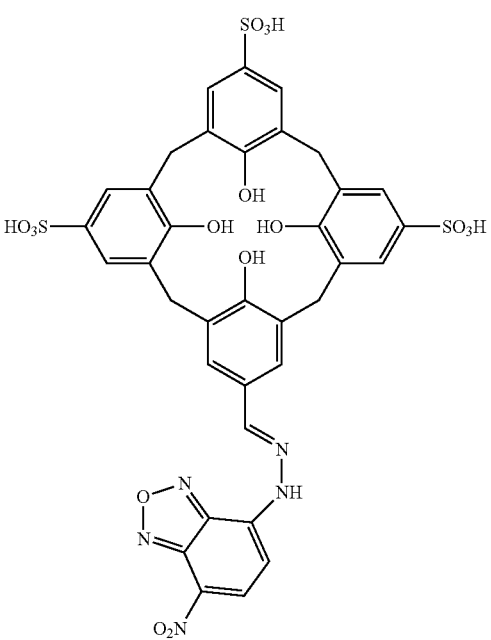 [SMILES: O=[N+]([O-])c1ccc(N/N=C/c2cc3c(O)c(c2)Cc2cc(S(=O)(=O)O)cc(c2O)Cc2cc(S(=O)(=O)O)cc(c2O)Cc2cc(S(=O)(=O)O)cc(c2O)C3)c2nonc12]

TABLE 2-continued
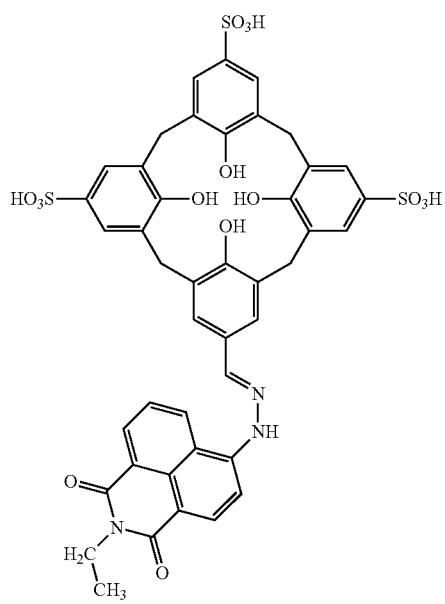 [SMILES: CCN1C(=O)c2cccc3c(N/N=C/c4cc5c(O)c(c4)Cc4cc(S(=O)(=O)O)cc(c4O)Cc4cc(S(=O)(=O)O)cc(c4O)Cc4cc(S(=O)(=O)O)cc(c4O)C5)ccc(c23)C1=O]
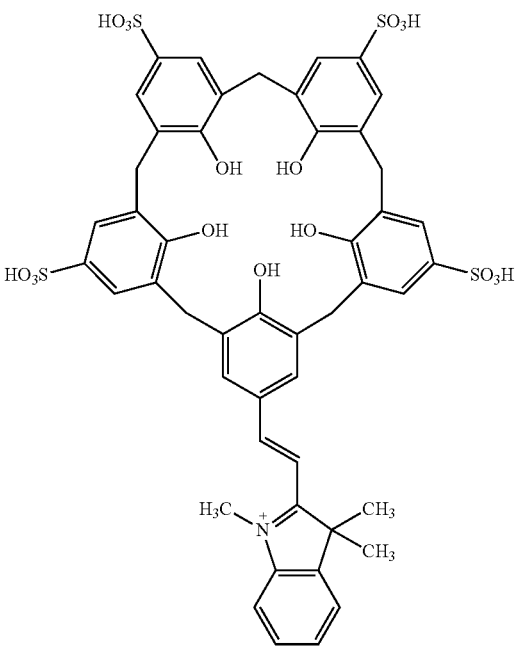
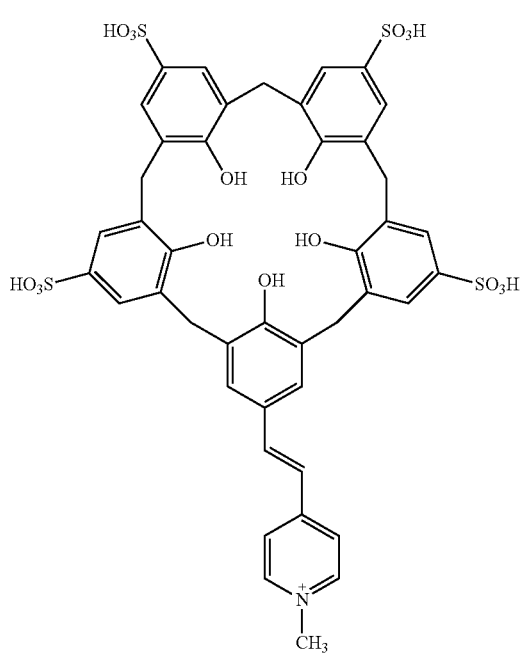
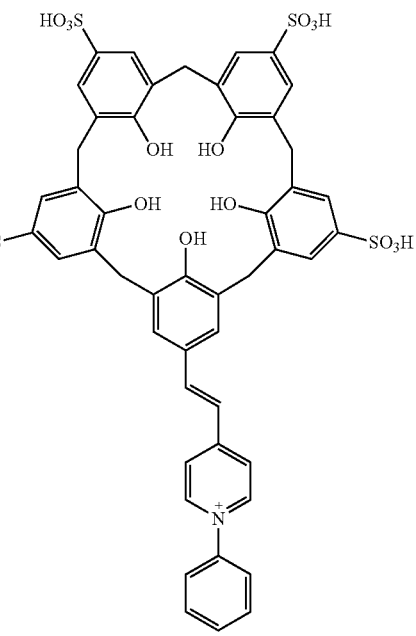
In an independent embodiment, the compound is not, or is other than, the compounds illustrated below. Nevertheless, such compounds can be used in array embodiments disclosed herein, particularly when combined with one or more of the compound embodiments provided in Table 2 above.

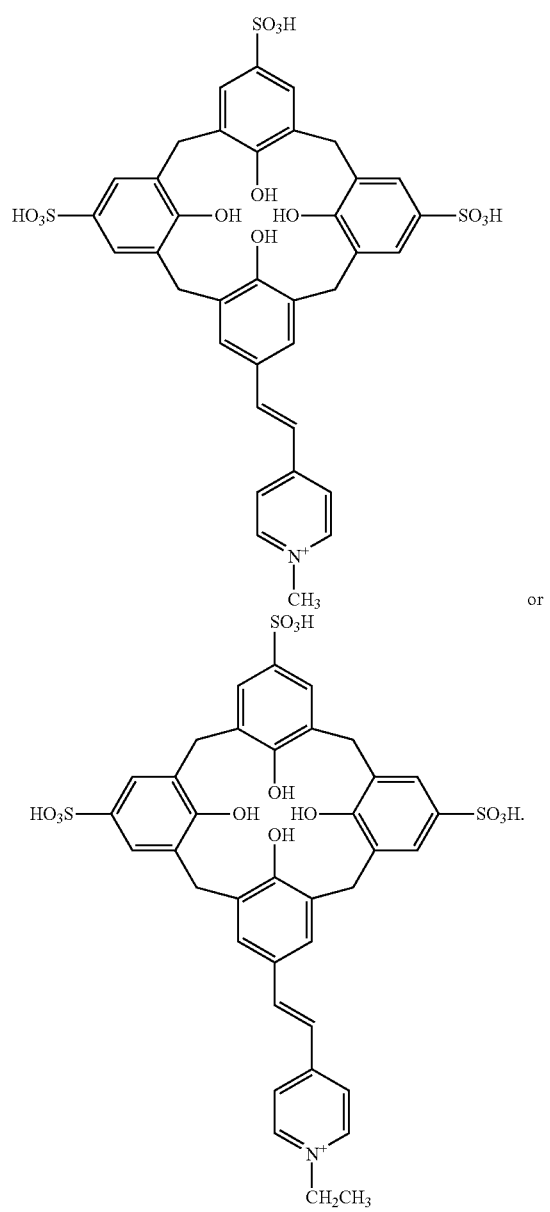

or

Also disclosed herein are array embodiments comprising a plurality of the compounds discussed above. In some embodiments, the plurality of compounds can comprise two or more compounds, such as two to thousands of compounds, or two to hundreds of compounds, or 2 to 100 compounds, or 2 to 50 compounds, or 2 to 25 compounds, or 2 to 15 compounds, or 2 to 10 compounds, or 2 to 5 compounds. In some embodiments, the array can be provided in different platform embodiments. In some embodiments, the array comprises a test strip platform which comprises a substrate (e.g., a paper substrate, or other porous substrates; a plastic substrate; a well-plate; or the like) comprising one or more sample zones that comprise one or more compound embodiments. In other embodiments, the array comprises a tube platform in which one or more tubes are provided and wherein each tube comprises a single compound embodiment or wherein each tube comprises a plurality of compound embodiments.

The array can be exposed to a biological fluid or other aqueous solution and any detectable signals generated can be viewed and/or analyzed to determine whether any analytes are present. In some embodiments, the identity of the analyte and/or the concentration of the analyte can be assessed using the array. Images of exemplary arrays are provided in FIGS. 3A, 3B, and FIGS. 58A-58D.

IV. Methods of Use

Compound embodiments of the present disclosure can be used in methods for detecting the presence of analytes. In some embodiments, the analytes can be drugs (e.g., illicit drugs) and/or analogs and/or metabolites thereof. For example, such analytes can be recreational drugs, mood-altering drugs, performance enhancing drugs and drugs listed in the Controlled Substances Act (CSA) Database provided by the Drug Enforcement Administration (DEA) at https://www.dea.gov/, the relevant portion of which is incorporated herein by reference, or any metabolites and/or analogs thereof. In some independent embodiments, the analytes can be small molecules, drugs, drug analogs, drug metabolites, amino acids (e.g., phenylalanine, asymmetric dimethylarginine, or other amino acids), peptides, proteins, natural metabolites (including primary and secondary metabolites), or any combinations thereof. In yet additional independent embodiments, the method of using certain compound embodiments disclosed herein can comprise methods for detecting the presence of analytes (e.g., small molecules, drugs, drug analogs, drug metabolites, amino acids, peptides, proteins, and natural metabolites) that comprise cations or hydrophobic cations. In embodiments where the method involves detecting the presence of any natural analytes, such natural analytes can comprise endogenous and exogenous metabolites, primary and secondary metabolites, and metabolites originating from food, plants, microbes, toxins, pollutants, cosmetics or drugs, including metabolites listed in the Human Metabolome Database provided by the Metabolomics Innovation Centre (TMIC) at http://www.hmdb.ca/, the relevant portion of which is incorporated herein by reference.

The compounds have a unique ability to operate in many and varied biological fluids, such as saliva, urine, nasal washes, synovial fluid, cerebrospinal fluid, gastric fluid, serum, plasma, cell growth medium, and cell lysates. The compounds also act as sensors in aqueous solutions, with or without buffer, with pH values ranging from 0-14.

Disclosed herein are method embodiments where the compounds embodiments are used as mixtures of sensor compounds. Multiple sensor compounds are mixed in the same solution or solid-phase sample. The sensor compounds interact with each other, generating a visible signal at multiple wavelengths that is characteristic for the starting state of the mixture of fluorescent and/or color-changing elements. The mixture of sensor compounds is treated with the fluid sample in order to generate a change in fluorescence and/or color that arises from the collective change in assembled state and sensor-analyte binding states in the presence of analytes. The spectral responses at multiple wavelengths of light provides a pattern of signals that uniquely determines the identity and/or concentration of a given analyte. Signal analysis can be done with multivariate statistics or machine learning or artificial intelligence-based analyses. In each case, data from multiple authentic samples are used to train the method and operator as to the signal expected to arise from a given analyte and/or concentration, and the sensor array then is used on unknown samples in order to identify a given analyte and/or concentration.

Also disclosed herein are method embodiments where the compounds are used in an array. In array embodiments, multiple sensors are used in parallel by distributing them in different liquid holding vessels or in different locations on a solid substrate. Each parallel element of the sensor array is treated with the fluid sample in order to generate responses for each sensor element that are read individually. The pattern of responses to a given analyte provides a signal that uniquely determines the identity and/or concentration of a given analyte. Using disclosed compounds in a sensor array can be used to measure a large number of analytes by generating a unique fingerprint to each analyte. Multivariate analysis, including methods like principal component analysis (PCA) and linear discriminant analysis (LDA), can analyze the 'fingerprints' by both reducing the dimensionality of the data and creating a useful way to represent the differential responses.

In yet additional embodiments, compounds disclosed herein can act as sensors that can operate while present on the surface of or embedded within the pores of a solid support. The sensors, once dried onto solid substrates (paper, etc.), provide sensor spots that respond to the presence of their targeted analytes. They can also be embedded in gel phases and applied in medical devices such as wound dressings. This enables the creation of test strips or wound dressings that can be treated with a biological fluid or other aqueous solution and visualized by color change or fluorescence change in order to ascertain the presence of, identity of, and/or the concentration of a given analyte.

In some embodiments, compound embodiments assemble into dimers in water (e.g., homodimers and/or heterodimers), regardless of having different detectable moieties attached thereto. In some embodiments, $^1$H NMR can be used to confirm that each compound exists as a homodimer when dissolved in buffered-$D_2O$. One feature of homodimerization is upfield shift and broadening of pendant group resonances due to encapsulation in the electron-rich calixarene pocket. In some embodiments, aromatic resonances in certain compounds can shift upfield by 1.23-3.69 ppm, while aliphatic (methyl) resonances shifted upfield by 0.46-3.60 ppm. In some embodiments, protons farthest out on the coupling partner component had the greatest upfield shifts, which can indicate that those protons are the most deeply buried in the pocket of the opposing calixarene of the dimer.

Figure 1B:
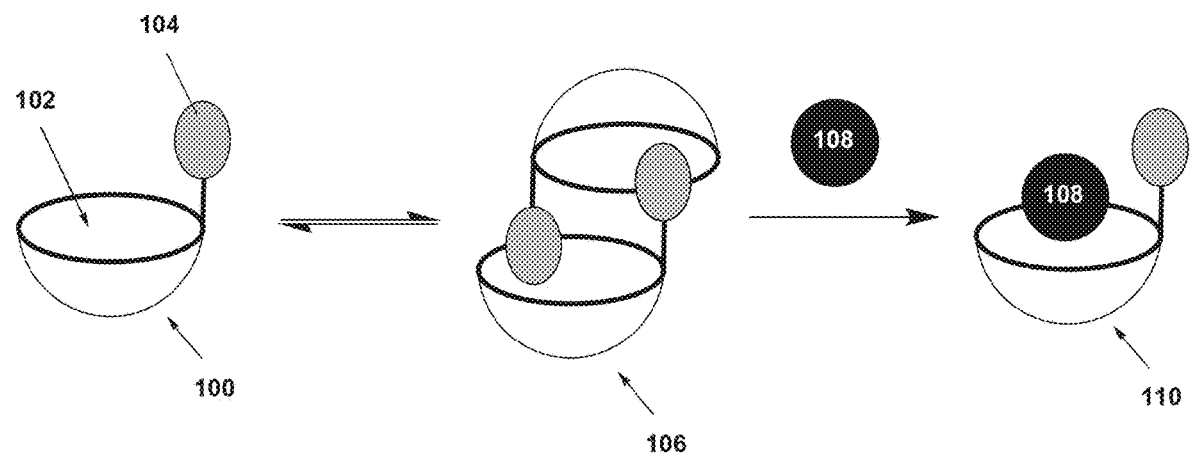
Figure 1C:
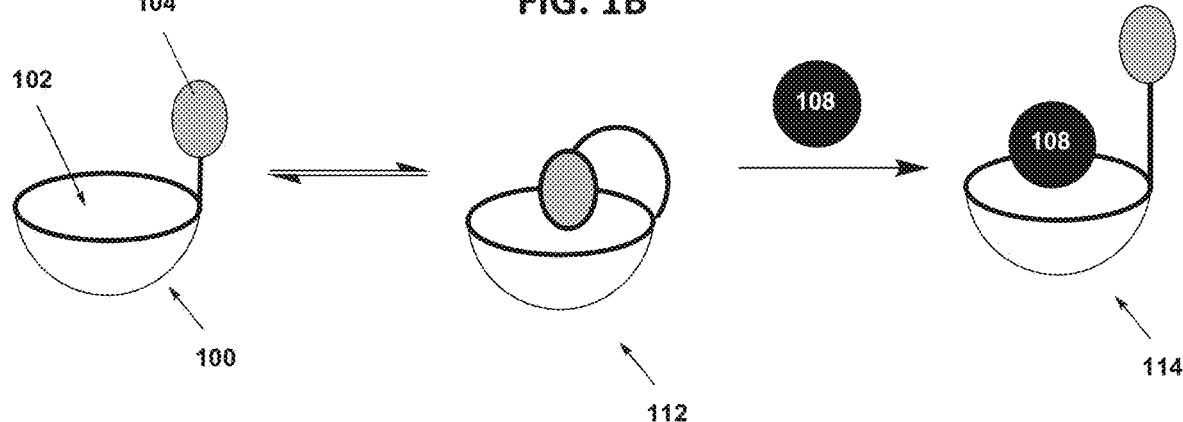

In some embodiments, fluorescence responses arise from the disassembly of each compound (that is, disruption of a dimer, such as illustrated in FIG. 1A or 1B; or disruption of a folded compound embodiment, such as illustrated in FIG. 1C) and sequential complexation with an analyte. In FIG. 1C, a compound embodiment 100 comprising a reporter moiety 104 and a binding pocket 102 can undergo self-folding providing self-folded compound embodiment 112. Upon exposure to analyte 108, the compound embodiment can unfold to product a new detectable signal provided by the complexed product 114 formed by binding of then analyte to the binding pocket. In certain embodiments, $^1$H NMR titrations of an analyte into each compound show resonances broadening partially or completely, indicating dimer disassembly and analyte complexation at an intermediate timescale relative to NMR. The disclosed compound embodiments provide turn-on fluorescence detection of different drugs at low micromolar concentrations in water and in saliva, as well as in other biological samples.

Figure 3A:
FIGS. 3A-3C provide an overview of a method embodiment for making compound and embodiments of the present disclosure and then using the compounds to provide dimer complexes that can detect drugs of interest, wherein (i)
Figure 3B:
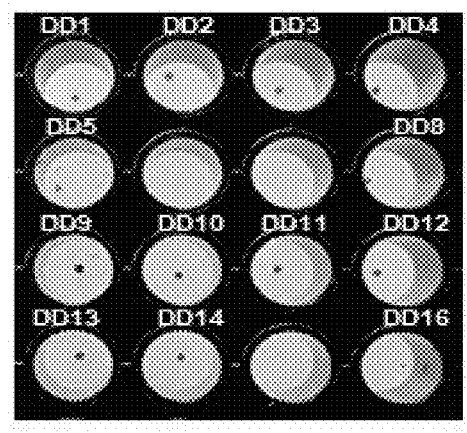
Figure 3C:
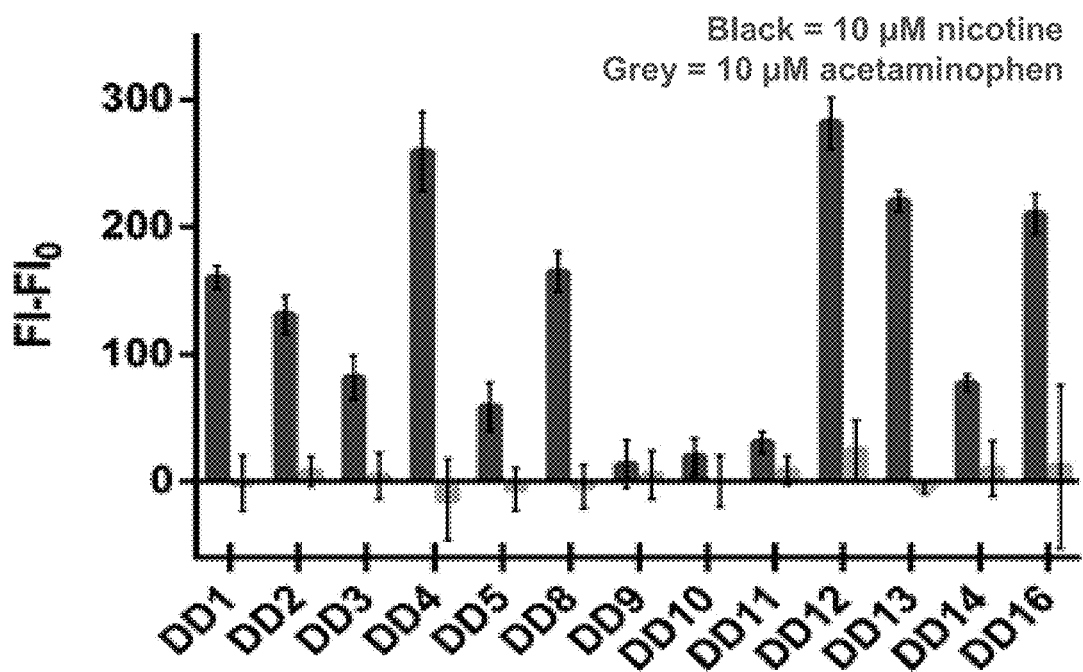

In some embodiments, sensing capabilities can be determined using a test analyte (e.g., nicotine). Increases in any fluorescence in a well of the well-plate indicates the creation of good nicotine sensors. To confirm that the fluorescence change arises from host-guest binding, the library can be counter-screened against acetaminophen, which is neutral and should not bind the compounds. As shown by FIG. 3C, acetaminophen generates little to no fluorescence in all cases.

V. Methods of Making

Compound embodiments disclosed herein can be made by combining a compound precursor with a coupling partner comprising a ring system capable of producing a detectable signal. In some embodiments, the compound precursor has a structure satisfying Formula A, wherein each variable can be as described above for Formula I.

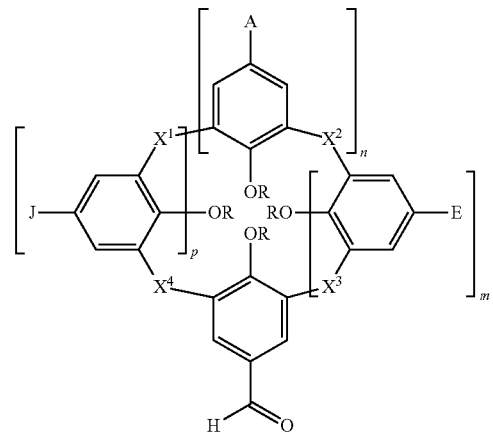

Formula A

In some embodiments, the coupling partner comprising a ring system capable of producing a detectable signal can be an N-functionalized nitrogen-containing ring system, a 2-ethyl-1H-benzo[de]isoquinoline-1,3(2H)-dione functional group, a nitrobenzo[c][1,2,5]oxadiazole functional group, or other detectable moiety. In such embodiments, the N-functionalized nitrogen-containing ring system can be 5- to 10-membered ring system, such as a 5- to 10-membered aromatic ring system comprising at least one nitrogen atom that is functionalized with H, aliphatic, or aromatic. Representative coupling partner embodiments are provided by Table 1.

In some embodiments, the method can further comprise heating the compound precursor and the coupling partner in a solvent with a base (e.g., pyridine or morpholine) at temperature ranging from ambient temperature to a refluxing temperature of the solvent, such as 25° C. to 70° C., or 25° C. to 65° C.

Exemplary compound precursors and coupling partners are disclosed herein, such as in the Examples section. Exemplary method embodiments for making compound embodiments also are described in the Examples section.

Figure 2A:
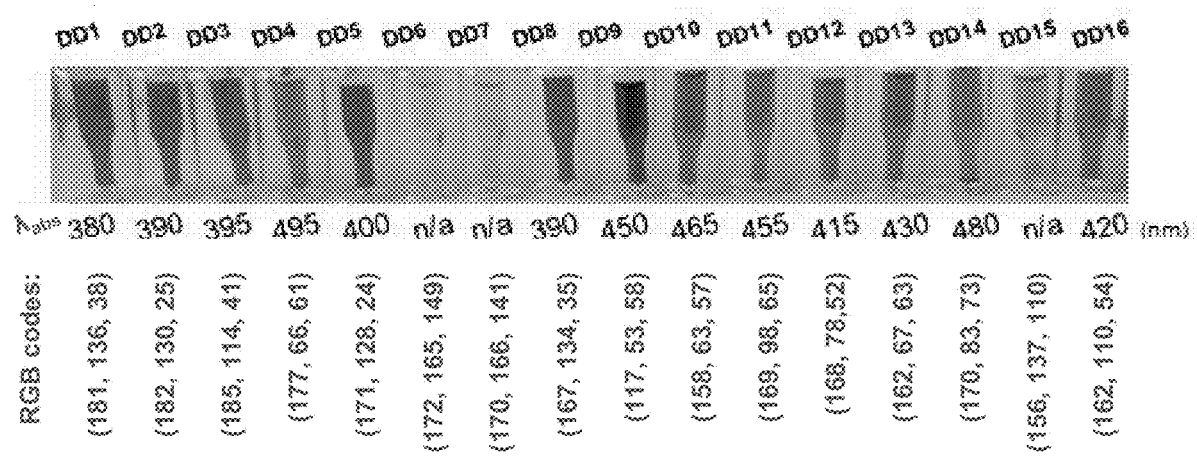
Figure 2B:
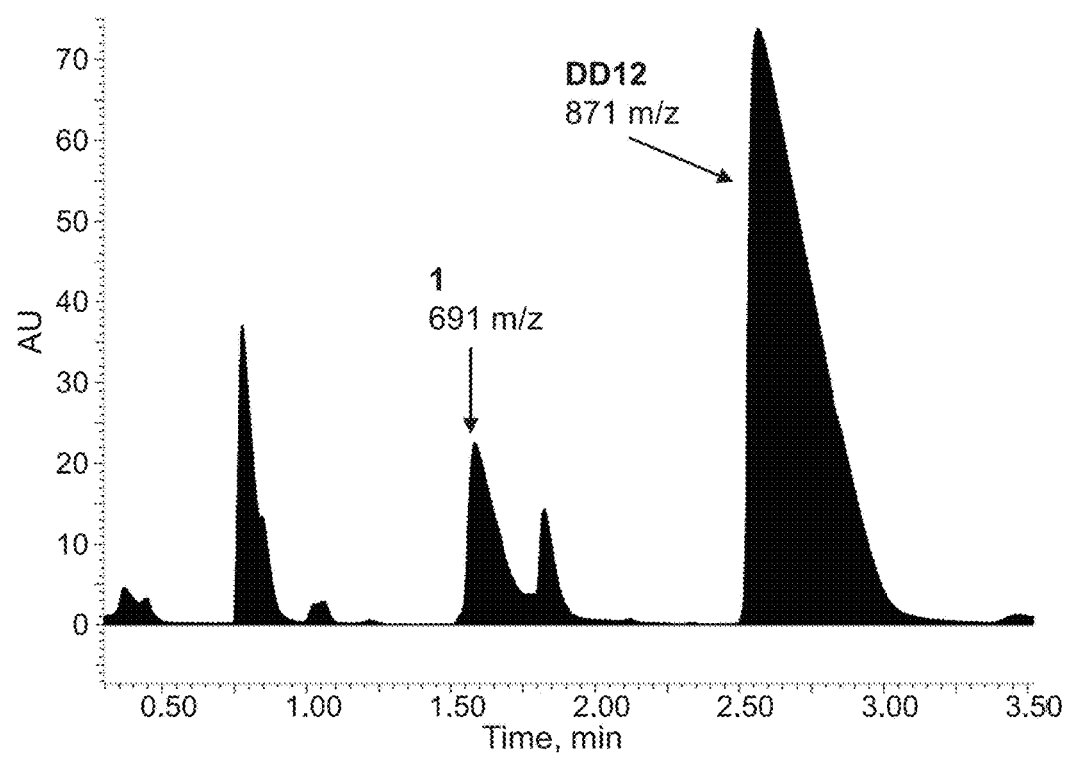
Figure 2C:
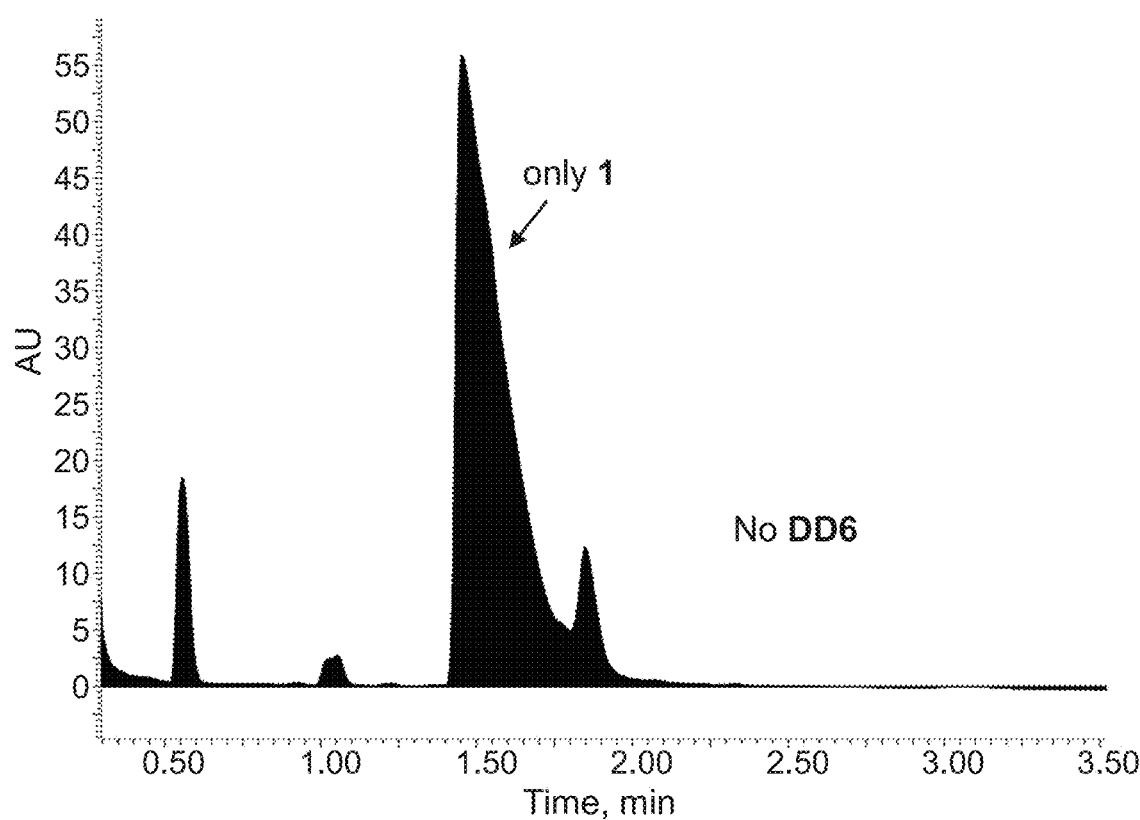
Figure 15A:
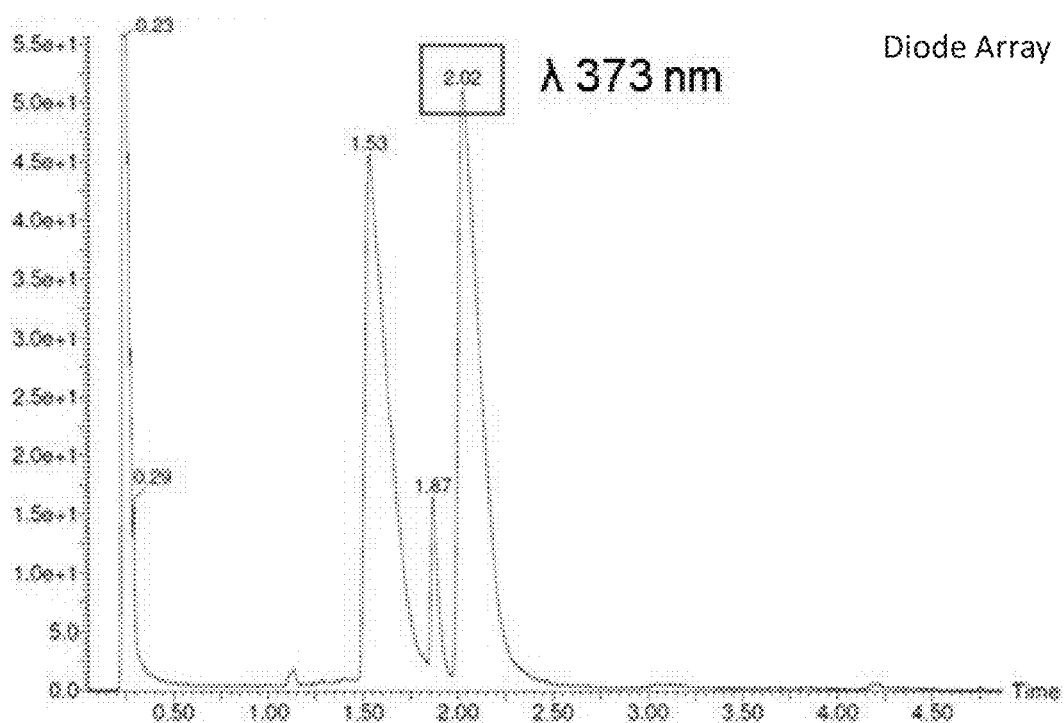
FIGS. 15A and 15B show a UPLC trace (FIG. 15A) and the corresponding mass spectrum (FIG. 15B) obtained after using a method embodiment to make compound embodiment DD1.
Figure 15B:
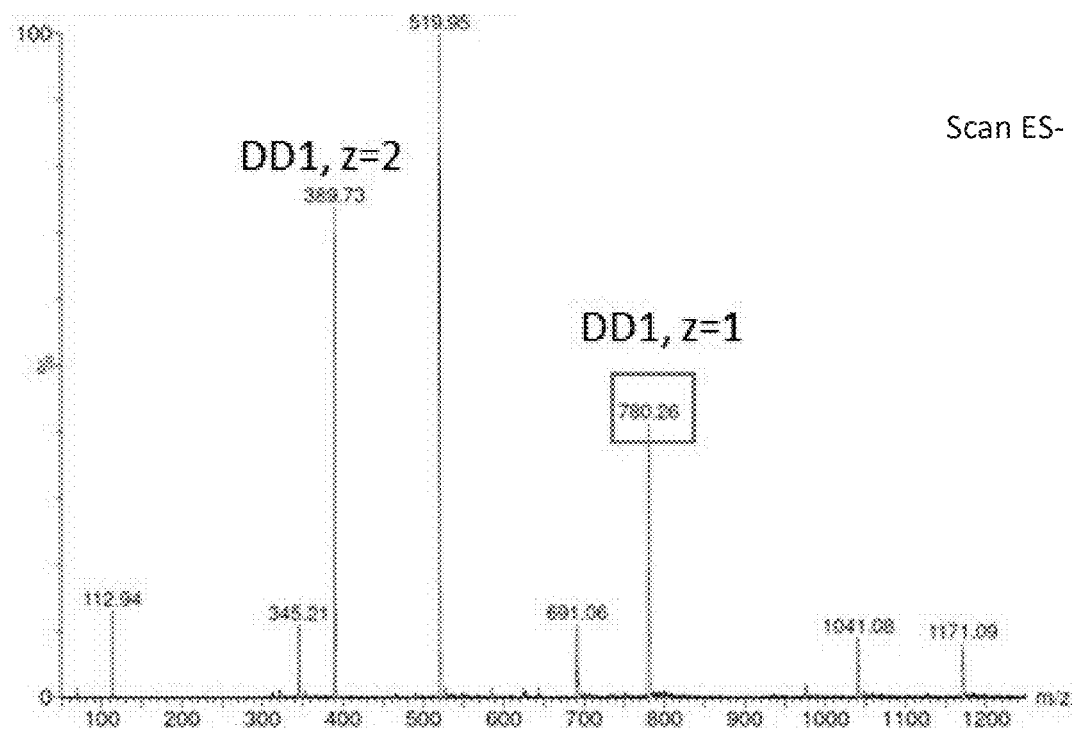
Figure 16A:
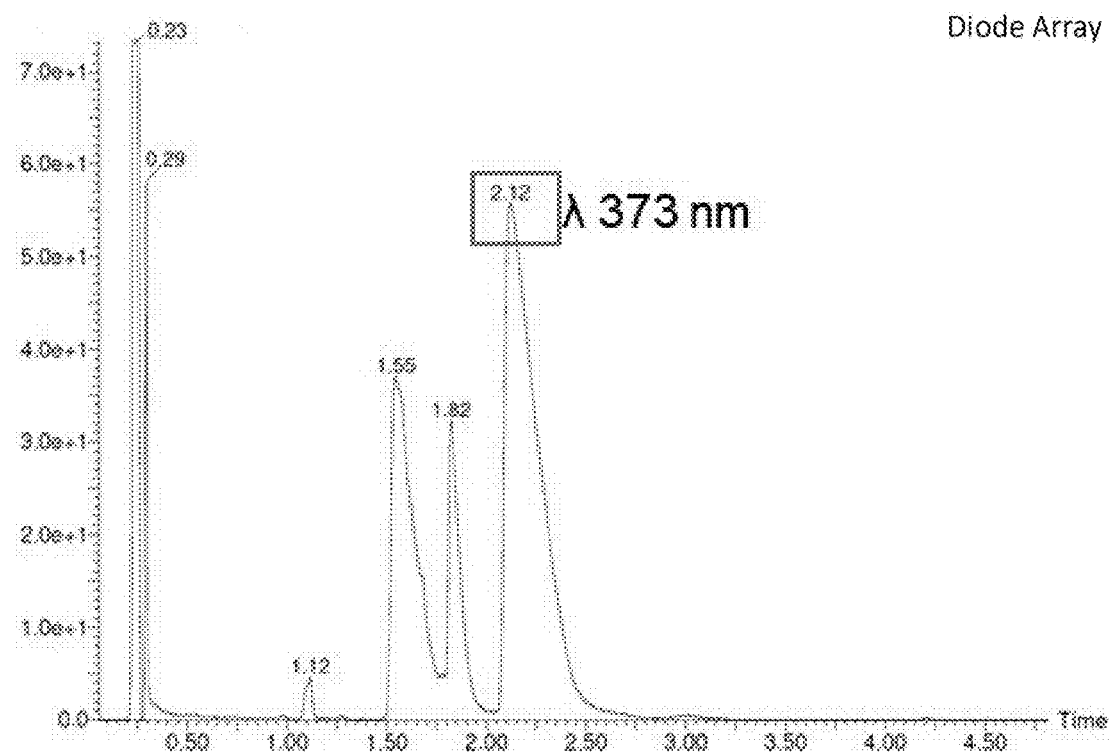
FIGS. 16A and 16B show a UPLC trace (FIG. 16A) and the corresponding mass spectrum (FIG. 16B) obtained after using a method embodiment to make compound embodiment DD2
Figure 16B:
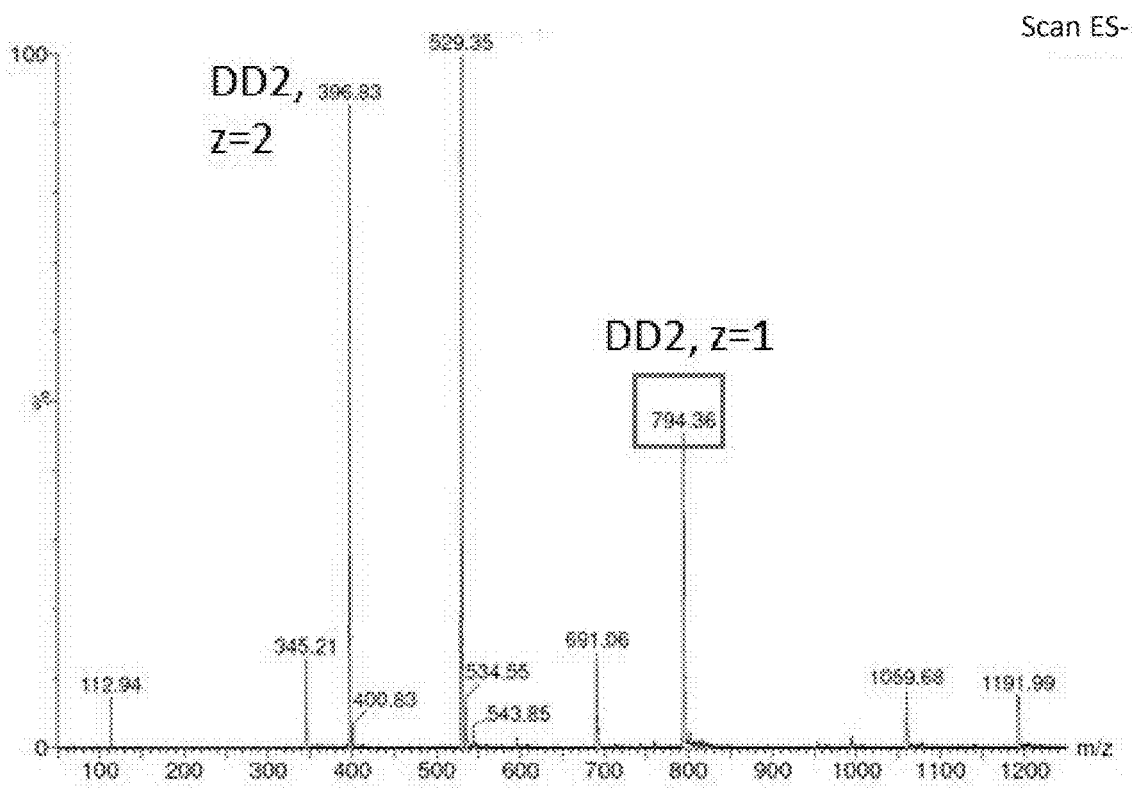
Figure 17A:
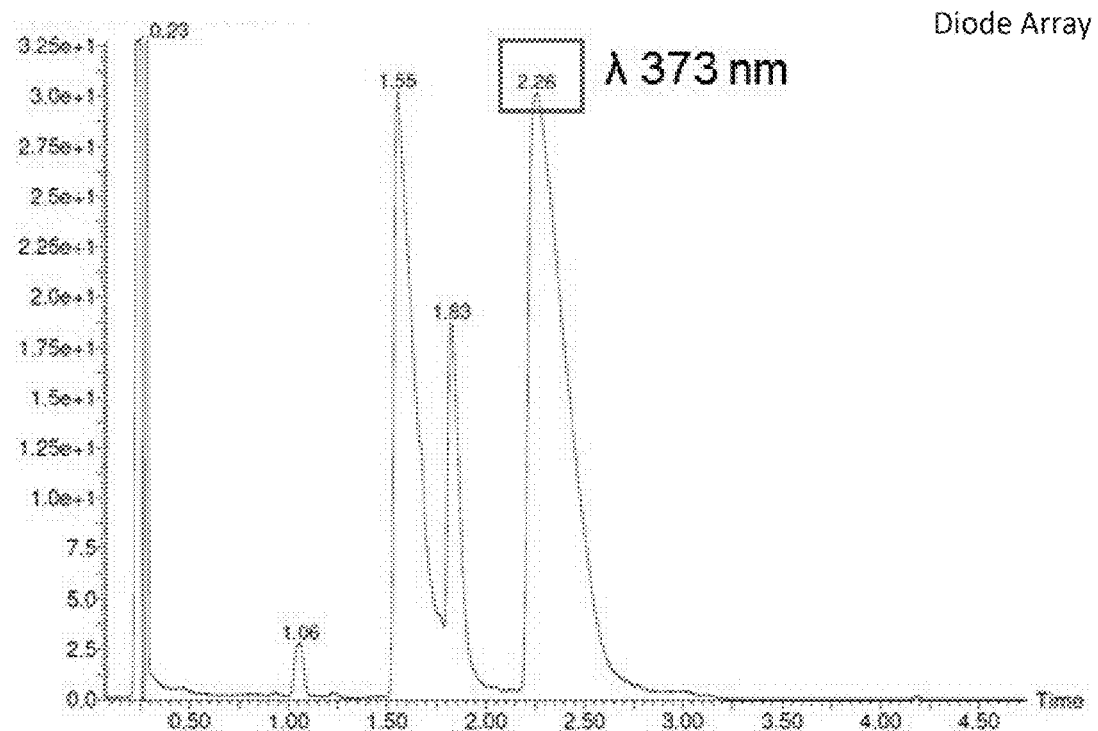
FIGS. 17A and 17B show a UPLC trace (FIG. 17A) and the corresponding mass spectrum (FIG. 17B) obtained after using a method embodiment to make compound embodiment DD3.
Figure 17B:
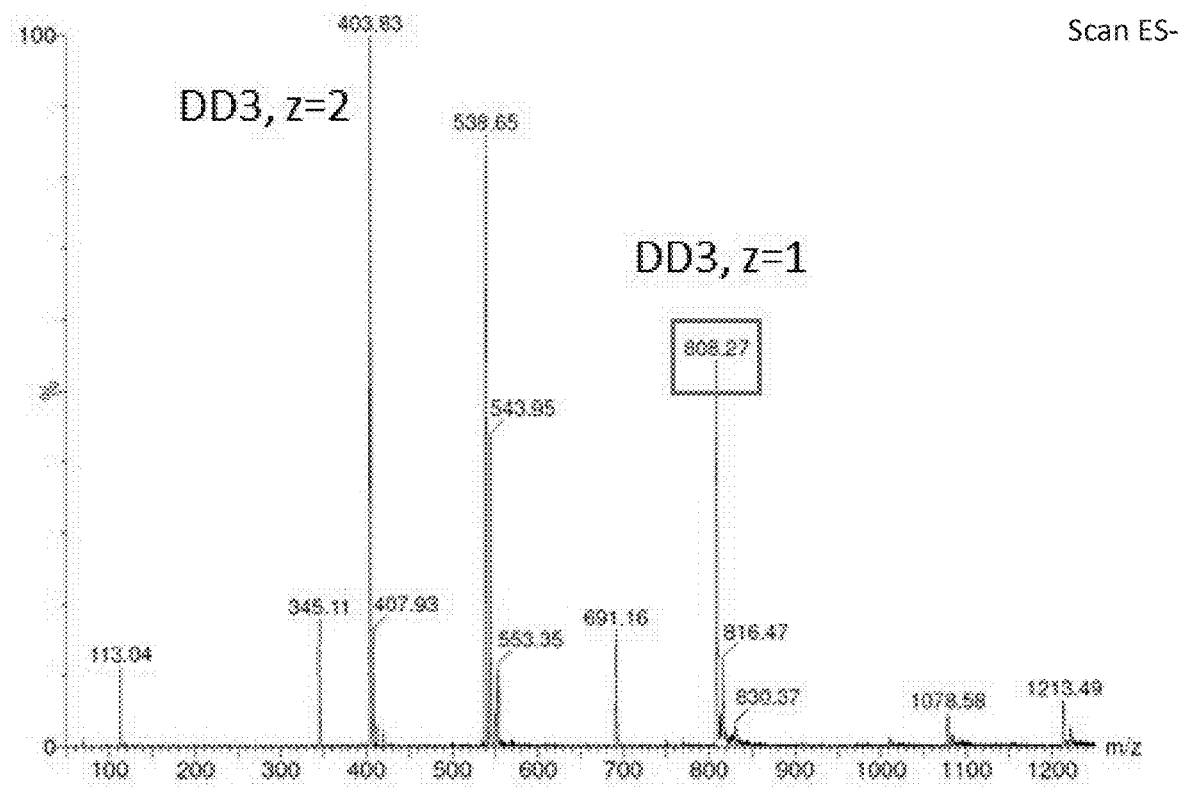
Figure 18A:
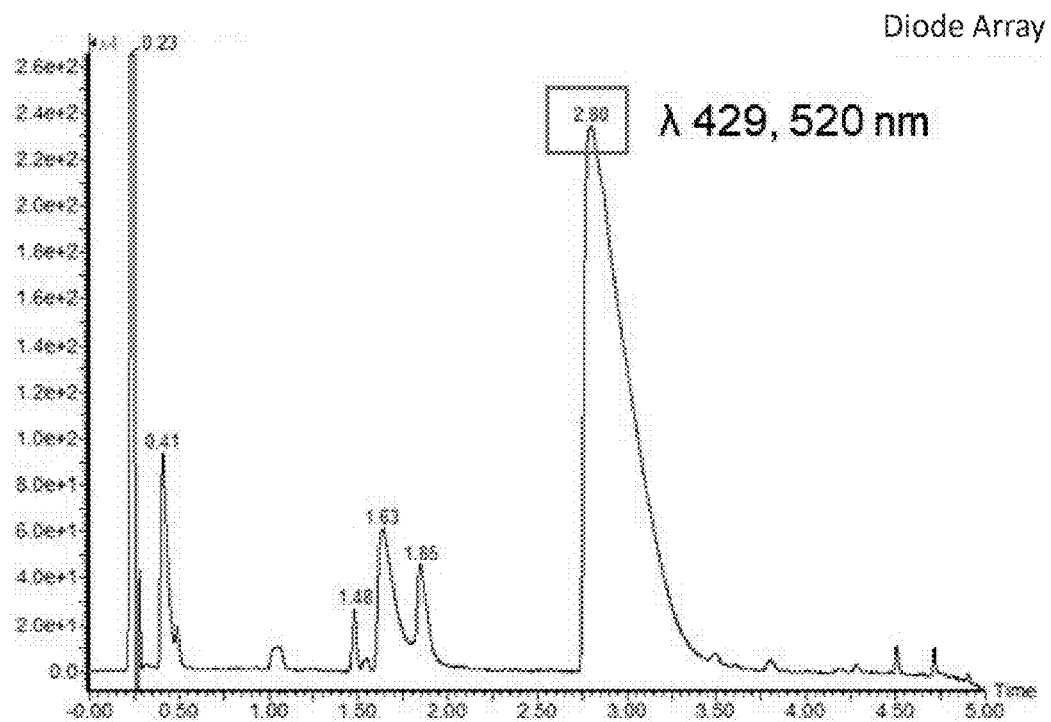
FIGS. 18A and 18B show a UPLC trace (FIG. 18A) and the corresponding mass spectrum (FIG. 18B) obtained after using a method embodiment to make compound embodiment DD4.
Figure 18B:
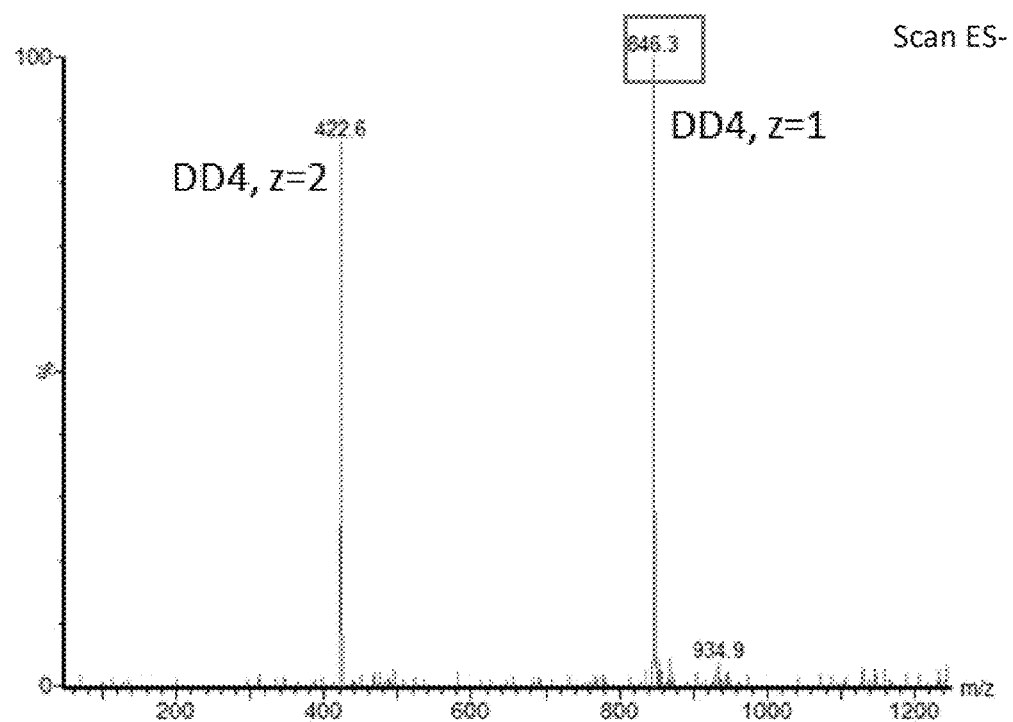
Figure 19A:
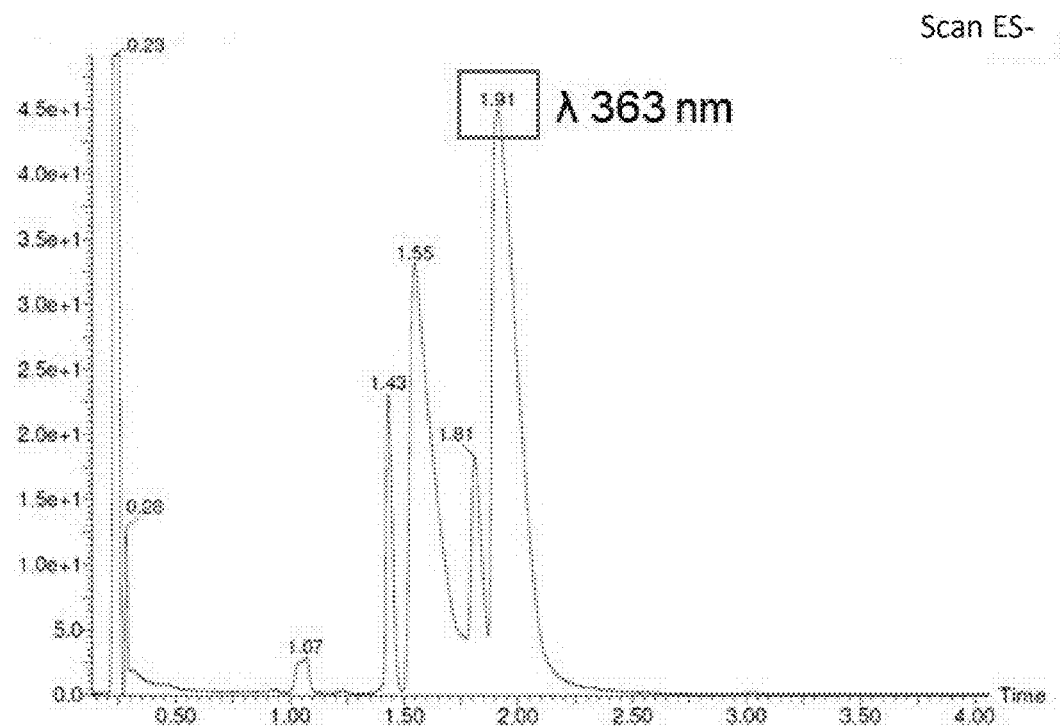
FIGS. 19A and 19B show a UPLC trace (FIG. 19A) and the corresponding mass spectrum (FIG. 19B) obtained after using a method embodiment to make compound embodiment DD5.
Figure 19B:
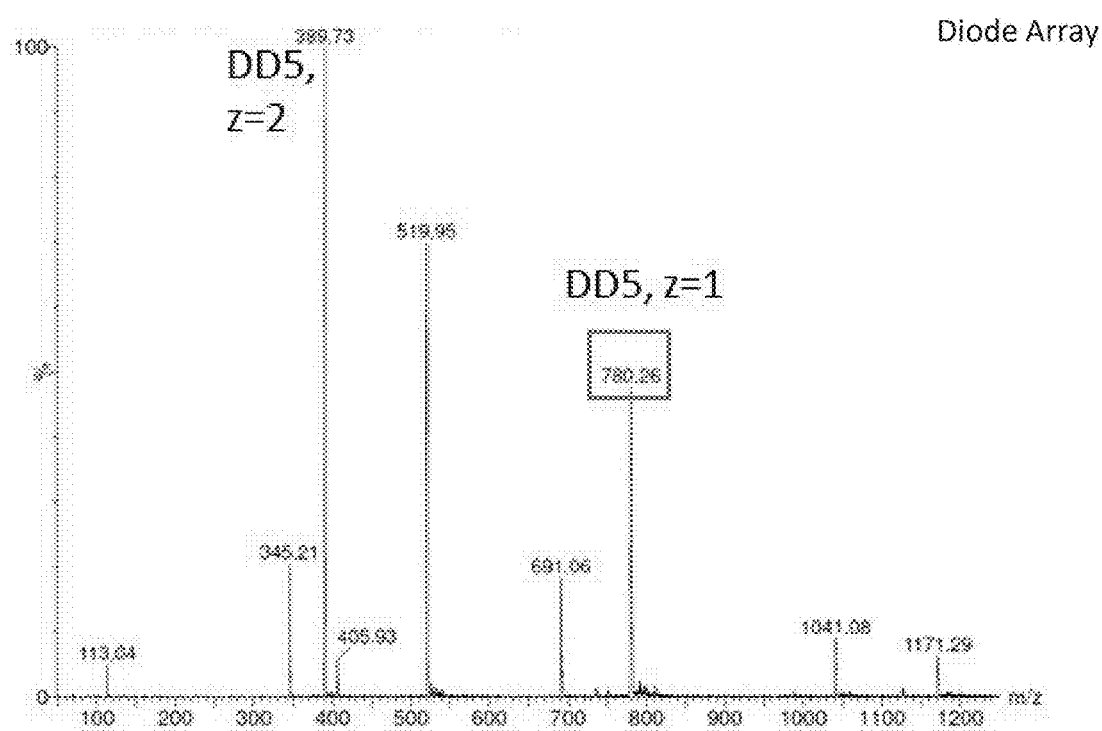
Figure 20A:
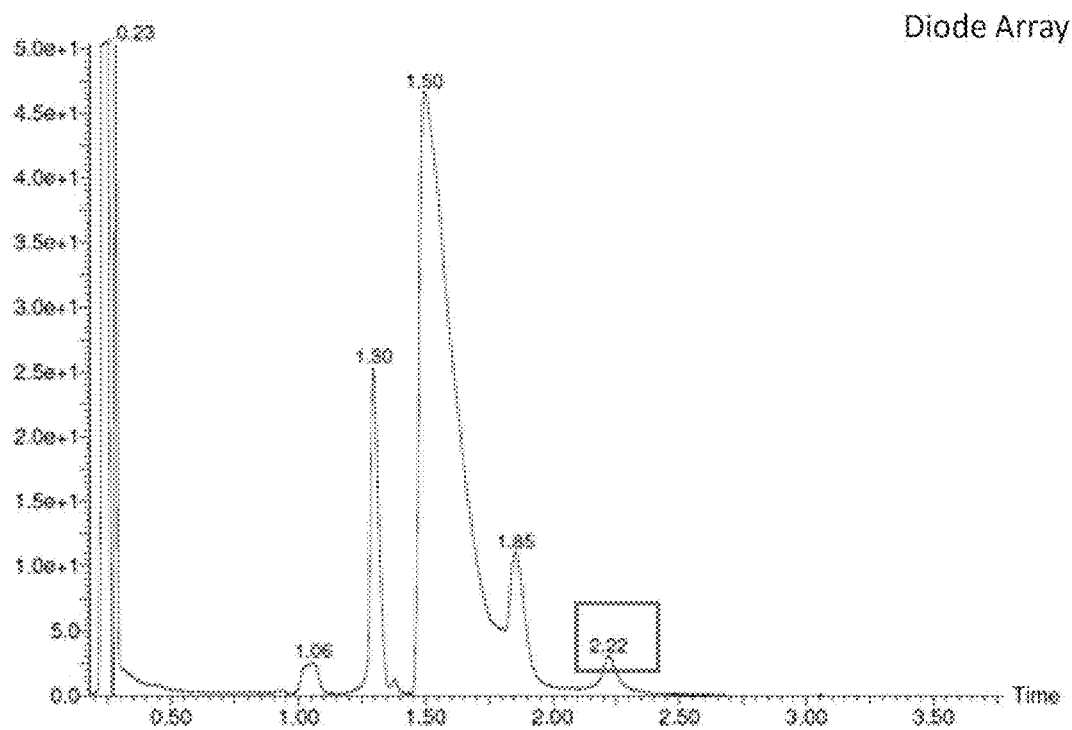
FIGS. 20A and 20B show a UPLC trace (FIG. 20A) and the corresponding mass spectrum (FIG. 20B) obtained after using a method embodiment to make compound embodiment DD7.
Figure 20B:
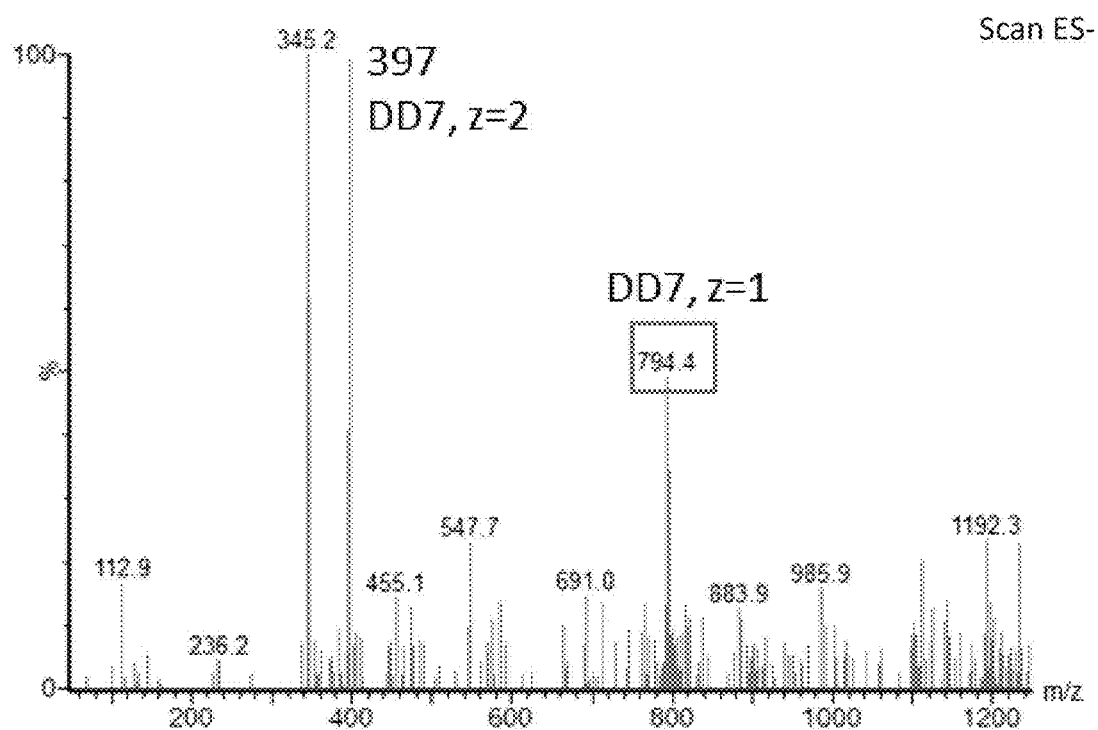
Figure 21A:
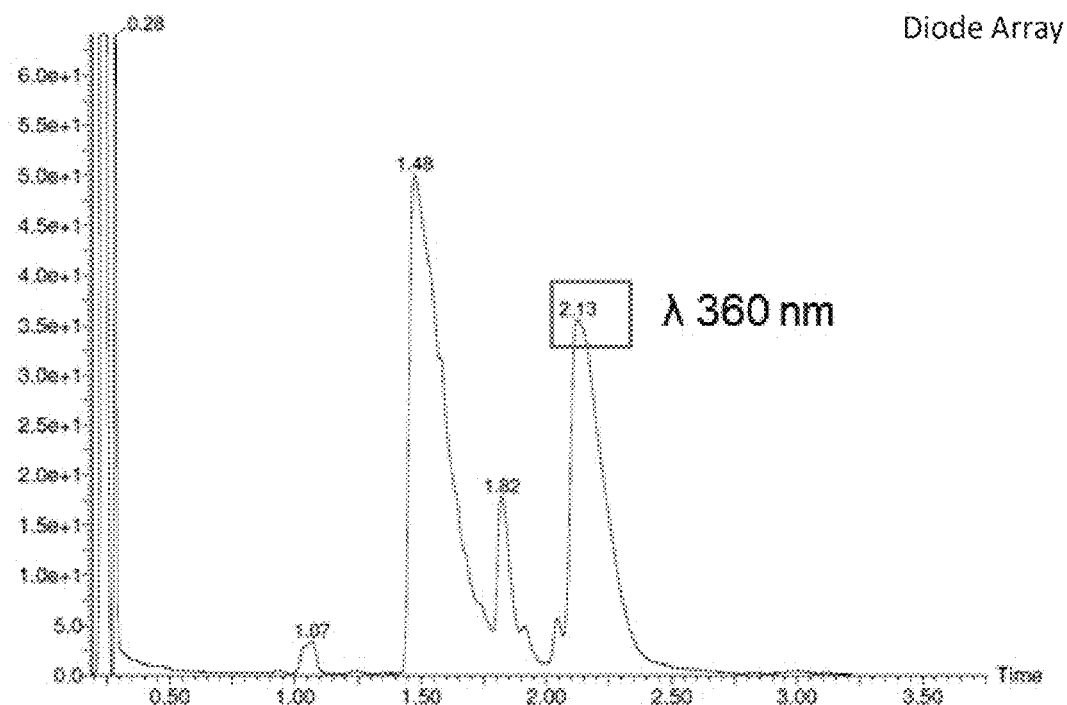
FIGS. 21A and 21B show a UPLC trace (FIG. 21A) and the corresponding mass spectrum (FIG. 21B) obtained after using a method embodiment to make compound embodiment DD8.
Figure 21B:
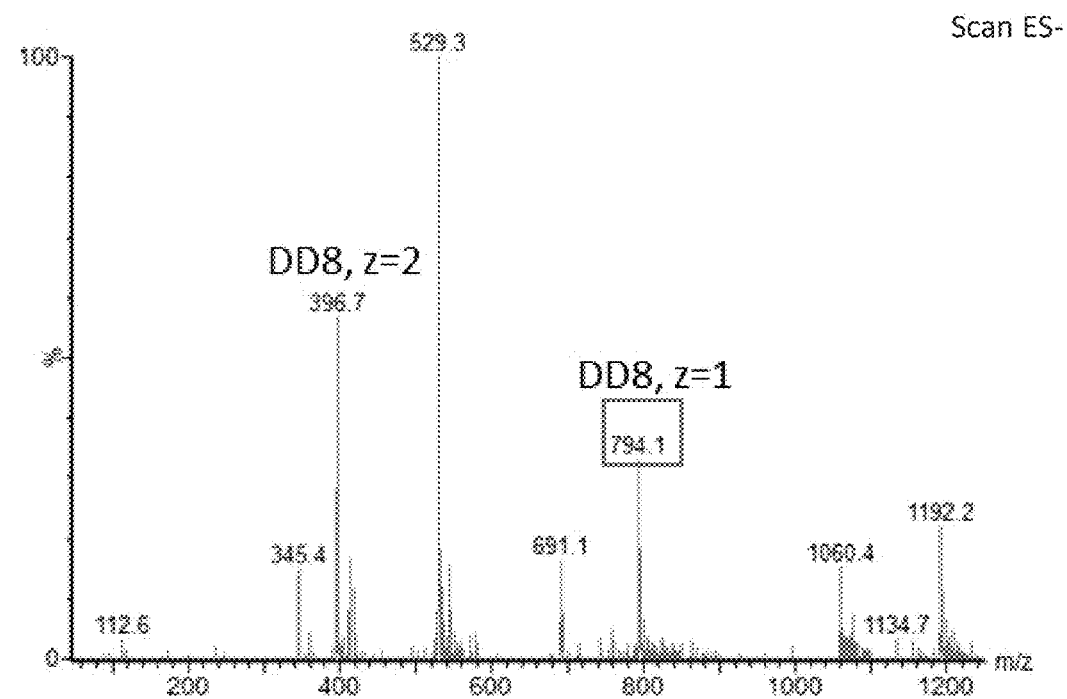
Figure 22A:
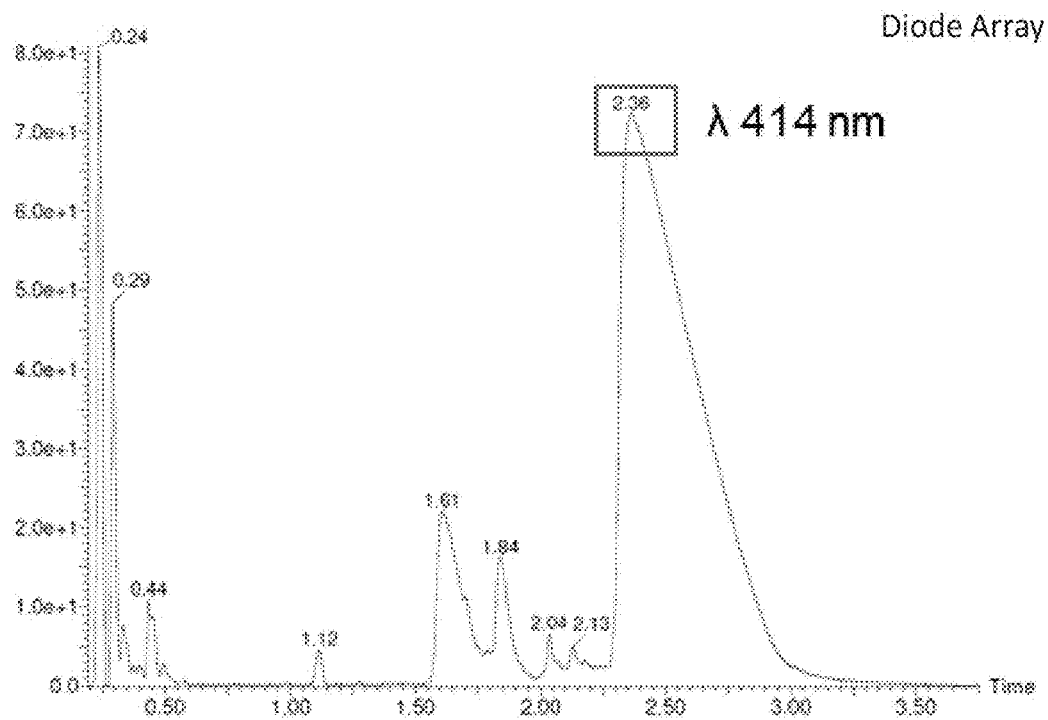
FIGS. 22A and 22B show a UPLC trace (FIG. 22A) and the corresponding mass spectrum (FIG. 22B) obtained after using a method embodiment to make compound embodiment DD9.
Figure 22B:
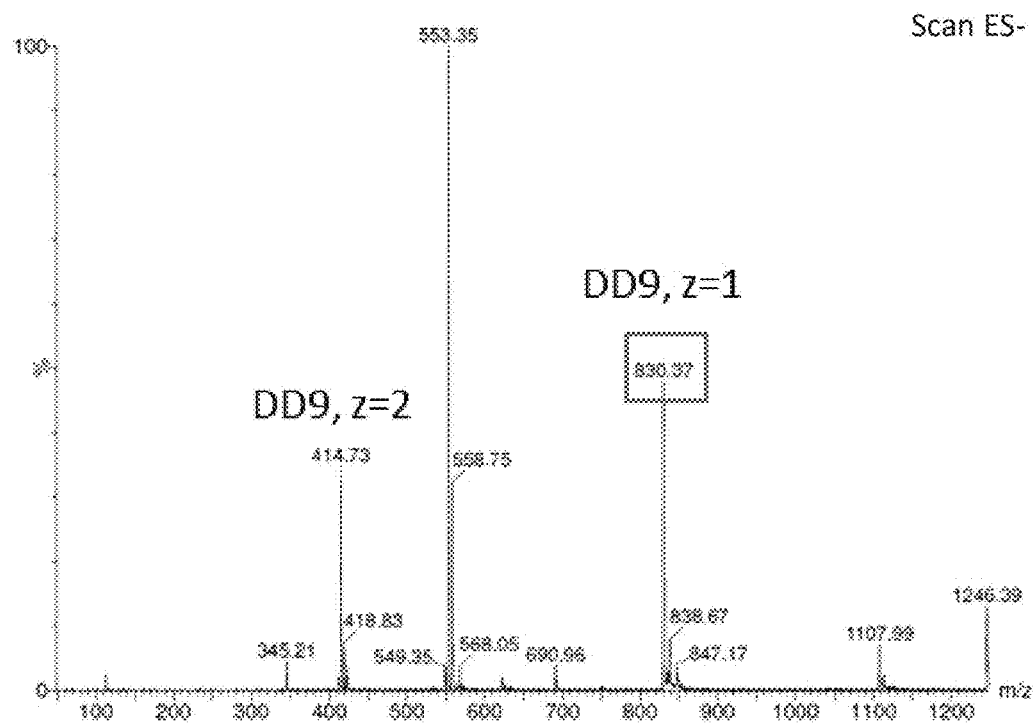
Figure 23A:
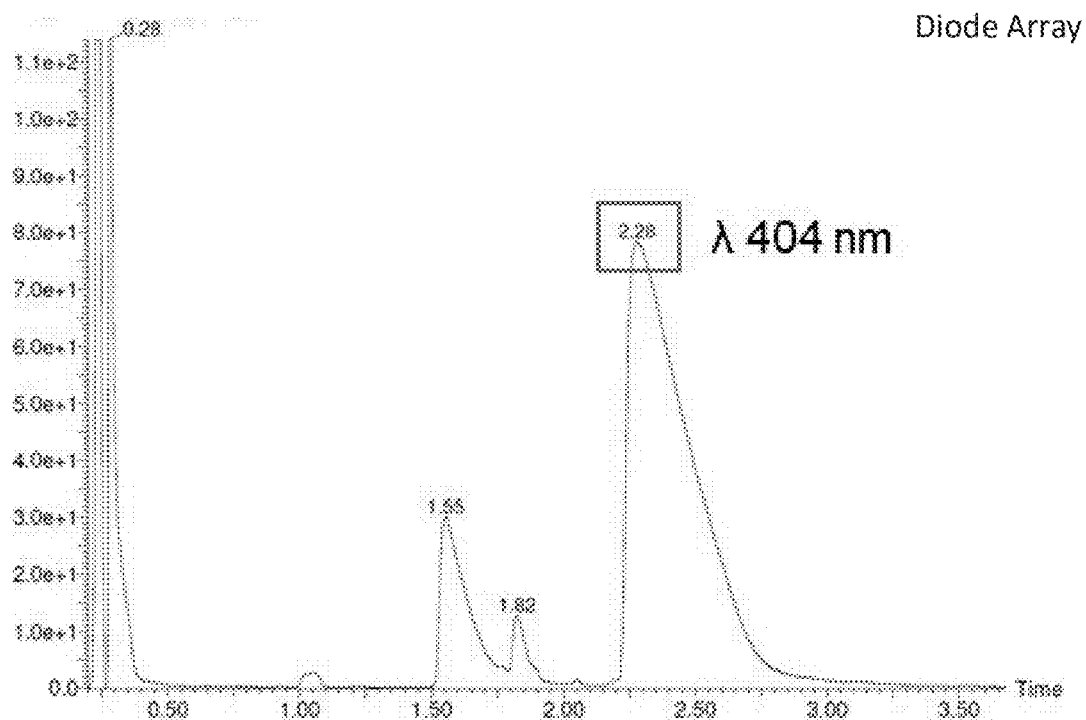
FIGS. 23A and 23B show a UPLC trace (FIG. 23A) and the corresponding mass spectrum (FIG. 23B) obtained after using a method embodiment to make compound embodiment DD10.
Figure 23B:
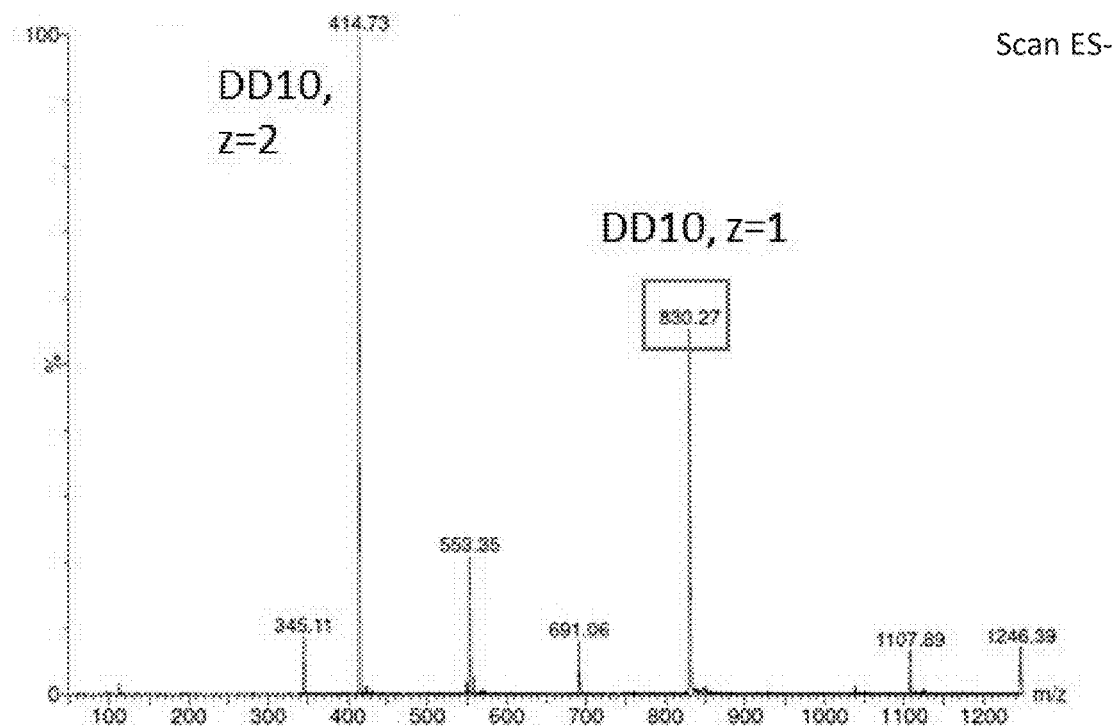
Figure 24A:
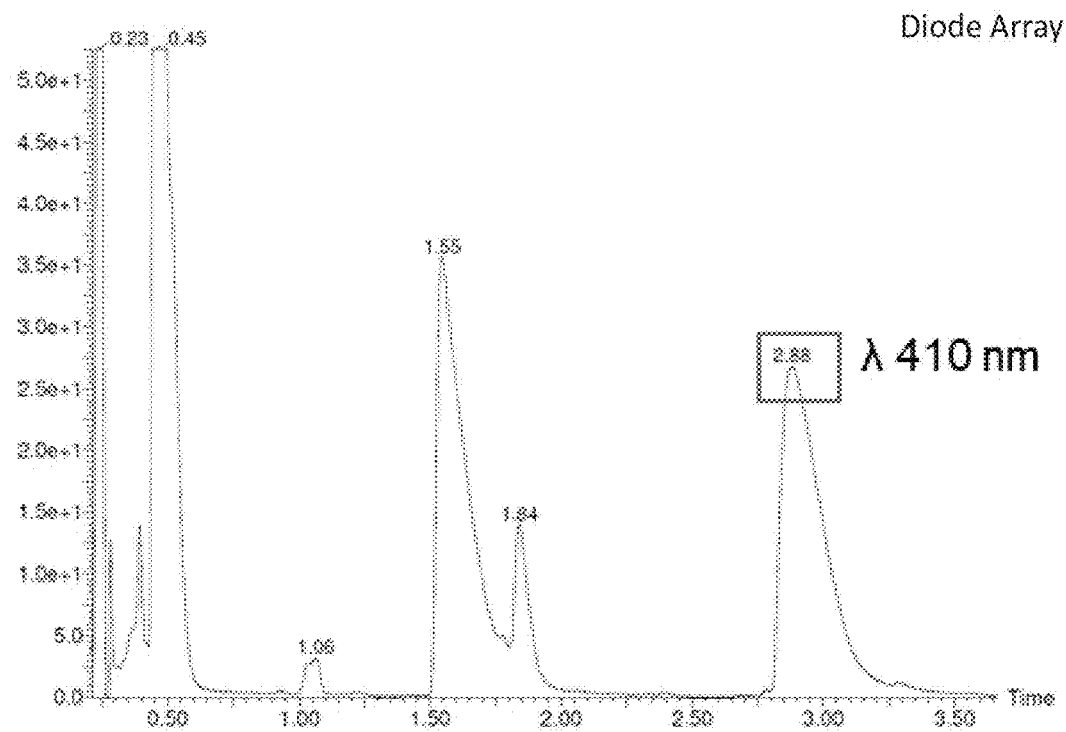
FIGS. 24A and 24B show a UPLC trace (FIG. 24A) and the corresponding mass spectrum (FIG. 24B) obtained after using a method embodiment to make compound embodiment DD11.
Figure 24B:
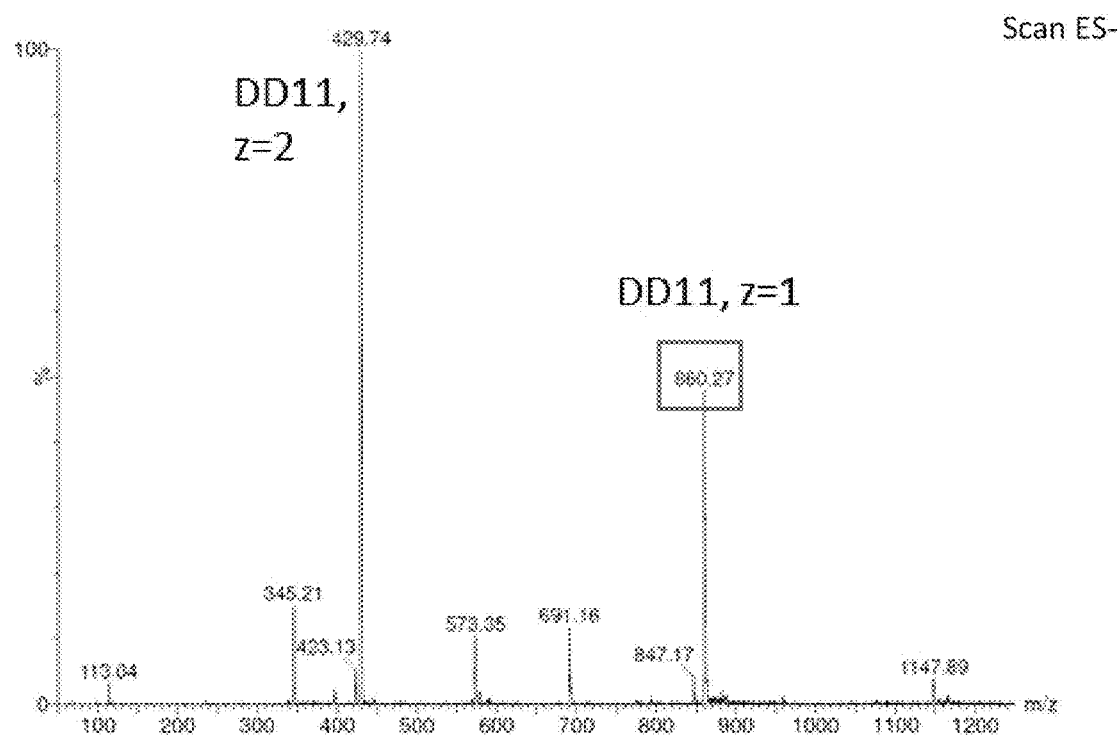
Figure 25A:
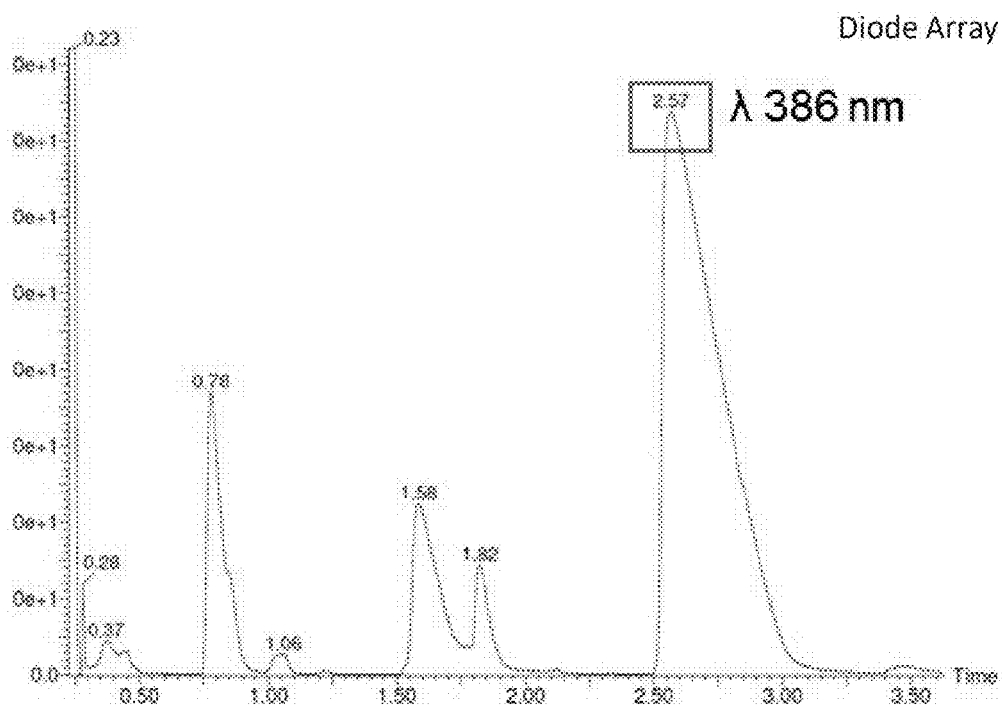
FIGS. 25A and 25B show a UPLC trace (FIG. 25A) and the corresponding mass spectrum (FIG. 25B) obtained after using a method embodiment to make compound embodiment DD12.
Figure 25B:
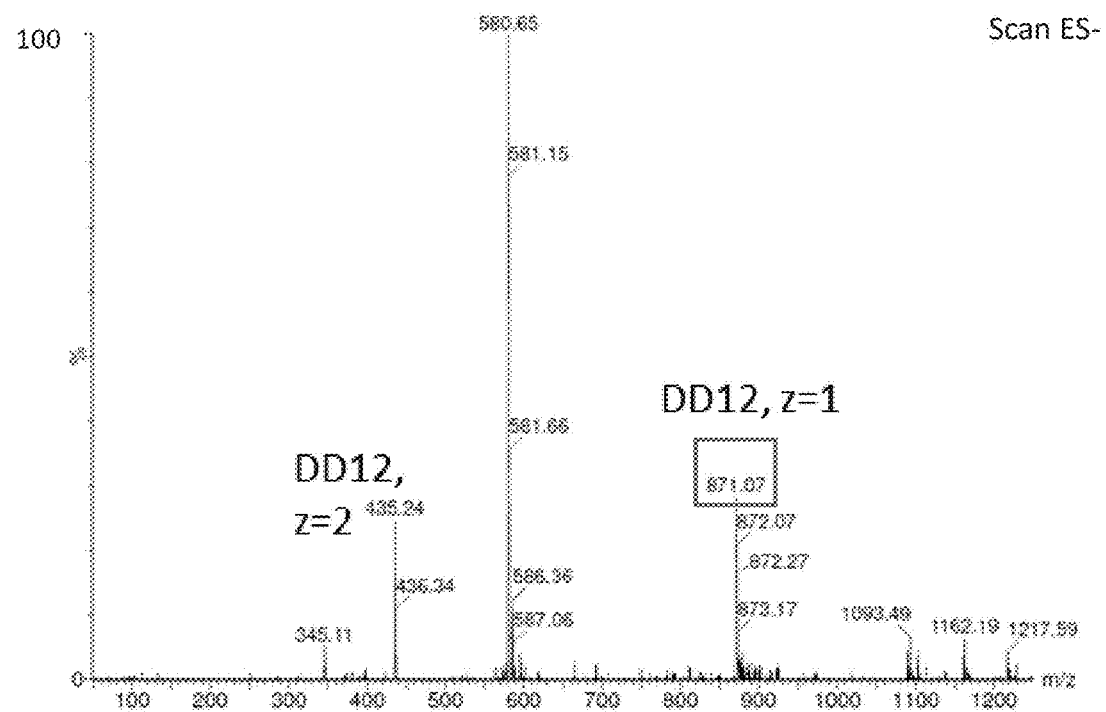
Figure 26A:
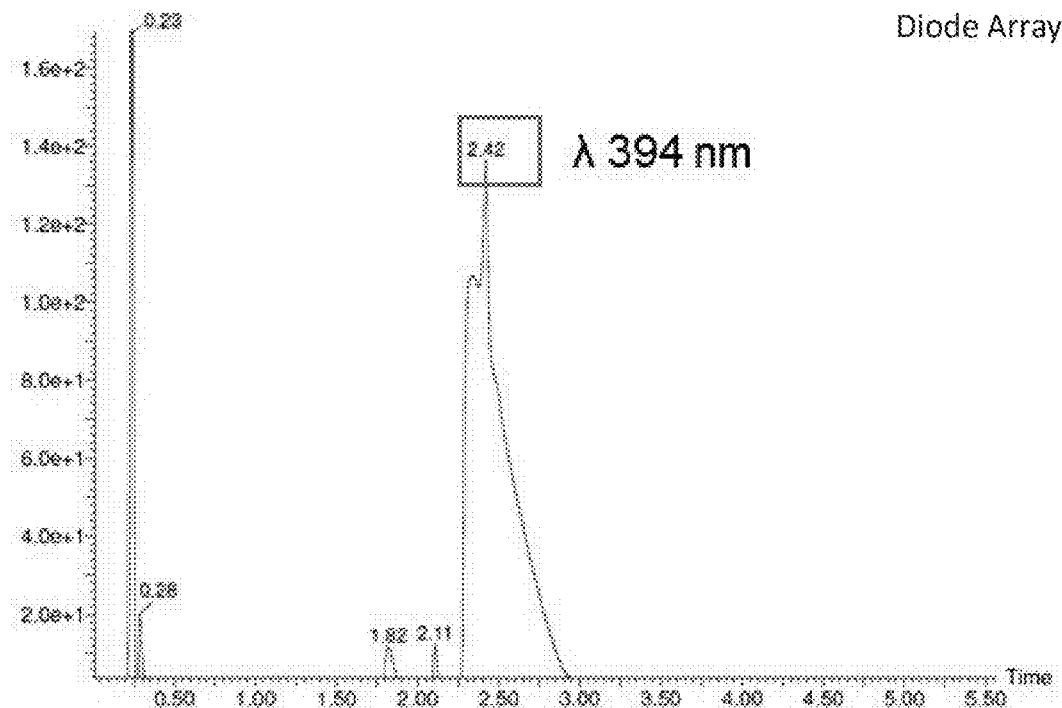
FIGS. 26A and 26B show a UPLC trace (FIG. 26A) and the corresponding mass spectrum (FIG. 26B) obtained after using a method embodiment to make compound embodiment DD13.
Figure 26B:
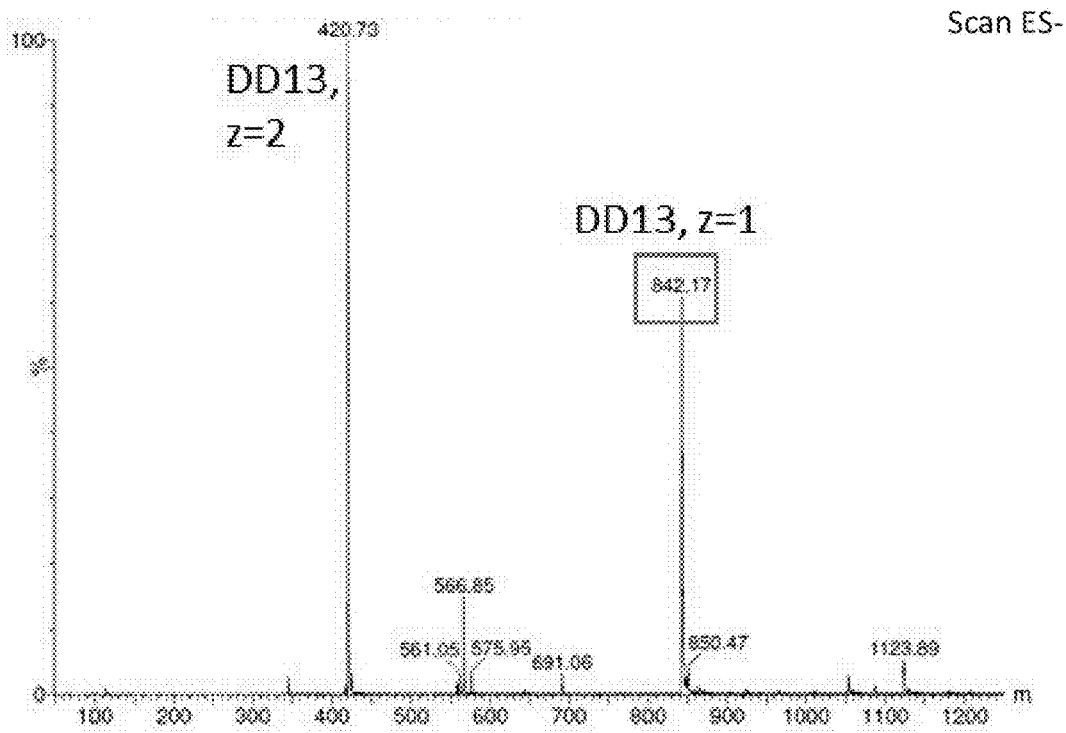
Figure 27A:
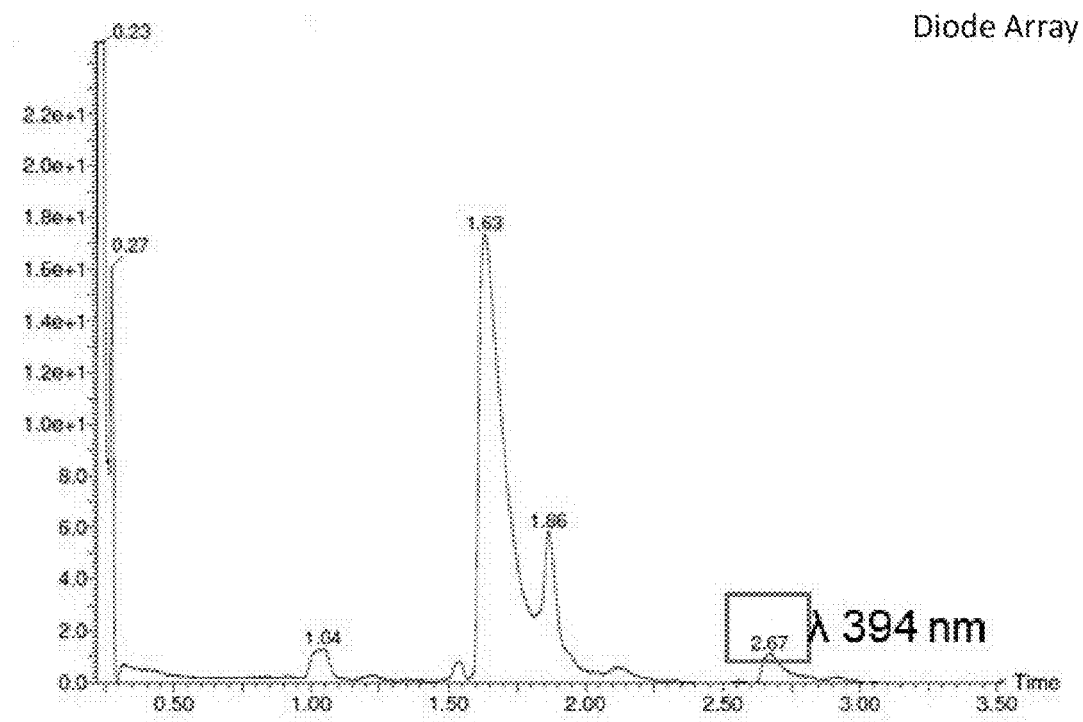
FIGS. 27A and 27B show a UPLC trace (FIG. 27A) and the corresponding mass spectrum (FIG. 27B) obtained after using a method embodiment to make compound embodiment DD14.
Figure 27B:
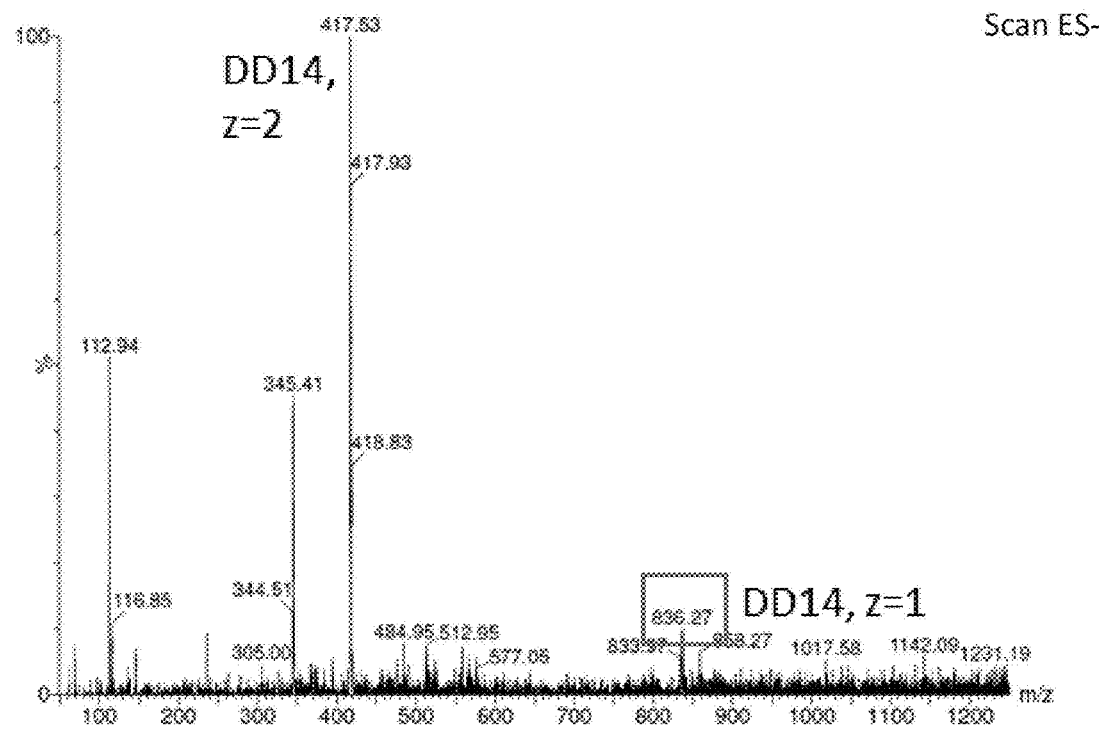
Figure 28A:
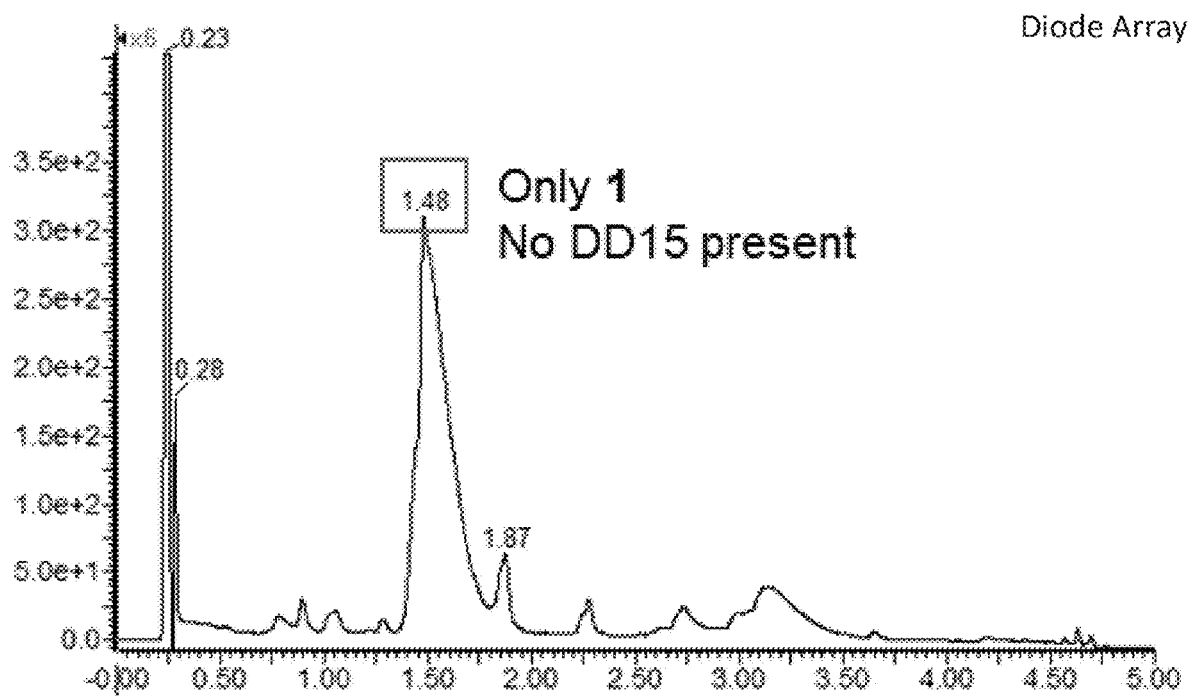
FIGS. 28A and 28B show a UPLC trace (FIG. 28A) and the corresponding mass spectrum (FIG. 28B) obtained after using a method embodiment in an attempt to make compound embodiment DD15.
Figure 28B:
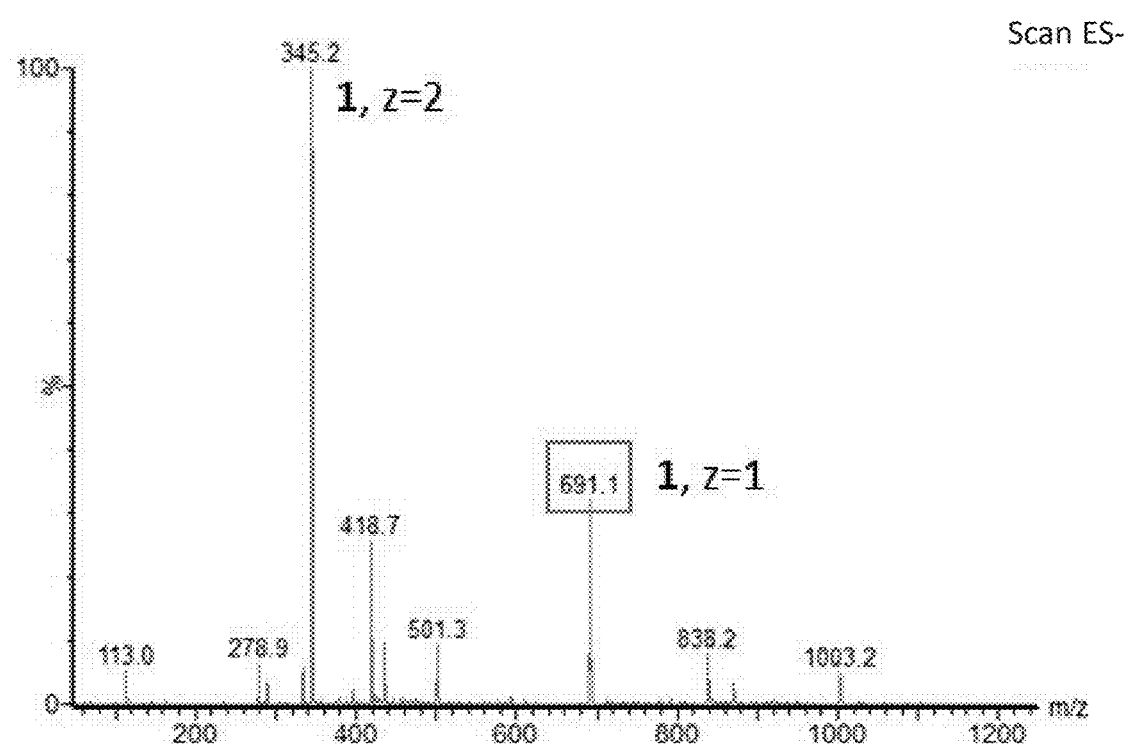
Figure 29A:
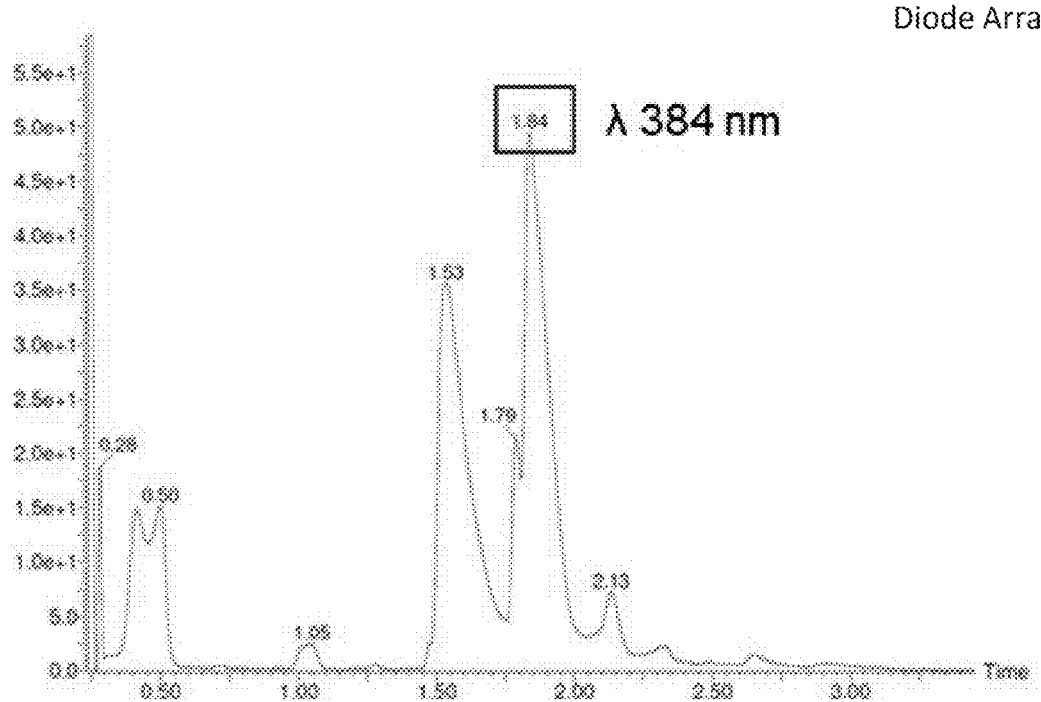
FIGS. 29A and 29B show a UPLC trace (FIG. 29A) and the corresponding mass spectrum (FIG. 29B) obtained after using a method embodiment to make compound embodiment DD16.
Figure 29B:
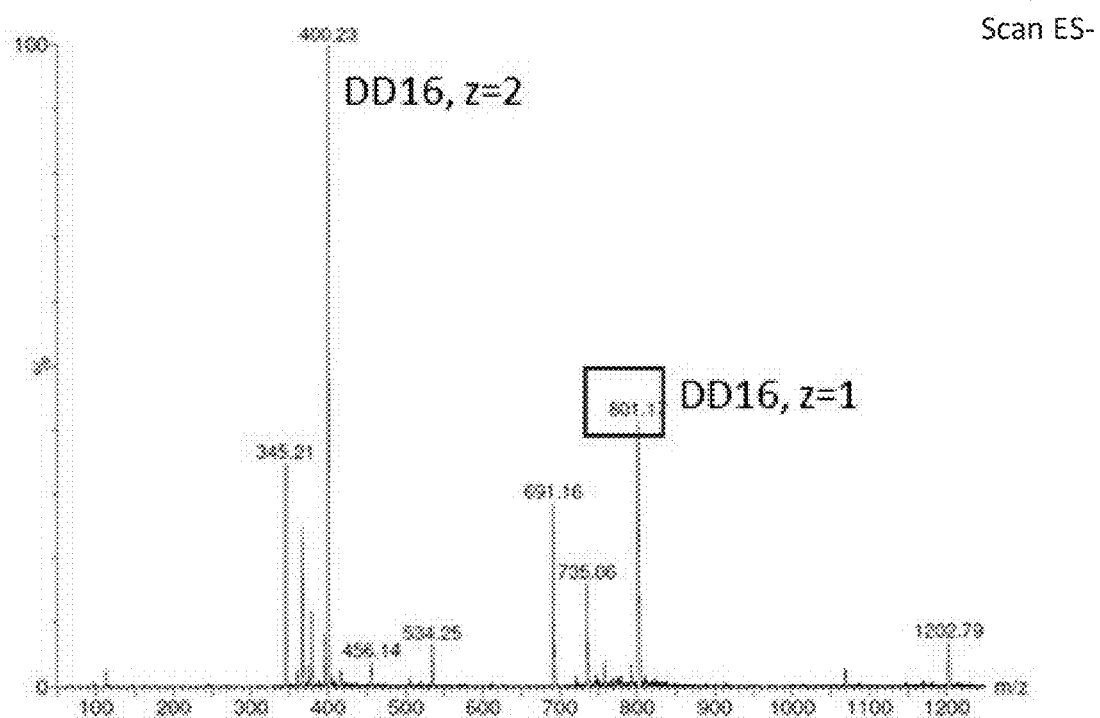

In some embodiments, a parallel synthesis method is used. In such embodiments, varying the detectable moiety-included in the compound can provide compound embodiments with diverse homodimerization affinities and guest-binding selectivities. Such compound embodiments retain the general features of self-assembly-driven molecular sensing and salt tolerance. In some such embodiments, coupling partners capable of providing merocyanine fluorophores after condensation with an aldehyde-containing compound precursor can be used (see FIGS. 2A-2C). In some embodiments, the method comprises using morpholine as an amine-containing base as it exhibits less propensity for binding to the hydrophobic binding pockets of the compound embodiments. In some embodiments, the color of the reaction mixture including the compound precursor, the coupling partner, and the base changes after the reactions are heated, indicating successful condensation. UPLC-MS can be used to confirm product formation and can reveal the extent of each reaction. Exemplary UPLC-MS spectra are provided by FIGS. 15A/15B through 29A/29B.

In some embodiments, a rapid, crude screening process successfully identified compounds without first needing to purify each compound. The crude reactions can be directly aliquoted into wells of a well-plate and the reaction solvent can be allowed to evaporate. The dried pellets can be re-suspended in sodium phosphate buffer (e.g., 10 mM, pH 7.4).

VI. Overview of Several Embodiments

Disclosed herein are embodiments of compounds and dimer complexes comprising such compounds. In some embodiments, the compound has a structure satisfying Formula I as disclosed herein. In particular embodiments, the compound is not, or is other than,

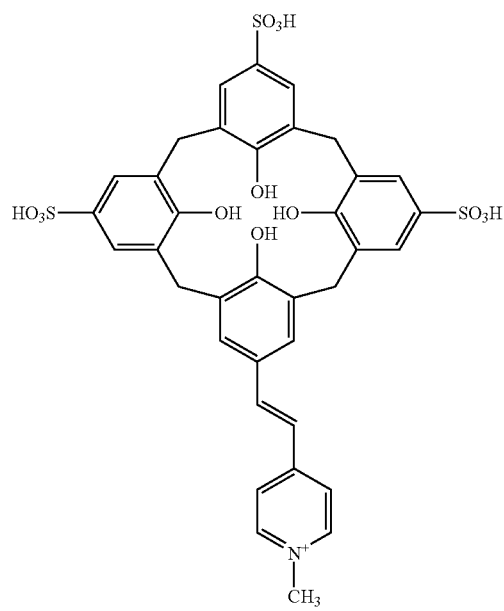

-continued

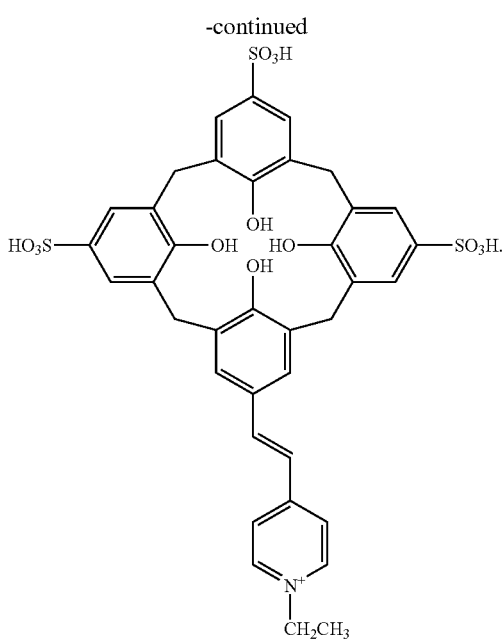

In some embodiments, the linker' group has a structure satisfying a Formula IA as disclosed herein.

In any or all of the above embodiments, the Ring B and/or the Ring$_{B'}$ groups independently comprise a detectable moiety.

In any or all of the above embodiments, the Ring B and/or the Ring$_{B'}$ groups independently comprise an N-functionalized nitrogen-containing ring system, a 2-ethyl-1H-benzo[de]isoquinoline-1,3(2H)-dione functional group, or a nitrobenzo[c][1,2,5]oxadiazole functional group.

In any or all of the above embodiments, the Ring B and/or the Ring$_{B'}$ groups independently are selected from:

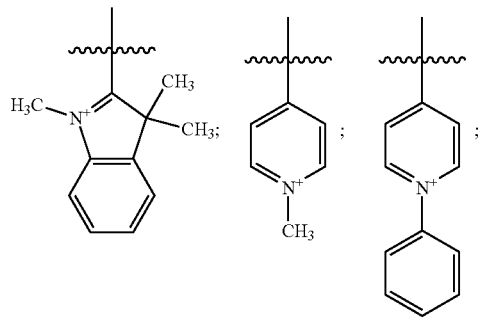

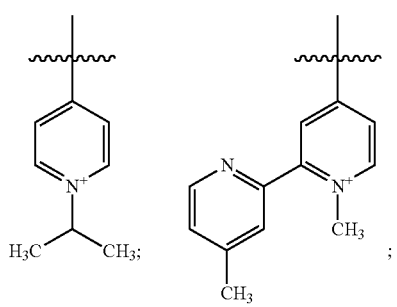

-continued

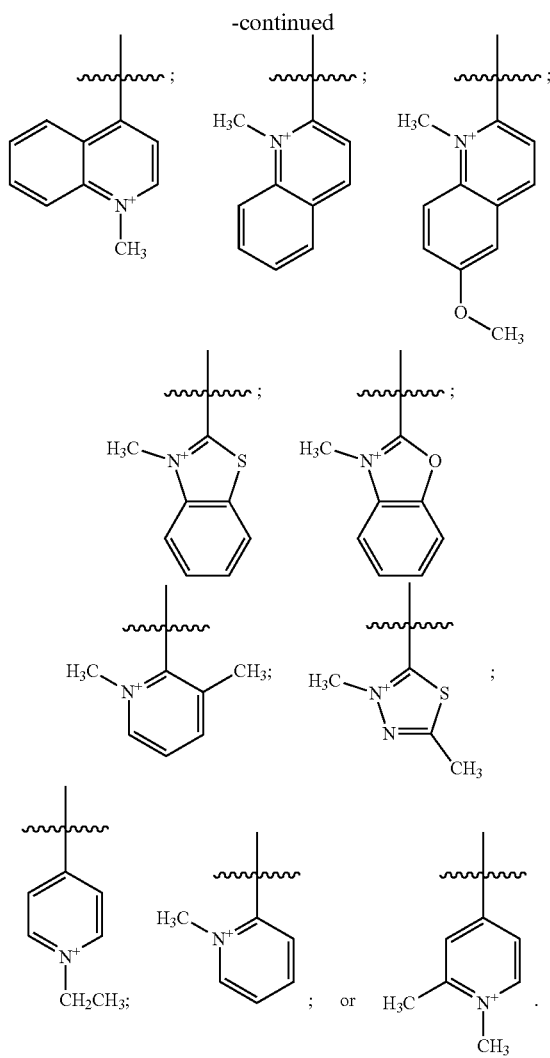

In any or all of the above embodiments, the compound has a structure satisfying any one or more of Formulas II-V as disclosed herein.

In any or all of the above embodiments, the compound has a structure according to Formula VA, as disclosed herein.

Also disclosed herein are embodiments of a sensor array, comprising: a substrate; and one or more compounds according to any or all of the above embodiments associated with the substrate.

Also disclosed herein are embodiments of a method, comprising: exposing a sample to one or more compounds according to one or all the above compound embodiments; and determining whether an analyte is present in the sample.

In some embodiments, the sample is an aqueous sample, a saliva sample, a urine sample, a nasal wash sample, a synovial fluid sample, a cerebrospinal fluid sample, a gastric fluid sample, a serum sample, a plasma sample, a cell growth medium sample, a cell lysate sample, or any combination thereof.

In any or all of the above embodiments, the compound interacts with any analytes present in the sample to produce a detectable signal.

In any or all of the above embodiments, the detectable signal is a colorimetric signal or a fluorescent signal and the analyte is an illicit drug.

In any or all of the above embodiments, the two detectable signals are produced wherein one detectable signal is a colorimetric signal and the other is a fluorescent signal.

In any or all of the above embodiments, determining whether the analyte is present in the sample comprises subjecting the sample, after compound exposure, to an ultraviolet light source to observe any fluorescent signal produced by an interaction between the analyte and the compound; or visual detection to observe any colorimetric signal produced by an interaction between the analyte and the compound.

Also disclosed herein are embodiments of a dimer complex, comprising: a first compound according to any or all of the above compound embodiments; and a second compound according to any or all of the above compound embodiments; wherein the first compound and the second compound chemically interact to form the dimer complex and wherein the dimer complex does not emit a detectable signal or wherein the dimer complex emits a dimer detectable signal that is different from any detectable signal provided by the first compound, the second compound, or both.

In any or all of the above embodiments, the first compound has the same structure as the second compound.

In any or all of the above embodiments, the first compound has a structure that is different from the second compound.

Also disclosed herein are embodiments of a method, comprising exposing the dimer complex of any one or all of the above dimer complex embodiments to an analyte, wherein the analyte disassembles the dimer complex to produce a detectable signal or wherein the analyte disassembles the dimer complex to produce a monomer detectable signal that is different from the dimer detectable signal.

In some embodiments, the analyte comprises a cation or a hydrophobic cation.

VII. Examples

General Methods and Materials—

$^1$H, $^{13}$C, and 1D DOSY were recorded on a Bruker Avance Neo 500 MHz spectrometer unless otherwise indicated and processed with MestReNova by Mestrelab Research S.L. Deuterated solvents were purchased from Sigma Aldrich and NaH$_2$PO$_4$/Na$_2$HPO$_4$ (50 mM, pD 7.4) in D$_2$O were prepared in lab and the pD was adjusted with 1 M NaOD/DCl solutions. Mass spectra of novel compounds were collected on a Thermo Scientific Ultimate 3000 ESI-Orbitrap Exactive. A Waters UPLC-MS equipped with UV/Vis and QDa detector was used with an Aquity UPLC BEH C18 1.7 uM (21×50 mm) column run with a gradient of 80% H$_2$O (+0.4% FA)/20% CH$_3$CN (+0.4% FA) to 50% H$_2$O (+0.4% FA)/50% CH$_3$CN (+0.4% FA) over 4 minutes at 0.6 ml/min. All UV-Vis and fluorescence titrations and spectra were collected on a Cytation-5 BioTek Imaging Reader. Titrations and dilutions were conducted in a NUNC black walled, optical bottom 96-well plate. Infrared (IR) spectra were obtained using a Perkin Elmer 1000 FT-IR spectrometer. Data are represented as follows: frequency of absorption (cm$^{-1}$), intensity of absorption (s=strong, m=medium, w=weak, br=broad). Melting points were collected on a Gallenkamp Melting Point apparatus.

Compound 1 was prepared following a literature protocol. Heterocyclic compounds were synthesized from previously reported literature.

All drugs (except nicotine) were purchased through Sigma Aldrich in 1 mg/ml ampules dissolved in methanol or acetonitrile. To avoid adding organic solvent to DD array, the ampules were evaporated of organic solvent over a gentle stream of nitrogen overnight. The residue was re-dissolved in water and aliquoted to form stock solutions (1 mM) in $NaH_2PO_4/Na_2HPO_4$ (10 mM, pH 7.4). S-(−)-nicotine was purchased from Alfa Aesar.

Stock solutions of compound embodiments 1, 4, 8, 12, 13 (1 mM) were prepared in $NaH_2PO_4/Na_2HPO_4$ (10 mM, pH 7.4) with concentrations accurately checked against a reference standard by quantitative NMR before being further diluted to a working stock (200 μM).

1D DOSY Procedure—

For each DOSY experiment, the 90° pulse is determined by measuring the pulse length at 360° by a zg pulse sequence and dividing by four. The T1 relaxation was estimated through an inversion recovery (t1ir1d) pulse sequence. The relaxation time for each experiment was set to be 10-times the estimated T1. For each experiment, the Δ was set to 50 or 100 ms. The δ was determined by finding a 90-95% intensity difference between the first and last spectra in the power array via a stebpgp1s1d pulse program, see calculation below for 5 used for each experiment. The pulse sequences used for 1D DOSY was stebpgp1s. After pre-processing through TopSpin, the area under the peaks of interest was selected and plotted as a function of the field gradient strength (G). These points were fitted to extract the diffusion coefficient, D. The hydrodynamic radius, $r_H$, was calculated with Stokes-Einstein equation with the following parameters: viscosity of water $8.7 \times 10^{-4}$ Pa·s at 300 K.

Fluorescence Titrations in Diluted Saliva—

Saliva was prepared for handling by centrifugation (3400 rpm, 15 min) at 4° C. The supernatant was pipetted into a second conical tube containing an equal volume of water. To avoid multiple transfers of saliva to form stocks, each compound embodiment was directly pipetted into empty wells of a NUNC black-walled plate in a set of triplicates. The 1:1 saliva:water mixture was added to form a final [DD]=12 μM at 100 μL. Separately, each drug (nicotine, MDMA, cocaine) was diluted in the 1:1 saliva:water mixture with a final [DD]=12 μM and [drug]=240 μM. This was serial diluted to achieve a [drug]=240 μM–4 μM.

General Synthesis of Select Compound Embodiments—

Figure 9A:
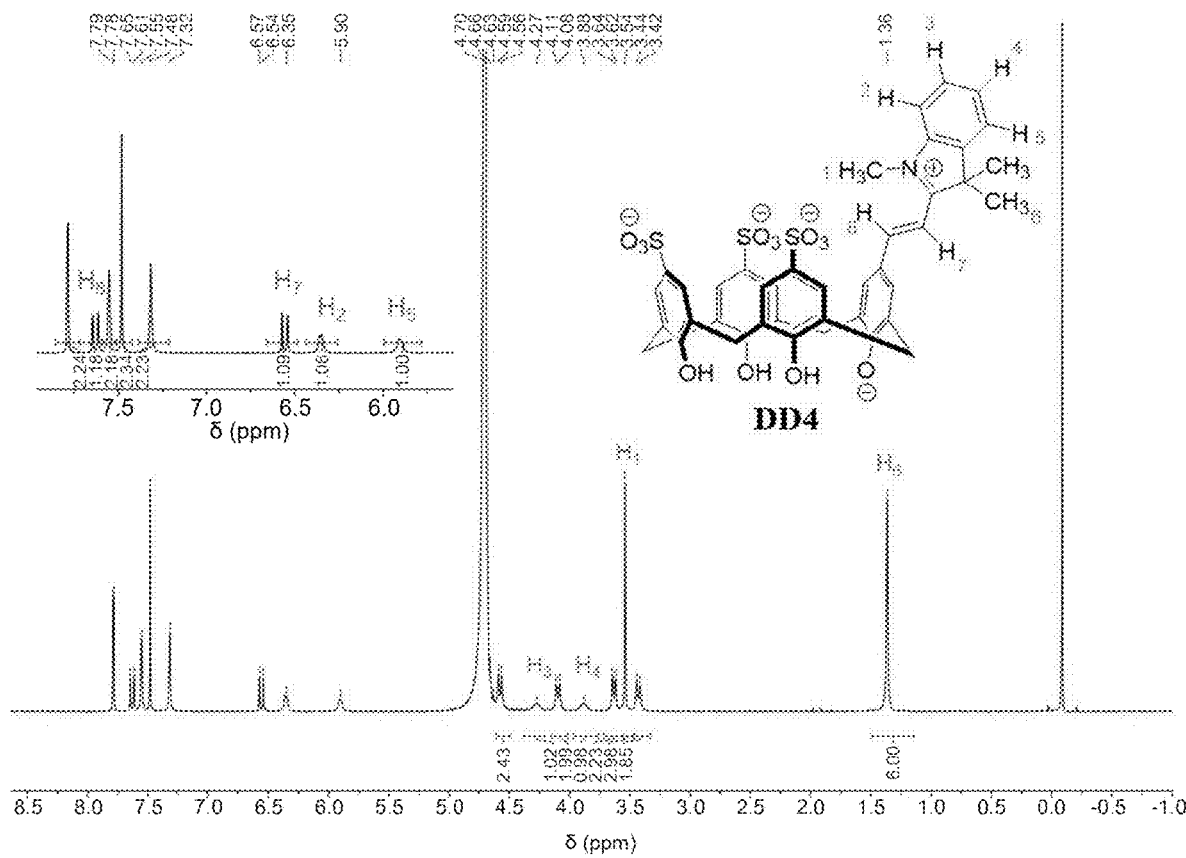
FIGS. 9A and 9B are nuclear magnetic resonance (NMR) spectra showing proton (FIG. 9A) and carbon (FIG. 9B) spectra for compound embodiment DD4.
Figure 9B:
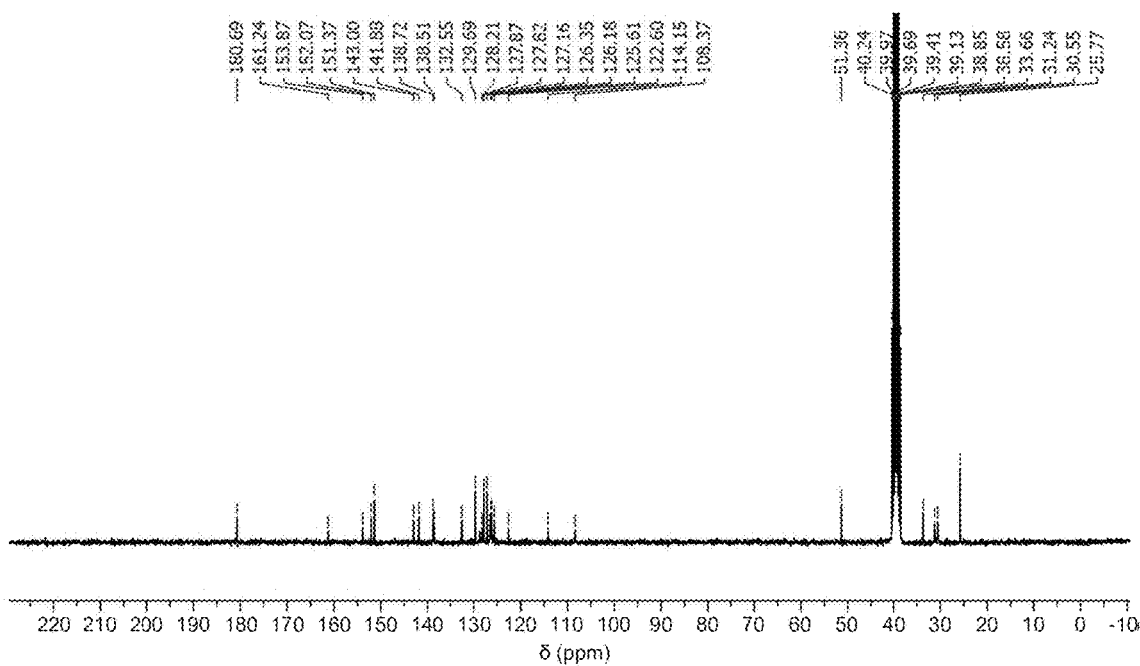
Figure 10A:
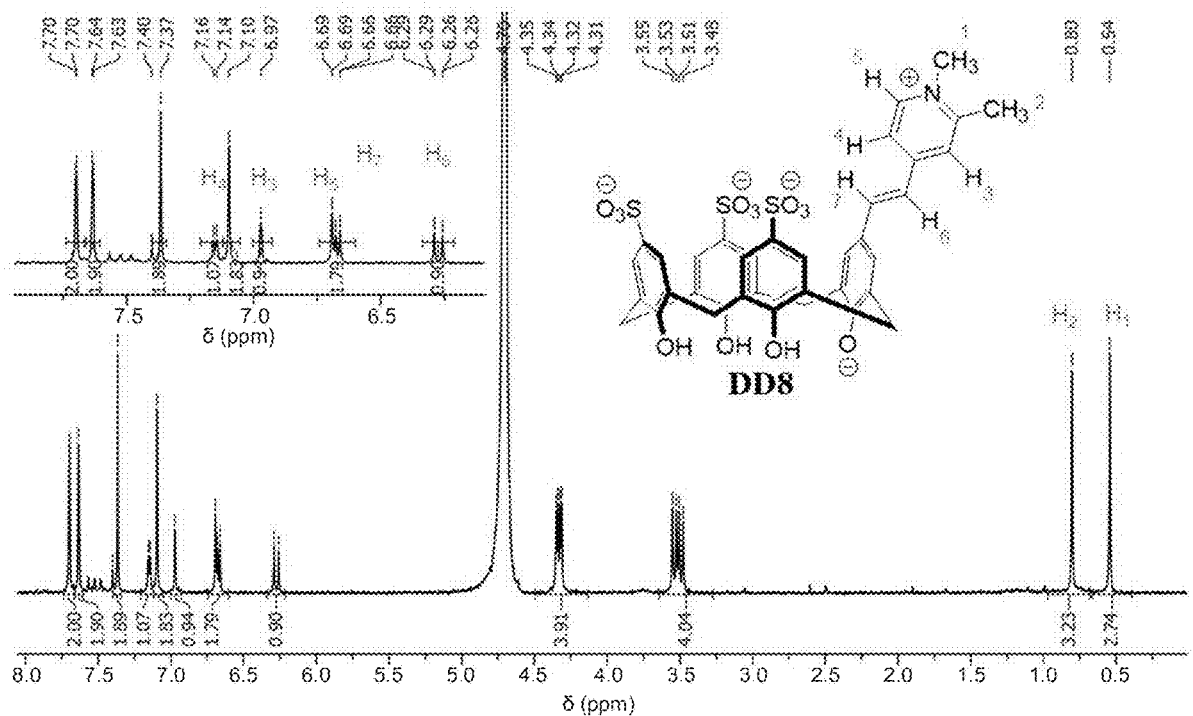
FIGS. 10A and 10B are nuclear magnetic resonance (NMR) spectra showing proton (FIG. 10A) and carbon (FIG. 10B) spectra for compound embodiment DD8.
Figure 10B:
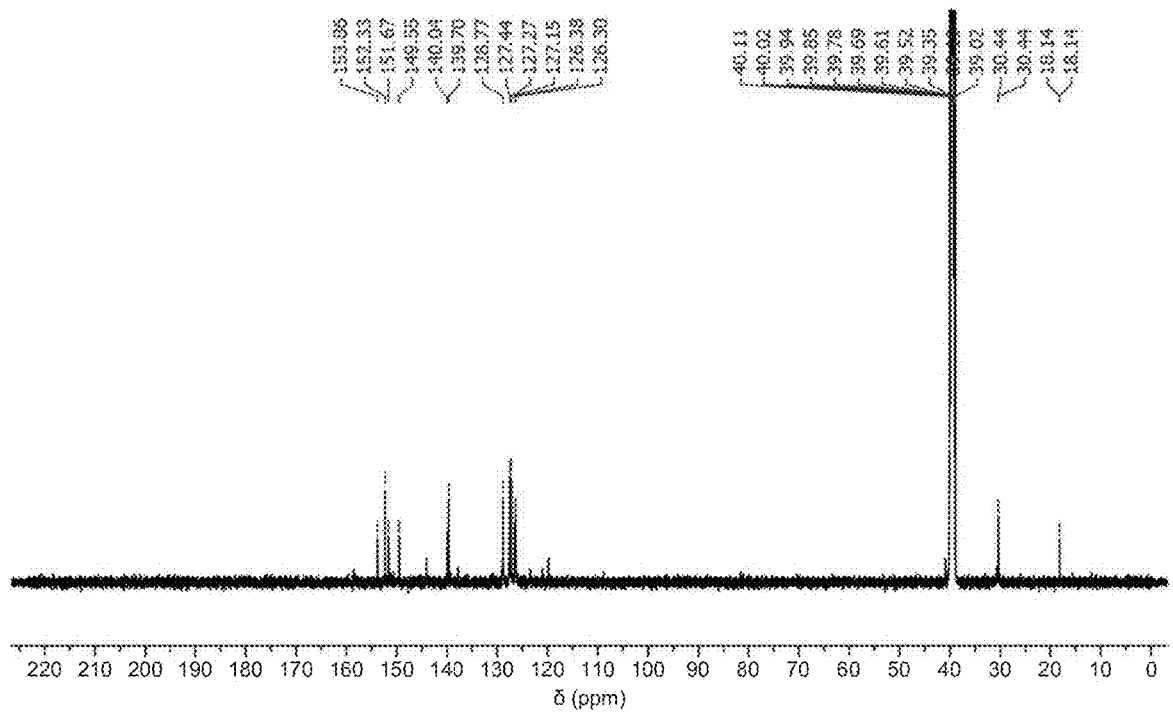
Figure 11A:
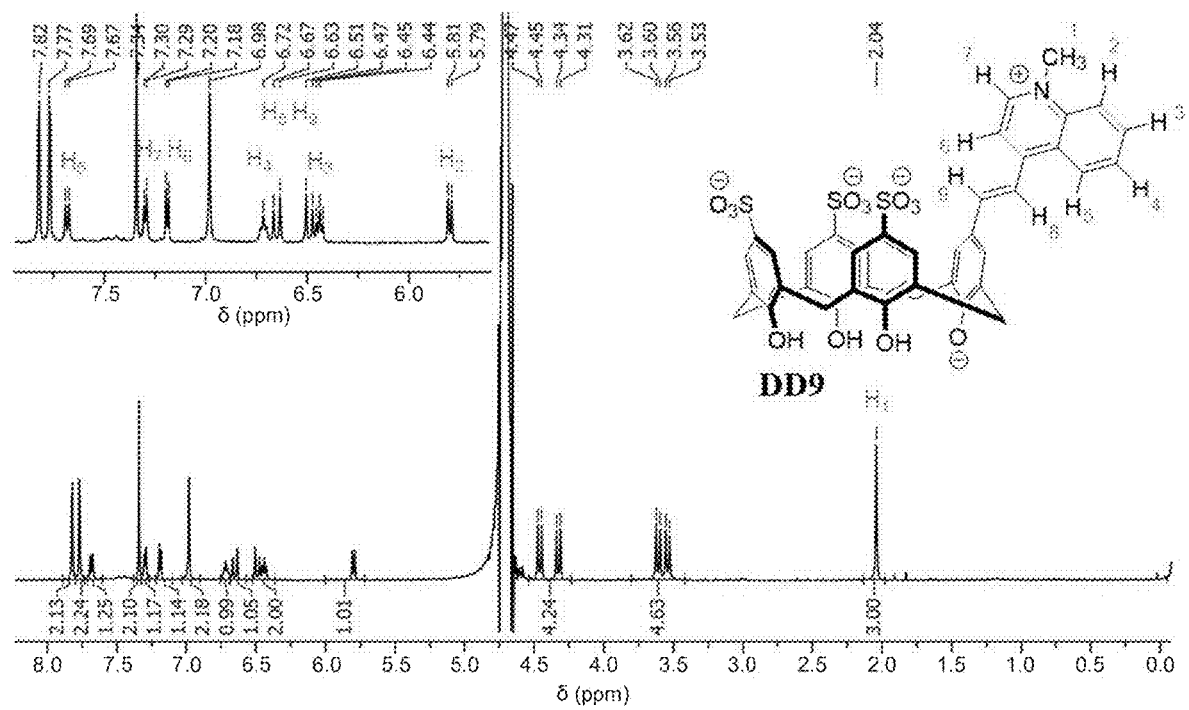
FIGS. 11A and 11B are nuclear magnetic resonance (NMR) spectra showing proton (FIG. 11A) and carbon (FIG. 11B) spectra for compound embodiment DD9.
Figure 11B:
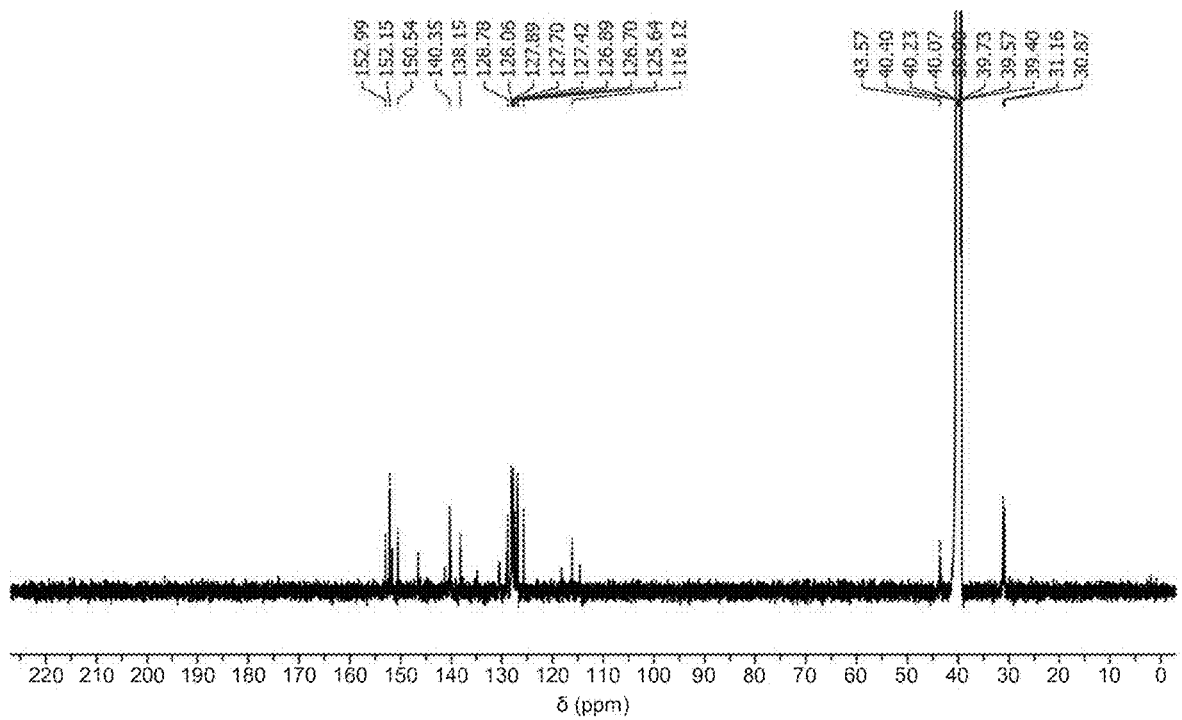
Figure 12A:
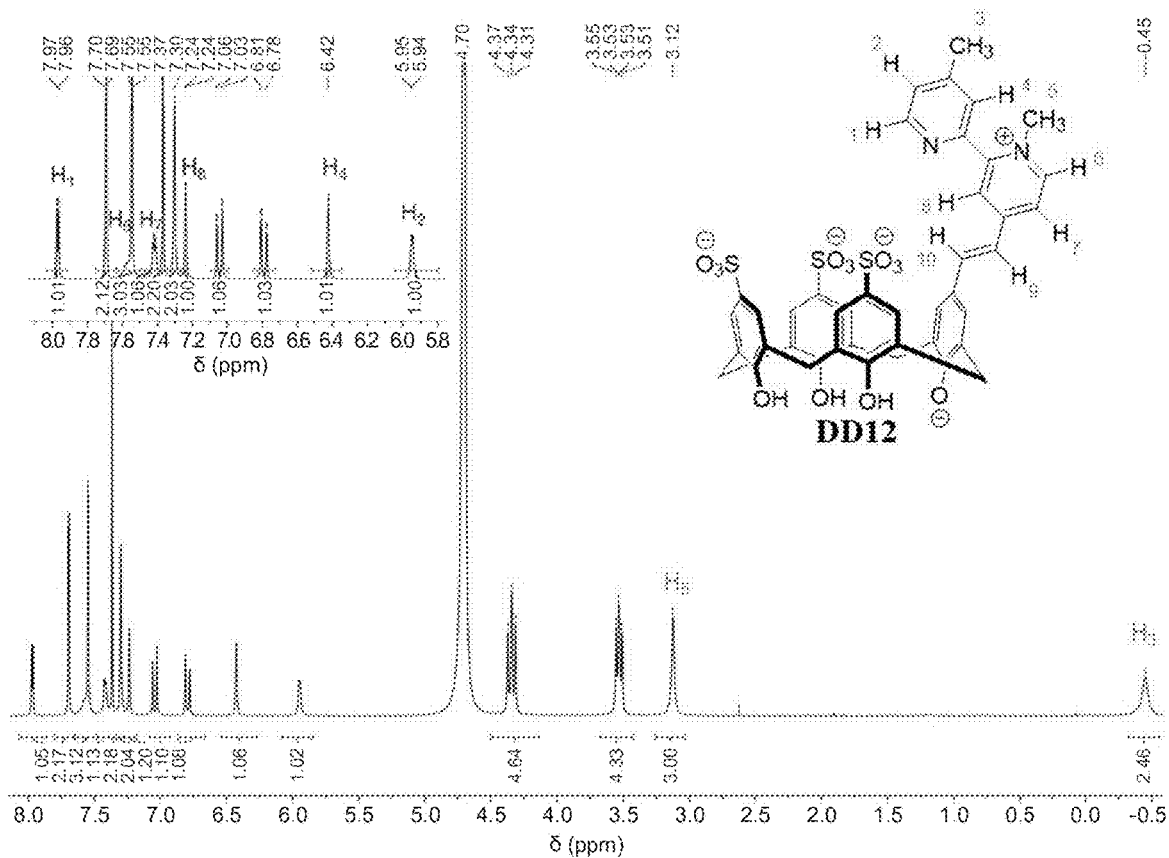
FIGS. 12A and 12B are nuclear magnetic resonance (NMR) spectra showing proton (FIG. 12A) and carbon (FIG. 12B) spectra for compound embodiment DD12.
Figure 12B:
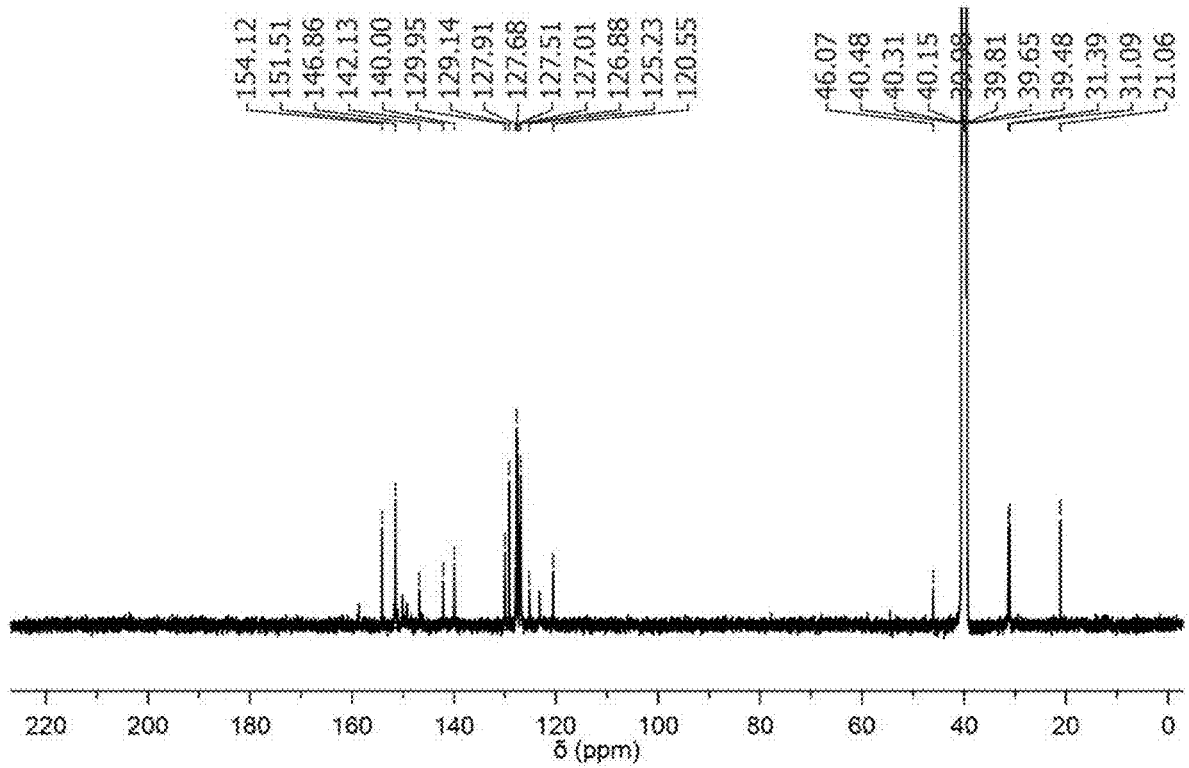
Figure 13A:
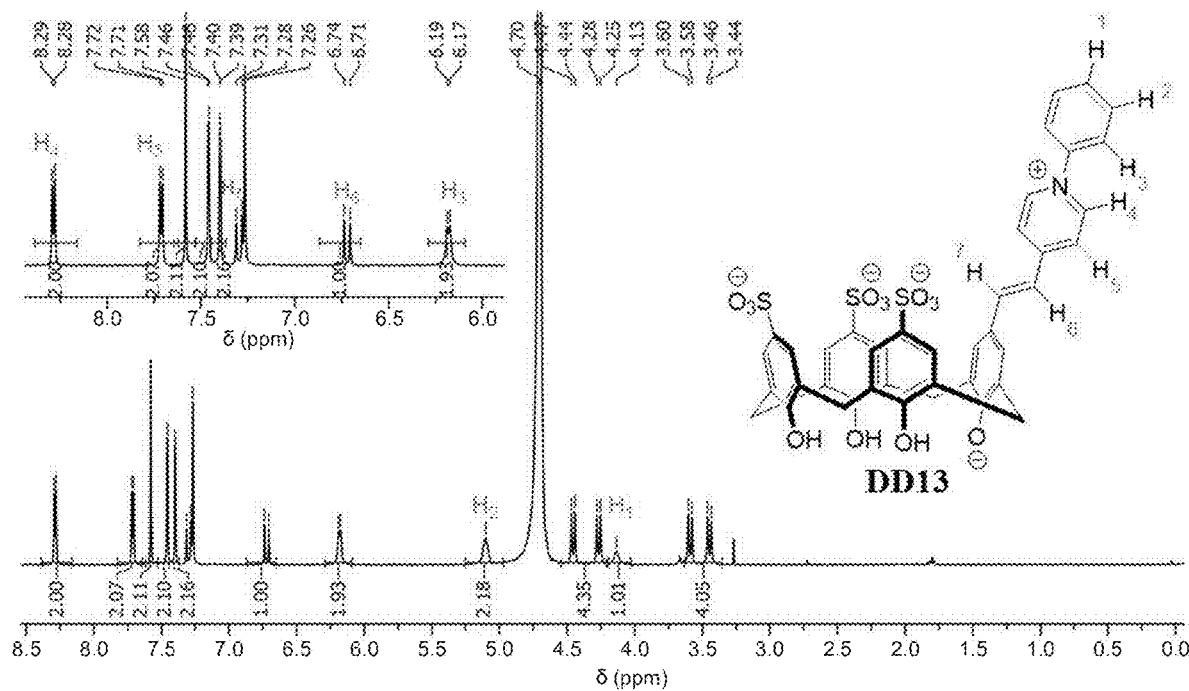
FIGS. 13A and 13B are nuclear magnetic resonance (NMR) spectra showing proton (FIG. 13A) and carbon (FIG. 13B) spectra for compound embodiment DD13.
Figure 13B:
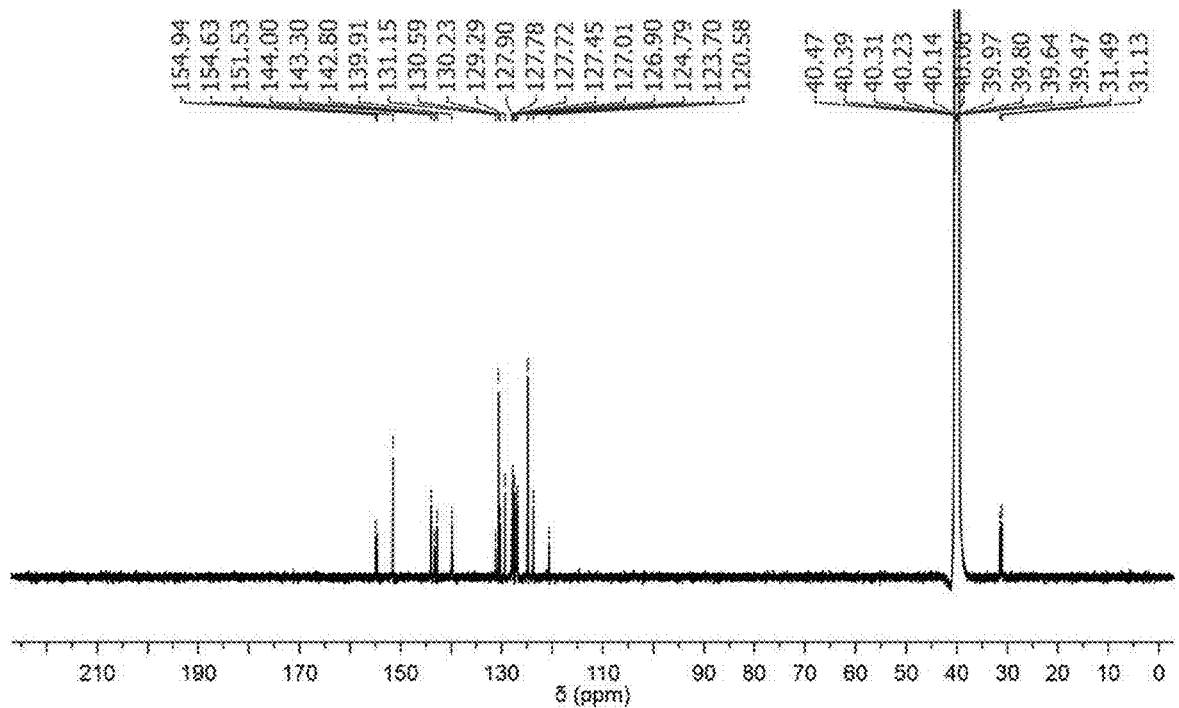

For all compound embodiments the synthesis was as follows: 1 (50 mg) and Het4/8/9/12/13 (1.1 eq.) were dissolved in methanol (2 mL) along with morpholine (40 eq.) and heated at reflux for 12 hours. Cold ether was added to induce precipitation and the suspension was transferred to a 50 mL conical tube. After centrifugation (3400 rpm, 5 min) a pellet was formed and the supernatant was decanted and discarded. The pellet was re-suspended in fresh cold ether and the centrifugation, decanting process was repeated two more times. The pellet was re-dissolved in the indicated eluent composition and filtered. A Shimadzu HPLC with a 280 nm and 370 nm detector was used to purify the final product with a Phenomenex Luna C18, 250 mm×22 mm, 5 μM preparative column. $^1$H and $^{13}$C NMR spectra for certain compound embodiments are provided by FIGS. 9A/9B-13A/13B.

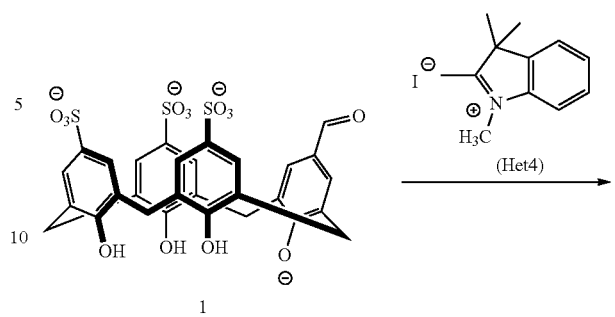

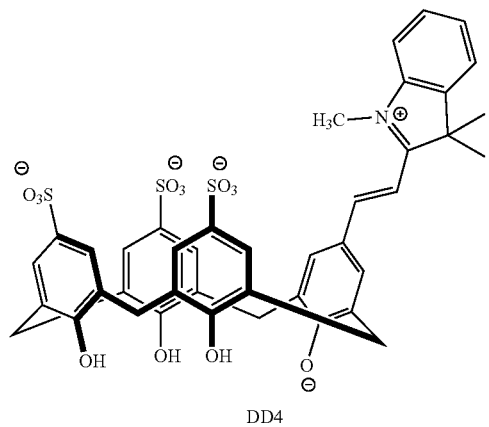

DD4.

Purified with a gradient of 85% $H_2O$ (+0.1% TFA)/15% $CH_3CN$ (+0.1% TFA) to 50% $H_2O$ (+0.1% TFA)/50% $CH_3CN$ (+0.1% TFA) over 20 minutes. The fractions were collected and lyophilized to yield a yellow/orange fluffy solid (27 mg, 44%). Mp: decomposed >260° C. FT-IR (cm$^{-1}$): 3229 (br), 1585 (m), 1535 (w), 1479 (m), 1447 (w), 1292 (w), 1163 (s), 1135 (s), 1036 (s), 786 (m), 749 (w), 626 (s), 543 (m). $^1$H NMR (500 MHz, $D_2O$): δ 7.79 (s, 1H), 7.78 (s, 1H), 7.63 (d, J=16.3 Hz, 1H), 7.55 (s, 2H), 7.48 (s, 2H), 7.32 (s, 2H), 6.55 (d, J=15.7 Hz, 1H), 6.35 (d, J=6.7 Hz, 1H), 5.90 (br, 1H), 4.57 (d, J=13.7 Hz, 2H), 4.27 (br, 1H), 4.10 (d, J=12.2 Hz, 2H), 3.88 (br, 1H), 3.63 (d, J=12.2 Hz, 2H), 3.54 (s, 3H), 3.43 (d, J=13.7 Hz, 2H), 1.36 (s, 6H). $^{13}$C NMR (76 MHz, DMSO): δ 180.7, 161.2, 153.9, 152.1, 151.4, 143.0, 141.9, 138.7, 138.5, 132.6, 129.7, 128.2, 127.9, 127.8, 127.2, 126.4, 126.2, 125.6, 122.6, 114.2, 108.4, 51.4, 33.7, 31.2, 30.6, 25.8. HR-MS (M$^+$ m/z): Calculated for $C_{41}H_{38}NO_{13}S_3{}^+$ 848.14998, Found 848.14938.

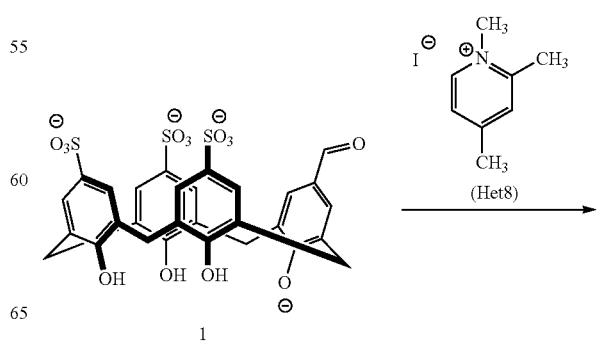

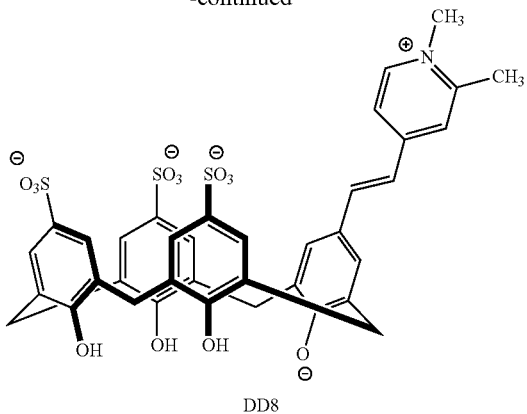

DD8.

Purified with a gradient of 90% H$_2$O (+0.1% TFA)/10% CH$_3$CN (+0.1% TFA) to 70% H$_2$O (+0.1% TFA)/30% CH$_3$CN (+0.1% TFA) over 23 minutes. The fractions were collected and lyophilized to yield a yellow fluffy solid (20 mg, 35%). Mp: decomposed >300° C. FT-IR (cm$^{-1}$): 3288 (br), 1621 (m), 1598 (m), 1451 (w), 1132 (s), 1111 (s), 891 (w), 786 (w), 732 (w), 623 (s), 583 (s). $^1$H NMR (500 MHz, D$_2$O): δ 7.69 (d, J=1.4 Hz, 2H), 7.63 (d, J=1.8 Hz, 2H), 7.36 (s, 2H), 7.14 (d, J=6.1 Hz, 1H), 7.09 (s, 2H), 6.96 (s, 1H), 6.67 (d, J=6.1 Hz, 1H), 6.67 (d, J=15.5 Hz, 1H), 6.27 (d, J=16.5 Hz, 1H), 4.34 (d, J=3.5 Hz, 2H), 4.32 (d, J=3.1 Hz, 2H), 3.53 (d, J=13.4 Hz, 2H), 3.48 (d, J=13.8 Hz, 2H), 0.79 (s, 3H), 0.54 (s, 3H). $^{13}$C NMR (126 MHz, DMSO): δ 153.9, 152.3, 151.7, 149.6, 140.0, 139.7, 128.8, 127.4, 127.3, 127.2, 126.4, 126.3, 30.4, 18.2. HR-MS (M$^+$ m/z): Calculated for C$_{37}$H$_{34}$NO$_{13}$S$_3$$^+$ 796.11868, Found 796.11754.

DD9.

Purified with a gradient of 85% H$_2$O (+0.1% TFA)/15% CH$_3$CN (+0.1% TFA) to 50% H$_2$O (+0.1% TFA)/50% CH$_3$CN (+0.1% TFA) over 18 minutes. The fractions were collected and lyophilized to yield an orange fluffy solid (30 mg, 50%). Mp: decomposed >300° C. FT-IR (cm$^{-1}$): 3287 (br), 1593 (m), 1567 (m), 1535 (w), 1476 (w), 1449 (w), 1134 (s), 1109 (s), 1035 (s), 626 (s), 544 (s). $^1$H NMR (500 MHz, D$_2$O): δ 7.81 (d, J=2.3 Hz, 2H), 7.76 (d, J=1.9 Hz, 2H), 7.67 (d, J=8.6 Hz, 1H), 7.33 (s, 2H), 7.30 (d, J=6.5 Hz, 1H), 7.17 (d, J=6.5 Hz, 1H), 6.97 (s, 2H), 6.68 (br, 1H), 6.64 (d, J=15.6 Hz, 1H), 6.47 (d, J=16.2 Hz, 1H), 6.41 (br, 1H), 5.79 (d, J=9.1 Hz, 1H), 4.45 (d, J=13.6 Hz, 2H), 4.31 (d, J=13.7 Hz, 2H), 3.60 (d, J=13.1 Hz, 2H), 3.53 (d, J=13.1 Hz, 2H), 2.05 (s, 3H). $^{13}$C NMR (126 MHz, DMSO) δ: 153.0, 152.2, 150.5, 140.4, 138.2, 128.8, 128.1, 127.9, 127.7, 127.4, 126.9, 126.7, 125.6, 116.1, 43.6, 31.2, 30.9. HR-MS (M$^+$ m/z): Calculated for C$_{40}$H$_{34}$NO$_{13}$S$_3$$^+$ 832.11868, Found 832.11788.

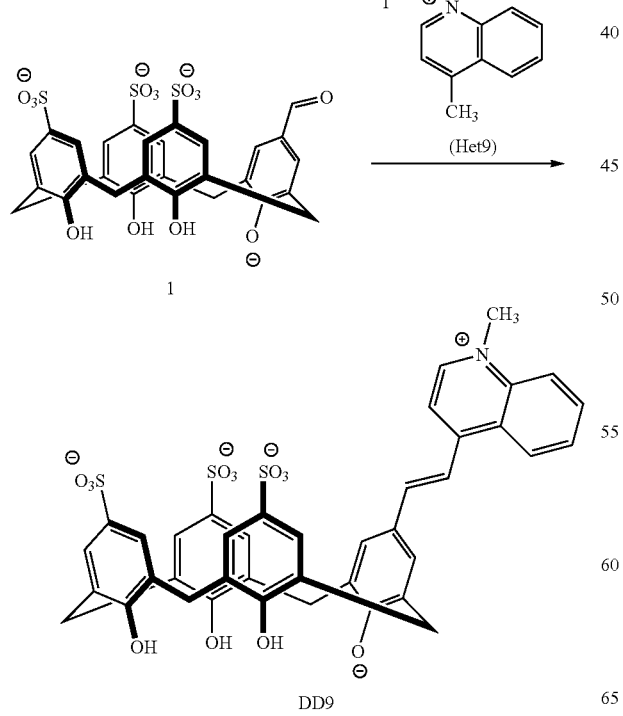

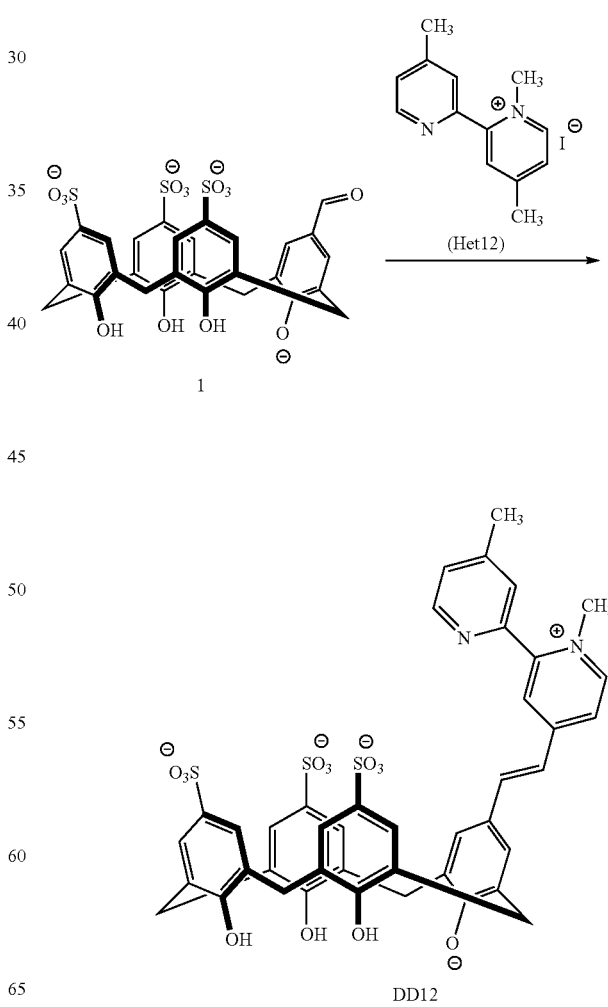

DD12.

Purified with a gradient of 85% H$_2$O (+0.01% TFA)/15% CH$_3$CN (+0.01% TFA) to 50% H$_2$O (+0.01% TFA)/50% CH$_3$CN (+0.01% TFA) over 23 minutes. The fractions were collected and lyophilized to yield an orange fluffy solid (35 mg, 55%). Mp: decomposed >300° C. FT-IR (cm$^{-1}$): 3240 (br), 1615 (m), 1591 (m), 1453 (w), 1156 (s), 1111 (s), 1037 (s), 886 (w), 785 (w), 657 (m), 624 (s), 547 (s).). $^1$H NMR (500 MHz, D$_2$O): δ 7.67 (d, J=5.1 Hz, 1H), 7.69 (d, J=2.1 Hz, 2H), 7.58 (br, 1H), 7.55 (d, J=2.1 Hz, 2H), 7.42 (d, J=6.1 Hz, 1H), 7.38 (s, 2H), 7.30 (s, 2H), 7.24 (s, 2H), 7.05 (d, J=16.1 Hz, 1H), 6.80 (d, J=16.1 Hz, 1H), 6.42 (s, 1H), 5.94 (br, 1H), 4.36 (d, J=14.4 Hz, 2H), 4.33 (d, J=14.4 Hz, 2H), 3.55 (d, J=12.4 Hz, 2H), 3.52 (d, J=12.8 Hz, 2H), 3.12 (s, 3H), 0.45 (s, 3H). $^{13}$C NMR (126 MHz, DMSO): δ 154.1, 151.5, 146.9, 142.1, 140.0, 123.0, 129.1, 127.9, 127.7, 127.5, 127.0, 126.9, 125.2, 120.6, 46.1, 31.4, 31.1, 21.1. HR-MS (M$^+$ m/z): Calculated for C$_{42}$H$_{37}$N$_2$O$_{13}$S$_3^+$ 873.14523, Found 873.14435.

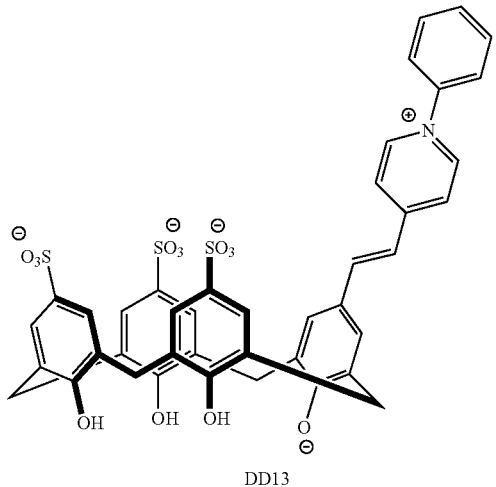

DD13

DD13.

Purified with a gradient of 85% H$_2$O (+0.1% TFA)/15% CH$_3$CN (+0.1% TFA) to 50% H$_2$O (+0.1% TFA)/50% CH$_3$CN (+0.1% TFA) over 20 minutes. The fractions were collected and lyophilized to yield an orange fluffy solid (14 mg, 23%). Mp decomposed >280° C. FT-IR (cm$^{-1}$): 3229 (br), 1618 (m), 1587 (m), 1489 (w), 1451 (w), 1200 (s), 1133 (s), 1110 (s), 1036 (s), 878 (w), 760 (w), 624 (s), 549 (s). $^1$H NMR (500 MHz, D$_2$O): δ 8.28 (d, J=6.8 Hz, 2H), 7.72 (d, J=7.0 Hz, 2H), 7.58 (s, 2H), 7.46 (d, J=2.1 Hz, 2H), 7.40 (d, J=2.1 Hz, 2H), 7.30 (d, J=15.8 Hz, 1H), 7.26 (s, 2H), 6.72 (d, J=16.1 Hz, 1H), 6.18 (d, J=6.92 Hz, 2H), 5.10 (br, 2H), 4.45 (d, J=12.7 Hz, 2H), 4.27 (d, J=12.7 Hz, 2H), 4.13 (br, 1H), 3.59 (d, J=13.3 Hz, 2H), 3.45 (d, J=12.7 Hz, 2H). $^{13}$C NMR (126 MHz, DMSO): δ 155.0, 154.6, 151.5, 144.0, 143.3, 142.8, 139.9, 131.2, 130.6, 130.2, 129.3, 127.9, 127.8, 127.7, 127.5, 127.0, 126.9, 124.8, 123.7, 120.6, 31.5, 31.1. HR-MS (M$^+$ m/z): Calculated for C$_{41}$H$_{34}$NO$_{13}$S$_3^+$ 844.11868, Found 844.11786.

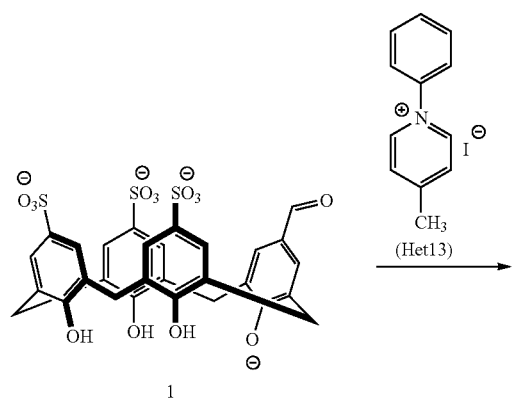

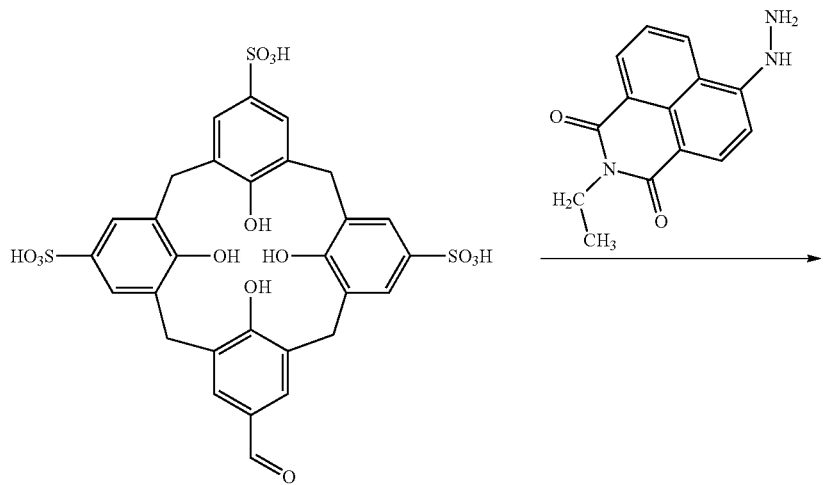

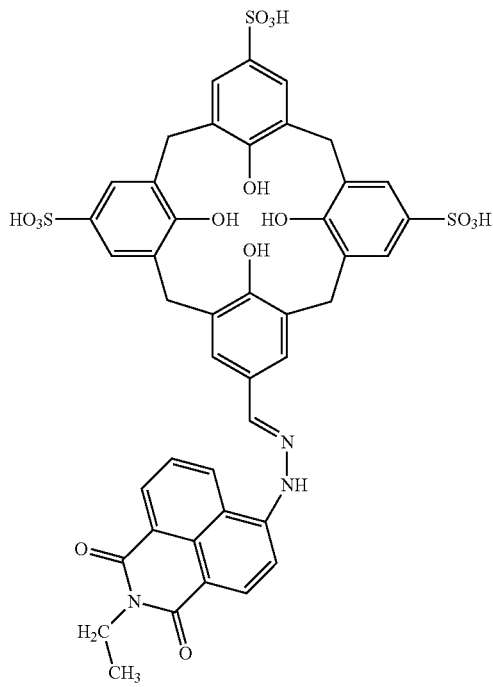

5-(N-ethyl-1,8-naphthalimide-4-hydrazono)-25,26,27,28-tetrahydroxy-11,17,23-trisulfonatoccalix[4]arene (NIM-Cx)

Aldehyde-trisulfonate calixarene (50 mg, 0.072 mmol) was dissolved in 4 mL MeOH, followed by addition of NIM-hydrazine (20.2 mg, 1.1 eq). Reaction was heated to 50° C. and left overnight. Reaction mixture was reduced by rotary evaporator and purified by semi-preparative HPLC (UV detection at 280 nm and 360 nm) with gradient of 90% $H_2O$ (+0.1% TFA)/10% $CH_3CN$ (+0.1% TFA) to 60% $H_2O$ (+0.1% TFA)/140% $CH_3CN$ (+0.1% TFA) over 20 minutes. Bright orange fractions were collected and lyophilized to yield fluffy dark orange solid. (16.8 mg, 26%). H NMR (300 MHz, $D_2O$): δ 9.37 (s, 1H), 7.70 (s), 7.67 (m), 7.56 (s), 7.49 (s), 3.85 (d, broad).

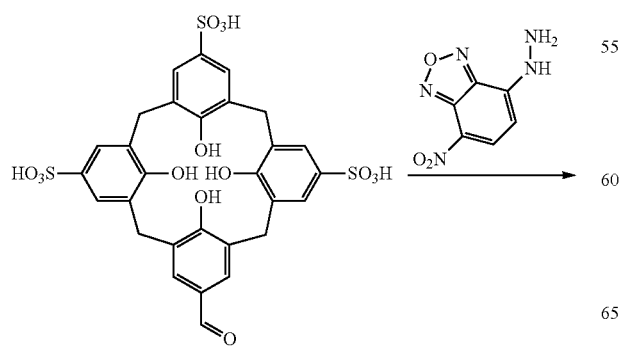

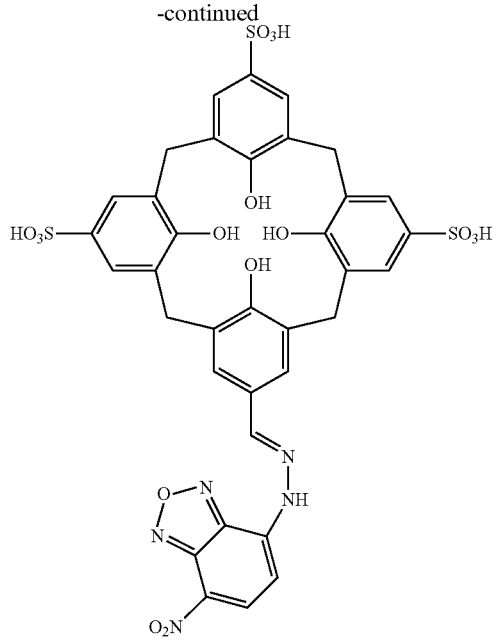

5-(7-nitrobenzo-2,1,3-oxadiazol-4-hydrazono)-25,26,27,28-tetrahydroxy-11,17,23-trisulfonatoccalix[4]arene (NBD-Cx)

Figure 57:
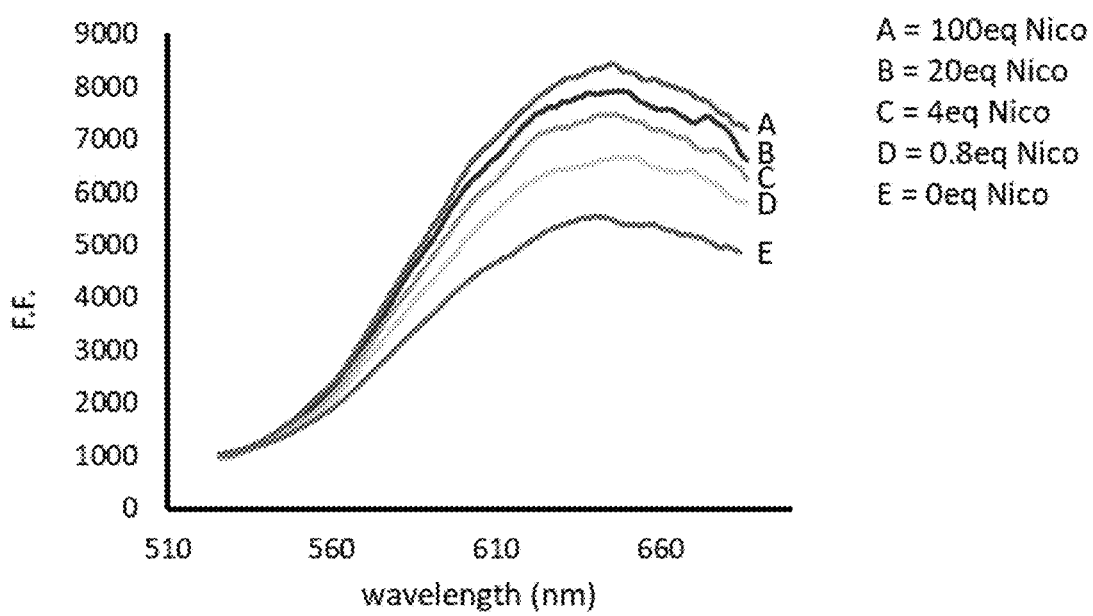
FIG. 57 is a graph showing fluorescence emission changes for 5-(7-nitrobenzo-2,1,3-oxadiazol-4-hydrazono)-25,26,27,28-tetrahydroxy-11,17,23-trisulfonatoccalix[4]arene ("NBD-Cx") upon addition of nicotine in pH 7.4 buffer, $\lambda_{ex}$=482 nm.
Figure 58A:
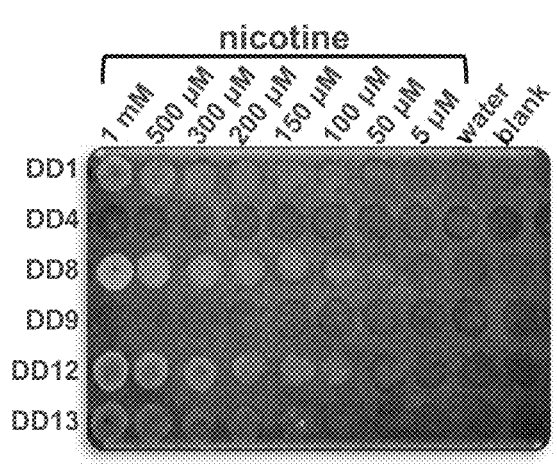
FIGS. 58A-58C are photographic images of representative fluorescent sensor devices and/or arrays after irradiation by a hand-held UV lamp ($\lambda_{ex}$ 364±20 nm) and which show that sensor devices comprising multiple dimer complex embodiments can be used to detect the presence of different drugs at difference concentrations, including nicotine (FIG. 58A); cocaine (FIG. 58B), benzoylecgonine (FIG. 58C); as well as arrays comprising such dimer complex embodiments (FIG. 58D).
Figure 58B:
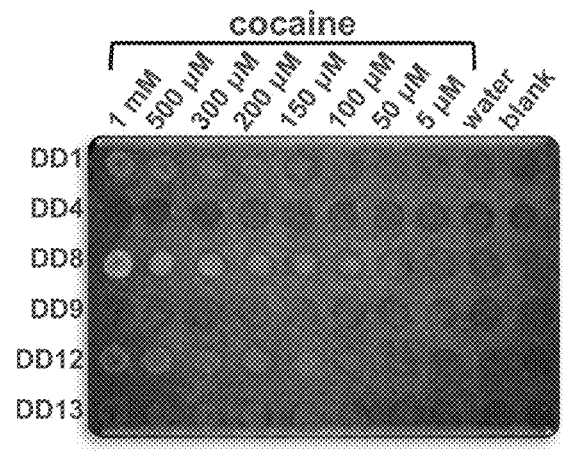
Figure 58C:
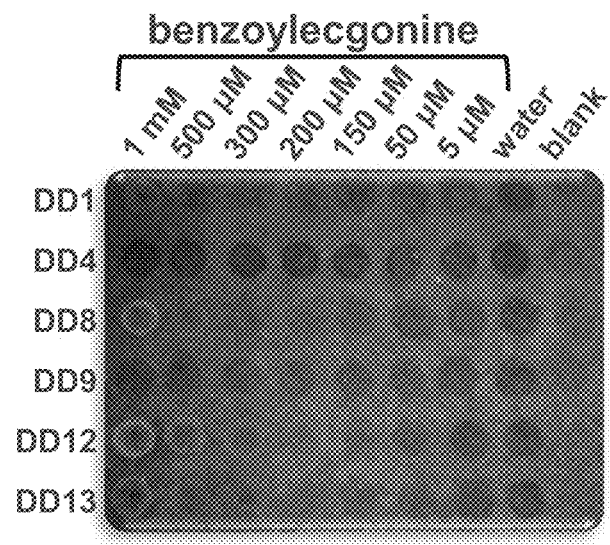
Figure 58D:
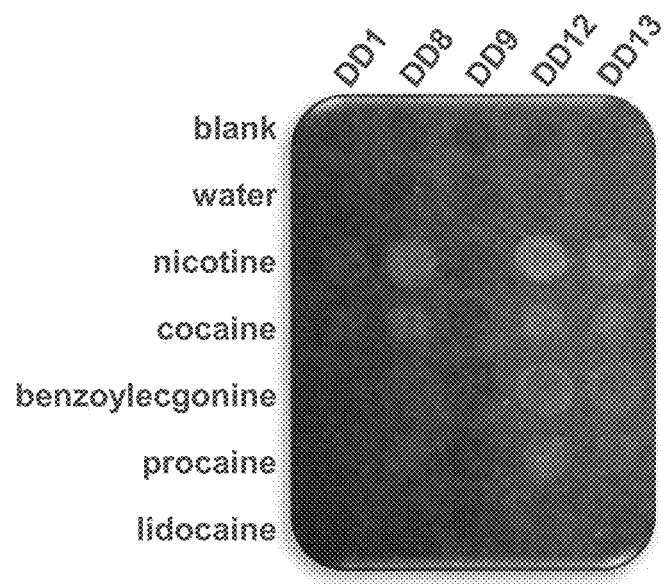

Aldehyde-trisulfonate calixarene (50 mg, 0.072 mmol) was dissolved in 4 mL MeOH, followed by addition of NBD-hydrazine (15.5 mg, 1.1 eq). Reaction was heated to 50° C. and left overnight. Reaction mixture was reduced by rotary evaporator and purified by semi-preparative HPLC (UV detection at 280 nm and 360 nm) with gradient of 90% H$_2$O (+0.1% TFA)/10% CH$_3$CN (+0.1% TFA) to 60% H$_2$O (+0.1% TFA)/140% CH$_3$CN (+0.1% TFA) over 20 minutes. Bright pink fractions were collected and lyophilized to yield fluffy deep purple solid. (23 mg, 37%). H NMR (300 MHz, D$_2$O): δ 9.37 (s, 1H), 7.70 (s), 7.67 (m), 7.56 (s), 7.49 (s), 3.85 (d, broad). (MS, m/z): Calculated for C$_{35}$H$_{23}$N$_5$O$_{16}$S$_3^-$ 865.8, found 866.1. Performance results for this compound embodiment are shown by FIG. 57.

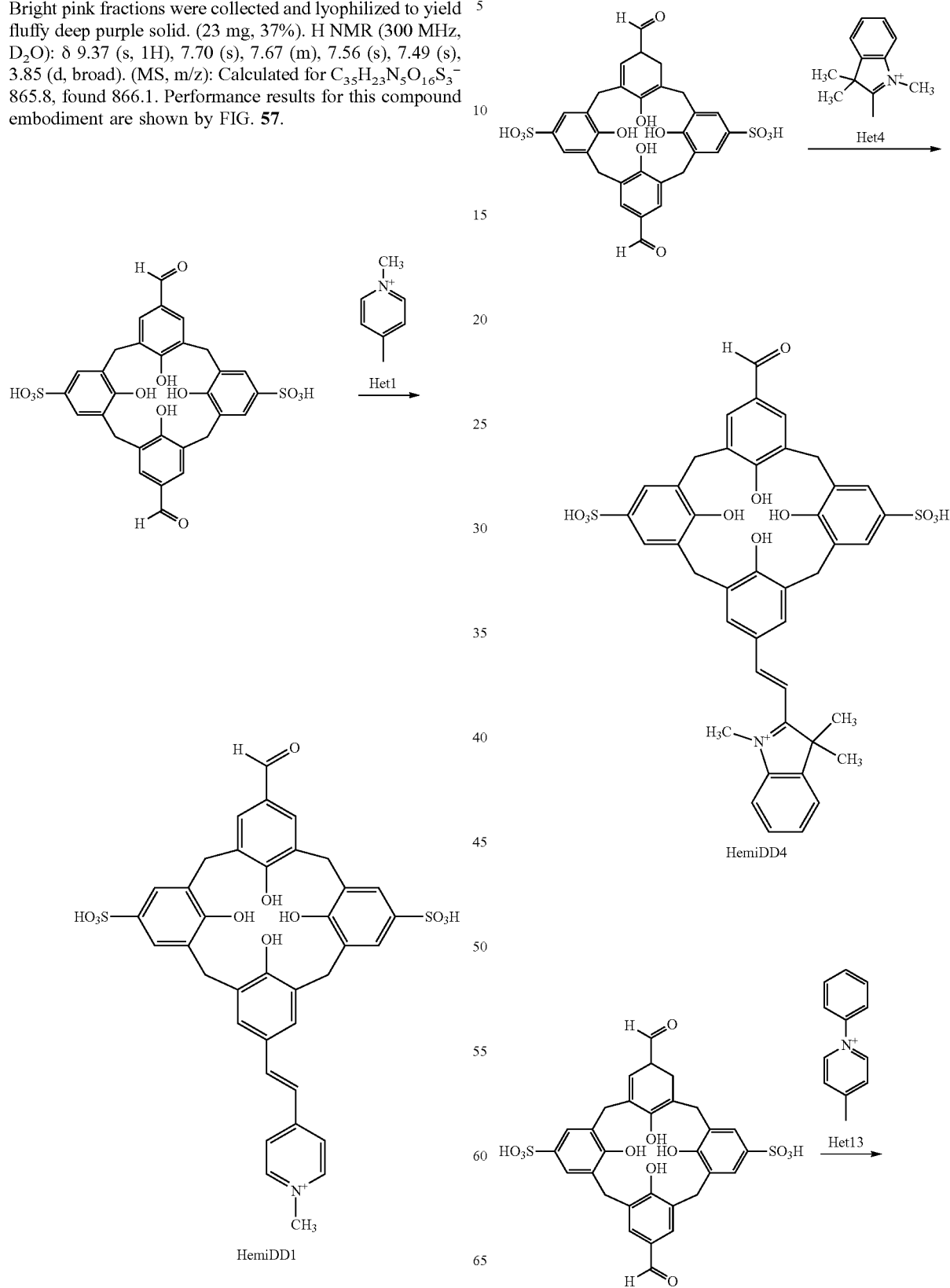

-continued

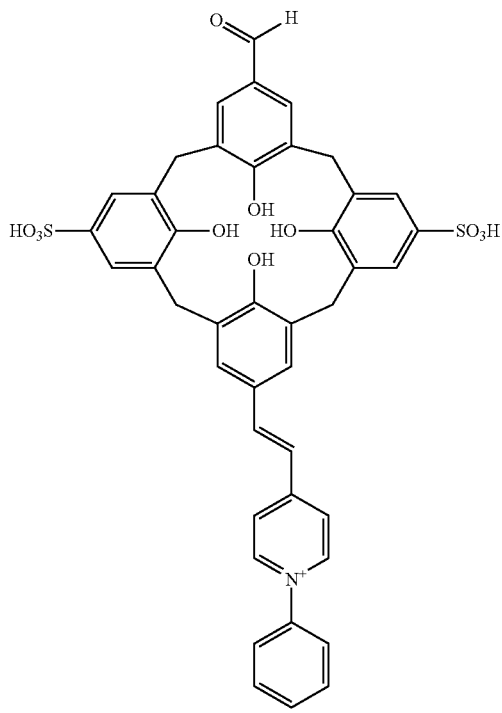

HemiDD13

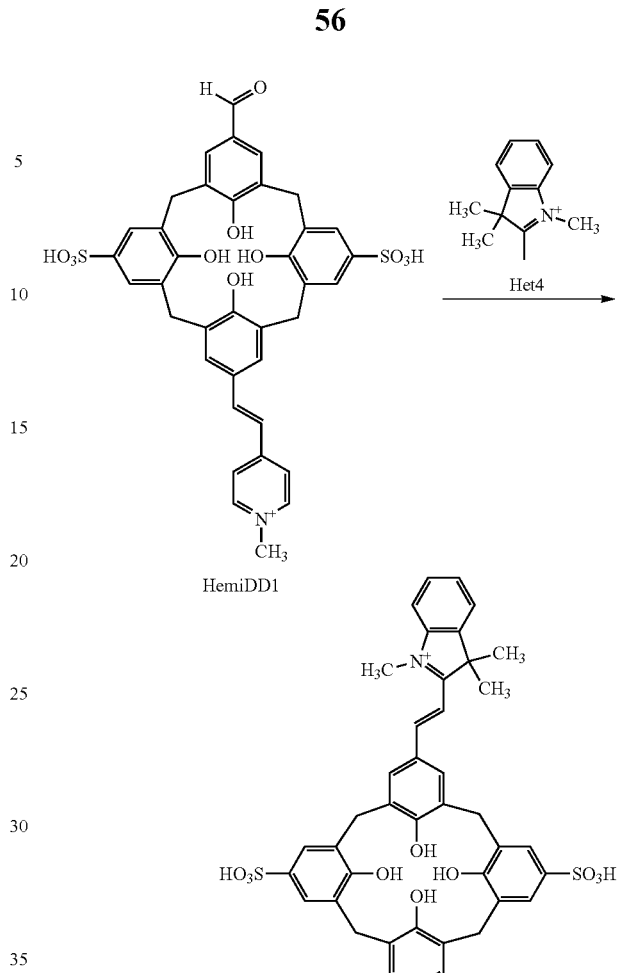

HemiDD1

DiDD1+4

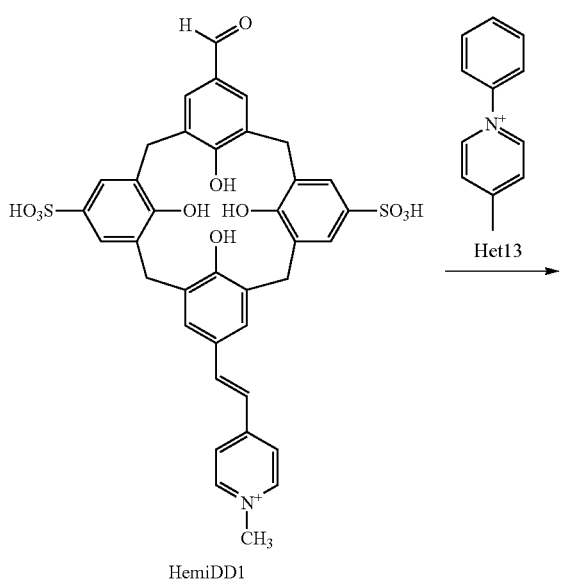

HemiDD1

HemiDD1/4/13.

5,17-formyl-25,26,27,28-tetrahydroxy-11,23-disulfonatocalix[4]arene and morpholine (8 eq) were dissolved in minimal MeOH. Het1/Het4/Het13 (1 eq) was dissolved in MeOH and added dropwise to the reaction. The mixture was gradually heated and left overnight forming a precipitate. Cold ether was added to further induce precipitation. The reaction mixture was transferred to a conical tube, centrifuged (3400 rpm, 10 min) and the supernatant was discarded. The pellet was resuspended in cold ether, centrifuged and the supernatant was discarded two more times. The pellet was left to air dry overnight and purified by HPLC.

HemiDD1 $^1$H NMR (300 MHz, 50 mM $H_2PO_4/HPO_4$ in $D_2O$): δ 9.46 (s, 1H), 7.79 (s, 2H), 7.77 (d, J=2.2 Hz, 2H), 7.72 (d, J=2.2 Hz, 2H), 7.40 (d, J=6.5 Hz, 2H), 7.20 (s, 2H), 6.94 (d, J=16.3 Hz, 1H), 6.54 (d, J=16.3 Hz, 1H), 6.45 (d, J=6.5 Hz, 2H), 4.41 (m, 4H), 3.70 (d, J=13.3 Hz, 2H), 3.56 (d, J=13.1 Hz, 2H), 0.54 (s, 3H)

HemiDD4 $^1$H NMR (300 MHz, 50 mM $H_2PO_4/HPO_4$ in $D_2O$): δ 8.92 (s, 1H), 7.82 (d, J=2.3, 2H), 7.69 (d, J=2.3, 2H), 7.46 (s, 2H), 7.45 (d, J=15.8 Hz, 1H), 7.35 (s, 2H), 6.50 (d, J=16.0 Hz, 1H), 6.10 (m, 2H), 4.57 (d, J=13.7 Hz, 2H), 4.28 (d, J=13.4 Hz, 2H), 4.05 (br, 2H), 3.66 (d, J=13.4 Hz, 2H), 3.55 (d, J=13.7 Hz, 2H), 3.50 (s, 3H), 1.11 (s, 6H).

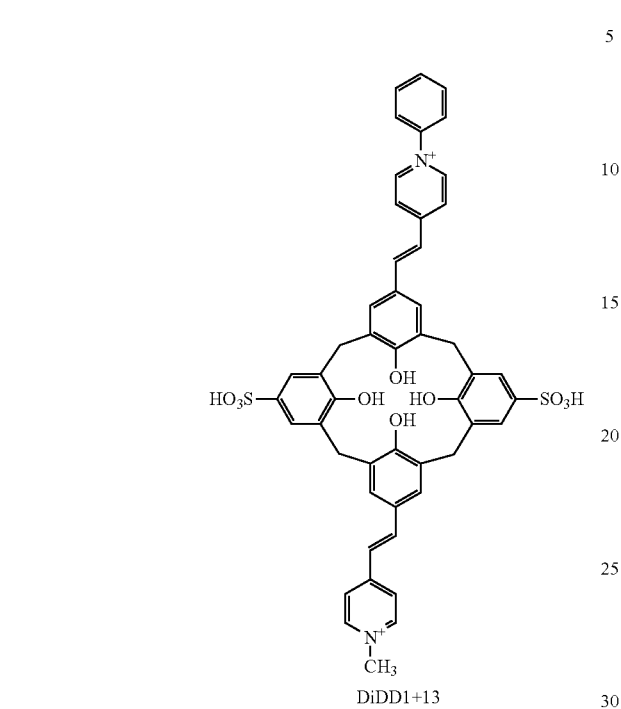

DiDD1+13

DiDD.

HemiDD1/4/13 (1eq), Het1/Het4/Het13 (1 eq) and morpholine (8 eq) were dissolved in MeOH. The reaction was heated and stirred overnight forming a precipitate. Cold ether was added to further induce precipitation. The reaction mixture was transferred to a conical tube, centrifuged (3400 rpm, 10 min) and the supernatant was discarded. The pellet was resuspended in cold ether, centrifuged and the supernatant was discarded two more times. The pellet was left to air dry overnight and purified by HPLC.

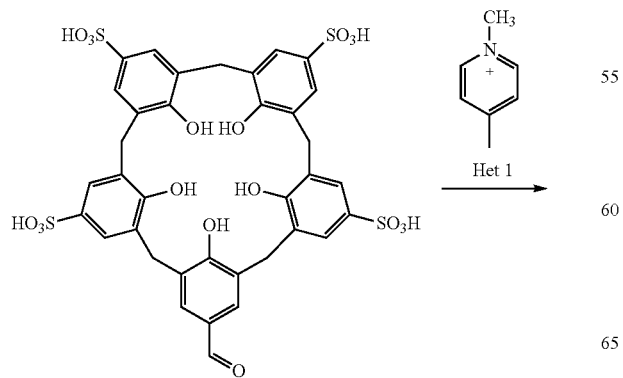

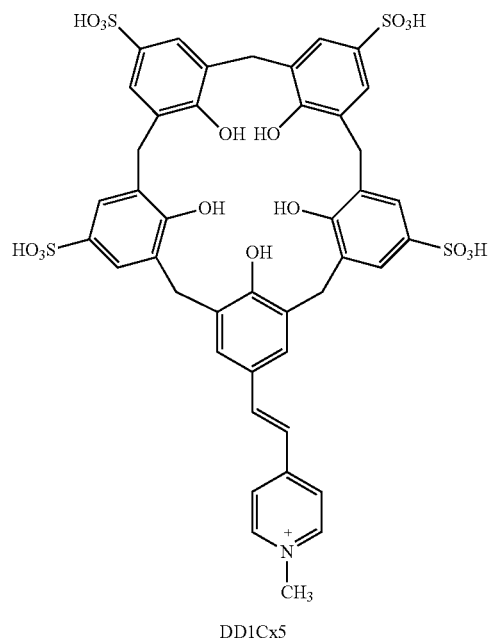

DD1Cx5

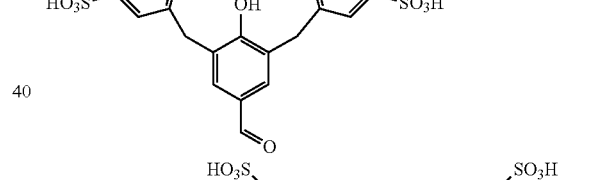

DD4Cx5

-continued

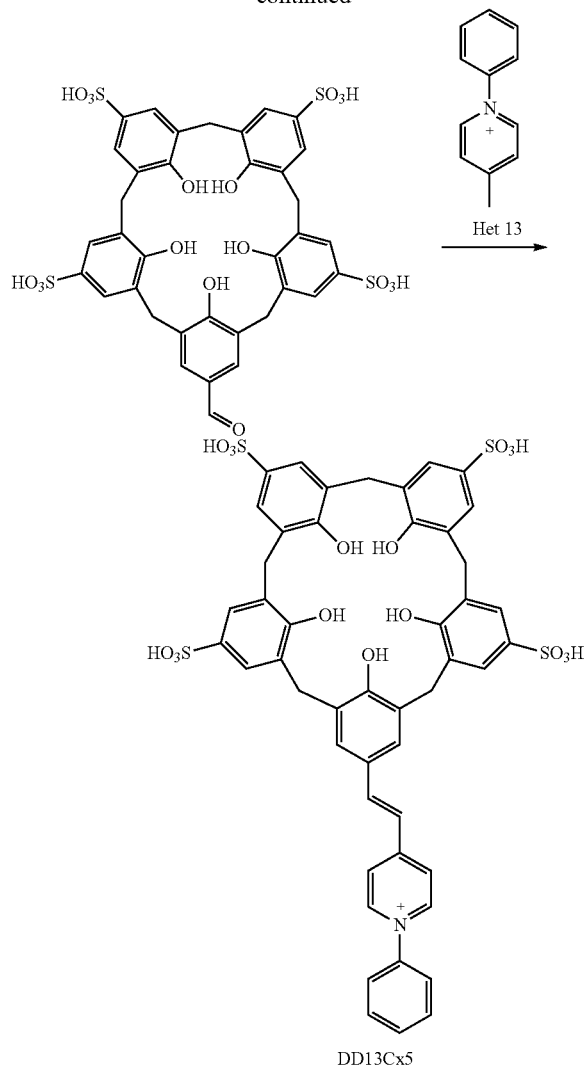

DD13Cx5

DD1/4/13Cx5.

Aldehyde-tetrasulfonate calix[5]arene (50 mg), morpholine (8 eq) and Het1/Het4/Het13 (1.1 eq) were dissolved in minimal MeOH (2 mL) and heated at reflux overnight. The reaction mix was cooled and transferred to a conical tube. Minimal ethyl acetate and sonication was used to remove residue from the reaction flask and added to the conical tube. Cold ether was added to precipitate the product, then centrifuged (3400 rpm, 10 min) and the supernatant was discarded. The pellet was resuspended in cold ether, centrifuged and the supernatant was discarded two more times. The pellet was left to air dry overnight and purified by HPLC.

Procedure for Parallel Synthesis of DDs:

An aluminum heating block (CombiBlocks, ChemGlass) held 4 dram vials which each contained a 1:1 mixture of 1 and one heterocyclic nucleophile (1.5 mM), along with morpholine (40 eq., 5 µL) in methanol (1 mL). The mixtures were capped, heated and stirred for 6 hours at 50° C. to afford colored solutions (use a blast shield in case of overpressure). The solutions were sonicated to re-dissolve dried compound embodiments along the walls. The solutions were aliquoted (10 µL) into NUNC black-walled, clear-bottomed 96-well plates and dried in a 37° C. oven for 4 hours. The dried pellets were re-suspended in phosphate buffer (10 mM, pH 7.4), centrifuged and mixed. Each solution was diluted by transferring aliquots into a separate 96-well plate containing the same phosphate buffer. Fluorescence endpoint measurements were taken for each compound embodiment, the $\lambda_{ex.}$ and $\lambda_{em.}$ that were used are listed below. A stock of nicotine prepared in phosphate buffer was added to each well (10 µL for final concentration of 10 µM) and fluorescence endpoint measurements were collected again. The fluorescence differences between after and before nicotine were used to evaluate each compound embodiment. In some embodiments, merocyanines based on N-methylpyridinium (DD1 and DD8), indolinium (DD4), bipyridinium (DD12) and N-phenylpyridinium (DD13) worked well and exhibited tunable excitation and emission wavelengths ($\lambda_{exc}$ 380-475 nm, $\lambda_{em}$ 570-640 nm), with Stokes shifts observed between 95 nm and 215 nm. Additional data for compound embodiment DD1 is provided by FIGS. 14A and 14B. The variable structures in this small compound embodiment library also translated into different binding properties for different drugs. In some embodiments, other compound embodiments were not as responsive, such as the quinolinium dyes, DD9-DD11, due to an unpredicted photophysical deficiency rather than poor recognition. This highlights the strength of the parallel synthesis and crude screening process, as it allows a user to identify potential compound embodiments that may not be as effective as others. Even while some compound embodiments were less effective than others, this does not preclude using such compounds in methods and array embodiments disclosed herein.

Interestingly, inactive sensor DD9 also shows signs of dimerization with the N—CH₃ and ortho-proton shifted 2.50 ppm and 2.61 ppm, respectively. 1D DOSY NMR on DD4 confirmed that it had the hydrodynamic radius expected of a dimeric assembly (Table 3, Table 5, and Table 7) and is larger than the non-dimerizing aldehyde precursor, 1.

TABLE 3

1D DOSY obtained diffusion coefficients and hydrodynamic radii of 1, DD4 alone and DD4 complexed to nicotine

| | Diffusion Coefficient, m²/s | $r_H$, Å |
|---|---|---|
| 1 | 3.31 × 10⁻¹⁰ | 7.63 |
| DD4 | 1.97 × 10⁻¹⁰ | 12.47 |
| DD4 + 20 eq. nicotine | 2.52 × 10⁻¹⁰ | 9.74 |

Figure 30:
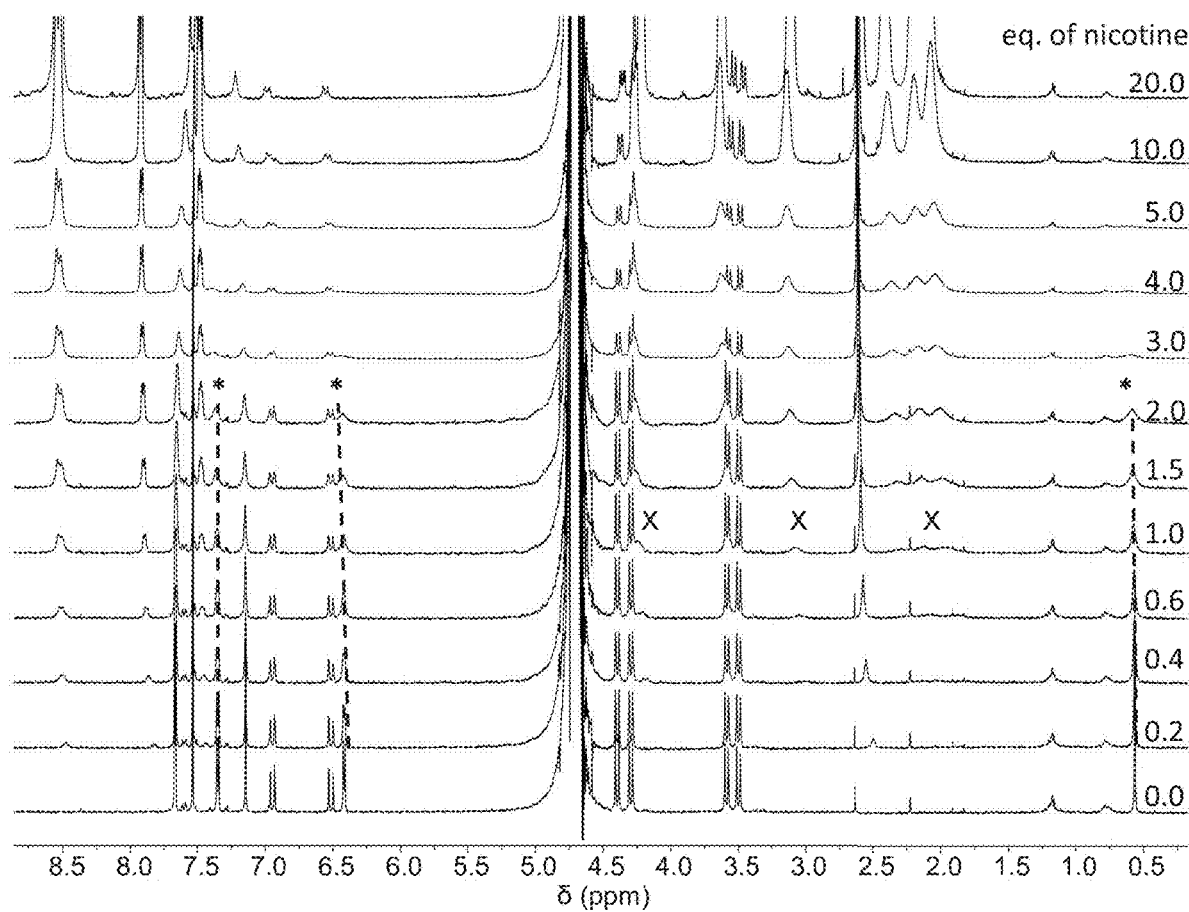
FIG. 30 shows proton NMR spectra obtained after performing nicotine titrations (10 mM stock solution) with a dimer complex comprising compound embodiment DD1 (500 µM), which show broadening of resonances most effected by dimer dissociation and complexation of DD with nicotine.
Figure 31:
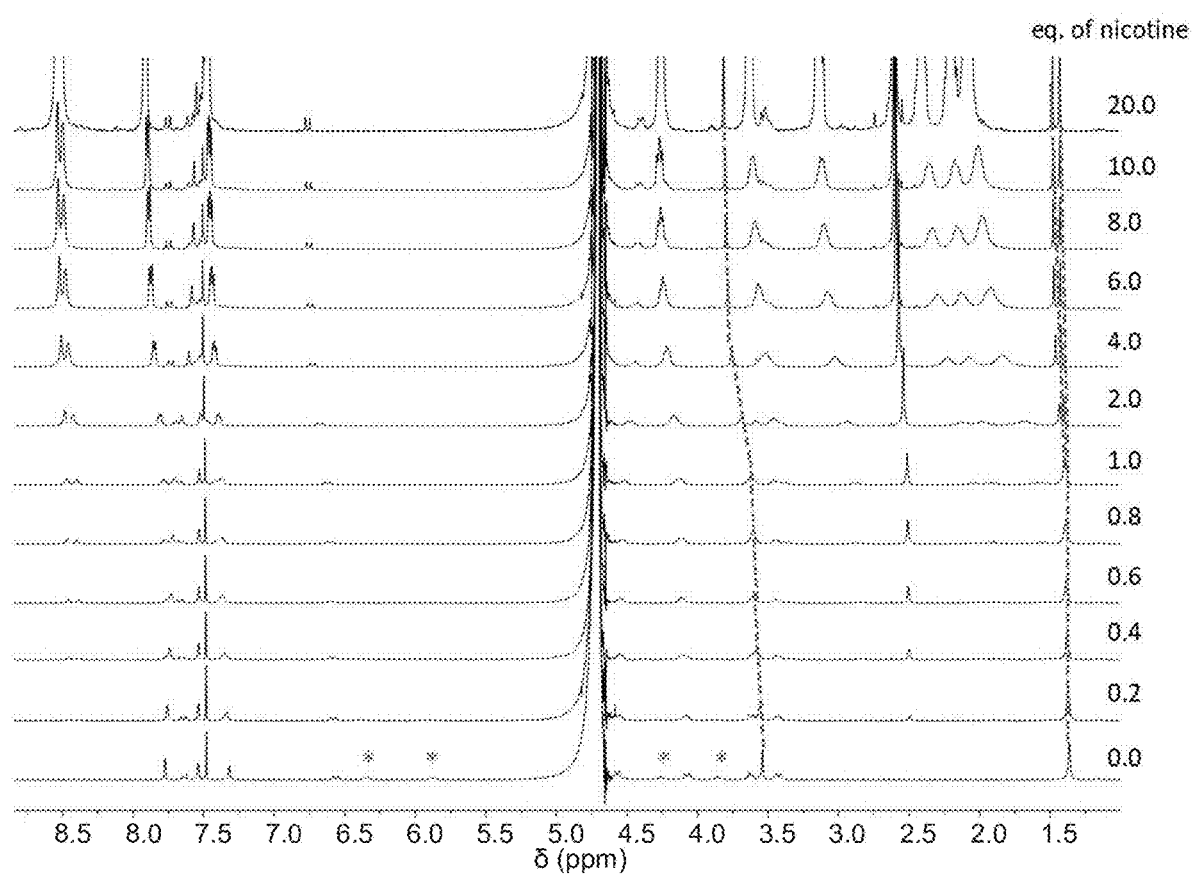
FIG. 31 shows proton NMR spectra obtained after performing nicotine titrations (10 mM stock solution) with a dimer complex comprising compound embodiment DD4 (500 µM), which show immediate broadening of particular resonances in DD4.
Figure 32:
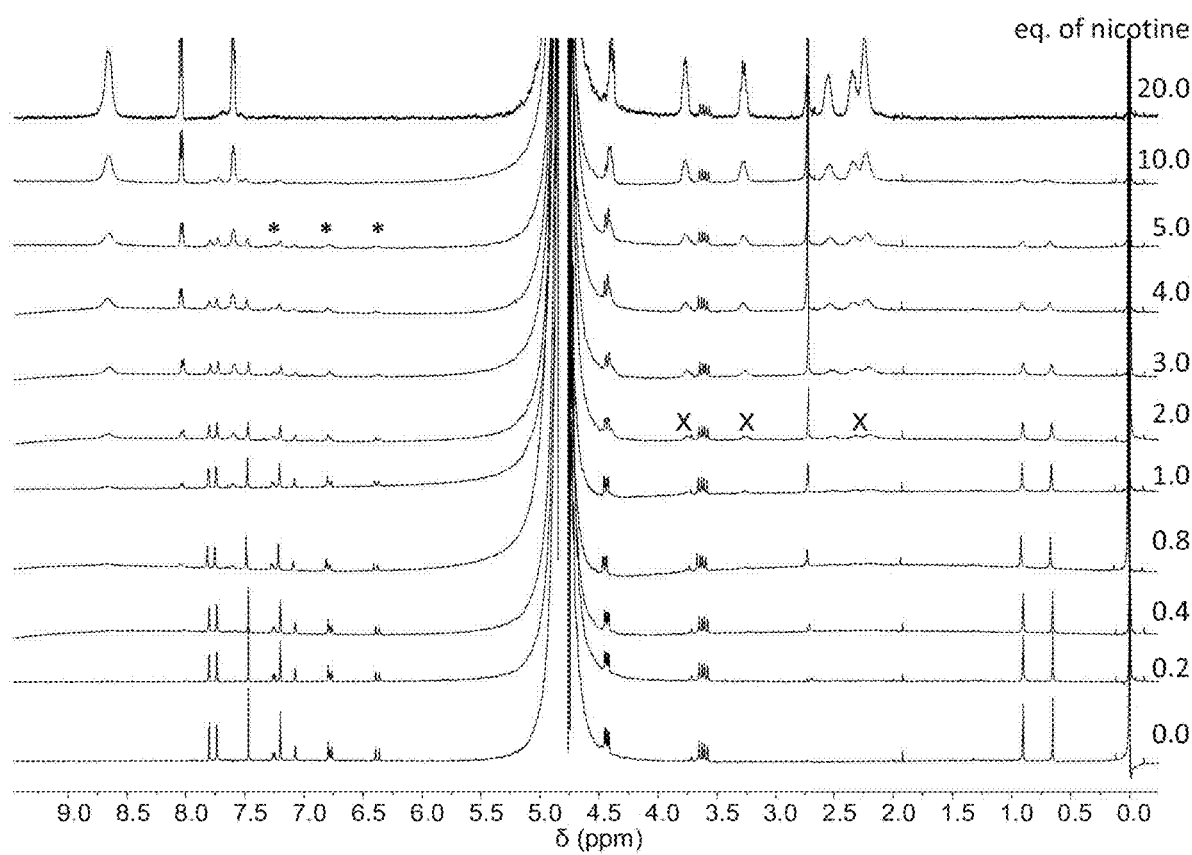
FIG. 32 shows proton NMR spectra obtained after performing nicotine titrations (4 mM stock solution) with a dimer complex comprising compound embodiment DD8 (200 µM), which show significant broadening of nicotine resonances.
Figure 33:
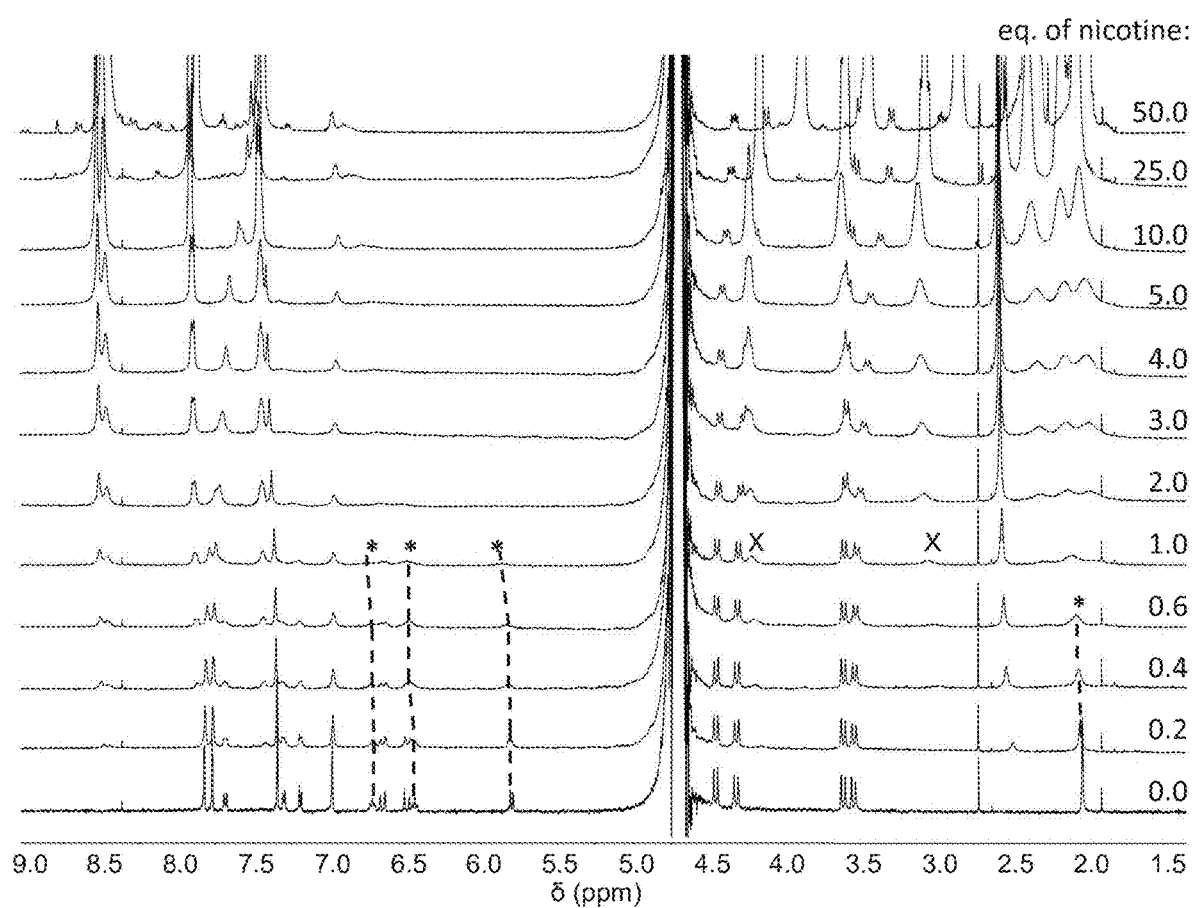
FIG. 33 shows proton NMR spectra obtained after performing nicotine titrations (25 mM stock solution) with a dimer complex comprising compound embodiment DD9 (500 µM), which show broadening of DD and nicotine resonances.
Figure 34:
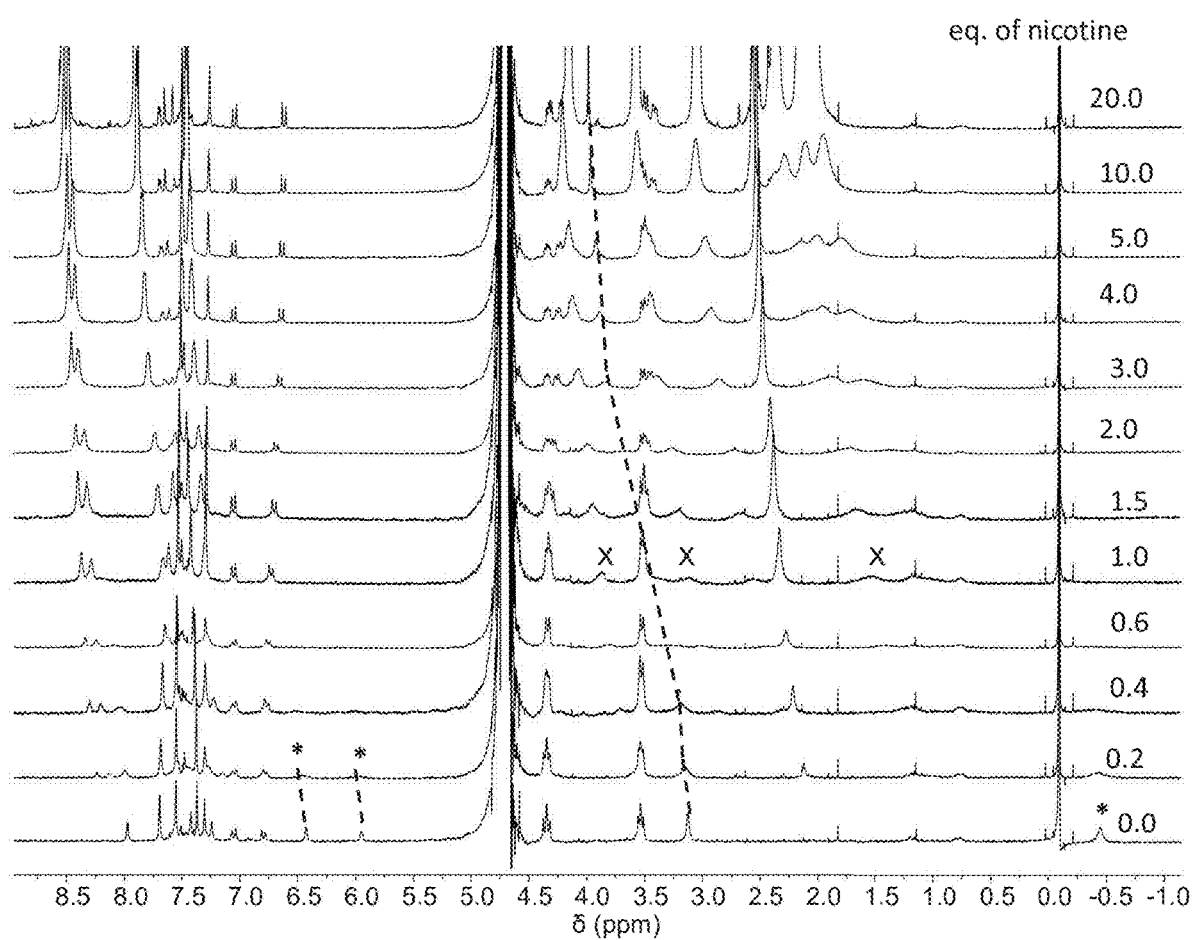
FIG. 34 shows proton NMR spectra obtained after performing nicotine titrations (10 mM stock solution) with a dimer complex comprising compound embodiment DD12 (500 µM), which show immediate broadening of key nicotine and DD12 resonances in DD12.
Figure 35:
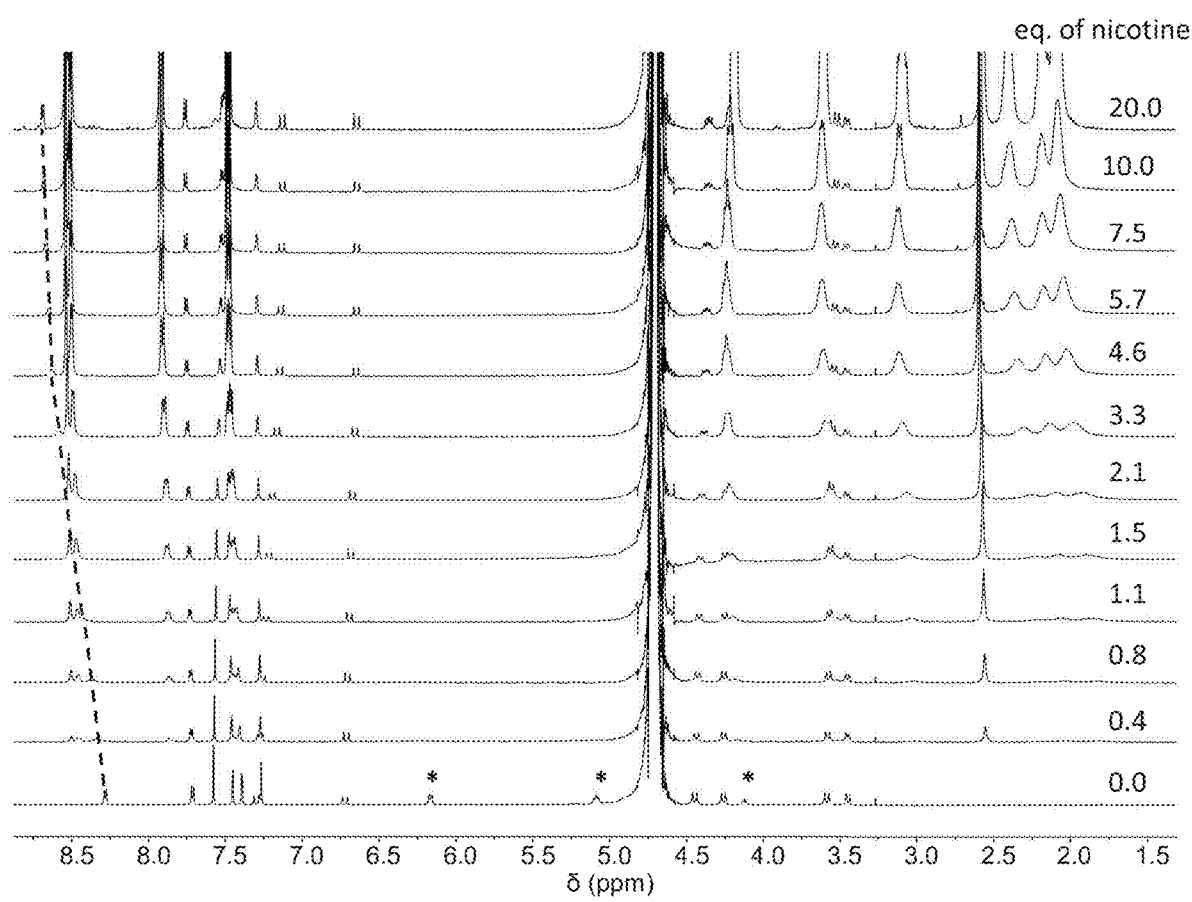
FIG. 35 shows proton NMR spectra obtained after performing nicotine titrations (10 mM stock solution) with a dimer complex comprising compound embodiment DD13 (500 µM) show immediate broadening of DD13 resonances.

The fluorescence responses arise from the disassembly of each compound embodiment and sequential complexation with nicotine. ¹H NMR titrations of nicotine into each compound embodiment show resonances broadening partially or completely, indicating dimer disassembly and nicotine complexation at an intermediate timescale relative to NMR. For example, see FIG. 4A and FIGS. 30-35. With reference to FIG. 30, the resonances of N—CH₃, ortho and meta pyridinium resonances on DD1, highlighted by stars, begin to broaden upon the addition of nicotine. While pyrrolidine protons of nicotine, highlighted with a cross, barely become visible at 1.0 eq and remain broad throughout the titration. Although resonances of a distinct DD1$_{monomer}$-nicotine complex are not present the broadening is evidence of two equilibria (dimer dissociation and nicotine complexation) occurring together in an intermediate timescale relative to the NMR experiment. With reference to FIG. 31, the encapsulated aromatic indolinium protons on DD4, highlighted by stars, broaden immediately upon the addition of nicotine. The methyl groups: N—CH$_3$ and the 3-dimethyl protons, can be followed with dashed lines and are in fast exchange relative to the NMR timescale. The two equivalent dimethyl groups, found as a 6H singlet at 0.0 eq, split into two chemically inequivalent singlets upon the addition of nicotine. In FIG. 32, the DD8 resonances did not shift but only broadened completely into the baseline, indicated with stars. Nicotine resonances began to appear at 2.0 eq. and remained broad throughout the titration. In FIG. 33, the DD9 quinolinium and N—CH$_3$ resonances broadened and shifted downfield slightly (indicated with stars and dashed lines) and eventually flattened into the baseline after 1.0 eq of nicotine was added. Nicotine pyrrolidine resonances appeared at 1.0 eq (marked with a cross) and remained broad throughout the titration. And, in FIG. 34, the encapsulated aromatic pyridinium protons and 4'-CH$_3$ on DD12, highlighted by stars, broaden immediately upon the addition of nicotine. However, the less shielded N—CH$_3$, can be followed with dashed lines and is in fast exchange relative to the NMR timescale, shifting by 0.86 ppm. The nicotine pyrrolidine resonances appear as broad signals near 1.0 eq. and remain broad throughout the titration. In FIG. 35 the encapsulated N-phenyl protons on DD13, highlighted by stars, broaden immediately upon the addition of nicotine. However, the less shielded ortho-pyridinium resonances, can be followed with dashed lines in slow exchange relative to the NMR timescale, shifting by 0.42 ppm.

Figure 4A:
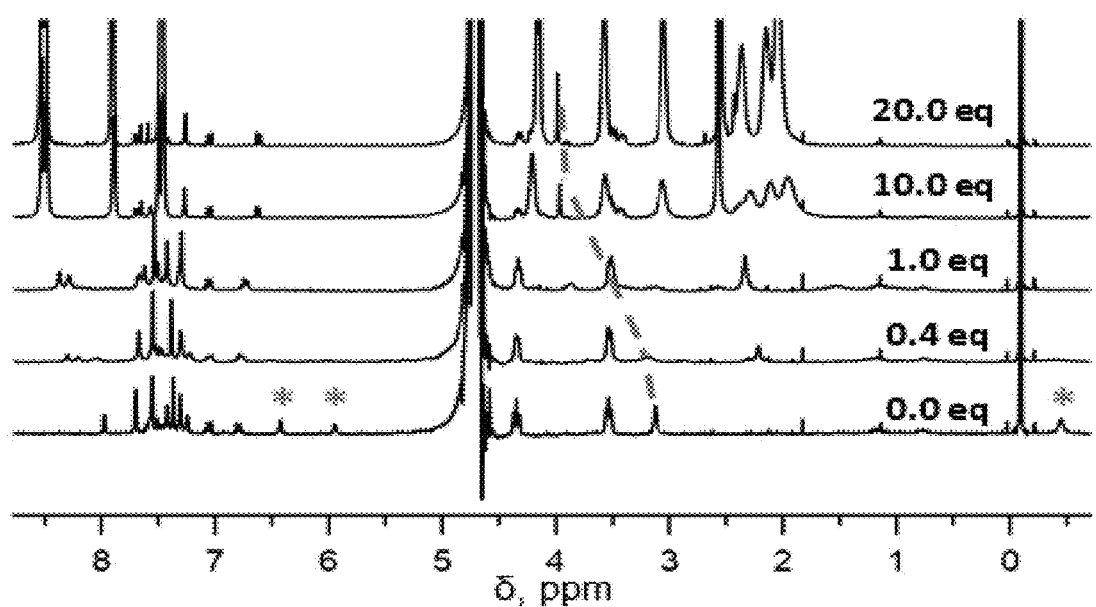
Figure 4B:
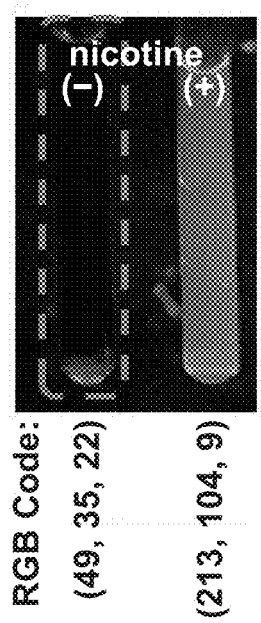
Figure 4C:
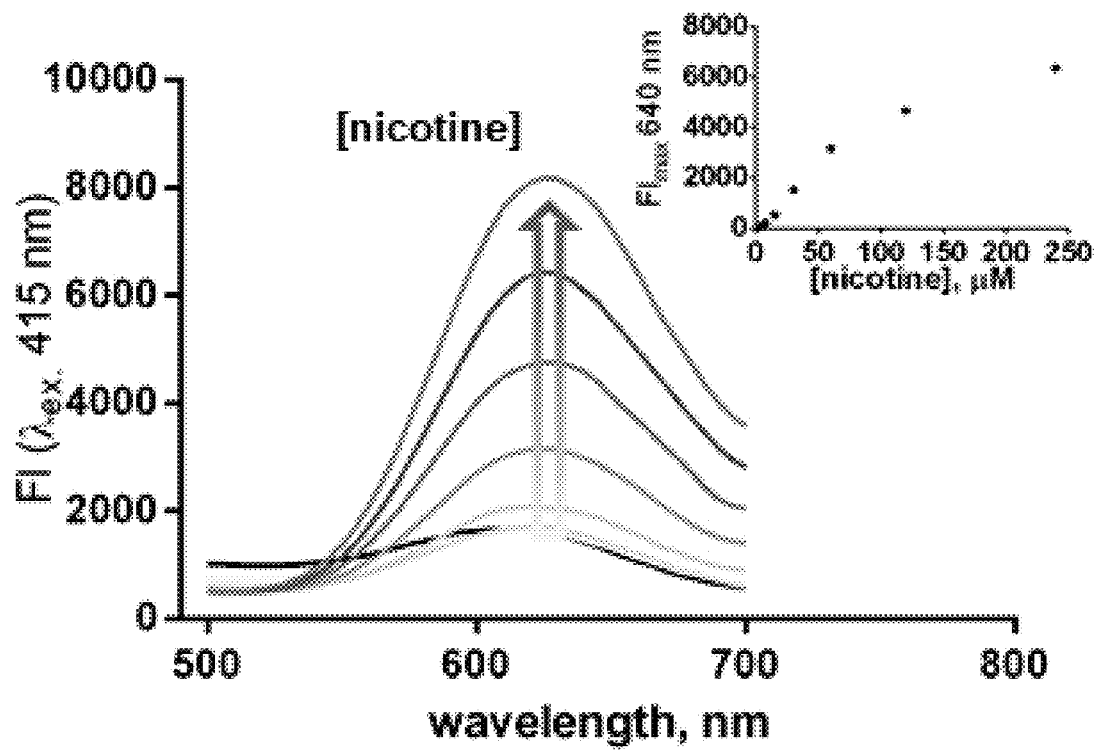
Figure 36:
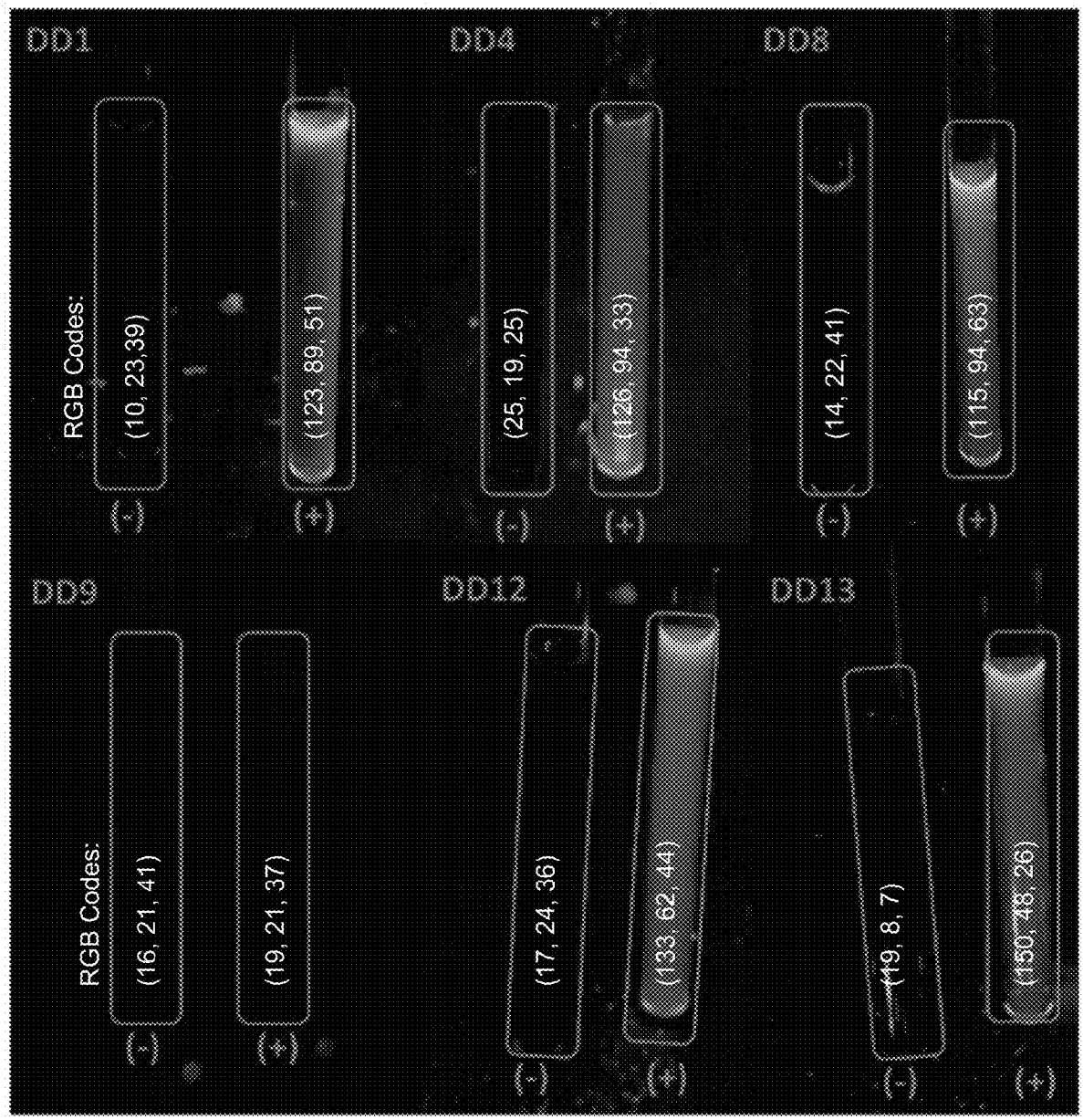
FIG. 36 is a photographic image showing NMR tubes comprising different dimer complex embodiments (DD1, DD4, DD8, DD9, DD12, and DD13; all at 500 µM) before and after nicotine addition; as can be seen, tubes without the nicotine addition (labeled as "−") are not fluorescent, but when 10 mM nicotine is added, most embodiments become fluorescent (labeled as "+"); each tube is irradiated with a hand-held UV lamp ($\lambda_{ex.}$ 364 nm±20 nm).

Nicotine titrations into DD4 and DD12, most clearly show the host resonances returning from upfield-shifted locations and/or broadening. DD4 resonances stay sharp enough in the presence of 20 eq. nicotine to conduct 1D DOSY experiments, and as expected the hydrodynamic radius of DD4 decreases to a value expected for a monomeric calixarene-nicotine complex (Table 3 and Table 6). Comparing the NMR tubes before and after the addition of nicotine shows visible DD fluorescence only for the nicotine-containing samples when irradiated at 365 nm with a hand-held UV lamp (FIG. 4B and FIG. 36). This behavior is further confirmed with titrations of nicotine into DD12 monitored by fluorescence spectroscopy. The dimer alone is barely fluorescent when irradiated at 415 nm but upon addition of nicotine the fluorescence increases at 640 nm (FIG. 4C). This turn-on fluorescence response is observed by all selected compound embodiments except for DD9, which shows nicotine complexation by NMR yet remains dark when irradiated with the UV hand-held lamp and minimal fluorescence is detected by fluorescence spectroscopy.

Figures 5A, 5B:
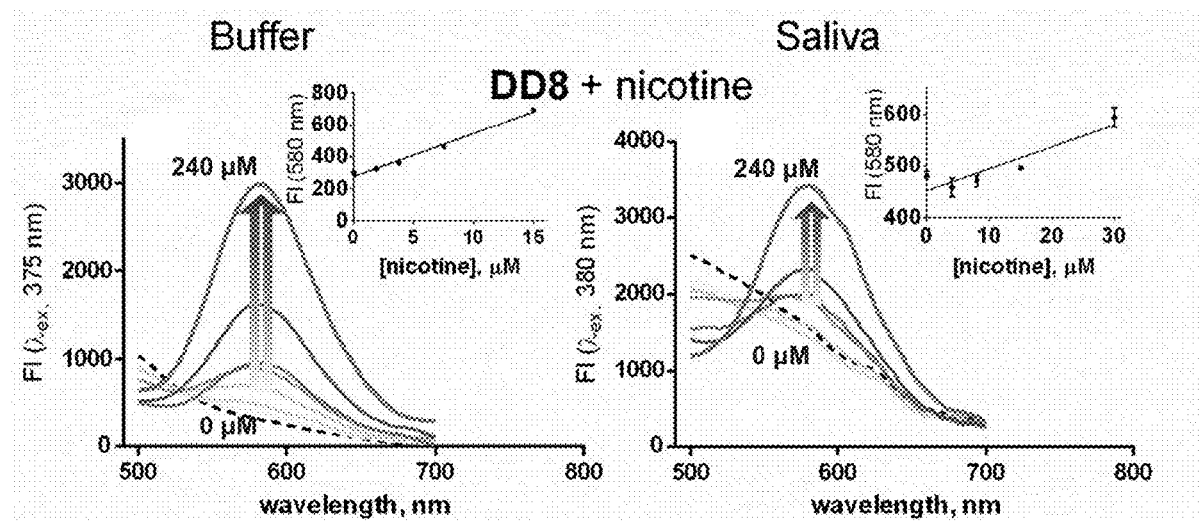
FIGS. 5A and 5B are fluorescence titration curves showing results obtained after adding nicotine to a dimer complex embodiment formed from compound embodiment DD8 in buffered water (NaH$_2$PO$_4$/Na$_2$HPO$_4$ (10 mM, pH 7.4), FIG. 5A) and saliva (1:1 dilution of saliva with water, FIG. 5B), wherein dimer complex concentration was 12 µM, drug concentration was 240 µM, and wherein the dashed black line indicates no drug present.
Figures 6A, 6B:
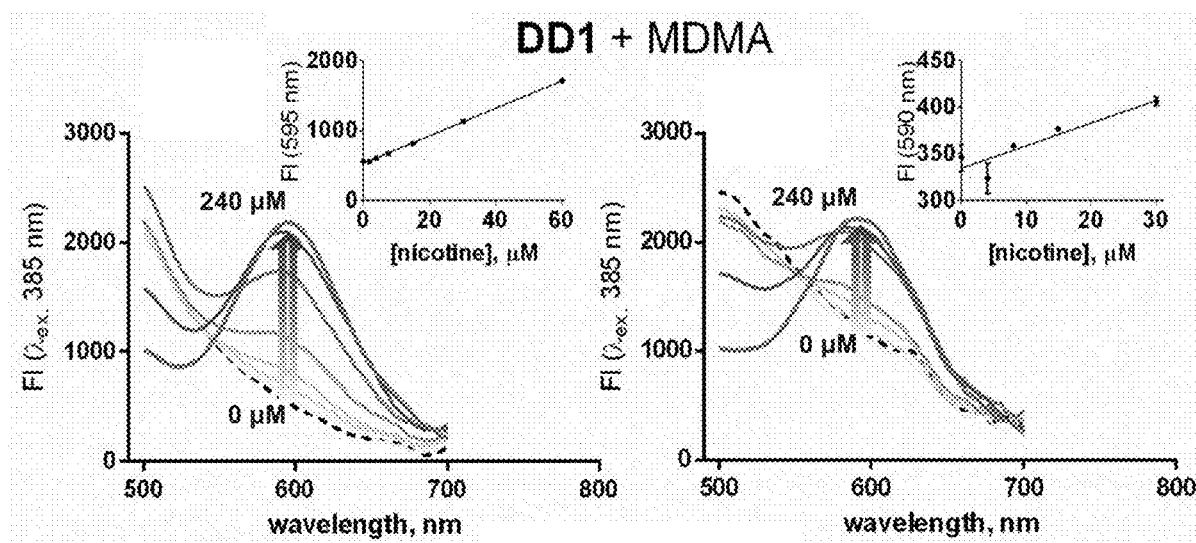
FIGS. 6A and 6B are fluorescence titration curves showing results obtained after adding MDMA to a dimer complex embodiment comprising compound embodiment DD1 in buffered water (NaH$_2$PO$_4$/Na$_2$HPO$_4$ (10 mM, pH 7.4), FIG. 6A) and saliva (1:1 dilution of saliva with water, FIG. 6B).
Figure 37A:
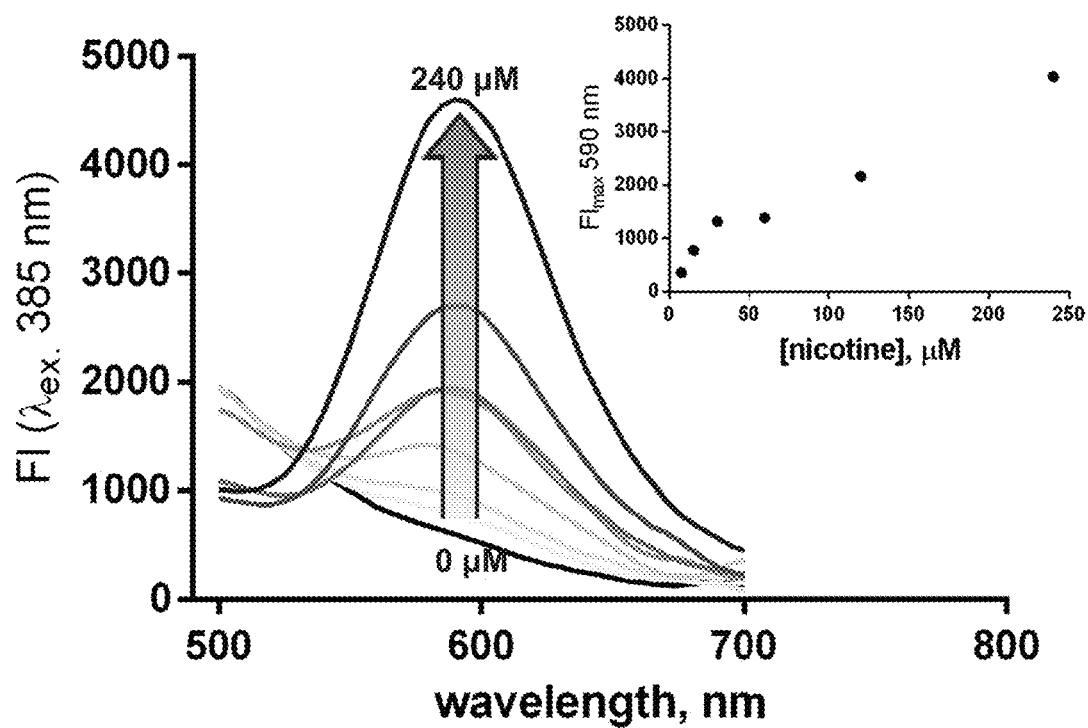
FIGS. 37A and 37B are graphs of titration curves obtained after combining a dimer complex comprising compound embodiment DD1 (12 µM) with nicotine in different media and monitoring the reaction using fluorescence spectroscopy.
Figure 37B:
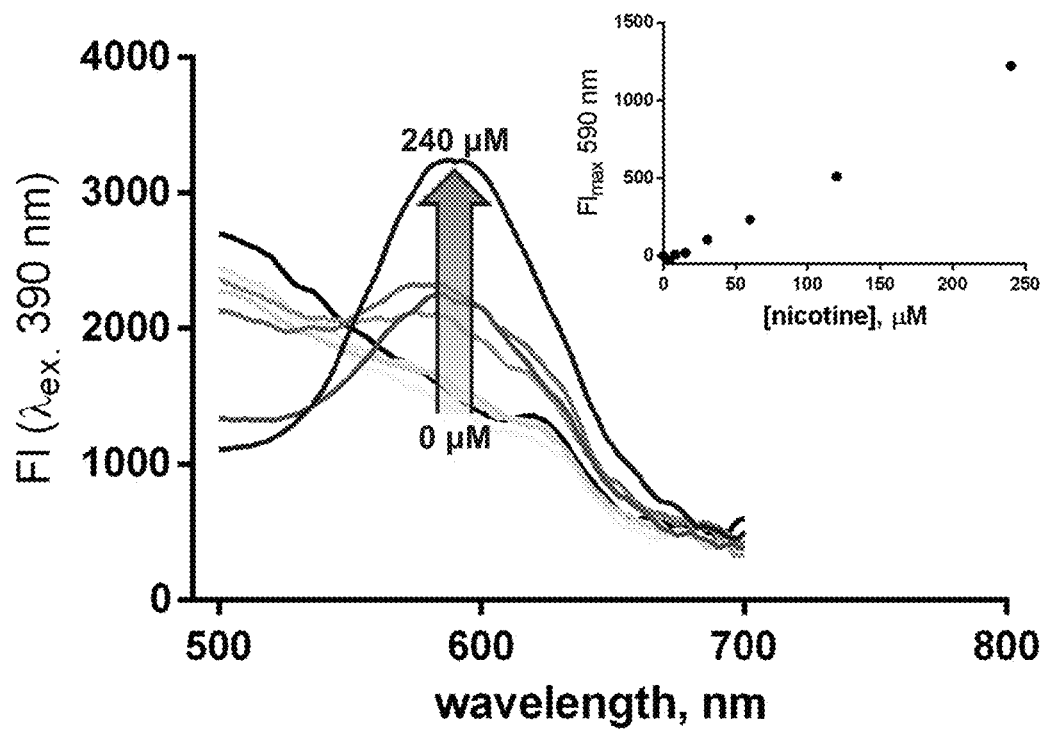
Figure 38A:
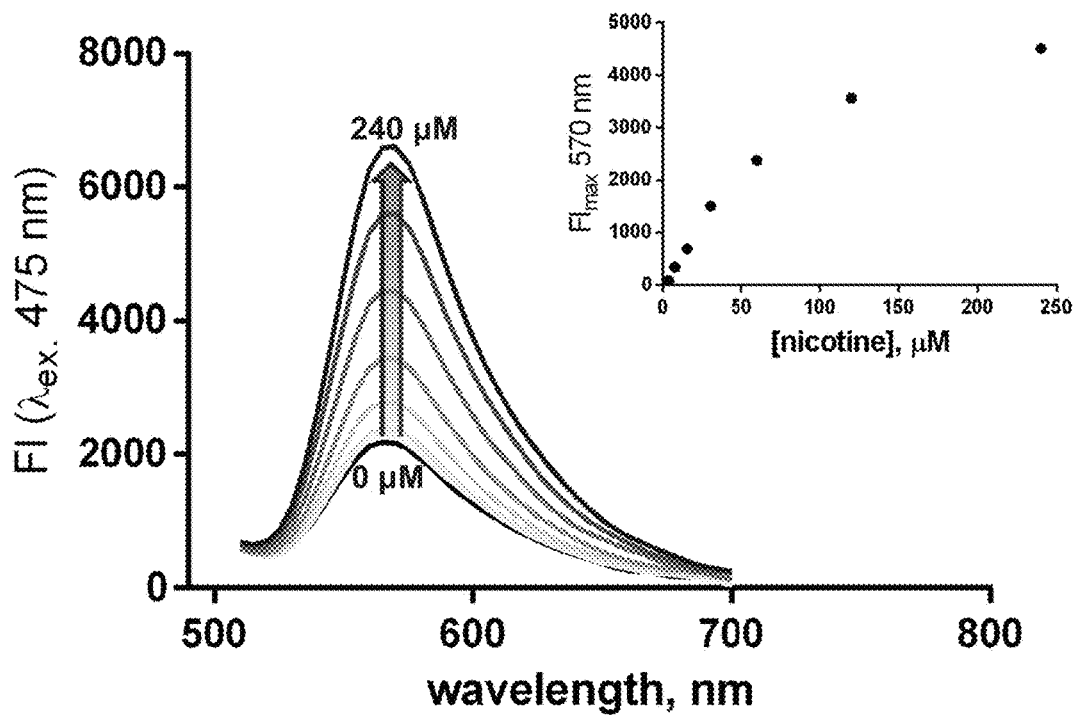
FIGS. 38A and 38B are graphs of titration curves obtained after combining a dimer complex comprising compound embodiment DD4 (12 µM) with nicotine in different media and monitoring the reaction using fluorescence spectroscopy.
Figure 38B:
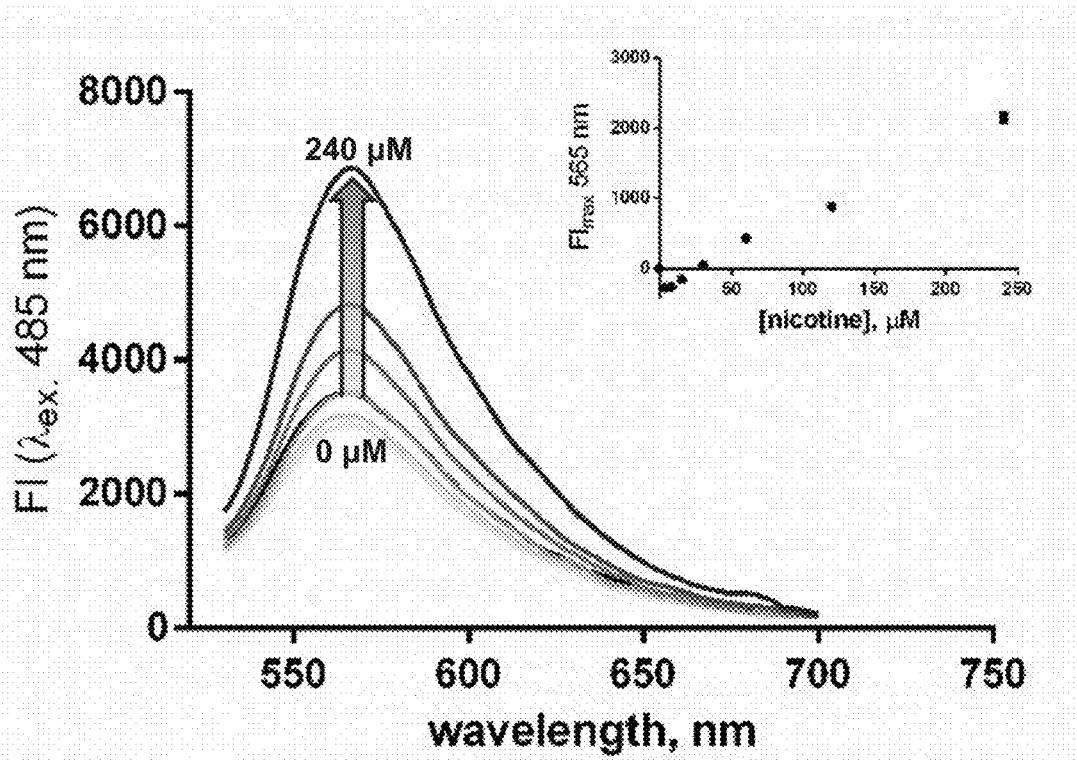
Figure 39A:
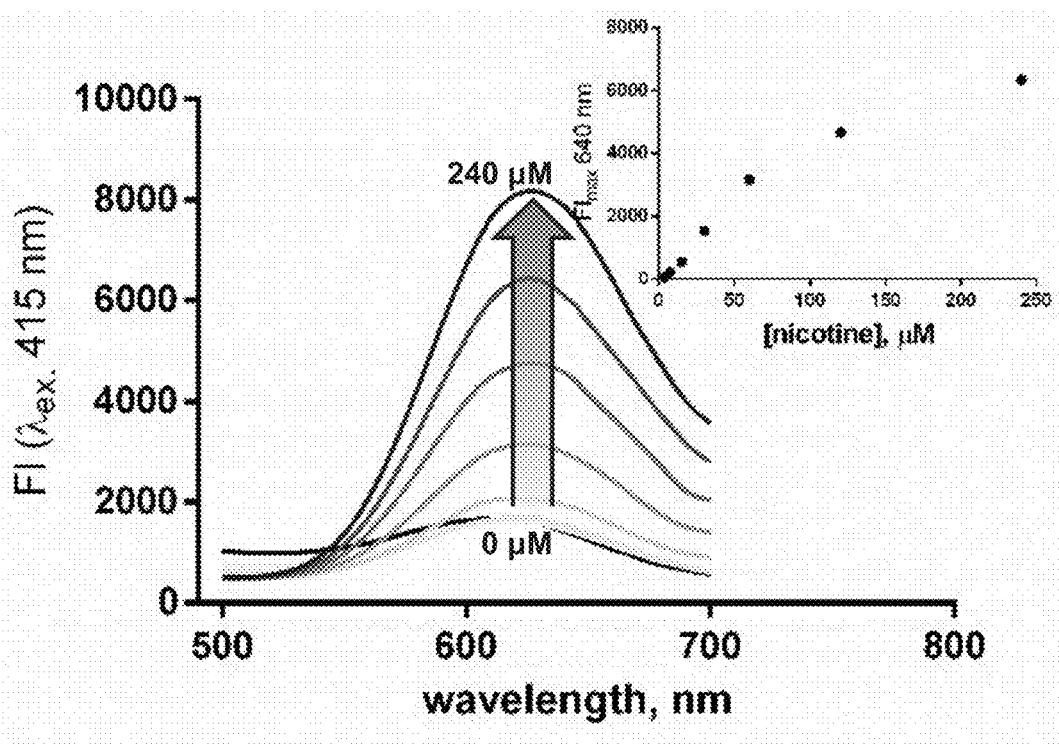
FIGS. 39A and 39B are graphs of titration curves obtained after combining a dimer complex comprising compound embodiment DD12 (12 µM) with nicotine in different media and monitoring the reaction using fluorescence spectroscopy.
Figure 39B:
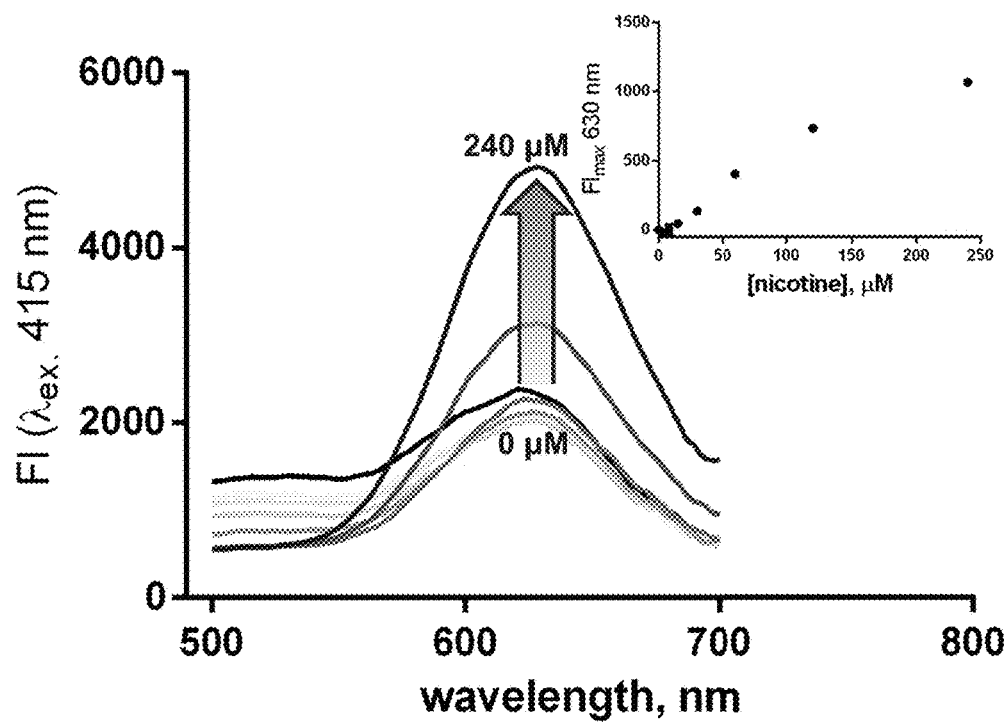
Figure 40A:
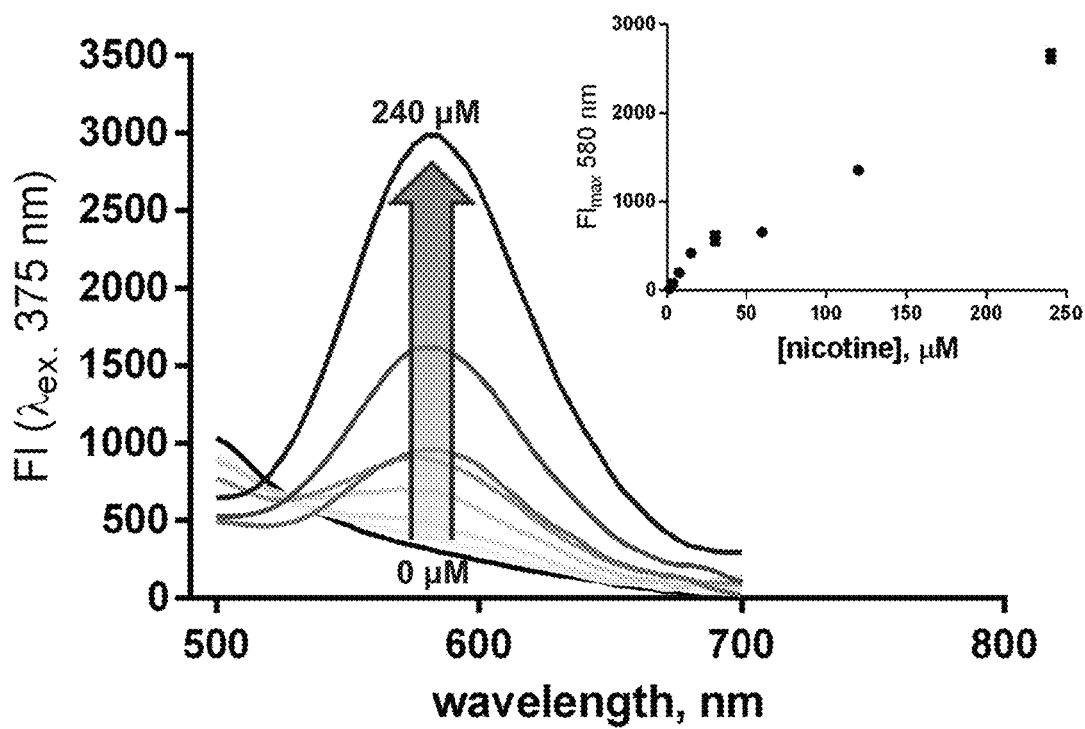
FIGS. 40A and 40B are graphs of titration curves obtained after combining a dimer complex comprising compound embodiment DD8 (12 µM) with nicotine in different media and monitoring the reaction using fluorescence spectroscopy.
Figure 40B:
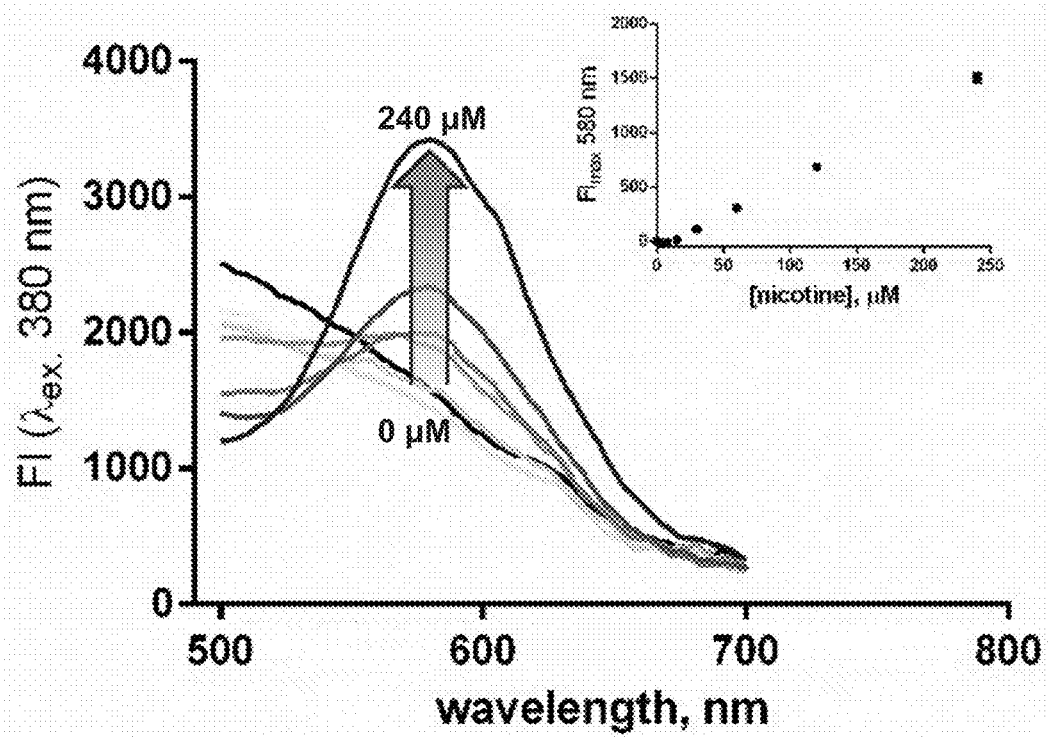
Figure 41A:
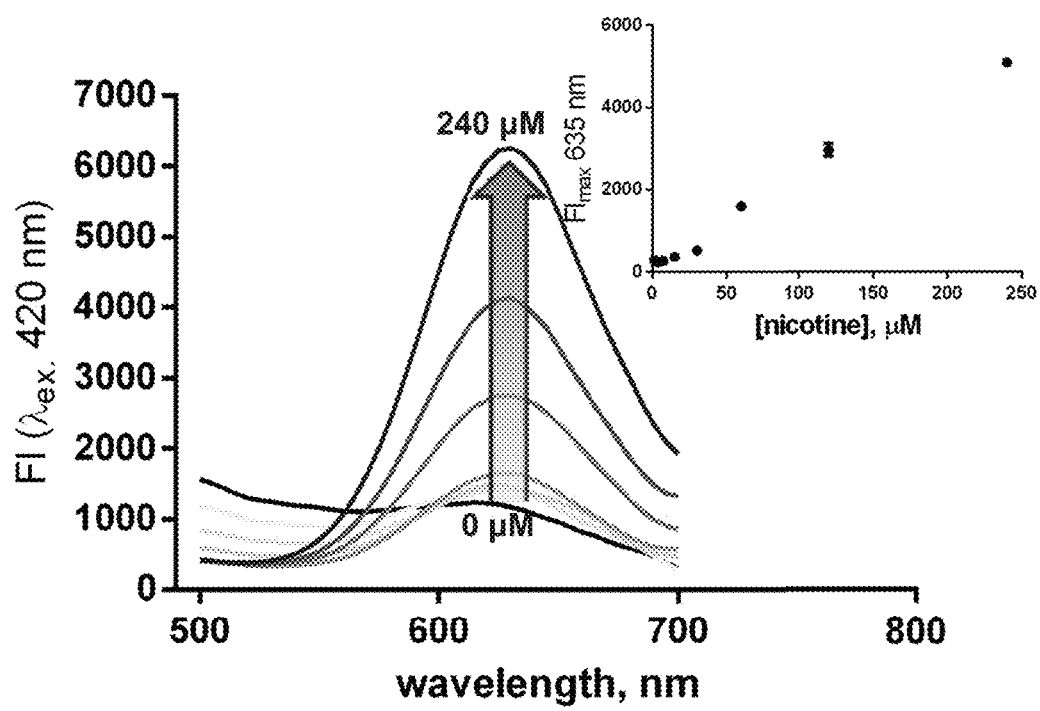
FIGS. 41A and 41B are graphs of titration curves obtained after combining a dimer complex comprising compound embodiment DD13 (12 µM) with nicotine in different media and monitoring the reaction using fluorescence spectroscopy.
Figure 41B:
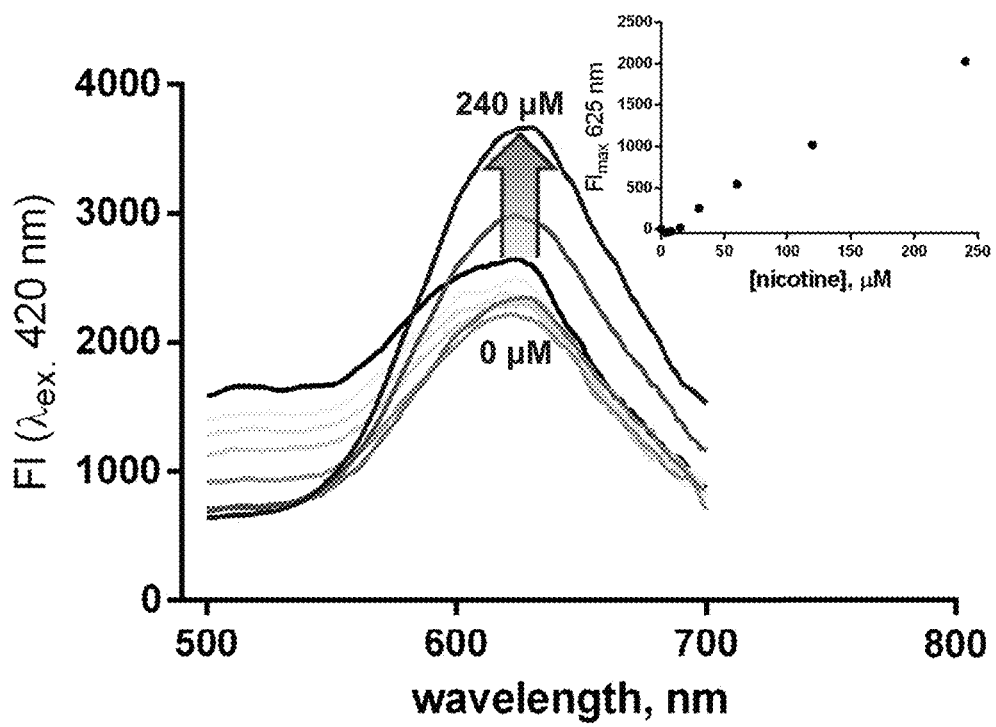
Figure 42A:
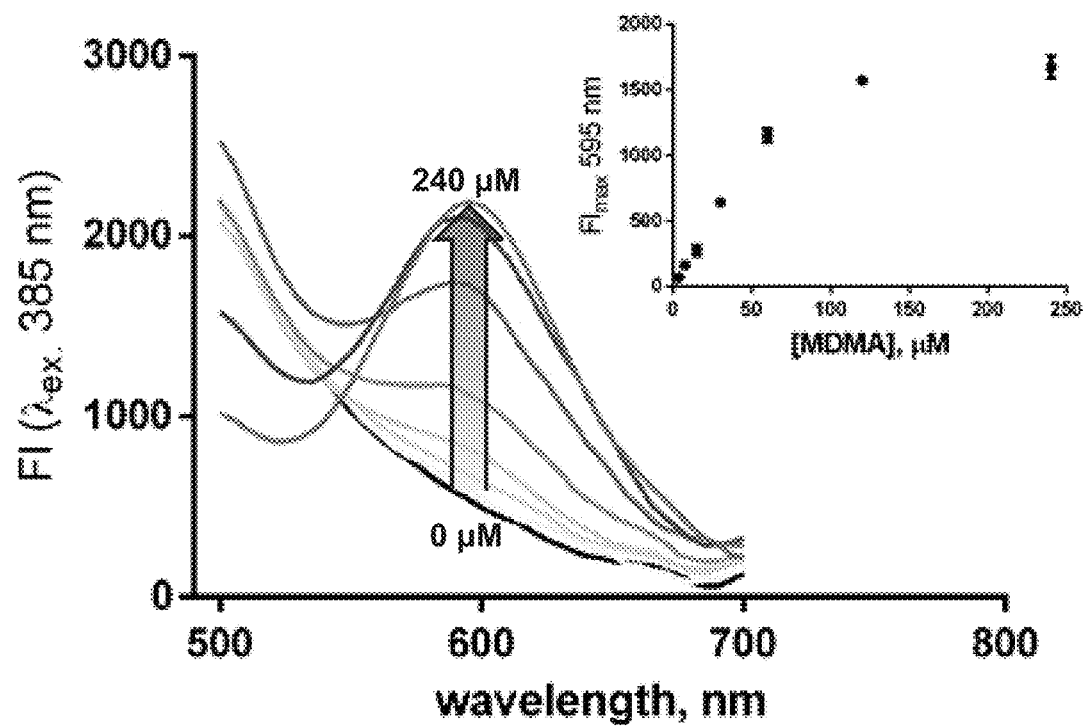
FIGS. 42A and 42B are graphs of titration curves obtained after combining a dimer complex comprising compound embodiment DD1 (12 µM) with MDMA in different media and monitoring the reaction using fluorescence spectroscopy.
Figure 42B:
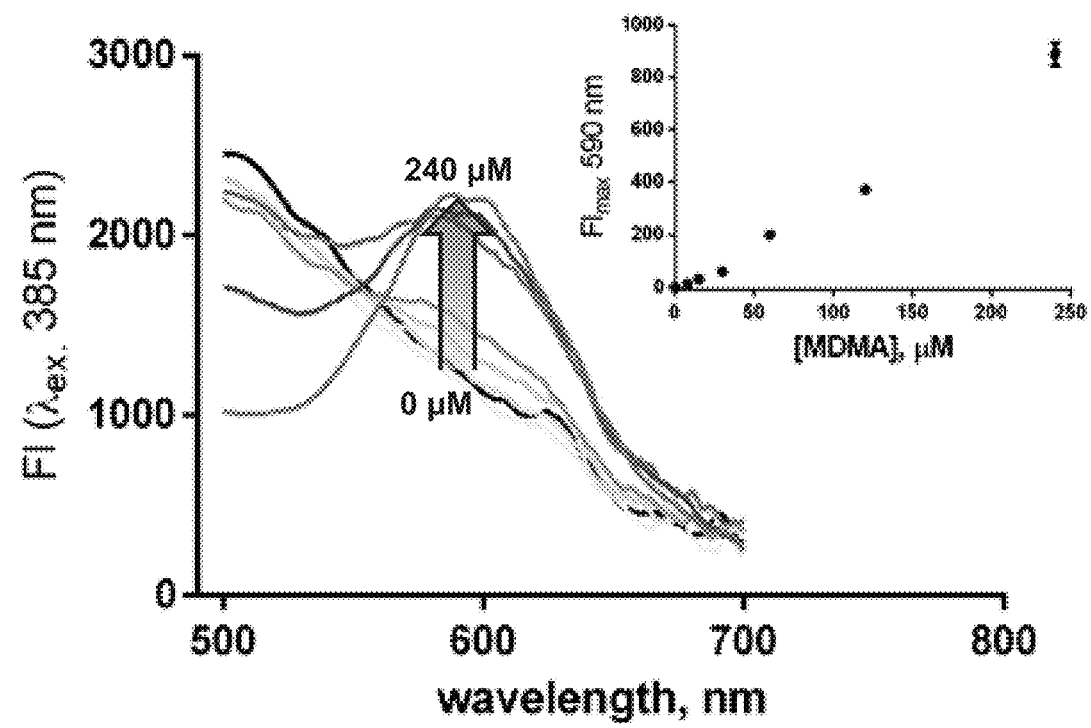
Figure 43A:
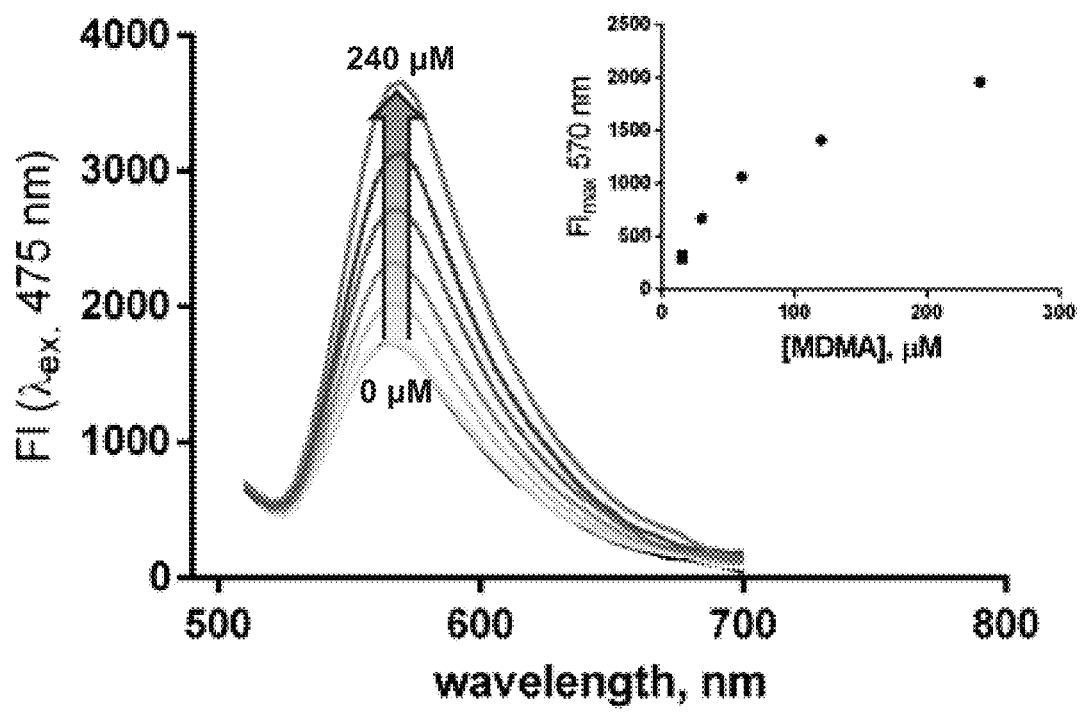
FIGS. 43A and 43B are graphs of titration curves obtained after combining a dimer complex comprising compound embodiment DD4 (12 µM) with MDMA in different media and monitoring the reaction using fluorescence spectroscopy.
Figure 43B:
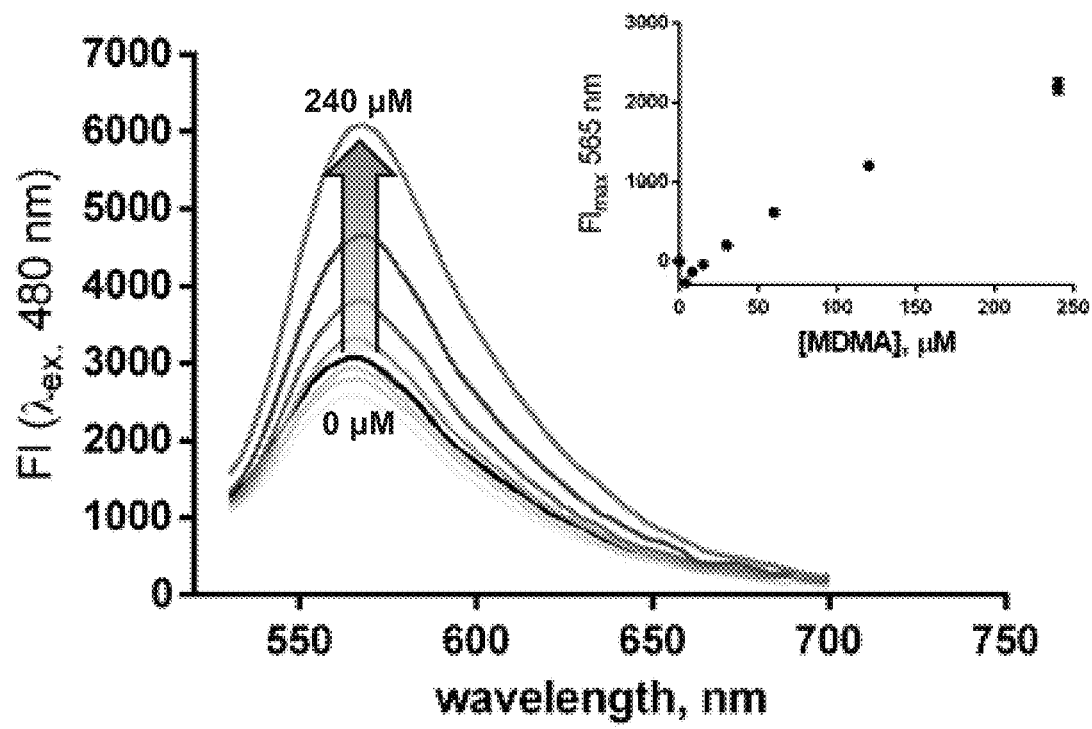
Figure 44A:
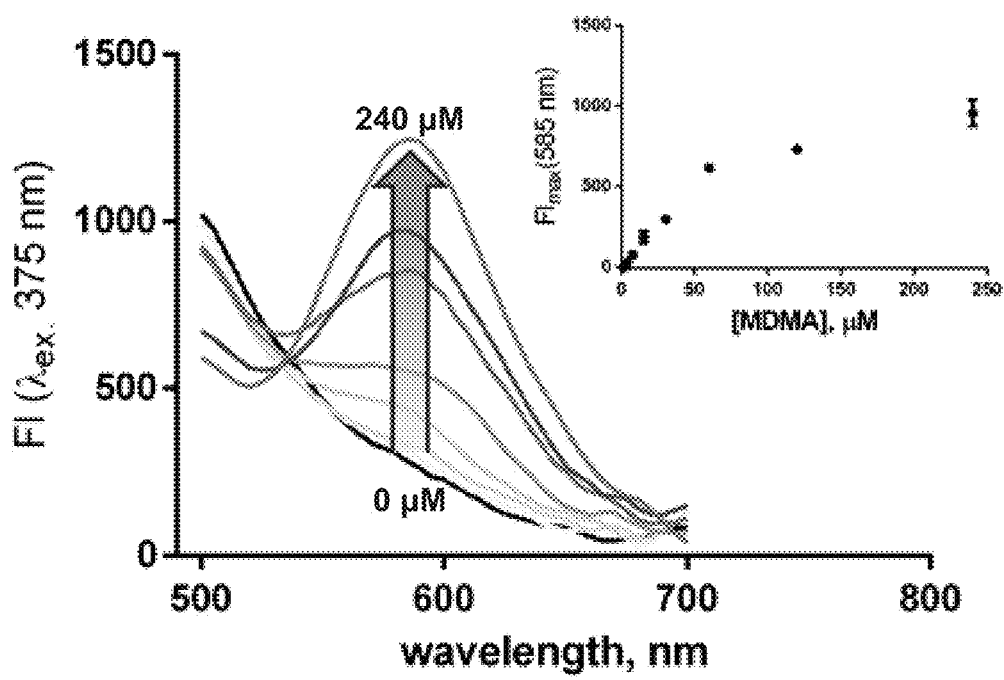
FIGS. 44A and 44B are graphs of titration curves obtained after combining a dimer complex comprising compound embodiment DD8 (12 µM) with MDMA in different media and monitoring the reaction using fluorescence spectroscopy.
Figure 44B:
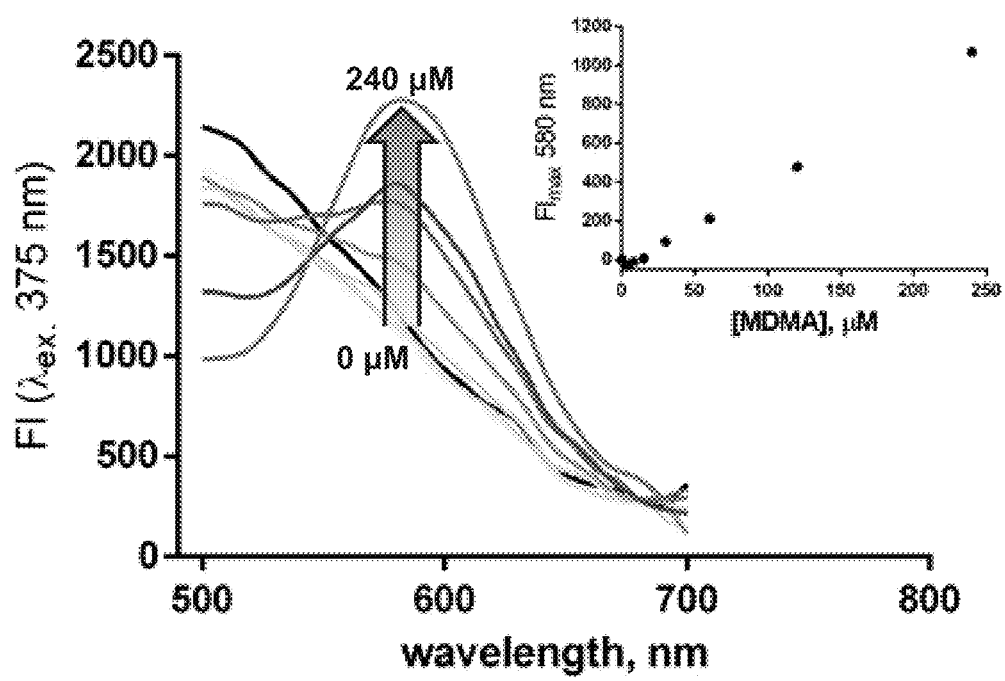
Figure 45A:
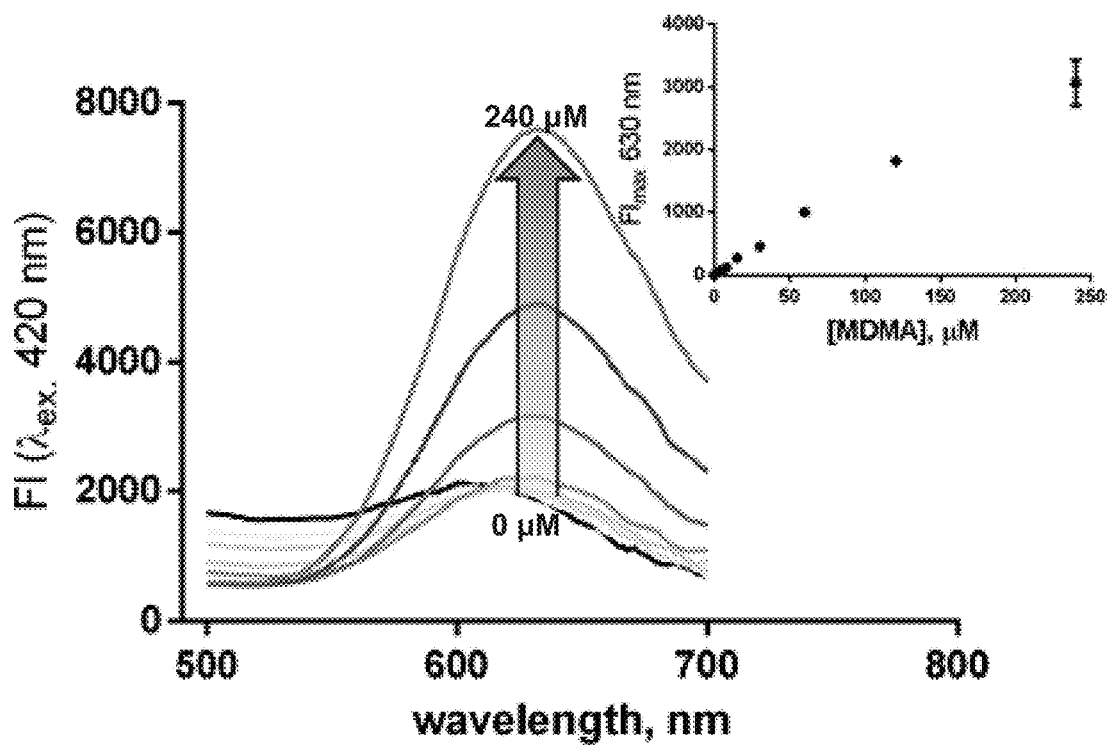
FIGS. 45A and 45B are graphs of titration curves obtained after combining a dimer complex comprising compound embodiment DD12 (12 µM) with MDMA in different media and monitoring the reaction using fluorescence spectroscopy.
Figure 45B:
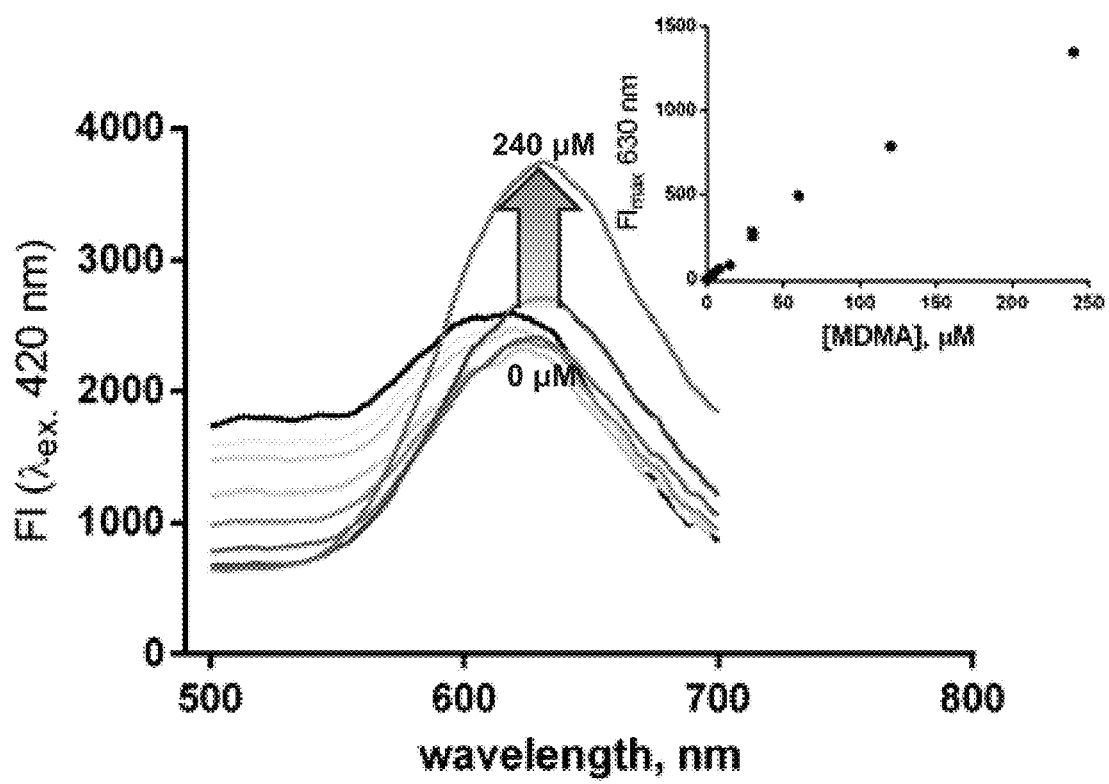
Figure 46A:
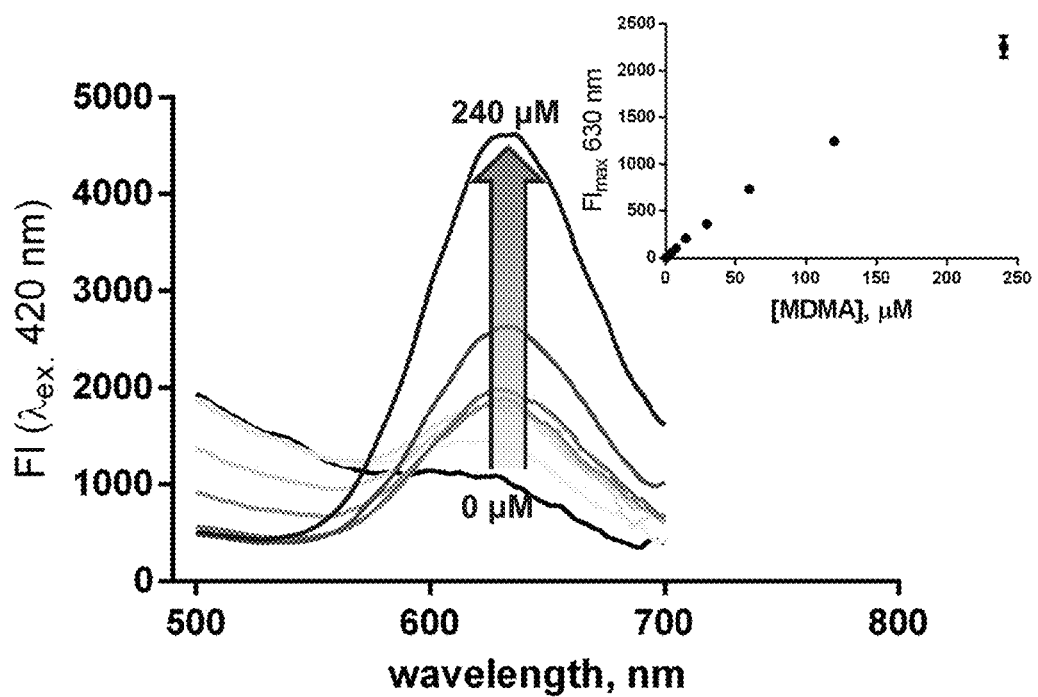
FIGS. 46A and 46B are graphs of titration curves obtained after combining a dimer complex comprising compound embodiment DD13 (12 µM) with MDMA in different media and monitoring the reaction using fluorescence spectroscopy.
Figure 46B:
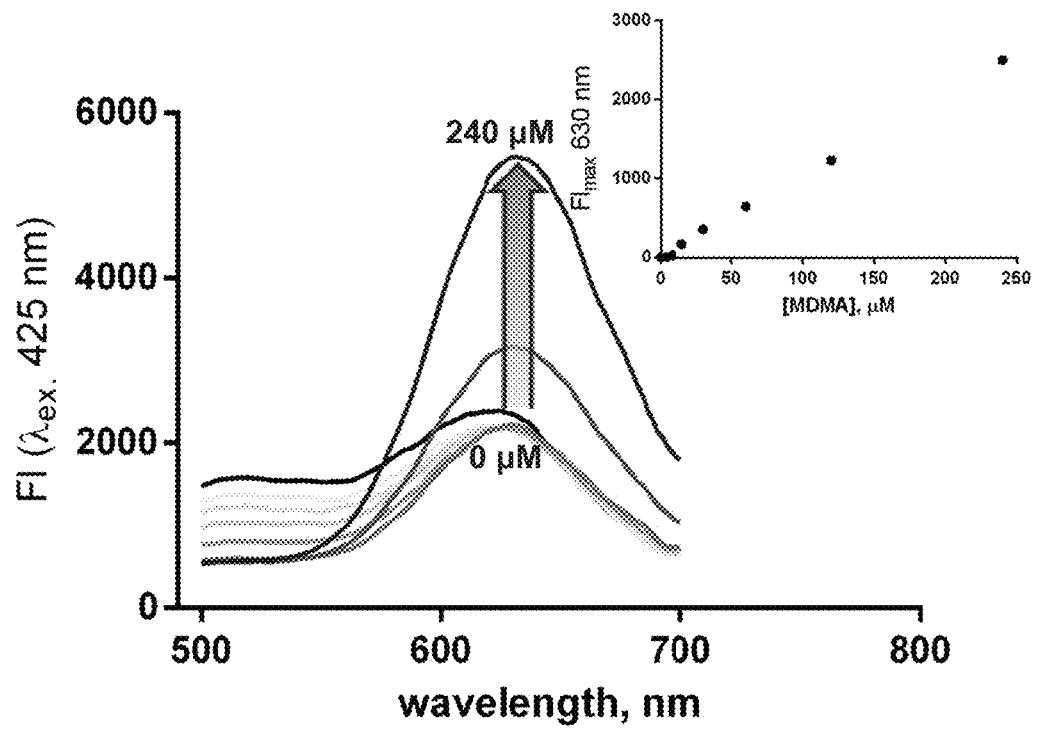
Figure 47A:
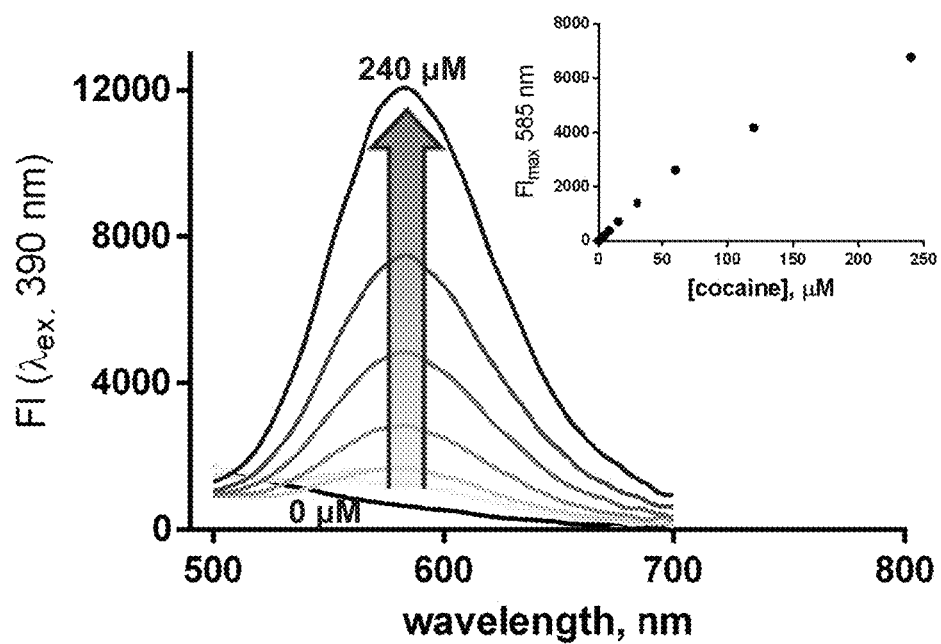
FIGS. 47A and 47B are graphs of titration curves obtained after combining a dimer complex comprising compound embodiment DD1 (12 µM) with cocaine in different media and monitoring the reaction using fluorescence spectroscopy.
Figure 47B:
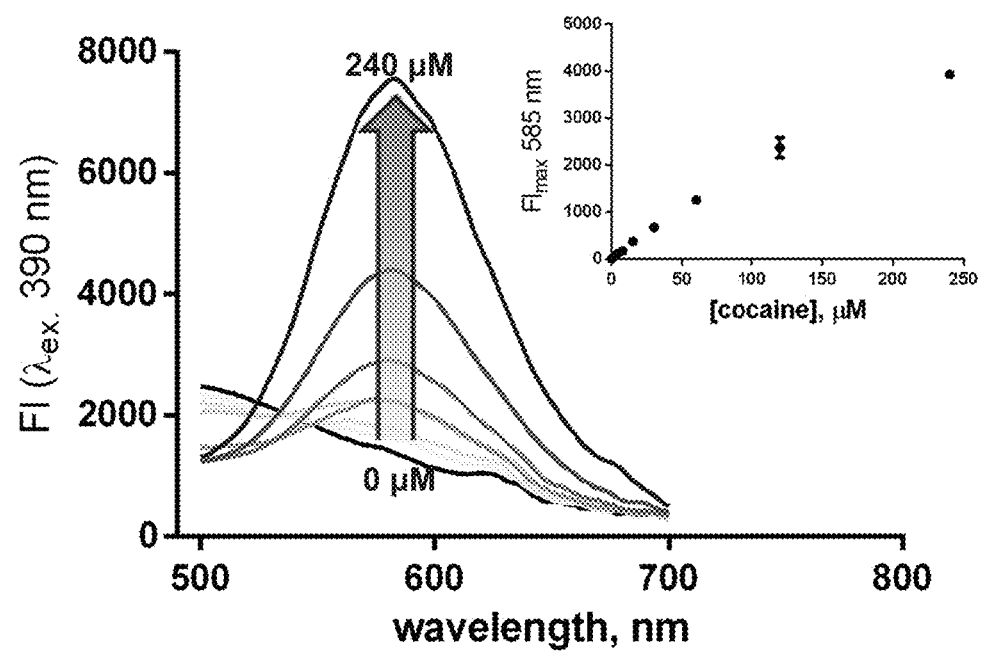
Figure 48A:
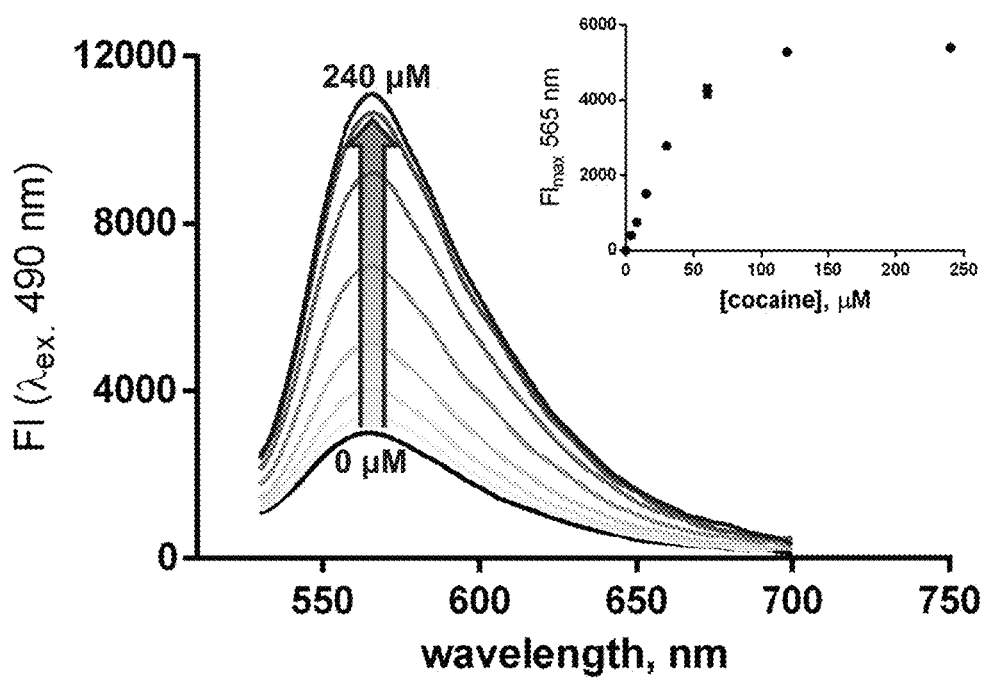
FIGS. 48A and 48B are graphs of titration curves obtained after combining a dimer complex comprising compound embodiment DD4 (12 µM) with cocaine in different media and monitoring the reaction using fluorescence spectroscopy.
Figure 48B:
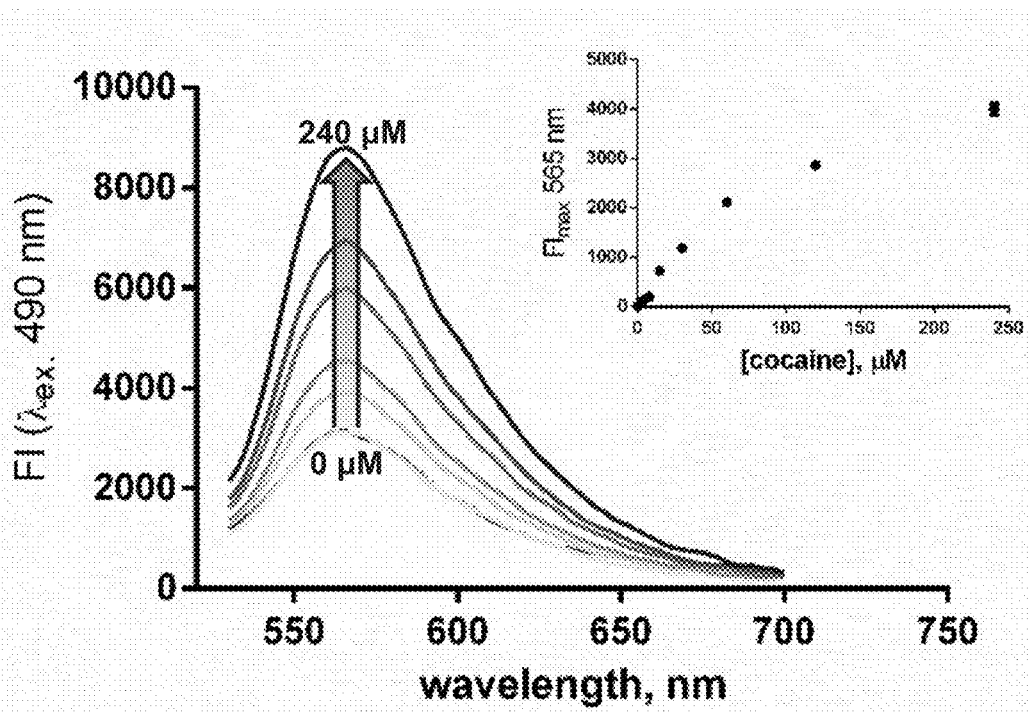
Figure 49A:
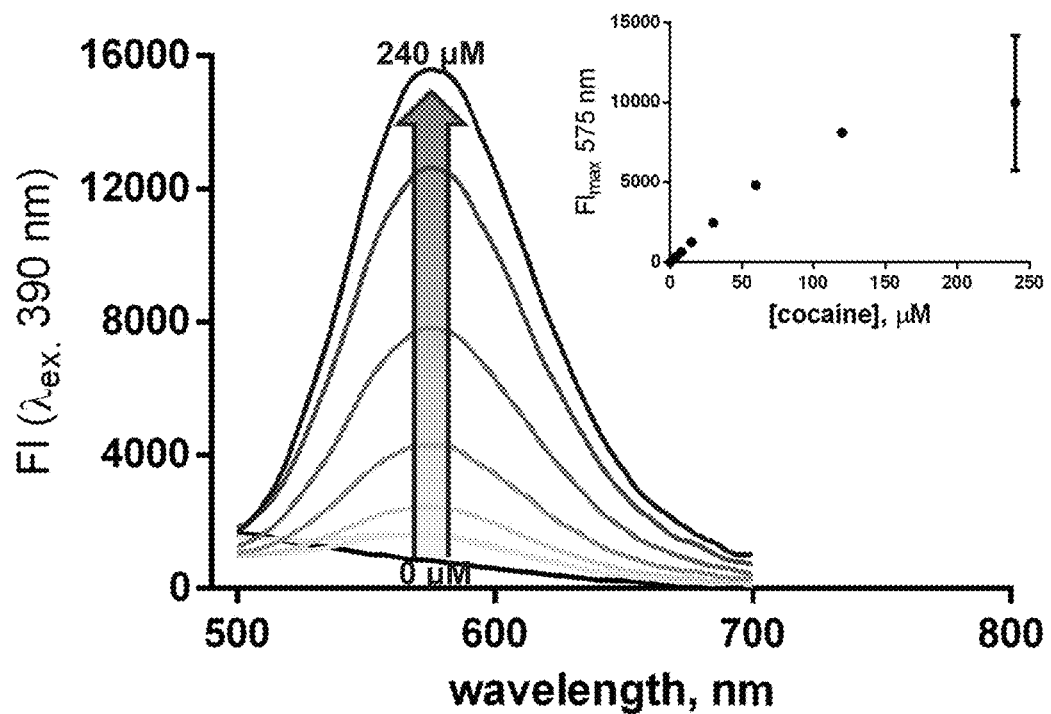
FIGS. 49A and 49B are graphs of titration curves obtained after combining a dimer complex comprising compound embodiment DD8 (12 µM) with cocaine in different media and monitoring the reaction using fluorescence spectroscopy.
Figure 49B:
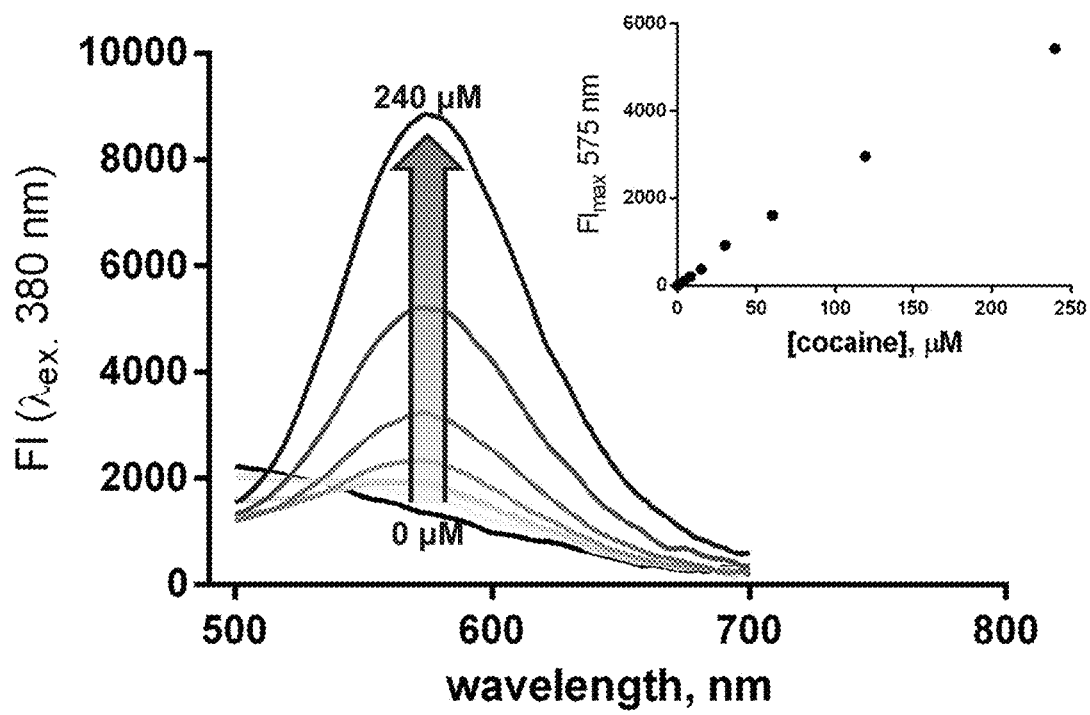
Figure 50A:
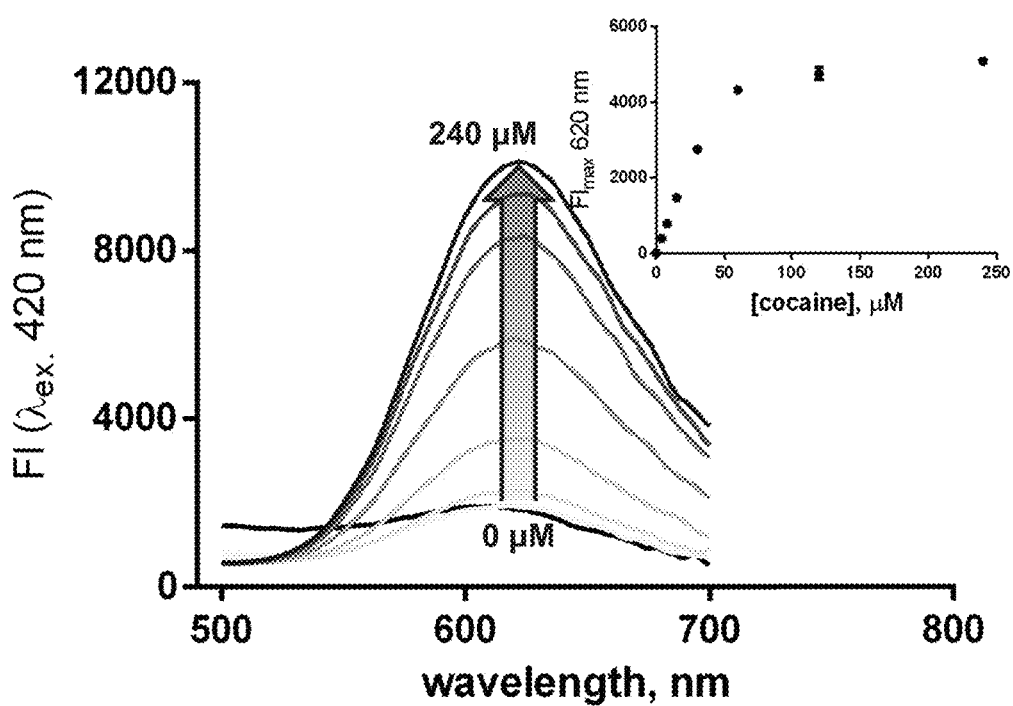
FIGS. 50A and 50B are graphs of titration curves obtained after combining a dimer complex comprising compound embodiment DD12 (12 µM) with cocaine in different media and monitoring the reaction using fluorescence spectroscopy.
Figure 50B:
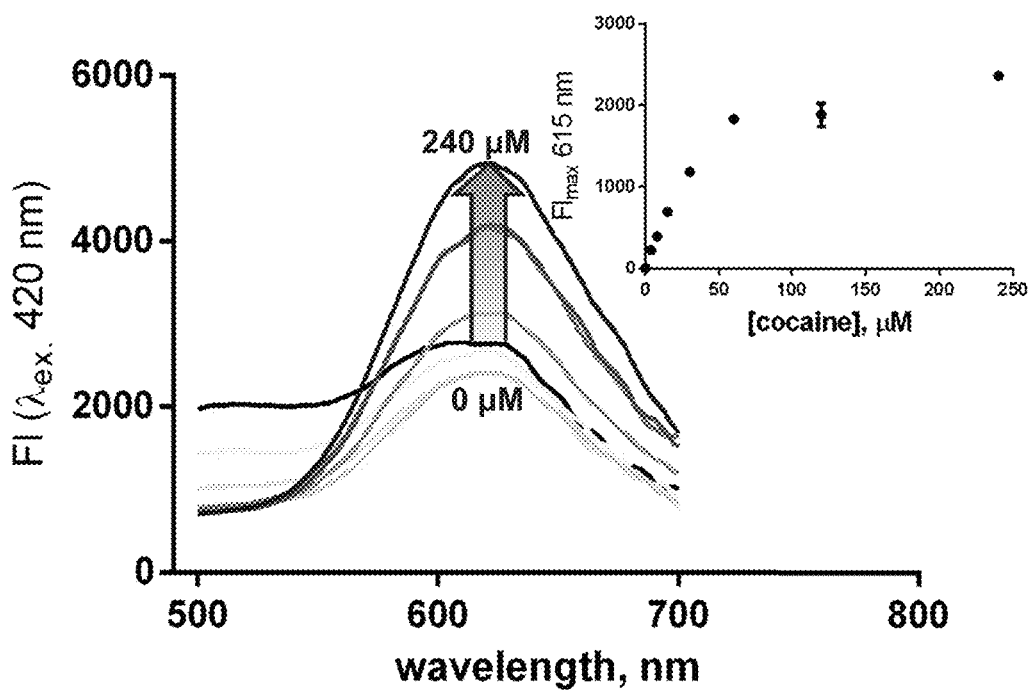
Figure 51A:
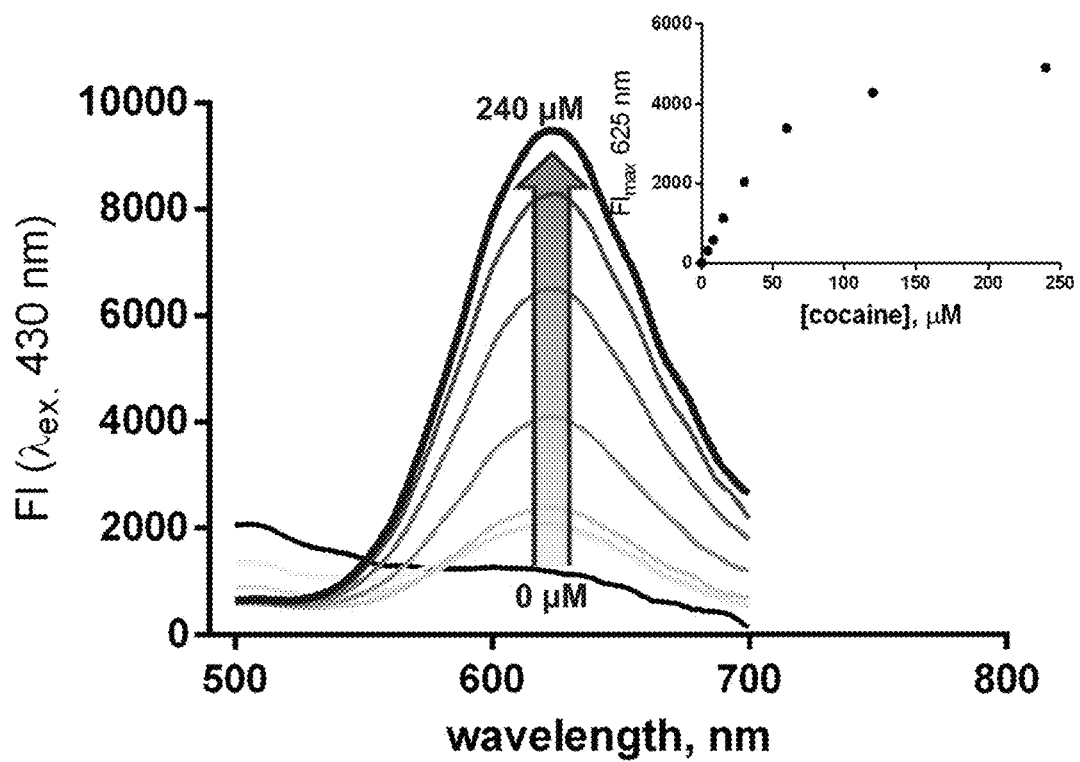
FIGS. 51A and 51B are graphs of titration curves obtained after combining a dimer complex comprising compound embodiment DD13 (12 µM) with cocaine in different media and monitoring the reaction using fluorescence spectroscopy.
Figure 51B:
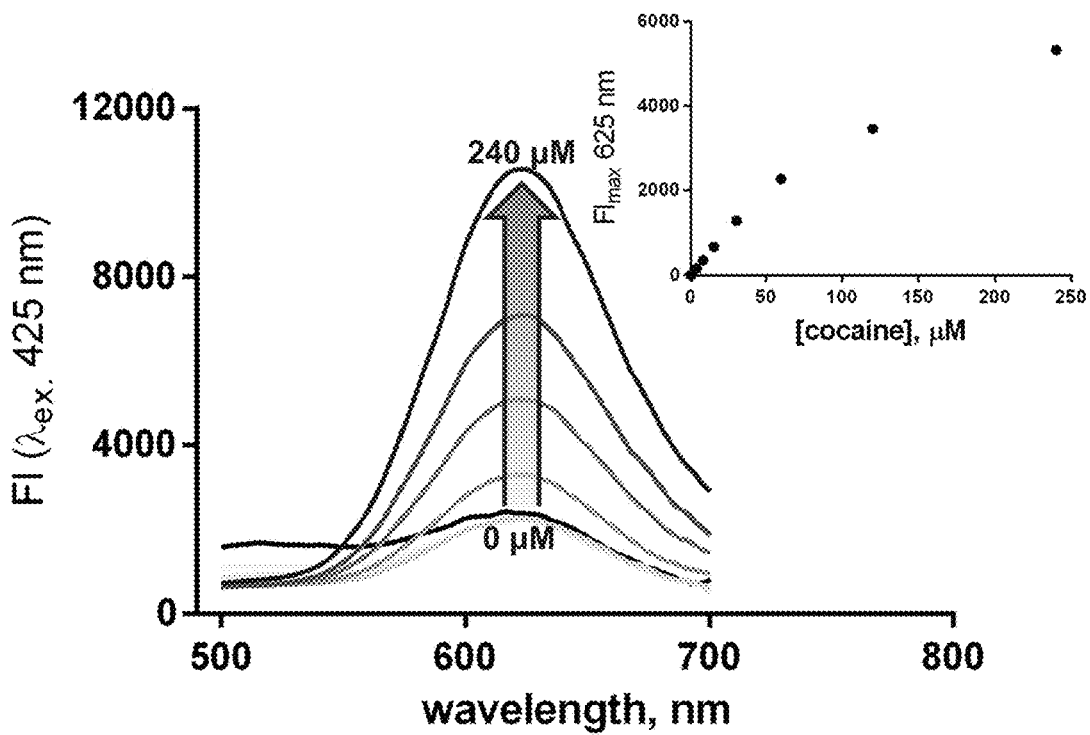
Figure 52A:
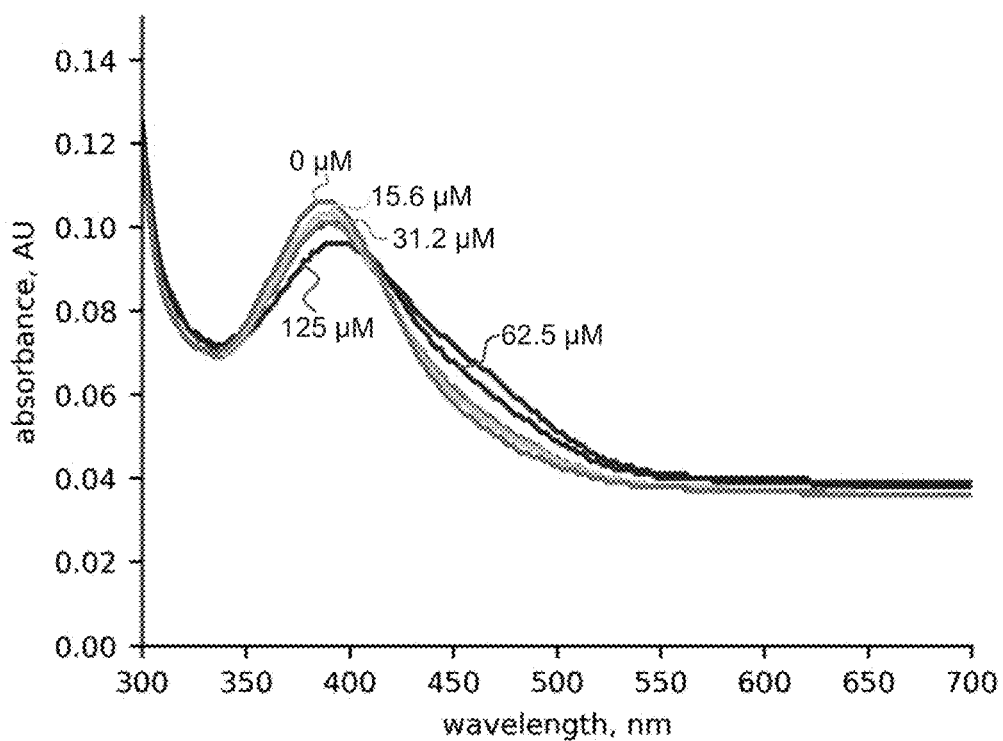
FIGS. 52A-52D are graphs of titration curves obtained after combining a dimer complex comprising compound embodiment DD1Cx5 (12 µM) with nicotine (FIGS. 52A and 52C) and cocaine (FIGS. 52B and 52D) as monitored by absorbance (FIGS. 52A and 52B) and fluorescence $\lambda_{ex}$ 380 nm (FIGS. 52C and 52D) in $NaH_2PO_4/Na_2HPO_4$ buffered water (10 mM, pH 7.4)
Figure 52B:
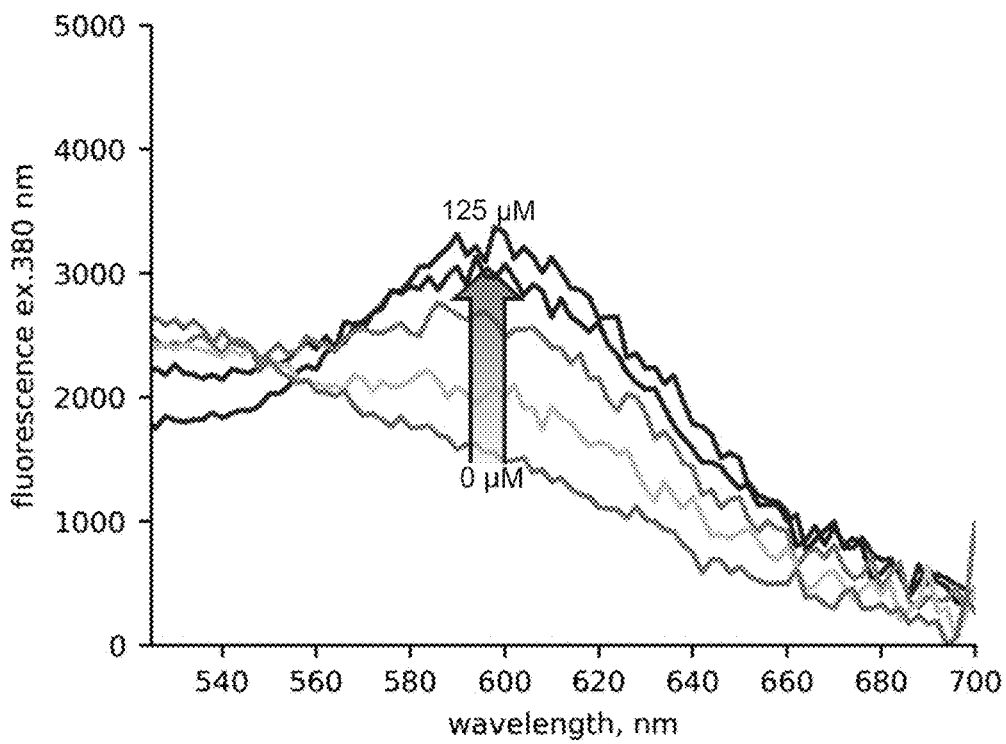
Figure 52C:
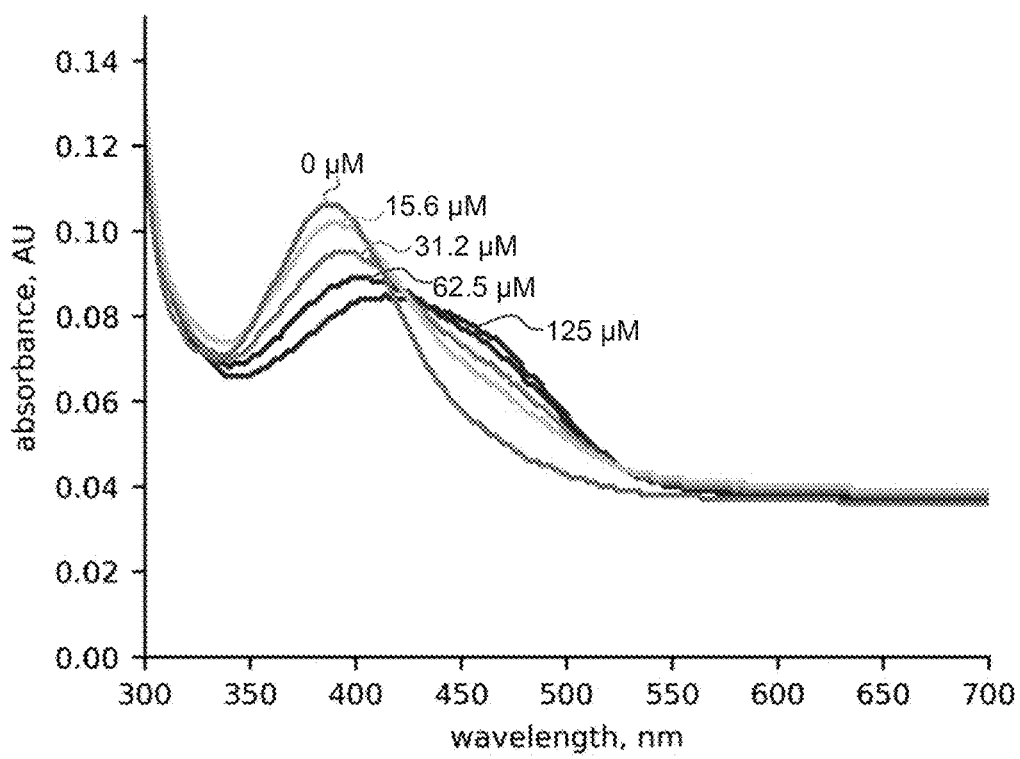
Figure 52D:
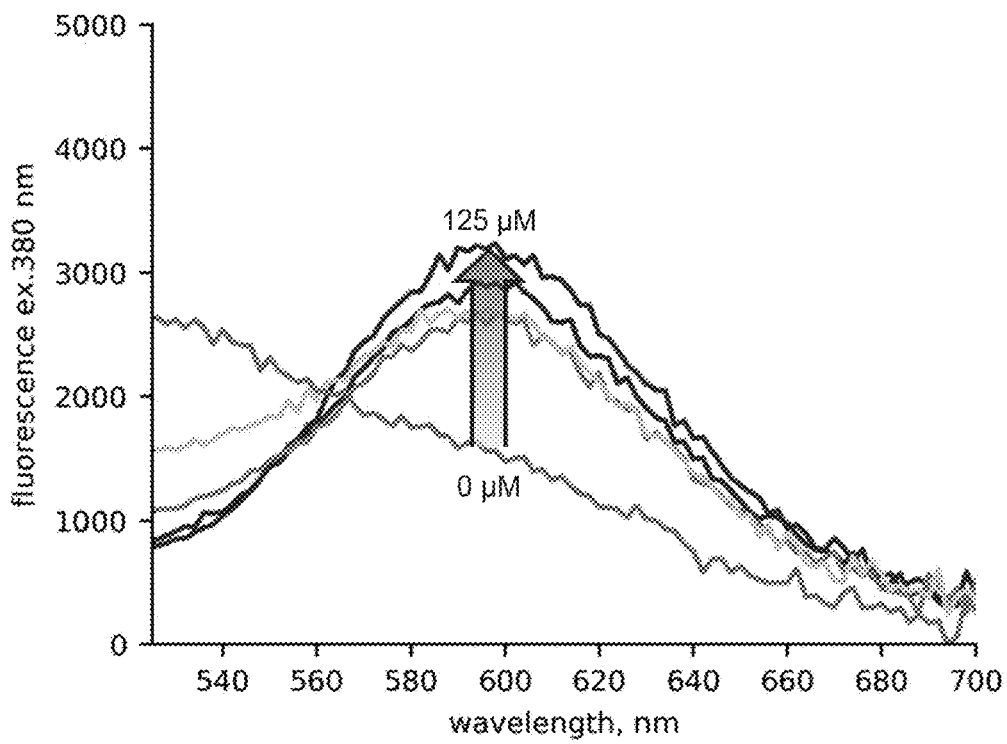
Figure 53A:
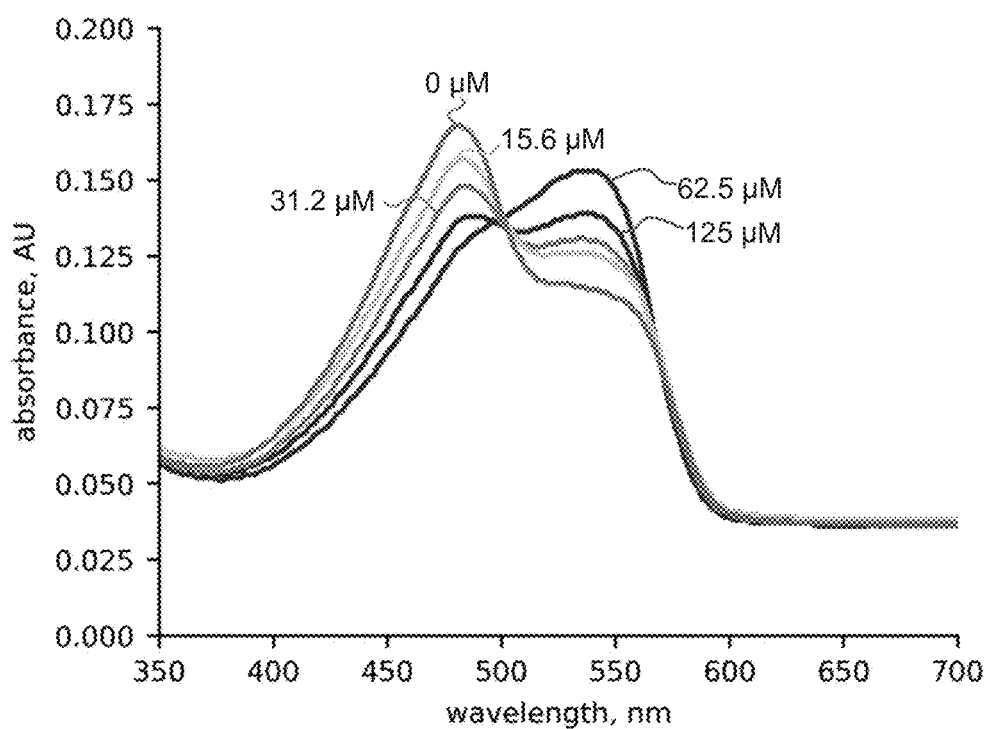
FIGS. 53A-53D are graphs of titration curves obtained after combining a dimer complex comprising compound embodiment DD4Cx5 (12 µM) with nicotine (FIGS. 53A and 53C) and cocaine (FIGS. 53B and 53D) as monitored by absorbance (FIGS. 53A and 53B) and fluorescence $\lambda_{ex}$ 380 nm (FIGS. 53C and 53D) in $NaH_2PO_4/Na_2HPO_4$ buffered water (10 mM, pH 7.4)
Figure 53B:
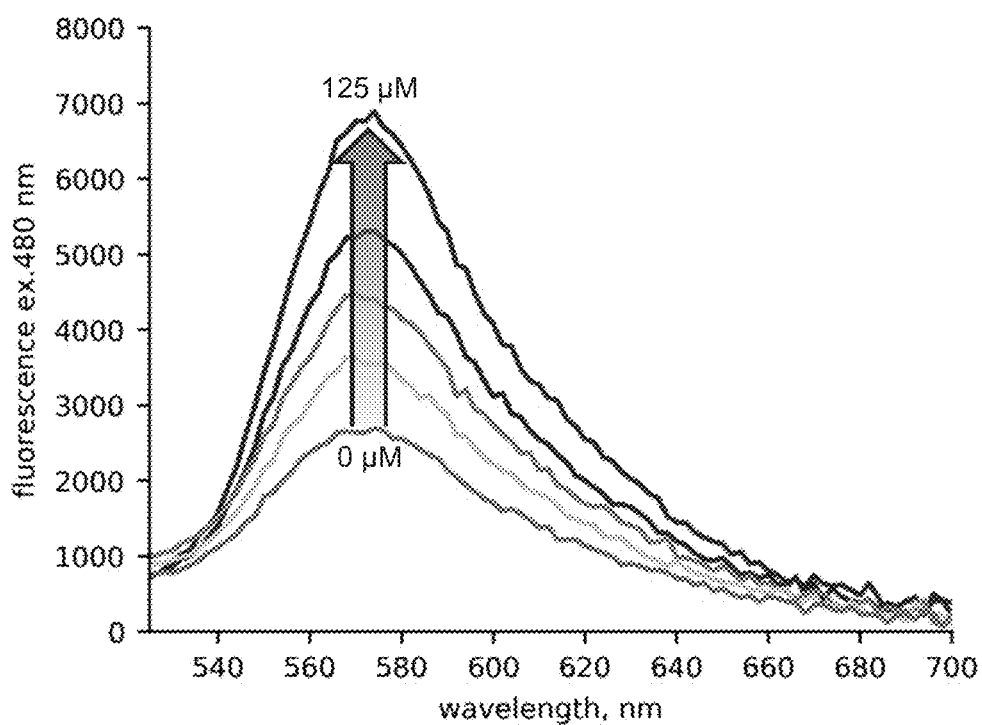
Figure 53C:
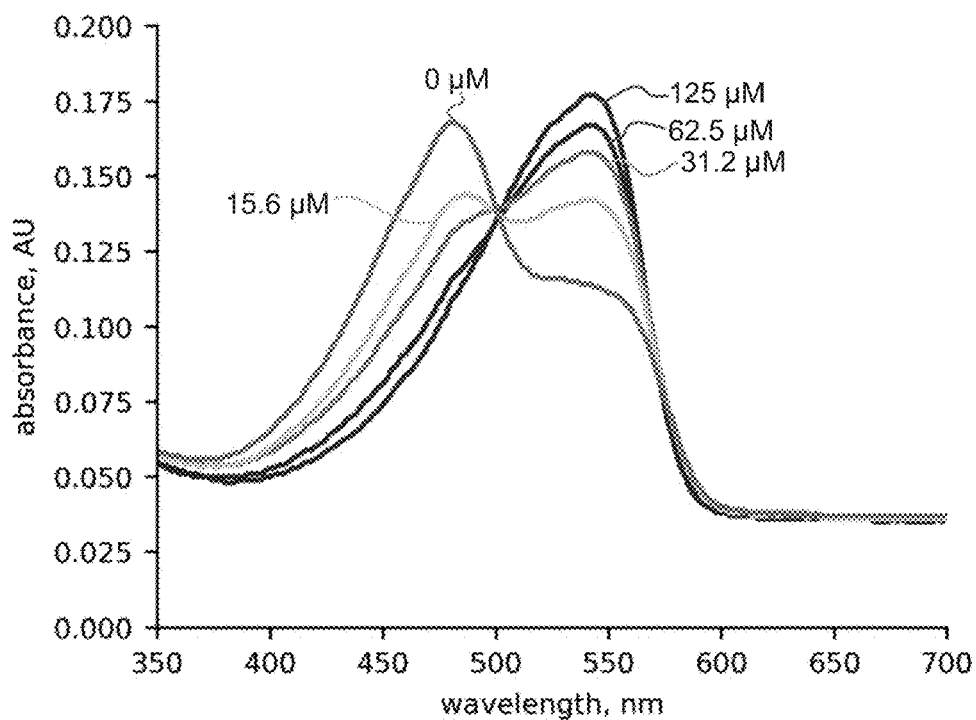
Figure 53D:
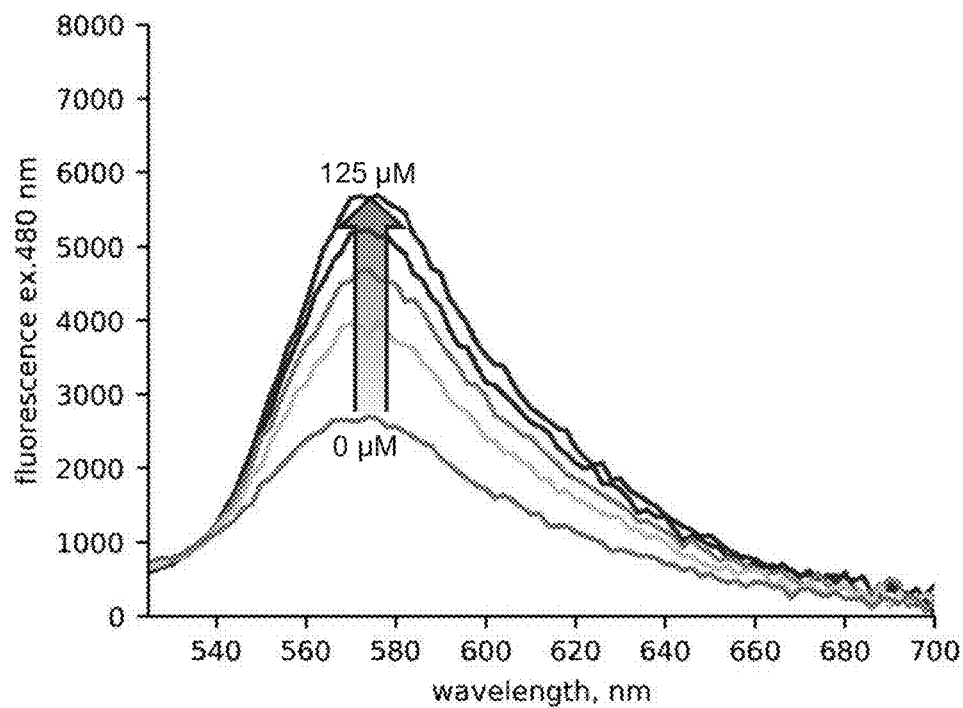
Figure 54A:
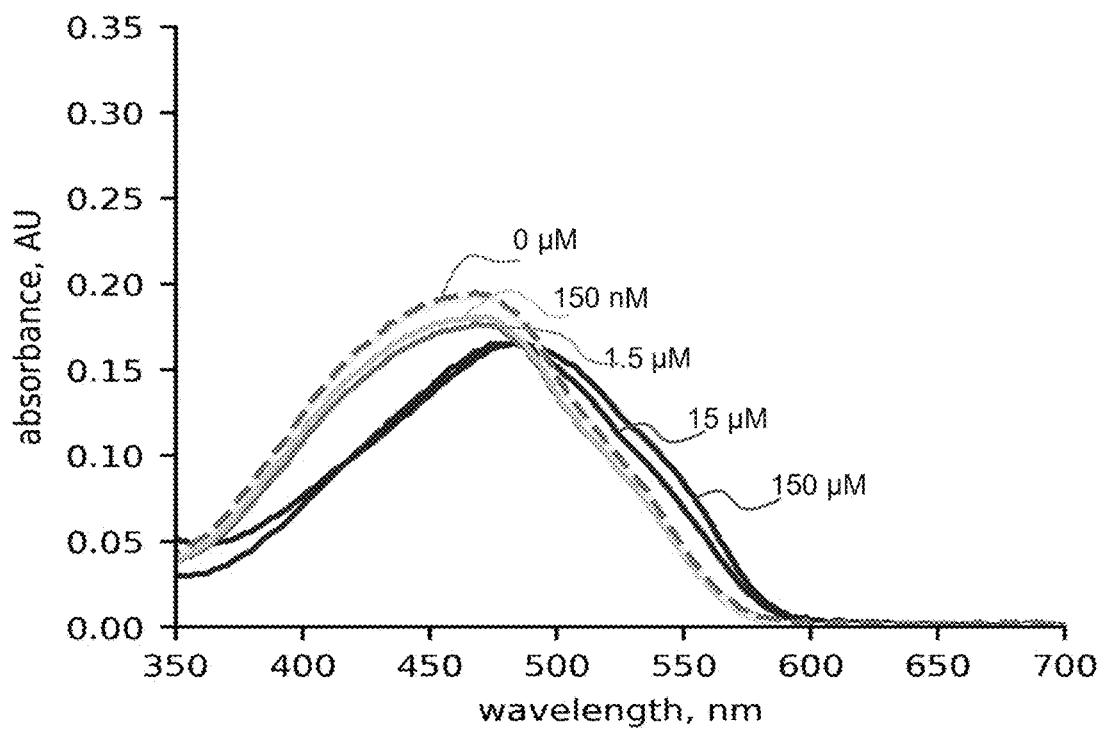
FIGS. 54A-54D are graphs of titration curves showing absorbance (FIG. 54A) and fluorescence (FIGS. 54B-54D) results after combining a mixture of HemiDD1, DD4 and DD13Cx5 (12 µM each) in $NaH_2PO_4/Na_2HPO_4$ buffered water (10 mM, pH 7.4) with bovine serum albumin.
Figure 54B:
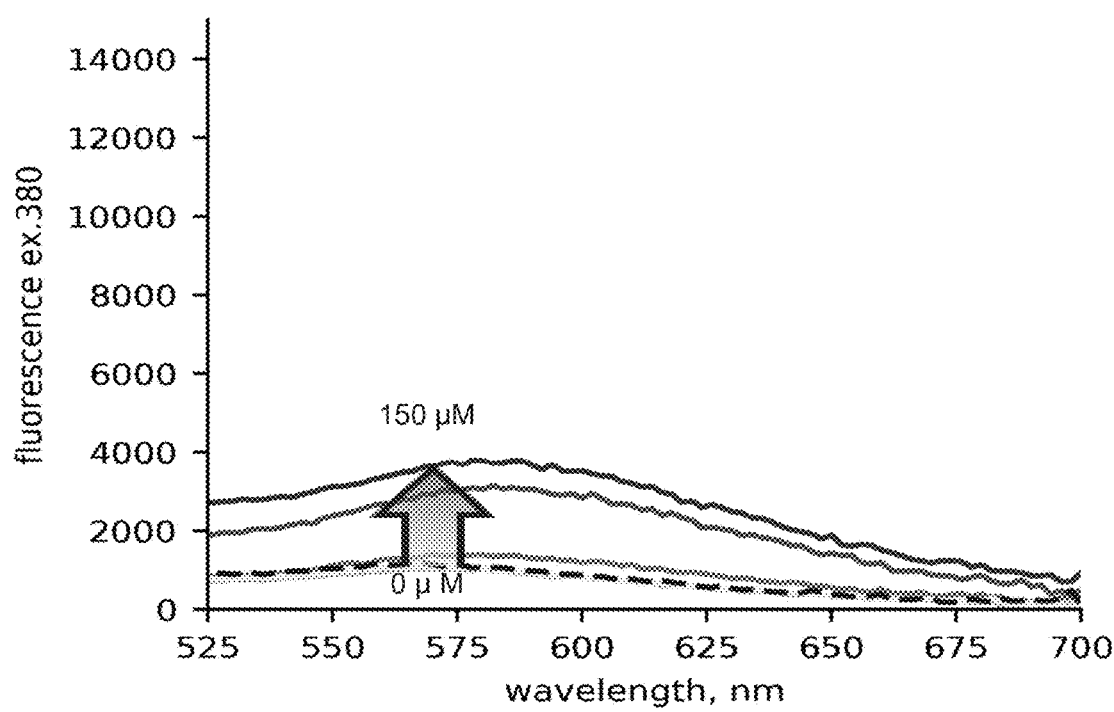
Figure 54C:
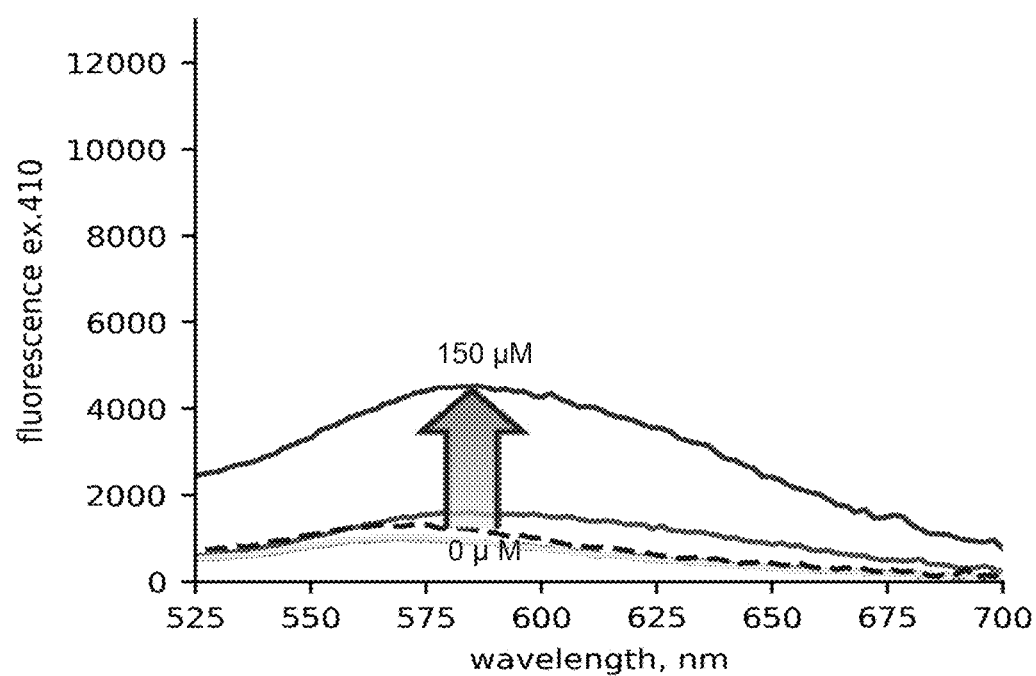
Figure 54D:
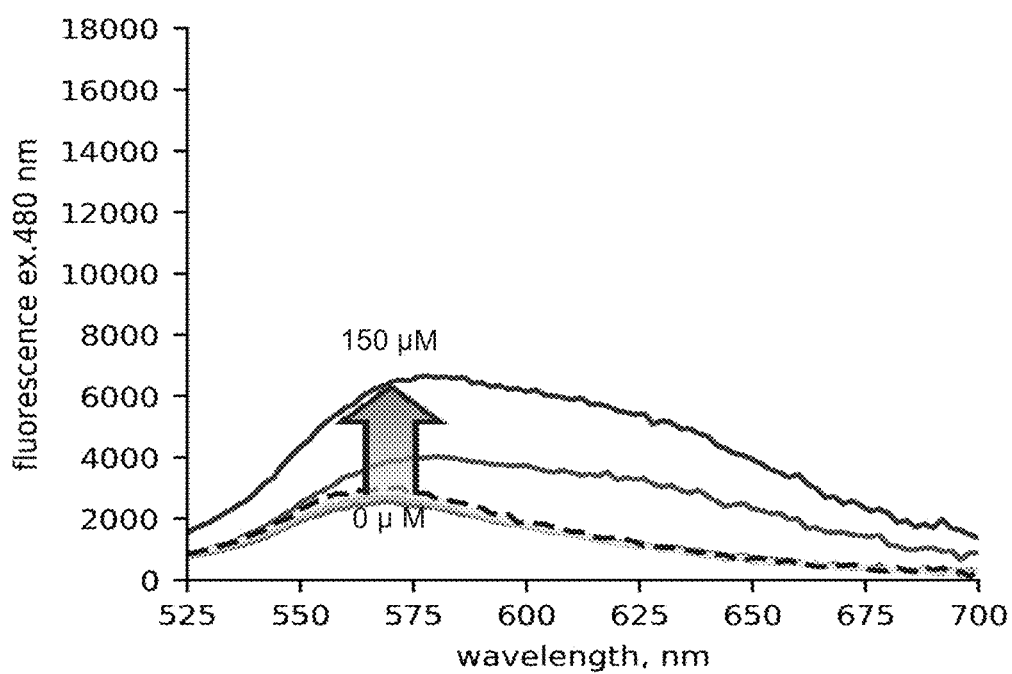
Figure 55A:
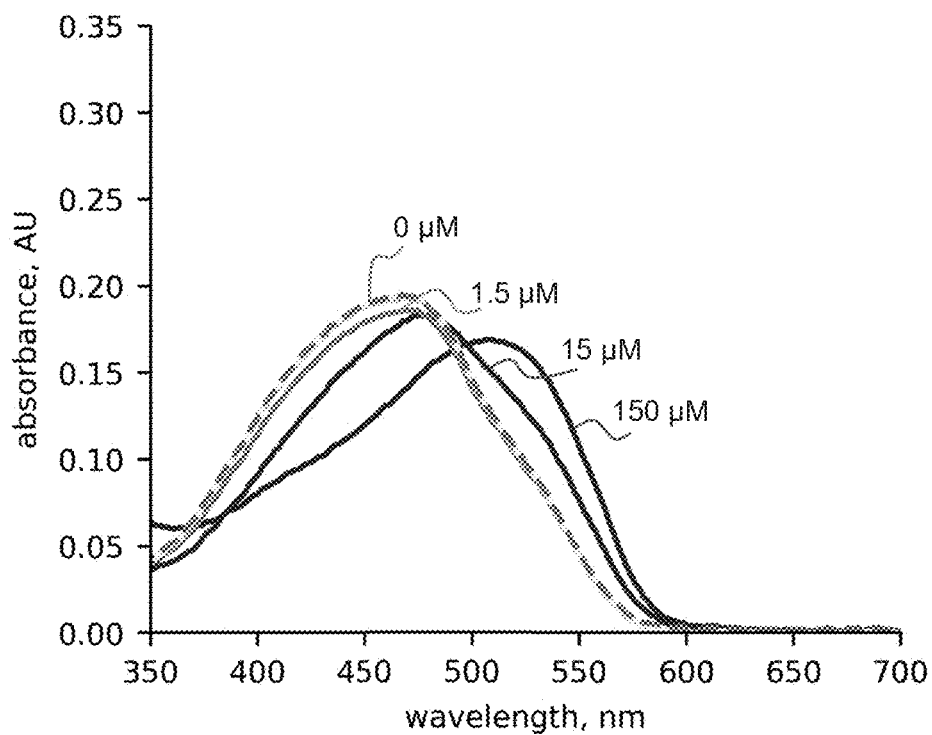
Figure 55B:
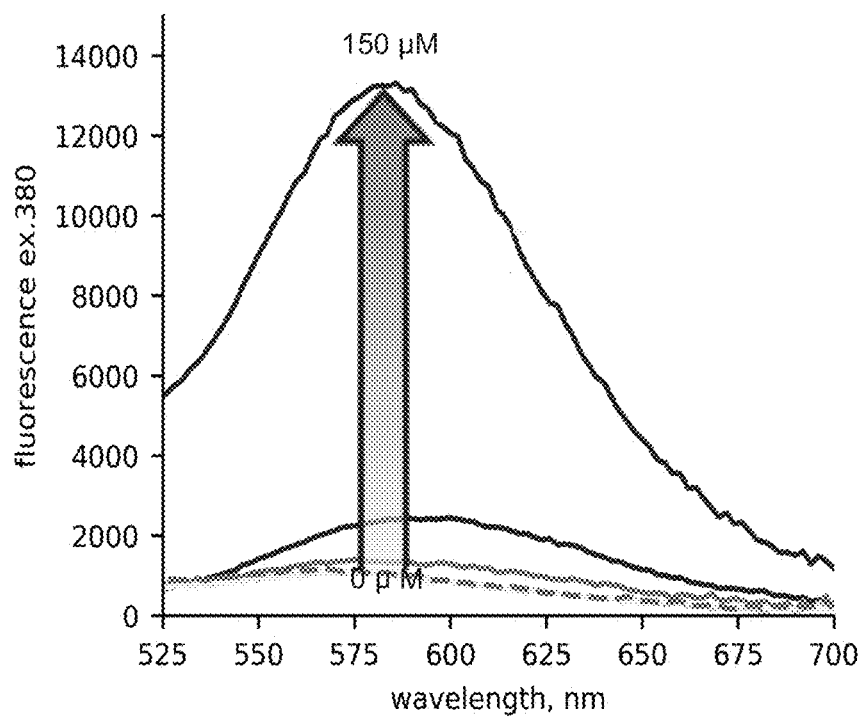
Figure 55C:
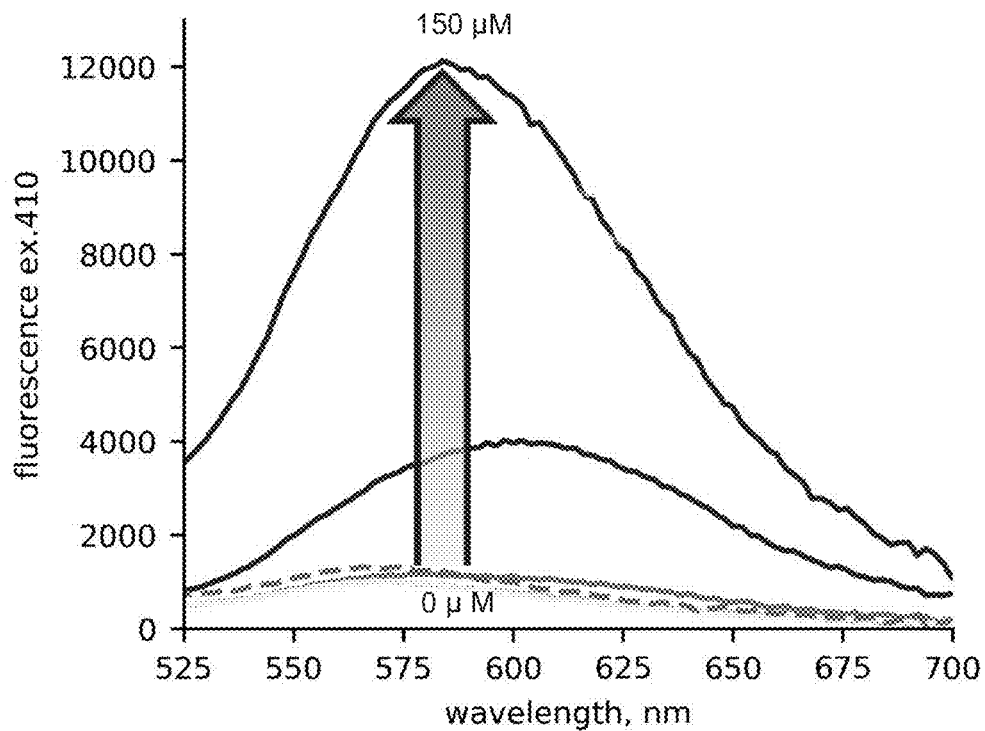
Figure 55D:
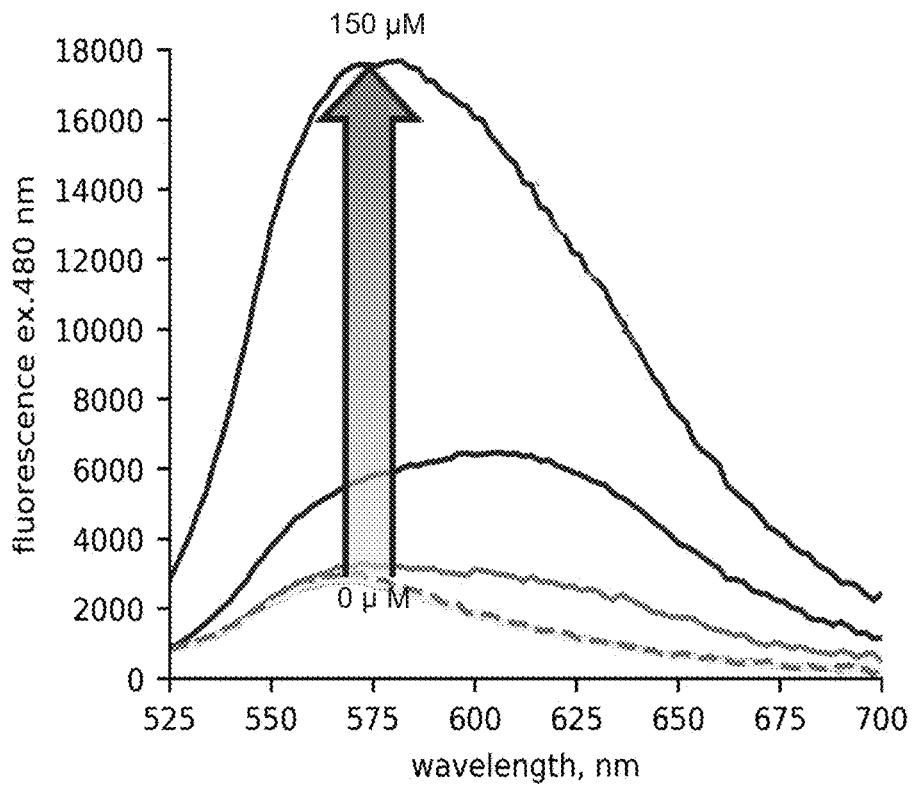

Compound embodiments provide turn-on fluorescence detection of different drugs at low micromolar concentrations in water and in saliva. Three exemplary drugs were chosen to study different drug classes: nicotine, methylenedioxymethamphetamine (Ecstasy, or MDMA), and cocaine. In both water and saliva, all five compound embodiments detect all three drugs at low μM concentrations (Table 8 and Table 9). DD8 detects nicotine in water and in saliva with limits of detection at 3.4 μM and 18.6 μM, respectively (FIG. 5A and FIG. 5B). Even MDMA, a secondary amine and therefore a weaker guest, induces a response from DD1 in both water and saliva with limits of detection at 2.7 μM and 41.2 μM, respectively (FIG. 6A and FIG. 6B). DD13 detects cocaine equally well in buffer and in saliva, with limits of detection of 2.7 μM in both fluids (FIG. 7A and FIG. 7B). Analyte titration results for compound embodiments are provided by FIGS. 37A/37B-51A/51B.

Figure 8B:
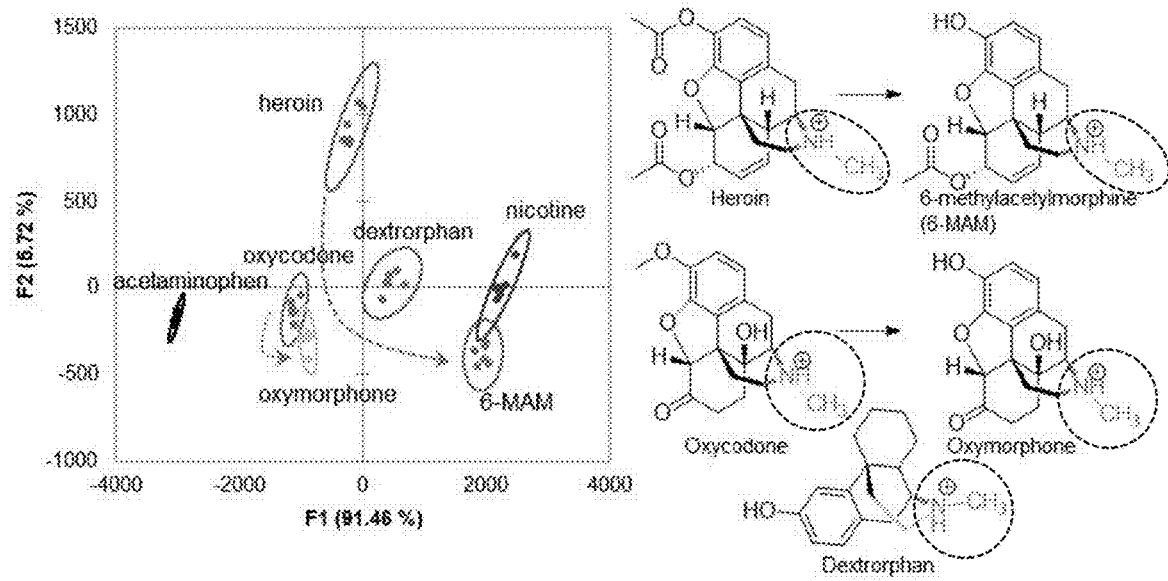
Figure 8C:
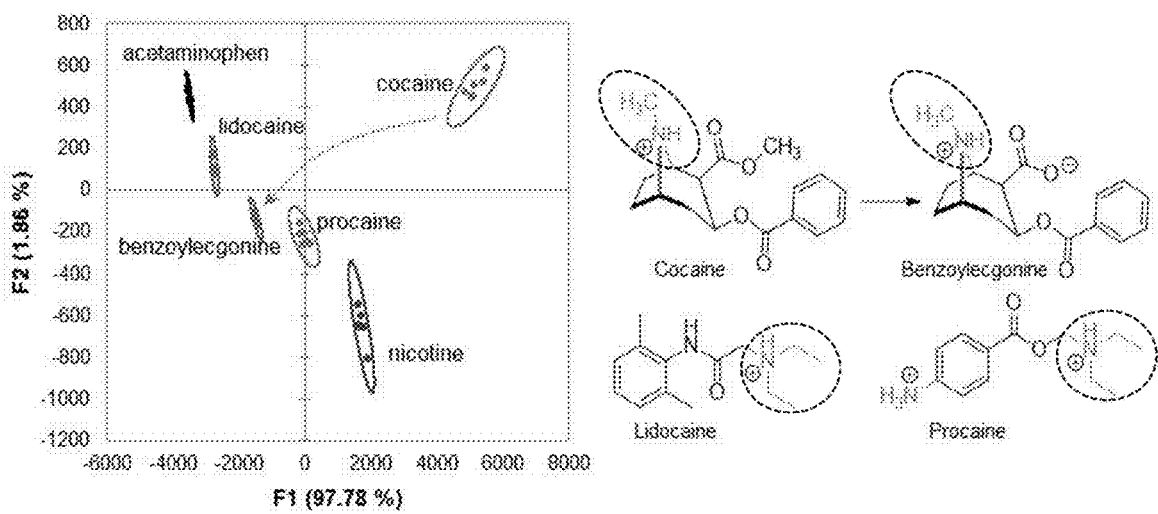

A sensor array of compound embodiments was successfully able to detect and discriminate between closely related drugs and metabolites in multiple drug families. We studied amphetamines, opiates, and alkaloids, and included nicotine and acetaminophen alongside each different drug family as these two drugs are commonly found in individuals. FIG. 8A shows that the active drugs, MDMA and methamphetamine (MA), are discriminated from their metabolites, 3,4-methylenedioxyamphetamine (MDA) and amphetamine (A), even though they differ by only a single methyl group in each case. FIG. 8B shows that heroin and its metabolite 6-monoacetylmorphine (6-MAM) were well discriminated, while oxycodone and oxymorphone are not perfectly discriminated with their 95% confidence ellipses slightly overlapping. The array also differentiated between cocaine, its main metabolite benzoylecgonine, as well as lidocaine and procaine, which are common adulterants found in illegally purchased cocaine (FIG. 8C).

Figure 56:
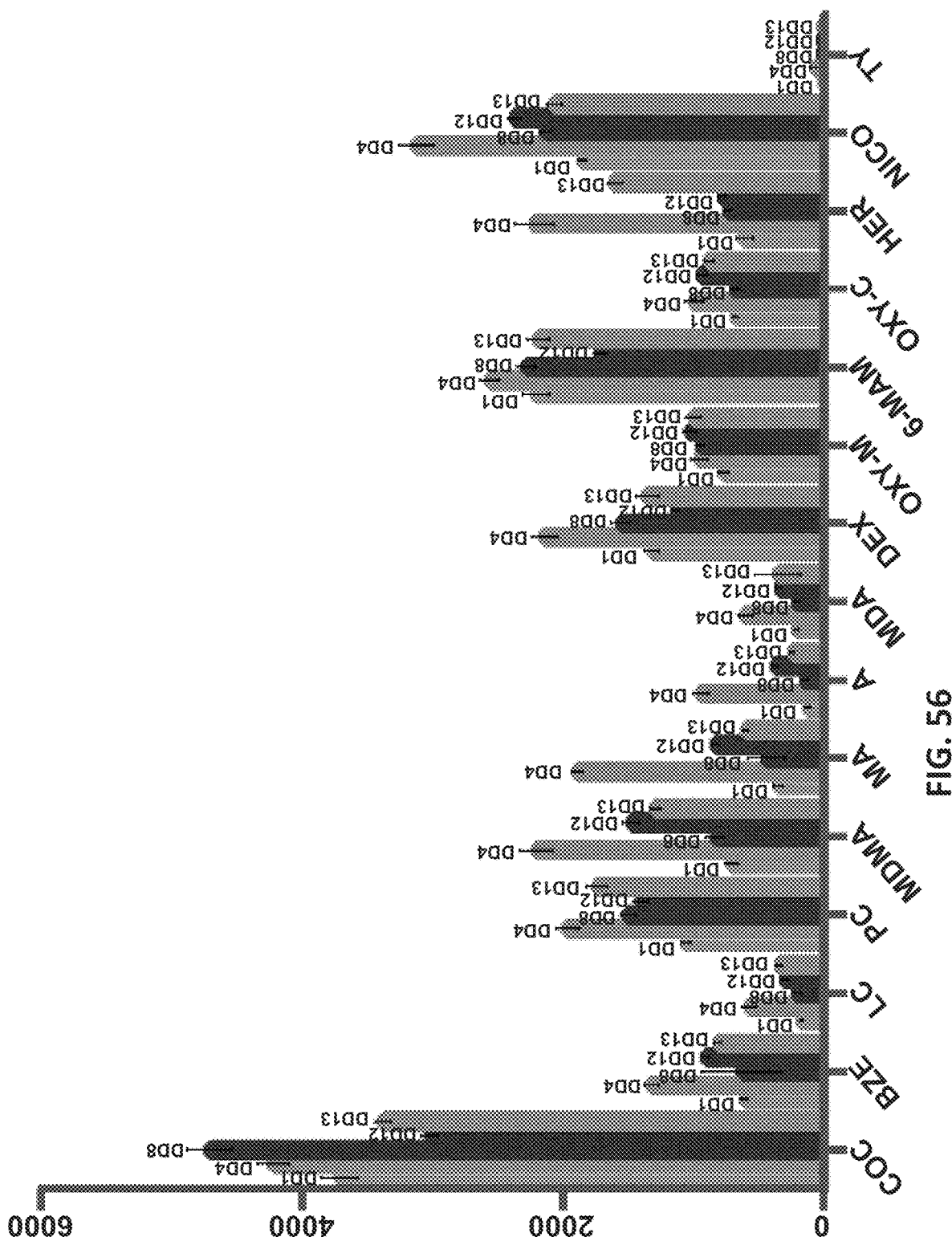
FIG. 56 is a bar graph showing average fluorescence data obtained from combining different dimer complex embodiments with cocaine ("COC"), benzoylecgonine ("BZE"), lidocaine ("LC"), procaine ("PC"), 3,4-methylenedioxymethamphatamine ("MDMA"), methamphetamine ("MA"), amphetamine ("A"), 3,4-methylenedioxoamphetamine ("MDA"), dextrorphan ("DEX"), oxymorphone ("OXY-M"), 6-acetylmorphine ("6-MAM"), oxycodone ("OXY-C"), heroin ("HER"), nicotine ("NICO"), acetaminophen ("TY").

Compound embodiments can function individually or as an array of sensors. Each sensor cross-reactivated with each drug but the uniqueness of the generated fluorescence fingerprint was limited. This is highlighted by the low variance (<5%) along the second principal component (F2) in the amphetamines and anaesthetics class. This suggests compound embodiments can operate independently and not necessarily within an array. However, the benefit of the DD array and using PCA is the visualization of the data. It is easier to map combinations of drugs with common adulterants or their metabolites by the PCA score plots rather than fluorescence bar graphs (FIG. 56).

TABLE 4

Excitation and emission wavelengths used for crude compound embodiment screening

| | $\lambda_{ex.}$, nm | $\lambda_{em.}$, nm |
|---|---|---|
| DD1 | 380 | 575 |
| DD2 | 390 | 575 |
| DD3 | 390 | 575 |
| DD4 | 480 | 560 |
| DD5 | 390 | 575 |
| DD8 | 380 | 575 |
| DD9 | 440 | 680 |
| DD10 | 450 | 600 |
| DD11 | 440 | 630 |
| DD12 | 410 | 615 |
| DD13 | 420 | 620 |
| DD14 | 470 | 565 |
| DD16 | 420 | 555 |

1D DOSY Calculations (1, DD4, DD4+20 Eq. Nicotine)

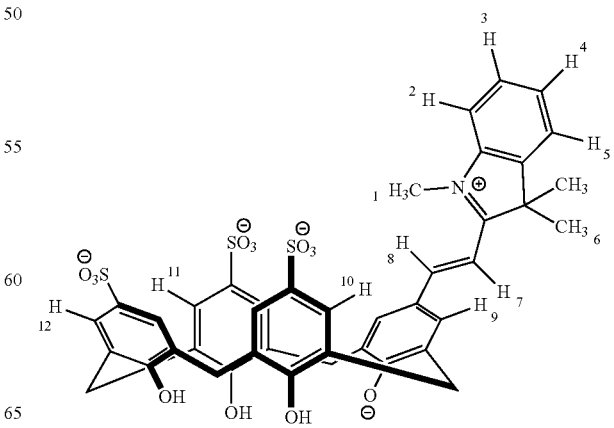

TABLE 5

Diffusion coefficients measured, and hydrodynamic radii calculated from indicated resonances in DD4 from 1D DOSY.

| Atom | D (m²/s) | r (Å) |
|---|---|---|
| H8 | 1.944E−10 | 12.64 |
| H7 | 1.986E−10 | 12.37 |
| H2 | 1.99E−10 | 12.35 |
| H1 | 1.952E−10 | 12.59 |
| H6 | 1.924E−10 | 12.77 |

DD4 was $NaH_2PO_4/Na_2HPO_4$ (50 mM, pD 7.4) in $D_2O$. P1=8.35 ρs, D1=18.75 s, δ=1800 ρs, Δ=100 ms.

The average hydrodynamic radius of DD4 ($r_H$) was calculated as 12.53±0.15 Å and the average diffusion coefficient (D) is $1.96 \times 10^{-10}$ m²/s.

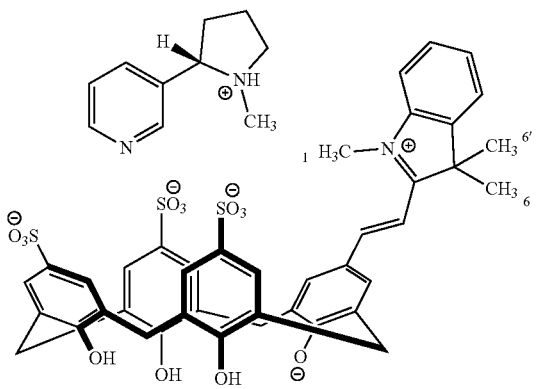

TABLE 6

Diffusion coefficients measured, and hydrodynamic radii calculated from indicated resonances in DD4-nicotine complex from 1D DOSY.

| Atom | D (m²/s) | r (Å) |
|---|---|---|
| H1 | 2.469E−10 | 9.95 |
| H6 | 2.517E−10 | 9.76 |
| H6' | 2.58E−10 | 9.52 |

DD4 (500 μM) and nicotine (10 mM) were dissolved in $NaH_2PO_4/Na_2HPO_4$ (50 mM, pD 7.4) in $D_2O$. P1=8.35 ρs, D1=10 s, δ=1200 ρs, Δ=100 ms.

The average hydrodynamic radius of DD4-nicotine complex ($r_H$) was calculated as 9.74±0.21 Å and the average diffusion coefficient (D) is $2.52 \times 10^{-10}$ m²/s.

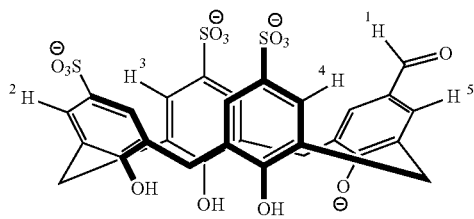

TABLE 7

Diffusion coefficients measured, and hydrodynamic radii calculated from indicated resonances in 1 from 1D DOSY.

| Atom | D (m²/s) | r (Å) |
|---|---|---|
| H1 | 3.3E−10 | 7.45 |
| H2 | 3.28E−10 | 7.50 |
| H3 | 3.27E−10 | 7.52 |
| H4 | 3.29E−10 | 7.48 |
| H5 | 3.28E−10 | 7.49 |

1 (4 mM) was dissolved in $NaH_2PO_4/Na_2HPO_4$ (100 mM, pD 7.4) in $D_2O$. P1=9.4 μs, D1=15.2 s, δ=2500 μs, Δ=50 ms.

The average hydrodynamic radius of 1 ($r_H$) was calculated as 7.49±0.02 Å and the average diffusion coefficient (D) is $3.28 \times 10^{-10}$ m²/s.

Limits of Detection—

Limits of detection were found through the linear regression of each data set and calculating: LOD=σ/slope*3.3

Where, σ and slope are the standard deviation and slope obtained from the regression line All LOD were measured with purified DDs, [DD]=12 μM.

TABLE 8

Limits of detection (LOD) determined of each compound embodiment for nicotine, MDMA and cocaine in sodium phosphate buffer

| | Nicotine | | | MDMA | | | Cocaine | | |
|---|---|---|---|---|---|---|---|---|---|
| | σ | SLOPE | LOD (μM) | σ | SLOPE | LOD (μM) | σ | SLOPE | LOD (μM) |
| DD1 | 45.91 | 43.42 | 3.489245 | 16.2 | 19.65 | 2.720611 | 12.87 | 46.51 | 0.913158 |
| DD4 | 64.27 | 44.19 | 4.799525 | 90.93 | 18.82 | 15.94416 | 52.02 | 92.76 | 1.850647 |
| DD8 | 21.43 | 26.94 | 2.625056 | 15.25 | 10.07 | 4.997517 | 32.12 | 80.26 | 1.320658 |
| DD12 | 82.56 | 33.99 | 8.015534 | 82.56 | 33.99 | 8.015534 | 57.65 | 91.09 | 2.088539 |
| DD13 | 58.65 | 97.59 | 1.983246 | 12.15 | 12.08 | 3.319123 | 54.44 | 67.62 | 2.656788 |

TABLE 9

Limits of detection determined of each compound embodiment for nicotine, MDMA and cocaine in diluted saliva

| | Nicotine | | | MDMA | | | Cocaine | | |
|---|---|---|---|---|---|---|---|---|---|
| | σ | SLOPE | LOD (μM) | σ | SLOPE | LOD (μM) | σ | SLOPE | LOD (μM) |
| DD1 | 17.38 | 2.08 | 27.57404 | 30.36 | 2.428 | 41.26359 | 28.54 | 22.23 | 4.236707 |
| DD4 | 134.8 | 6.003 | 74.10295 | 120.8 | 10.97 | 36.33911 | 94.71 | 41.11 | 7.602603 |
| DD8 | 23.88 | 4.233 | 18.61658 | 22.43 | 3.682 | 20.10293 | 45.95 | 30.63 | 4.950539 |
| DD12 | 26.85 | 5.149 | 17.2082 | 26.26 | 8.699 | 9.961835 | 47.81 | 38.76 | 4.070511 |
| DD13 | 52.71 | 9.283 | 18.7378 | 32.75 | 12.68 | 8.523265 | 35.11 | 43.05 | 2.691359 |

PCA and LDA Analysis—

Stocks of each compound embodiment (13.4 μM) were prepared in $NaH_2PO_4/Na_2HPO_4$ (10 mM, pH 7.4) and aliquoted (90 μL) into a 96-well plate to account for 6 replicates of each drug and 2 blanks. This was followed by additions of each drug/buffer (10 μL) to make a final [DD]=12 μM, [drug]=100 μM or 0 μM (blank) with a final volume of 100 μL. The fluorescence was measured with $\lambda_{ex.}$ and $\lambda_{em.}$ tabulated below. The raw fluorescence was subtracted from the blank before analysis. The PCA (type: covariance) and LDA analysis (cross-validation) were conducted with XLSTAT and Minitab 18.

TABLE 10

Excitation and fluorescence emission wavelengths used for each compound embodiment

| | $\lambda_{ex.}$ (nm) | $\lambda_{em.}$ (nm) |
|---|---|---|
| DD1 | 385 | 590 |
| DD4 | 475 | 570 |
| DD8 | 375 | 580 |
| DD12 | 415 | 640 |
| DD13 | 420 | 635 |

Drug Titrations with DDCx5—

Separately, stocks solutions of DD1Cx5, DD4Cx5, nicotine, and cocaine, were prepared in $NaH_2PO_4/Na_2HPO_4$ (10 mM, pH 7.4). DDCx5 and drug solutions were aliquoted into a NUNC black-walled 96 well plate in triplicate resulting in a final DDCx5 concentration of 12 μM and drug concentration of 125 μM in $NaH_2PO_4/Na_2HPO_4$ (10 mM, pH 7.4). A two-fold serial dilution was performed to achieve [drug]=125 μM–15.6 μM with a constant [DDCx5]=12 μM and final volume of 100 μL in each well. A blank of [DDCx5]=12 μM and [drug]=0 μM was also performed in triplicate. The absorbance spectra of each was measured. The fluorescence spectra of each was measured with the $\lambda_{ex}$ determined from the respective blank (DD1Cx5 $\lambda_{ex}$=380 nm, DD4Cx5 $\lambda_{ex}$=480 nm.)

Protein Titrations with Compound Mixtures—

A stock mixture comprising a combination of dimer complexes of compound embodiments (namely hemiDD1, DD4 and DD13Cx5) at a ratio of 1:1:1 hemiDD1, DD4 and DD13Cx5 was prepared in $NaH_2PO_4/Na_2HPO_4$ (10 mM, pH 7.4). Separate stock solutions of bovine serum albumin (BSA) and human serum albumin (HSA) were prepared on ice in $NaH_2PO_4/Na_2HPO_4$ (10 mM, pH 7.4), the solutions were mixed by slowly pipetting up and down to prevent foaming and aggregation of the protein. The dimer mixture and protein solutions were aliquoted into a NUNC black-walled 96 well plate in triplicate resulting in a final concentration of 12 μM of each hemiDD1, DD4 and DD13Cx5 and a final protein concentration of 150 μM in $NaH_2PO_4/Na_2HPO_4$ (10 mM, pH 7.4). A ten-fold serial dilution was performed to achieve [protein]=150 μM–1.5 nM with a constant [$DD_{mix}$]=12 μM and final volume of 100 μL in each well. A blank of [$DD_{mix}$]=12 μM and [protein]=0 μM was also performed in triplicate. The absorbance spectra of each was measured. Fluorescence spectra were measured with the excitation maxima of each compound embodiment in the mixture ($\lambda_{ex}$ 380, $\lambda_{ex}$ 410 and $\lambda_{ex}$ 480).

Test Strip Analysis— compound embodiment solutions (200 μM) were prepared in phosphate buffer (10 mM, pH 7.4) and spotted (2 μL) onto Whatman™ Qualitative Filter Paper: Grade 1 Circles. The filter paper was dried in a 37° C. oven for 4 hrs. Analytes prepared at various concentrations in water or saliva were spotted (2 μL) on top of dried compound embodiment spots. The filter paper was irradiated with a hand-held UV lamp ($\lambda_{ex}$ 364 nm±20 nm) and imaged using a smart phone camera (see FIGS. 58A-58D).

In view of the many possible embodiments to which the principles of the present disclosure may be applied, it should be recognized that the illustrated embodiments are only examples and should not be taken as limiting the scope. Rather, the scope is defined by the following claims. We therefore claim as our invention all that comes within the scope and spirit of these claims.

We claim:

1. A dimer complex, comprising:
   a first compound having a structure according to Formula I; and
   a second compound having a structure according to Formula I;
   wherein Formula I is

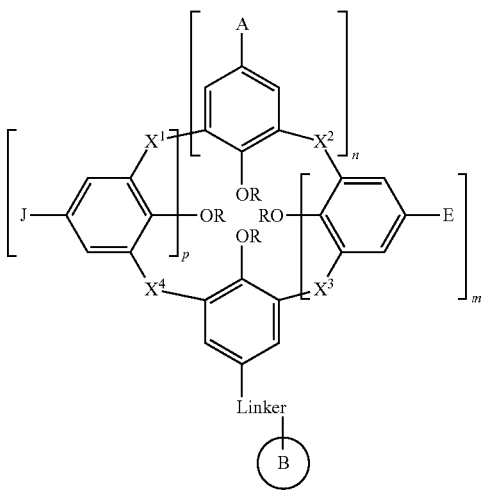

Formula I wherein
   each A independently is selected from C(O)H; $CH_2OH$; or —$SO_3R'$, wherein each R' independently is H or a counterion; or linker'-Ring$_{B'}$, wherein linker' is aliphatic or heteroaliphatic and Ring$_{B'}$ is a ring system capable of producing a detectable signal;

each E independently is selected from —SO$_3$R', wherein each R' independently is H or a counterion;

each J independently is selected from —SO$_3$R', wherein each R' independently is H or a counterion;

each of X$^1$, X$^2$, X$^3$, and X$^4$ independently is CH$_2$, O, S, CH$_2$OCH$_2$, CH$_2$SCH$_2$, or NR$^b$ wherein each R$^b$ independently is hydrogen, aliphatic, heteroaliphatic, or aromatic;

each R independently is H, aliphatic, or a counterion;

the linker group has a structure satisfying a Formula IA

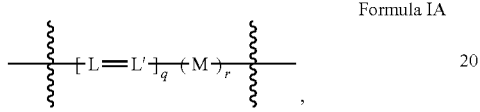

Formula IA wherein each L and L' independently is CH or N; M is NH; q is an integer selected from 1 to 3; and r is 0 or 1;

the B ring comprises an N-functionalized nitrogen-containing ring system, a 2-ethyl-1H-benzo[de]isoquinoline-1,3(2H)-dione functional group, or a nitrobenzo[c][1,2,5]oxadiazole functional group; and each of n, m, and p independently is an integer selected from 1 to 3;

and further wherein (i) the first compound and the second compound chemically interact to form the dimer complex and wherein the dimer complex does not emit a detectable signal or wherein the dimer complex emits a dimer detectable signal that is different from any detectable signal provided by the first compound, the second compound, or both; and (ii) the first compound has a structure that is different from the second compound.

2. The dimer complex of claim 1, wherein the linker' group has a structure satisfying a Formula IA

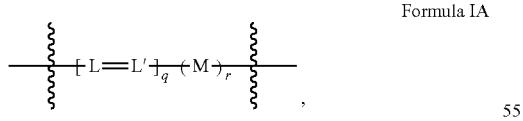

Formula IA wherein each L and L' independently is CH or N; M is NH; q is an integer selected from 1 to 3; and r is 0 or 1.

3. The dimer complex of claim 1, wherein the Ring B group comprises the N-functionalized nitrogen-containing ring system.

4. The dimer complex of claim 1, wherein the Ring$_{B'}$ group comprises an N-functionalized nitrogen-containing ring system, a 2-ethyl-1H-benzo[de]isoquinoline-1,3(2H)-dione functional group, or a nitrobenzo[c][1,2,5]oxadiazole functional group.

5. The dimer complex of claim 1, wherein the Ring B and/or the Ring$_{B'}$ groups independently are selected from:

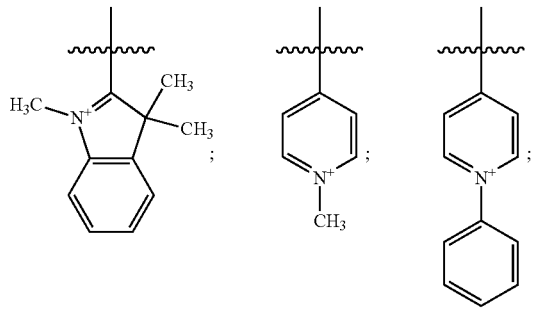

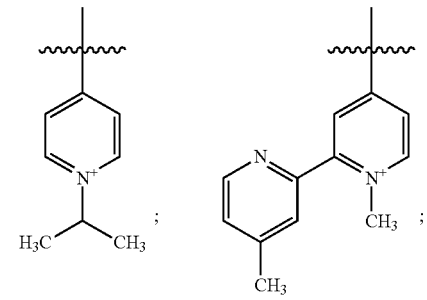

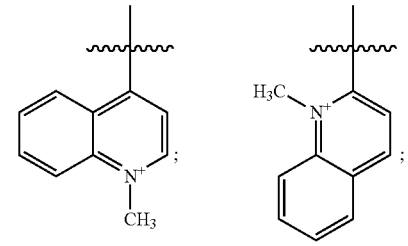

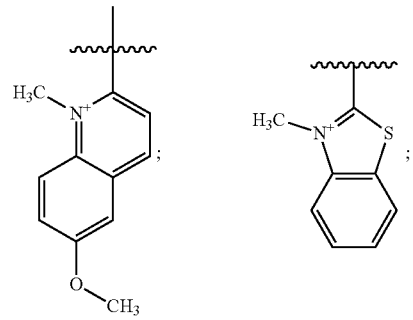

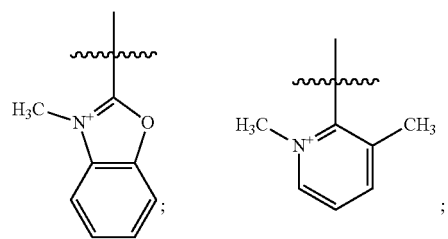

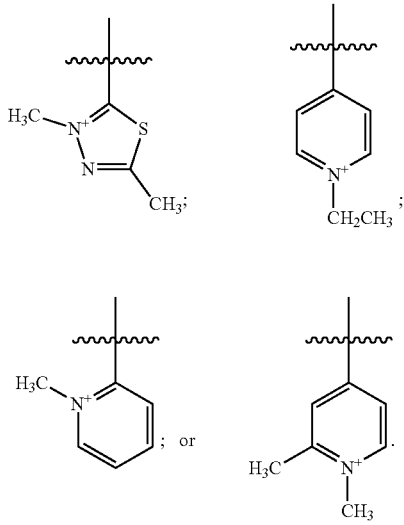

6. The dimer complex of claim 1, wherein each of the first compound and the second compound independently has a structure according to any one or more of Formulas II-V Formula II

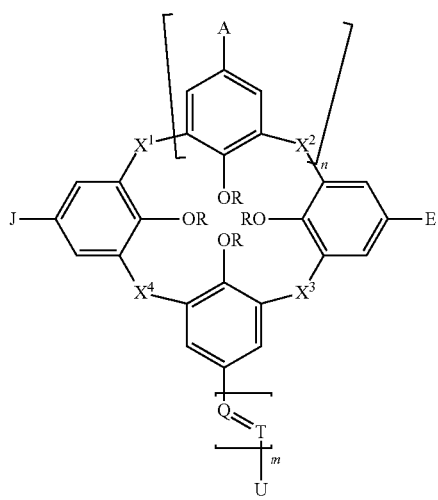

wherein n is an integer selected from 0, 1, or 2; m is an integer selected from 1, 2, or 3; each R independently is H or an aliphatic group; each of $X^1$, $X^2$, $X^3$, and $X^4$ independently is $CH_2$, O, S, $CH_2OCH_2$, or $CH_2SCH_2$; each A and each of E and J independently is $SO_3H$ or $SO_3$— balanced with a counterion provided by an aqueous solution, buffered aqueous solution, or any other counterion that may exist in the environment in which the compound is provided; each of Q and T independently is N or CH; and U comprises the N-functionalized nitrogen-containing ring system, the 2-ethyl-1H-benzo[de]isoquinoline-1,3(2H)-dione functional group, or the nitrobenzo[c][1,2,5]oxadiazole functional group;

Formula III

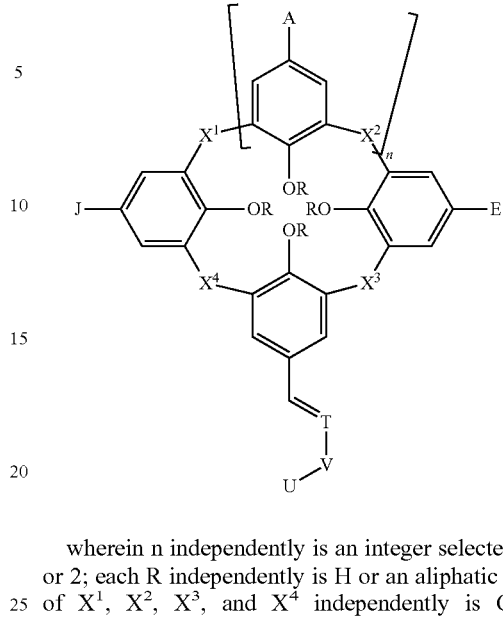

wherein n independently is an integer selected from 0, 1, or 2; each R independently is H or an aliphatic group; each of $X^1$, $X^2$, $X^3$, and $X^4$ independently is $CH_2$, O, S, $CH_2OCH_2$, or $CH_2SCH_2$; each of E and J independently is $SO_3H$ or $SO_3$— balanced with a counterion provided by an aqueous solution, buffered aqueous solution, or any other counterion that may exist in the environment in which the compound is provided; T is N or CH; V is NH; and U comprises the N-functionalized nitrogen-containing ring system, the 2-ethyl-1H-benzo[de]isoquinoline-1,3(2H)-dione functional group, or the nitrobenzo[c][1,2,5]oxadiazole functional group;

Formula IV

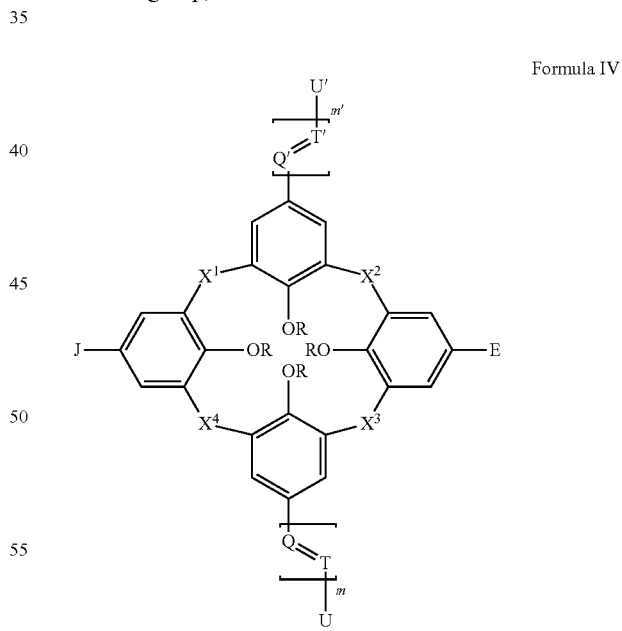

wherein each of m and m' independently is an integer selected from 1, 2, or 3; each R independently is H or an aliphatic group; each of $X^1$, $X^2$, $X^3$, and $X^4$ independently is $CH_2$, O, S, $CH_2OCH_2$, or $CH_2SCH_2$; each of E and J independently is $SO_3H$ or $SO_3$— balanced with a counterion provided by an aqueous solution, buffered aqueous solution, or any other counterion that may exist in the environment in which the compound is provided; each of Q, T, Q', and T' independently is N or CH; and U and U' independently comprises the N-functionalized nitrogen-containing ring system, the 2-ethyl-1H-benzo[de]isoquinoline-1,3(2H)-dione functional group, or the nitrobenzo[c][1,2,5]oxadiazole functional group; or Formula V

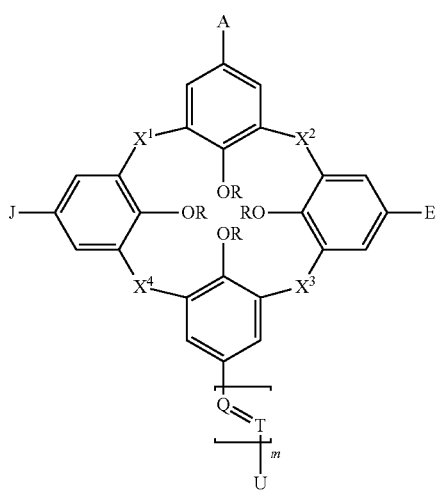

wherein m independently is an integer selected from 1, 2, or 3; each R independently is H or an aliphatic group; each of $X^1$, $X^2$, $X^3$, and $X^4$ independently is $CH_2$, O, S, $CH_2OCH_2$, or $CH_2SCH_2$; each of E and J independently is $SO_3H$ or $SO_3-$ balanced with a counterion provided by an aqueous solution, buffered aqueous solution, or any other counterion that may exist in the environment in which the compound is provided; each of Q and T independently is N or CH; U comprises the N-functionalized nitrogen-containing ring system, the 2-ethyl-1H-benzo[de]isoquinoline-1,3(2H)-dione functional group, or the nitrobenzo[c][1,2,5]oxadiazole functional group; and A is C(O)H or $CH_2OH$.

7. The dimer complex of claim 1, wherein each of the first compound and the second compound independently has structure according to Formula VA Formula VA

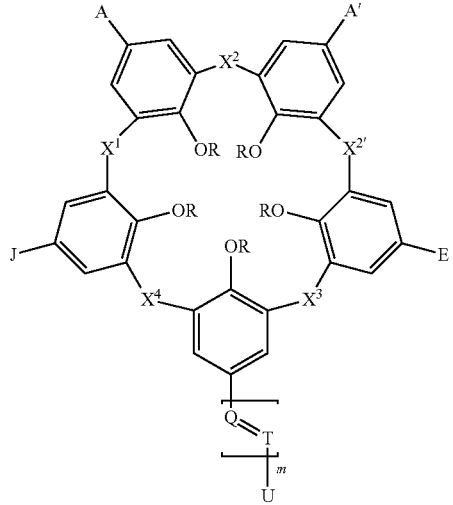

wherein m independently is an integer selected from 1, 2, or 3; each R independently is H or an aliphatic group; each of $X^1$, $X^2$, $X^{2'}$, $X^3$, and $X^4$ independently is $CH_2$, O, S, $CH_2OCH_2$, or $CH_2SCH_2$; each of E and J independently is $SO_3H$ balanced with a counterion provided by an aqueous solution, buffered aqueous solution, or any other counterion that may exist in the environment in which the compound is provided; each of Q and T independently is N or CH; U comprises the N-functionalized nitrogen-containing ring system, the 2-ethyl-1H-benzo[de]isoquinoline-1,3(2H)-dione functional group, or the nitrobenzo[c][1,2,5]oxadiazole functional group; and each of A and A' independently is C(O)H or $CH_2OH$.

8. The dimer complex of claim 1, wherein each of the first compound and the second compound independently is selected from

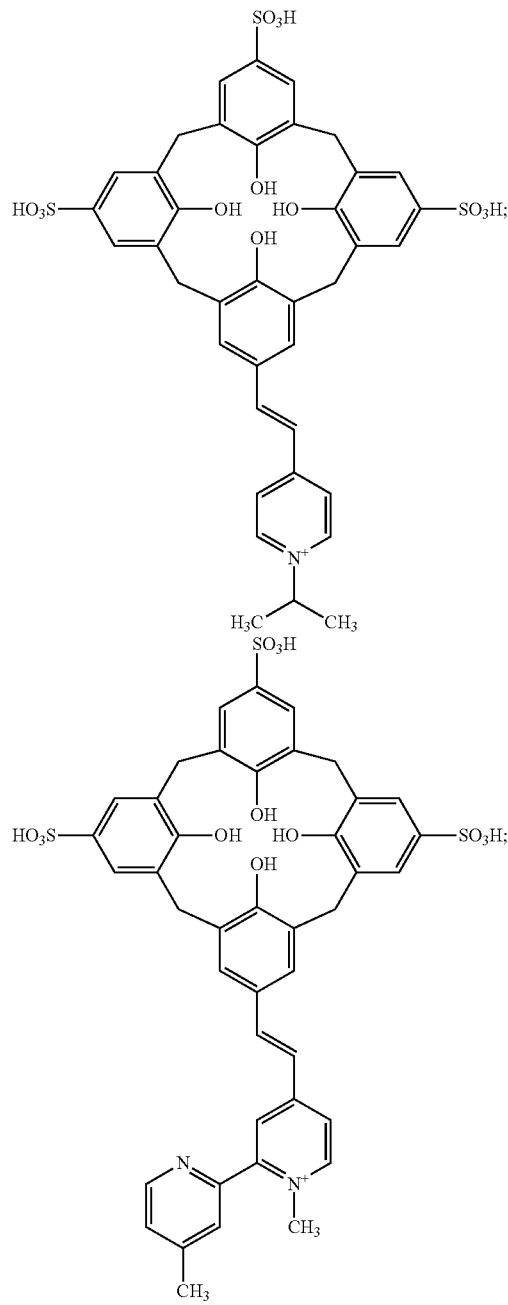

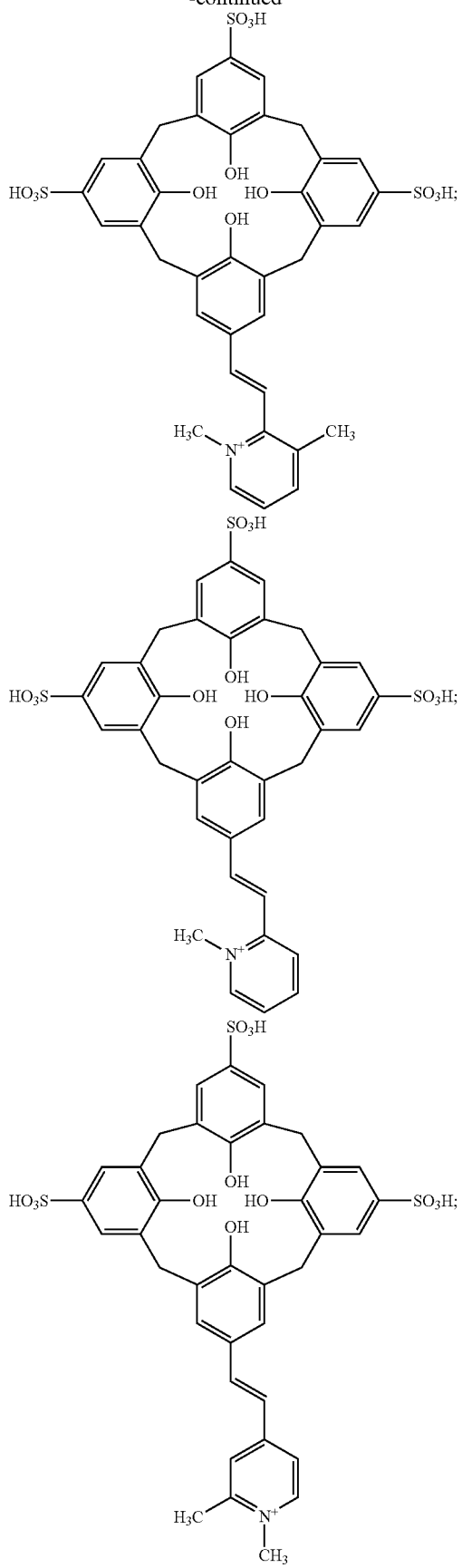
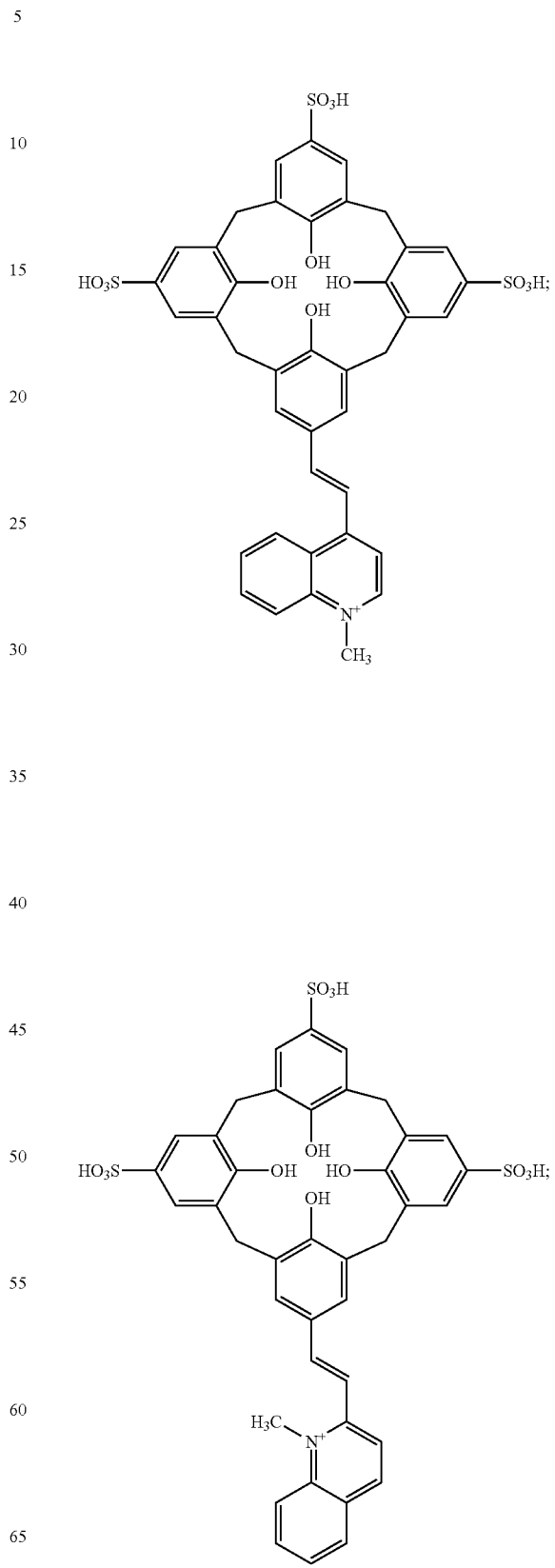

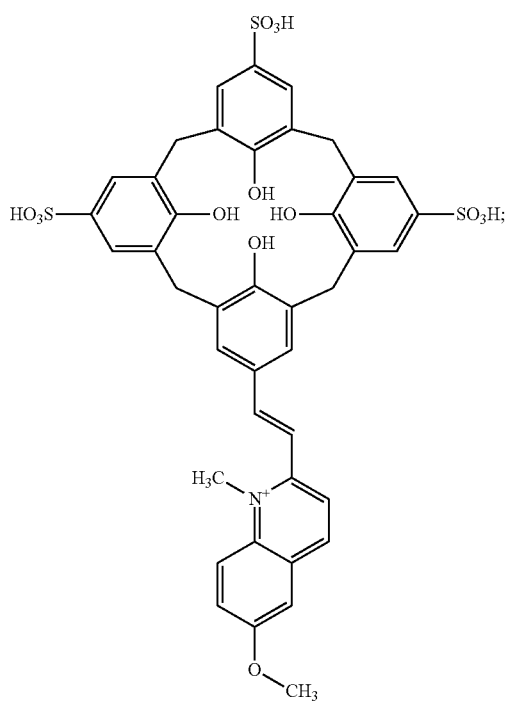
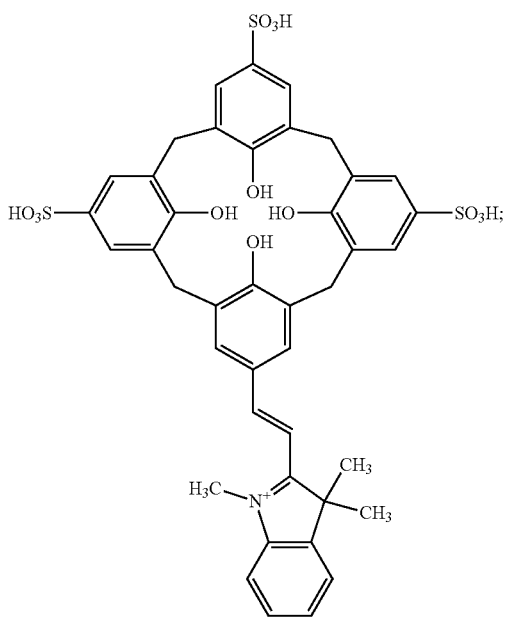
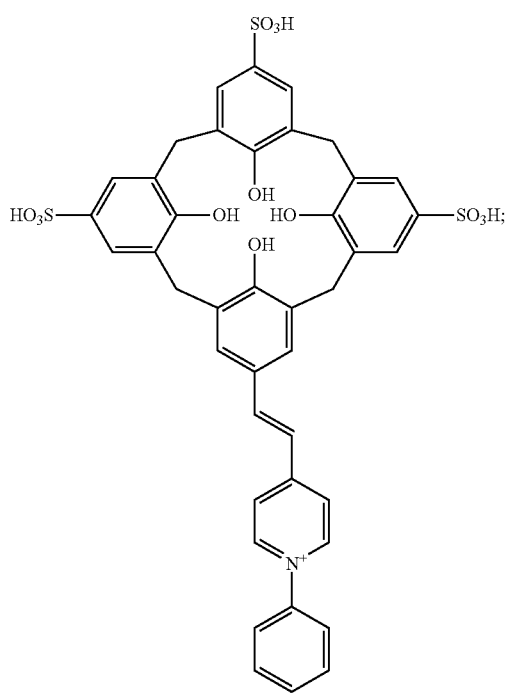

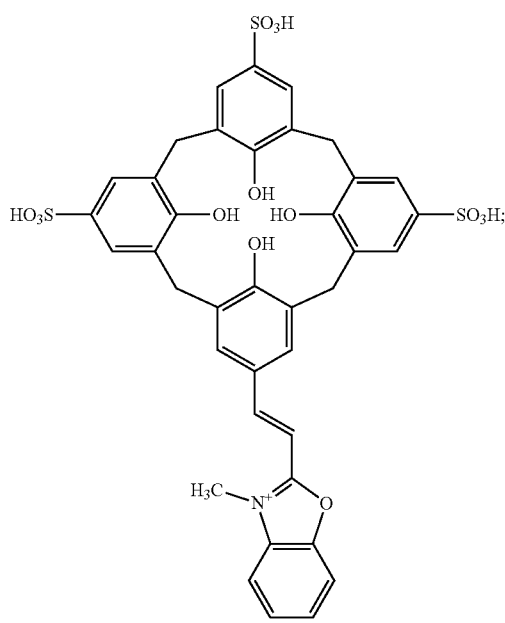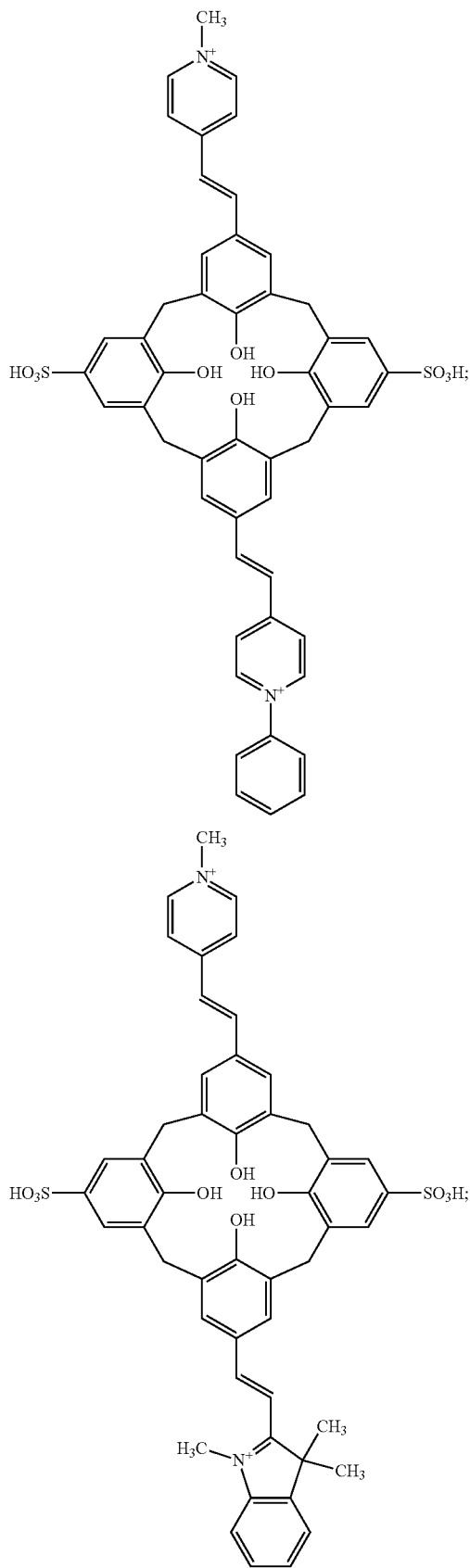

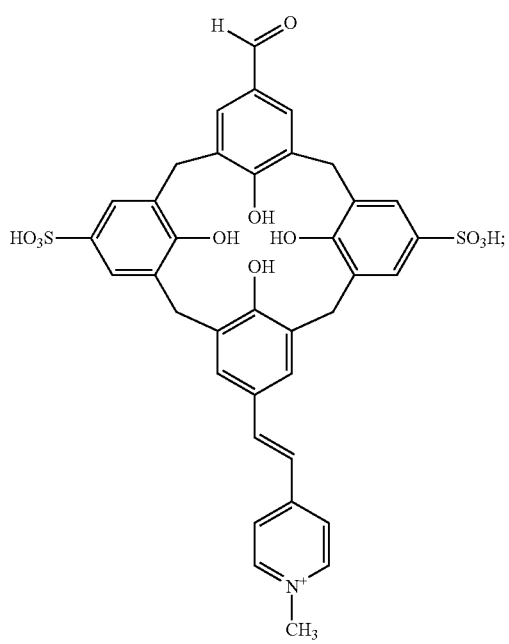
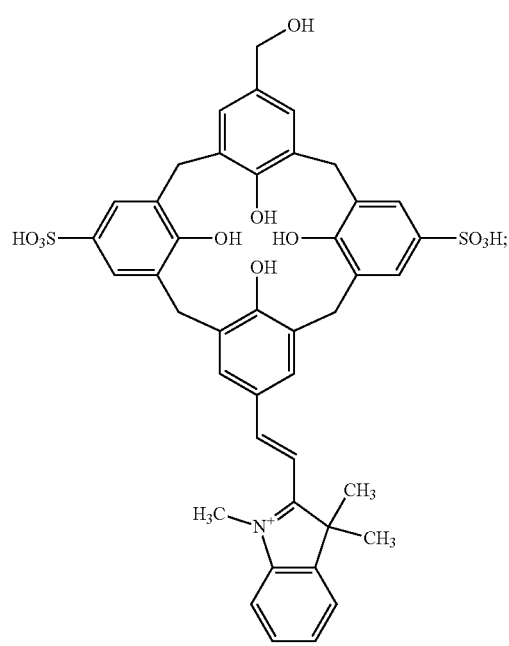
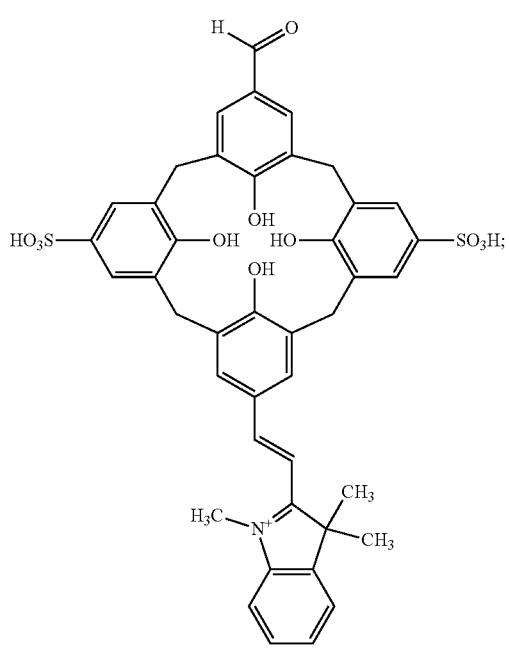
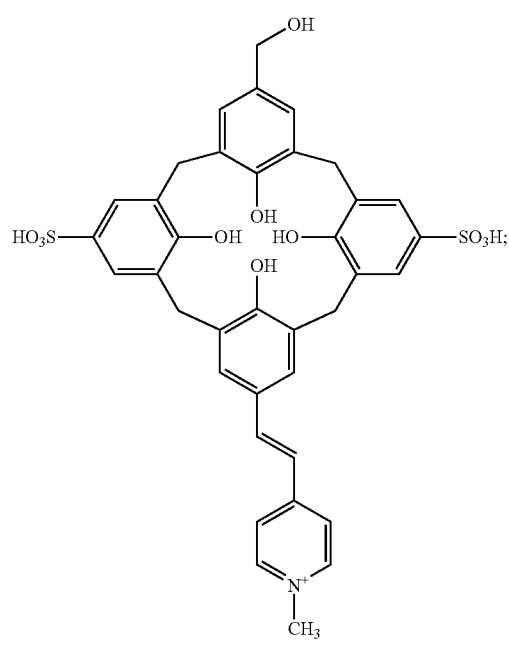

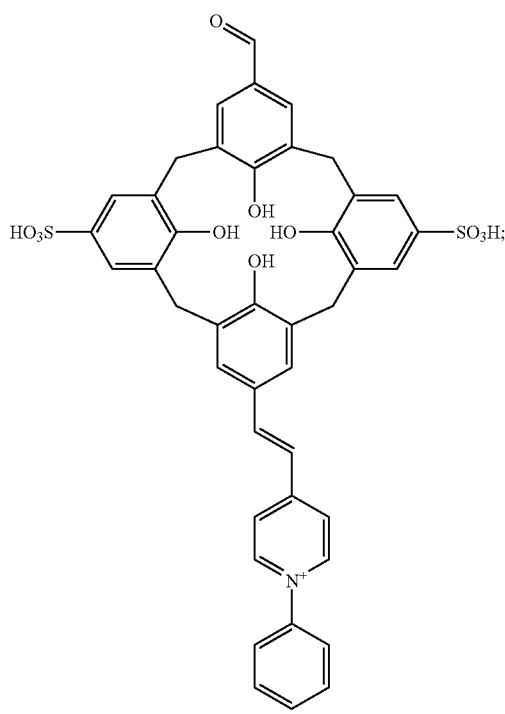
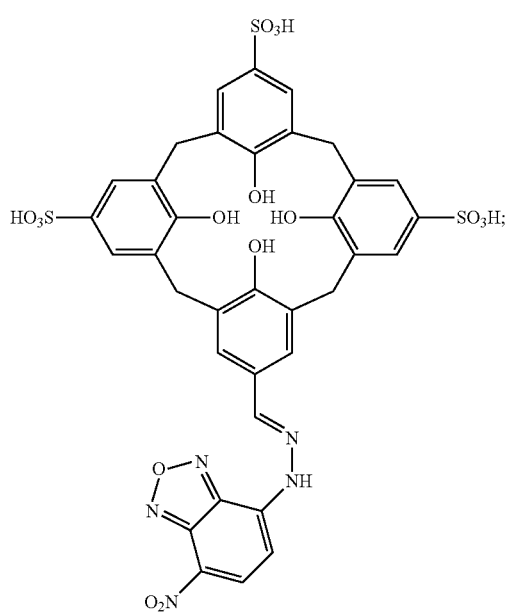
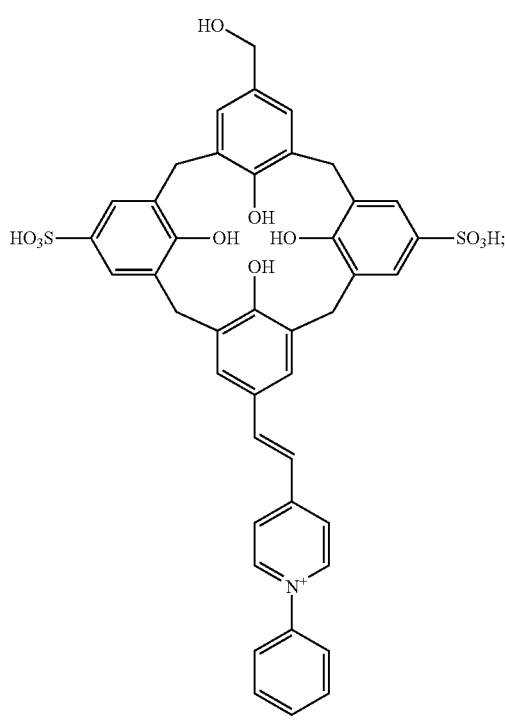

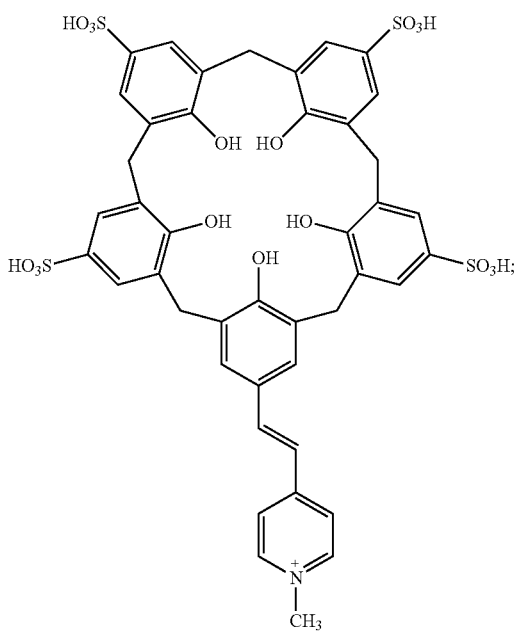

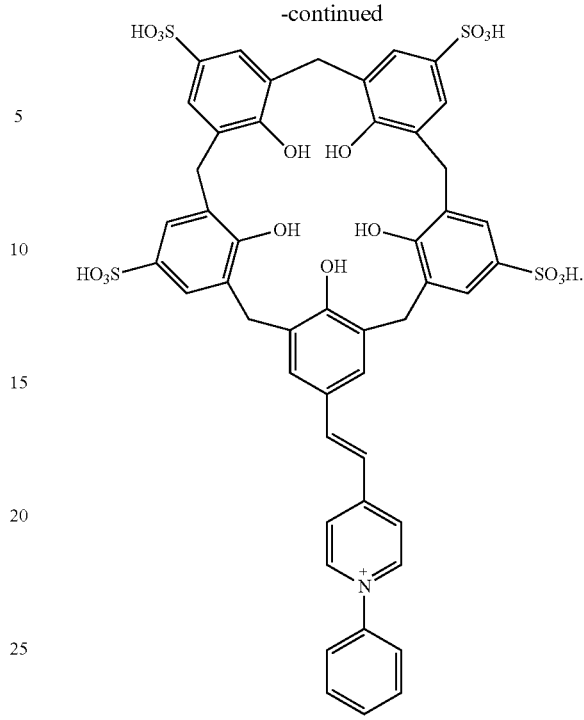

9. The dimer complex of claim 1, wherein each of the first compound and the second compound independently has structure according to Formula VA Formula VA wherein m independently is an integer selected from 1, 2, or 3; each R independently is H or an aliphatic group; each of $X^1$, $X^2$, $X^{2'}$, $X^3$, and $X^4$ independently is $CH_2$, O, S, $CH_2OCH_2$, or $CH_2SCH_2$; each of A, A', E, and J independently is $SO_3H$ or $SO_3^-$ balanced with a counterion provided by an aqueous solution, buffered aqueous solution, or any other counterion that may exist in the environment in which the compound is provided; each of Q and T independently is N or CH; and U comprises the N-functionalized nitrogen-containing ring system, the 2-ethyl-1H-benzo[de]isoquinoline-1,3(2H)-dione functional group, or the nitrobenzo[c][1,2,5]oxadiazole functional group.

10. A sensor array, comprising:
a substrate; and
one or more dimer complexes according to claim 1 associated with the substrate.

11. A method, comprising exposing the dimer complex of claim 1 to an analyte, wherein the analyte disassembles the dimer complex to produce a detectable signal or wherein the analyte disassembles the dimer complex to produce a monomer detectable signal that is different from the dimer detectable signal.

12. The method of claim 11, wherein the analyte comprises a cation or a hydrophobic cation.

13. The method of claim 11, wherein the analyte is provided by a sample selected from aqueous sample, a saliva sample, a urine sample, a nasal wash sample, a synovial fluid sample, a cerebrospinal fluid sample, a gastric fluid sample, a serum sample, a plasma sample, a cell growth medium sample, a cell lysate sample, or any combination thereof.

14. The method of claim 11, wherein the detectable signal is a colorimetric signal or a fluorescent signal and the analyte is an illicit drug.

15. A composition, comprising a plurality of homo- and heterodimer complexes, wherein the homo- and heterodimer complexes are formed from combining at least two compounds having structures according to Formula I, wherein the at least two compounds have different structures and wherein Formula I is

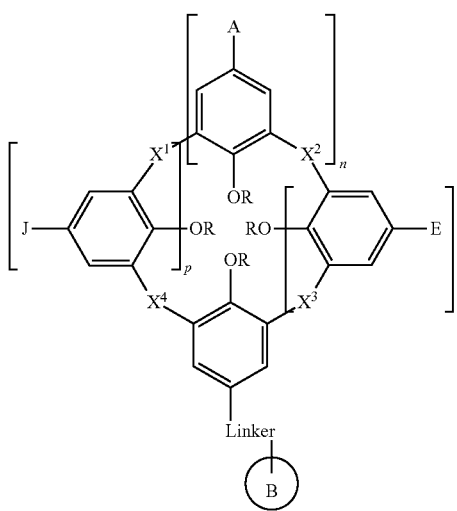

Formula I wherein
each A independently is selected from C(O)H; CH$_2$OH; or —SO$_3$R', wherein each R' independently is H or a counterion; or linker'-Ring$_{B'}$, wherein linker' is aliphatic or heteroaliphatic and Ring$_{B'}$ is a ring system capable of producing a detectable signal;

each E independently is selected from —SO$_3$R', wherein each R' independently is H or a counterion;

each J independently is selected from —SO$_3$R', wherein each R' independently is H or a counterion;

each of X$^1$, X$^2$, X$^3$, and X$^4$ independently is CH$_2$, O, S, CH$_2$OCH$_2$, CH$_2$SCH$_2$, or NR$^b$ wherein each R$^b$ independently is hydrogen, aliphatic, heteroaliphatic, or aromatic;

each R independently is H, aliphatic, or a counterion;

the linker group has a structure satisfying a Formula IA

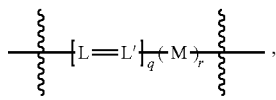

Formula IA wherein each L and L' independently is CH or N; M is NH; q is an integer selected from 1 to 3;
and r is 0 or 1;
the B ring comprises an N-functionalized nitrogen-containing ring system, a 2-ethyl-1H-benzo[de]isoquinoline-1,3(2H)-dione functional group, or a nitrobenzo[c][1,2,5]oxadiazole functional group; and
each of n, m, and p independently is an integer selected from 1 to 3.

16. The composition according to claim 15, wherein the homo- and heterodimer complexes are formed from combining at least three compounds having structures according to Formula I, wherein the at least three compounds have different structures.

* * * * *